US012344845B2

(12) United States Patent
Yan et al.

(10) Patent No.: US 12,344,845 B2
(45) Date of Patent: Jul. 1, 2025

(54) HIGHLY KNOTTED MOLECULAR TOPOLOGIES FROM SINGLE-STRANDED NUCLEIC ACIDS

(71) Applicant: ARIZONA BOARD OF REGENTS ON BEHALF OF ARIZONA STATE UNIVERSITY, Scottsdale, AZ (US)

(72) Inventors: Hao Yan, Chandler, AZ (US); Fei Zhang, Chandler, AZ (US); Xiaodong Qi, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 1233 days.

(21) Appl. No.: 17/050,918

(22) PCT Filed: Apr. 25, 2019

(86) PCT No.: PCT/US2019/029201

§ 371 (c)(1),
(2) Date: Oct. 27, 2020

(87) PCT Pub. No.: WO2020/036654

PCT Pub. Date: Feb. 20, 2020

(65) Prior Publication Data

US 2021/0230601 A1 Jul. 29, 2021

Related U.S. Application Data

(60) Provisional application No. 62/663,678, filed on Apr. 27, 2018.

(51) Int. Cl.

| | |
|---|---|
| ***C12N 15/117*** | (2010.01) |
| ***A61K 47/00*** | (2006.01) |
| ***B82Y 5/00*** | (2011.01) |
| ***C07H 21/00*** | (2006.01) |

(52) U.S. Cl.

CPC .......... *C12N 15/117* (2013.01); *C07H 21/00* (2013.01); *C12N 2310/17* (2013.01); *C12N 2310/18* (2013.01)

(58) Field of Classification Search

None

See application file for complete search history.

(56) References Cited

U.S. PATENT DOCUMENTS

| | | | |
|---|---|---|---|
| 4,559,157 | A | 12/1985 | Smith |
| 4,608,392 | A | 8/1986 | Jacquet |
| 4,820,508 | A | 4/1989 | Wortzman |
| 4,938,949 | A | 7/1990 | Borch |
| 4,992,478 | A | 2/1991 | Geria |
| 6,773,885 | B1 | 8/2004 | Walder |
| 2014/0363852 | A1 | 12/2014 | Efcavitch |
| 2016/0108382 | A1 | 4/2016 | Efcavitch |
| 2018/0044663 | A1 | 2/2018 | Yan |
| 2018/0274001 | A1 | 9/2018 | Efcavitch |

FOREIGN PATENT DOCUMENTS

| | | | |
|---|---|---|---|
| WO | WO2015/159023 | A1 | 10/2015 |
| WO | WO2016/034807 | A1 | 3/2016 |
| WO | WO2016/144755 | A1 | 9/2016 |
| WO | WO2019/030149 | A1 | 2/2019 |

OTHER PUBLICATIONS

Riccelli, NAR, 2001, 29: 996-1004.*
Zhang et al., J. Am. Chem. Soc., 2002, 124: 12940-12941.*
Zhu et al., Nature Commun., 2017, 8: 1-13.*
Ward et al., Adv. Immunol., 2016, 130: 1-40.*
Dai et al., Oncotarget, 2016, 7: 38257-38269.*
Shu et al., ACS Nano, 2015, 9: 9731-9740.*
Ackermann, D. et al., A double-stranded DNA rotaxane. Nat Nanotechnol 5, 436-442 (2010).
Acuna, G. P. et al., Fluorescence Enhancement at Docking Sites of DNA-Directed Self-Assembled Nanoantennas. Science 338, 506-510 (2012).
Alexander, J. W. Topological invariants of knots and links. Trans Am Math Soc 30, 275-306 (1928).
Altschul, Stephen F., et al. "Basic local alignment search tool." Journal of Molecular Biology 215.3 (1990): 403-410.
Beaucage, S. L., and M. H. Caruthers. "Deoxynucleoside phosphoramidites—a new class of key intermediates for deoxypolynucleotide synthesis." Tetrahedron Letters 22.20 (1981): 1859-1862.
Bellot, G., et al., (2013) DNA nanotubes for NMR structure determination of membrane proteins, Nat Protoc 8, 755-770.
Burton, A. S. et al., The elusive quest for RNA knots. RNA Biol 13, 134-139 (2016).
Champoux, J.J. DNA topoisomerases: Structure, function, and mechanism Annu Rev Biochem 70, 369-413 (2001).
Church, G. M. et al., Next-Generation Digital Information Storage in DNA. Science 337, 1628-1628 (2012).

(Continued)

*Primary Examiner* — Ileana Popa
(74) *Attorney, Agent, or Firm* — DUANE MORRIS LLP

(57) ABSTRACT

In some embodiments, complex molecular knots with high crossing numbers are achieved by folding, following a prescribed folding order, single-stranded DNA or RNA of customized sequences into target shapes. Such complex molecular knots with high crossing numbers are useful for biomedical applications including use as immunostimulatory agents and/or protein hosts and carriers.

17 Claims, 34 Drawing Sheets

Specification includes a Sequence Listing.

(56) References Cited

OTHER PUBLICATIONS

Ciengshin, T. et al., Automatic Molecular Weaving Prototyped by Using Single-Stranded DNA. Angew Chem Int Edit, 50, 4419-4422 (2011).
Corpet et al., Nucl. Acids Res., 16, 10881-10890 (1988).
Douglas, S. M. et al., A Logic-Gated Nanorobot for Targeted Transport of Molecular Payloads. Science 335, 831-834 (2012).
Du, S. M. et al. J Am Chem Soc 114, 9652-9655 (1992).
Du, S. M. et al. J Am Chem Soc 117, 1194-1200 (1995).
Forgan, R. S. et al., Chem Rev 111, 5434-5464 (2011).
Froehler et al., Nucl. Acid. Res. 14:5399-5407, 1986.
Gaffney et al., Tet. Let. 29:2619-2622, 1988.
Garegg, Per J., et al. "Nucleoside H-phosphonates. III. Chemical synthesis of oligodeoxyribonucleotides by the hydrogenphosphonate approach." Tetrahedron Letters 27.34 (1986): 4051-4054.
Garegg, Per J., et al. "Nucleoside H-phosphonates. IV. Automated solid phase synthesis of oligoribonucleotides by the hydrogenphosphonate approach." Tetrahedron Letters 27.34 (1986): 4055-4058.
Geary, C. et al., A single-stranded architecture for cotranscriptional folding of RNA nanostructures. Science 345, 799-804 (2014).
Goldman, N. et al., Towards practical, high-capacity, low-maintenance information storage in synthesized DNA. Nature 494, 77-80 (2013).
He, Y. et al., Self-assembly of hexagonal DNA two-dimensional (2D) arrays. J Am Chem Soc 127, 12202-12203 (2005).
He, Y. et al., On the Chirality of Self-Assembled DNA Octahedra. Angew Chem Int Ed 49, 748-751 (2010).
Higgins et al., CABIOS, 5, 151-153 (1989).
Hong, Fan, et al. "DNA origami: scaffolds for creating higher order structures." Chemical Reviews 117.20 (2017): 12584-12640.
Huang et al., CABIOS, 8, 155-165 (1992).
International Search Report/Written Opinion in International Patent Application No. PCT/US19/29201, dated Jul. 23, 2020, in 12 pages.
Karlin and Altschul, Proc. Natl. Acad. Sci. USA, 87, 2264-2268 (1990).
Karlin and Altschul, Proc. Natl. Acad. Sci. USA 90, 5873-5877 (1993).
Kocar, V. et al., Design principles for rapid folding of knotted DNA nanostructures. Nat Commun 7, (2016), 1-8.
Kuzyk, A. et al., DNA-based self-assembly of chiral plasmonic nanostructures with tailored optical response. Nature 483, 311-314 (2012).
Liu, L. F. et al., Nucleic Acids Red 9, 3979-3989 (1981).
Liu, L. F. et al., Proc. Natl Acad Sci-Biol 78, 5498-5502 (1981).
Liu, D. et al. Creating complex molecular topologies by configuring DNA four-way junctions. Nat Chem 8, 907-914 (2016).
Mansfield, M.L. Are There Knots in Proteins. Nat Struct Biol 1, 213-214 (1994).
Mao, C. D. et al. Nature 386, 137-138 (1997).
Marchi, A. N. et al., Nano Lett 14, 5740-5747 (2014).
Martin, T. G. et al., Design of a molecular support for cryo-EM structure determination. Proc Natl Acad Sci USA 113, E7456-E7463 (2016).
Mueller, J. E. et al. J Am Chem Soc 113, 6306-6308 (1991).
Myers and Miller, CABIOS, 4, 11-17 (1988).
Needleman and Wunsch, J Mol Biol, 48, 443-453 (1970).
Ohayon, Y. P. et al., ACS Nano 9, 10296-10303 (2015).
Ohayon, Y. R. et al., ACS Nano 9, 10304-10312 (2015).
Pearson and Lipman, Proc. Natl. Acad. Sci. USA, 85, 2444-2448 (1988).
Pearson et al., Meth. Mol. Biol., 24, 307-331 (1994).
Pinheiro, A. V. et al., Challenges and opportunities for structural DNA nanotechnology. Nat Nanotechnol 6, 763-772 (2011).
Schmidt, T. L. et al., Construction of a Structurally Defined Double-Stranded DNA Catenane. Nano Lett 11, 1739-1742 (2011).
Shih, W. M. et al., A 1.7-kilobase single-stranded DNA that folds into a nanoscale octahedron. Nature 427, 618-621 (2004).
Smith et al., Adv. Appl. Math., 2, 482-489 (1981).
Takusagawa, F. et al., J Am Chem Soc 118, 8945-8946 (1996).
Tang, G., et al., (2007) EMAN2: an extensible image processing suite for electron microscopy, Journal of Structural Biology 157, 38-46.
Taylor, W.R. A deeply knotted protein structure and how it might fold. Nature 406, 916-919 (2000).
Veneziano, R. et al., Designer nanoscale DNA assemblies programmed from the top down. Science 352, aaf4388—8 pages (2016).
Wagner, J. R. et al., A light-sensing knot revealed by the structure of the chromophore-binding domain of phytochrome Nature 438, 325-331 (2005).
Williams, S. et al., Tiamat: A Three-Dimensional Editing Tool for Complex DNA Structures. 5347, 90-101 (2009).
Yan, H. et al., DNA-templated self-assembly of protein arrays and highly conductive nanowires. Science 301, 1882-1884 (2003).
Zhang, F. et al., Structural DNA Nanotechnology: State of the Art and Future Perspective. J Am Chem Soc 136, 11198-11211 (2014).

* cited by examiner

① a → b →← c c

② a → c → b → c

③ b → a →← c c

④ b → c → a → c

⑤ c → a → b → c

⑥ c → a → c → b

⑦ c → b → a → c

⑧ c → b → c → a

FIG. 9A
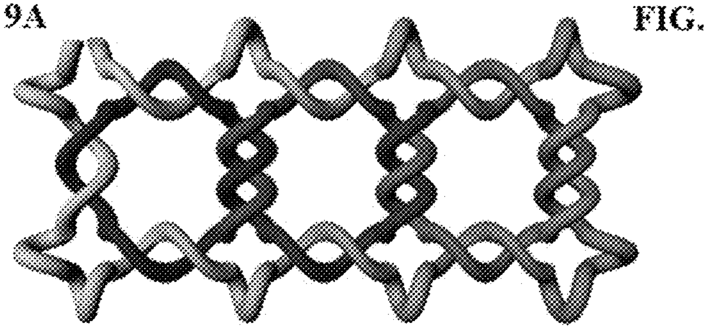
FIG. 9C
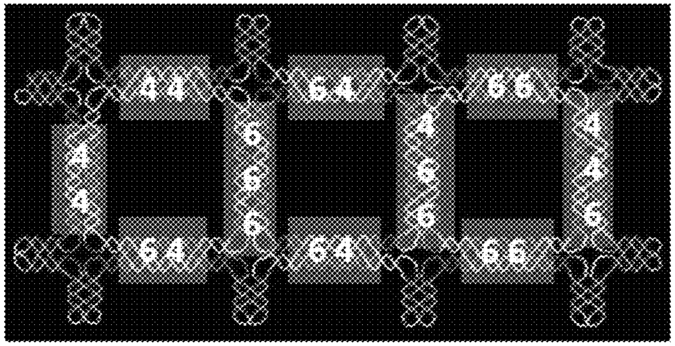
FIG. 9B
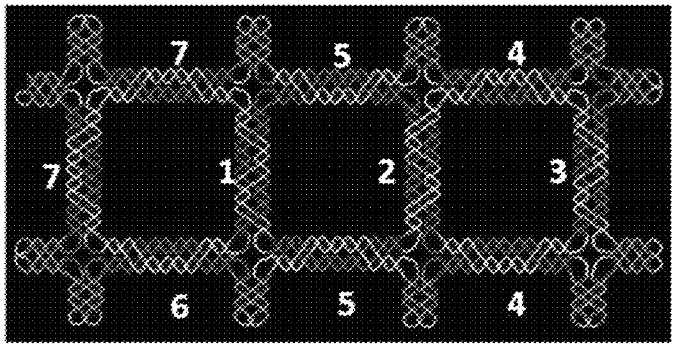
FIG. 9D
| Step | 1 | 2 | 3 | 4 | 5 | 6 | 7 |
|---|---|---|---|---|---|---|---|
| Cross number | 3 | 3 | 3 | 2 | 2 | 2 | 2 |
| length | 666 | 664 | 644 | 66 | 64 | 64 | 44 |
| bp | 36 | 32 | 28 | 24 | 20 | 20 | 16 |
| GC % | 69 | 66 | 61 | 58 | 60 | 55 | 50 |

FIG. 15A
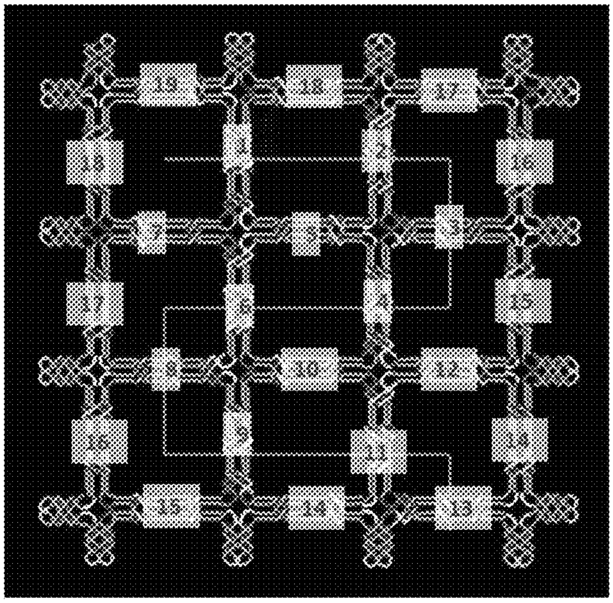
FIG. 15B
| Site | 1 | 2 | 3 | 4 | 5 | 6 | 7 | 8 | 9 | 10 | 11 | 12 | 13 | 14 | 15 | 16 | 17 | 18 | 19 |
|---|---|---|---|---|---|---|---|---|---|---|---|---|---|---|---|---|---|---|---|
| length | 6<br>6<br>6 | 4<br>6<br>6 | 4<br>6<br>6 | 4<br>4<br>6 | 6<br>6 | 4<br>4<br>4 | 6<br>6 | 4<br>4<br>4 | 4<br>4<br>4 | 6<br>6 | 4<br>4<br>4 | 6<br>6 | 4<br>4<br>4 | 4<br>6 | 4<br>6 | 4<br>6 | 4<br>6 | 4<br>4 | 4<br>4 |
| bp | 36 | 32 | 32 | 28 | 24 | 24 | 24 | 24 | 24 | 24 | 24 | 24 | 24 | 20 | 20 | 20 | 20 | 16 | 16 |
| GC % | 67 | 66 | 62 | 64 | 67 | 63 | 58 | 58 | 54 | 54 | 54 | 50 | 50 | 60 | 55 | 50 | 45 | 50 | 44 |
FIG. 15C
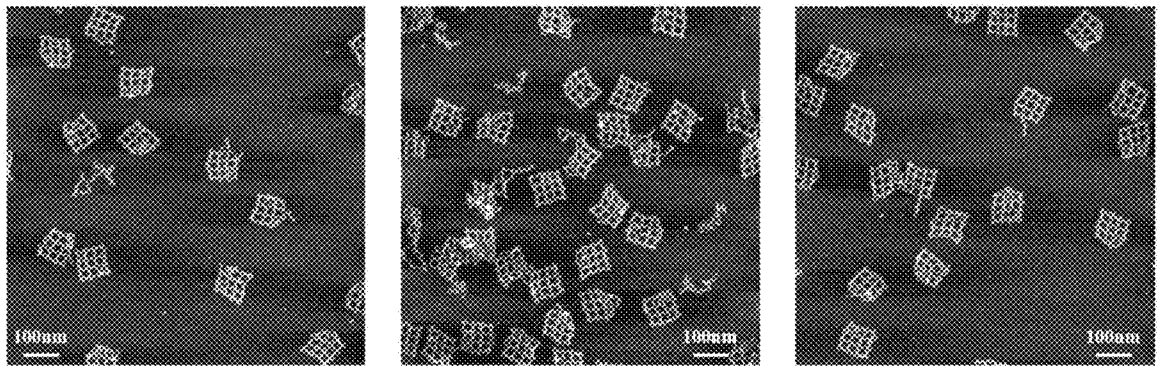

FIG. 18A
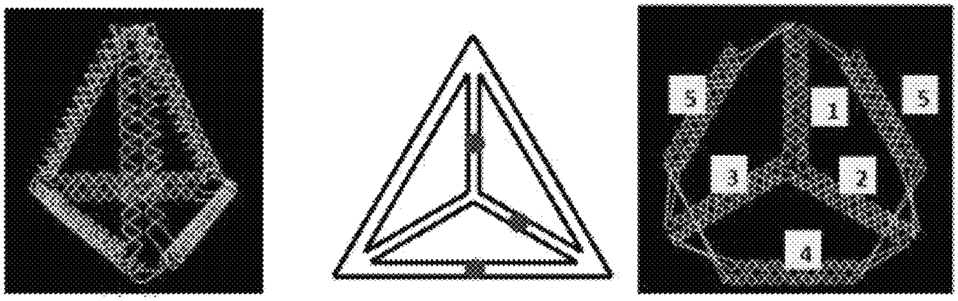
FIG. 18B
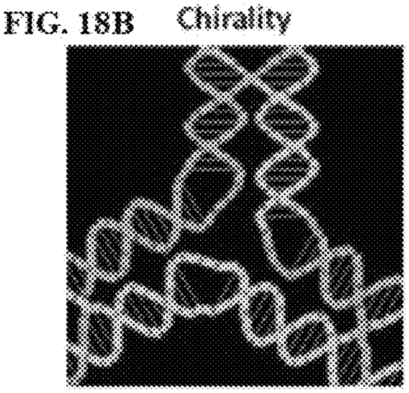
FIG. 18C
| Step | 1 | 2 | 3 | 4 | 5 |
|---|---|---|---|---|---|
| Cross number | 3 | 3 | 2 | 3 | 2 |
| length | 666 | 664 | 66 | 444 | 46 |
| bp | 36 | 32 | 24 | 24 | 20 |
FIG. 18D
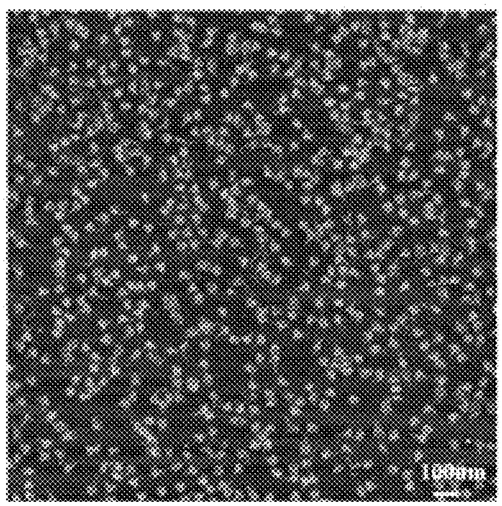

FIG. 19A
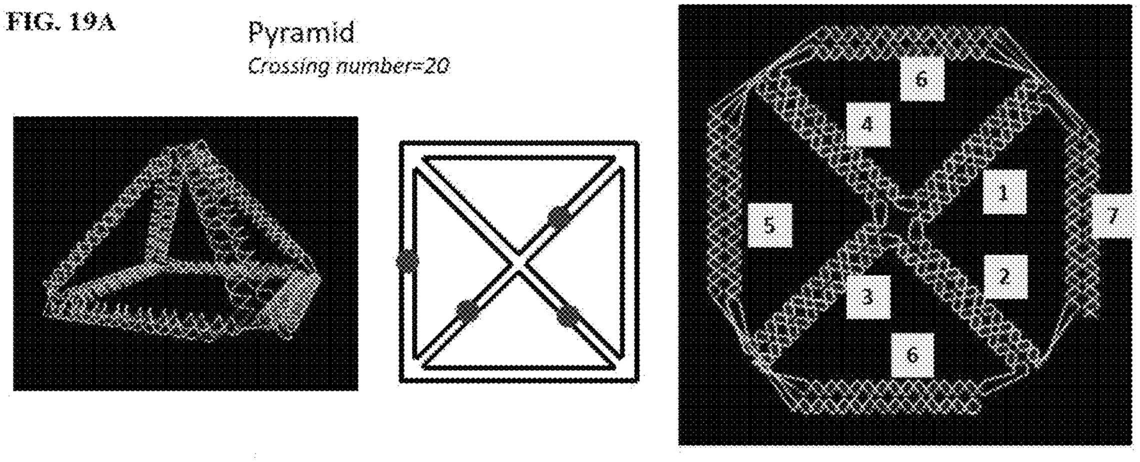
FIG. 19B
| Step | 1 | 2 | 3 | 4 | 5 | 6 | 7 |
|---|---|---|---|---|---|---|---|
| Cross number | 3 | 3 | 3 | 2 | 3 | 2 | 2 |
| length | 666 | 664 | 644 | 66 | 444 | 46 | 44 |
| Bp | 36 | 32 | 28 | 24 | 24 | 20 | 16 |
FIG. 19C
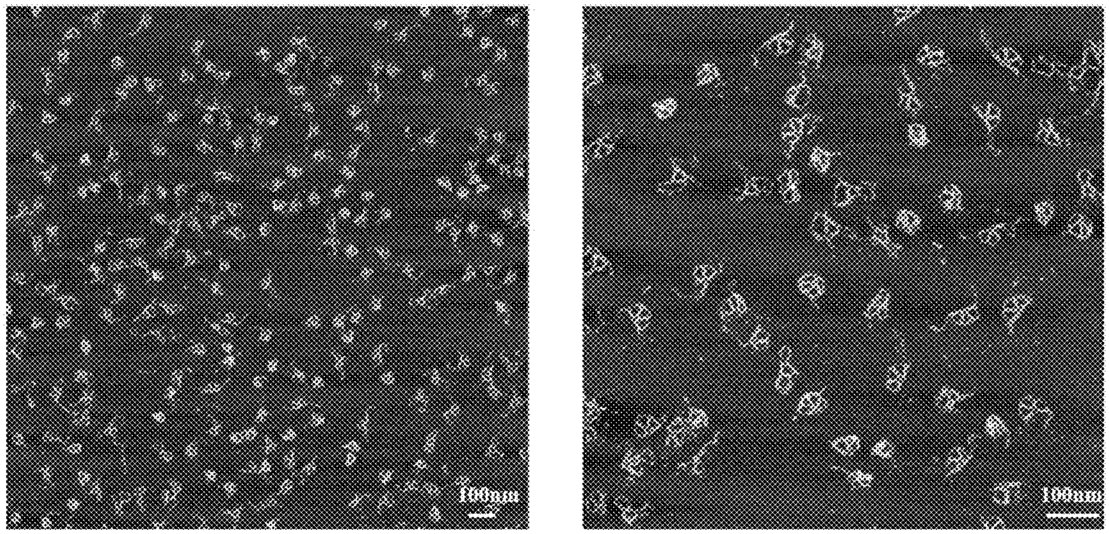

FIG. 20A
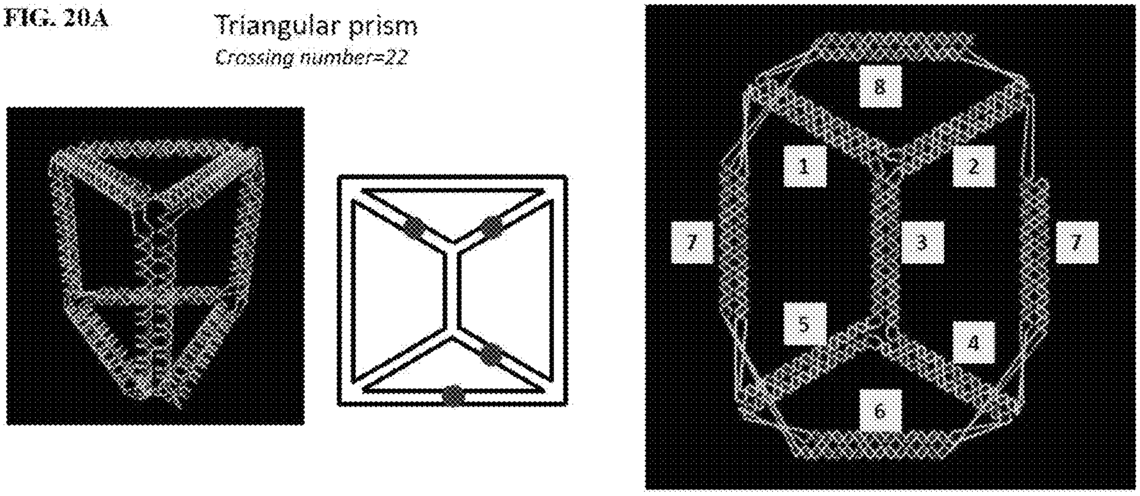
FIG. 20B
| Step | 1 | 2 | 3 | 4 | 5 | 6 | 7 | 8 |
|---|---|---|---|---|---|---|---|---|
| Cross number | 3 | 3 | 2 | 3 | 2 | 3 | 2 | 2 |
| length | 666 | 664 | 66 | 444 | 66 | 444 | 46 | 44 |
| bp | 36 | 32 | 24 | 24 | 24 | 24 | 20 | 16 |
FIG. 20C
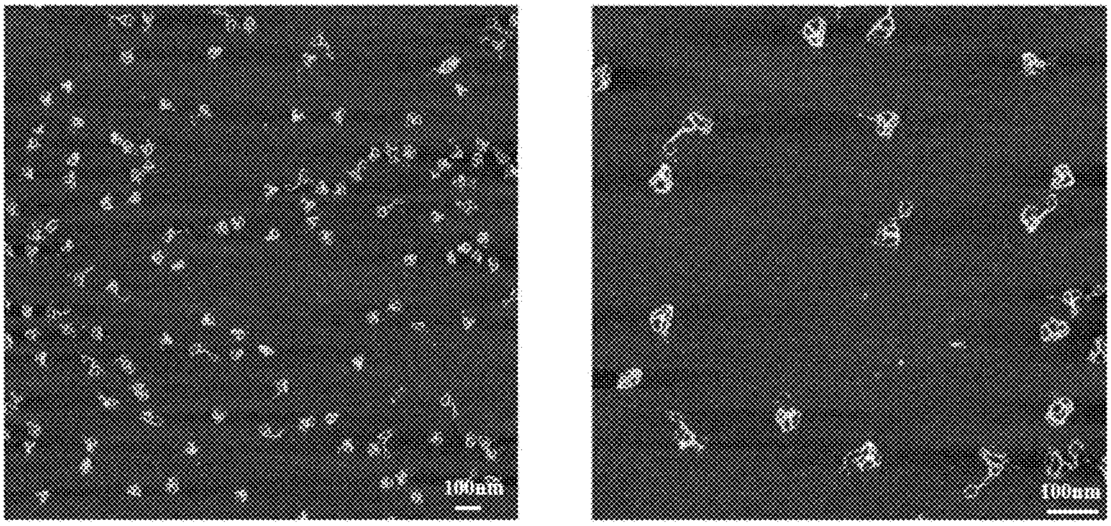

FIG. 21A
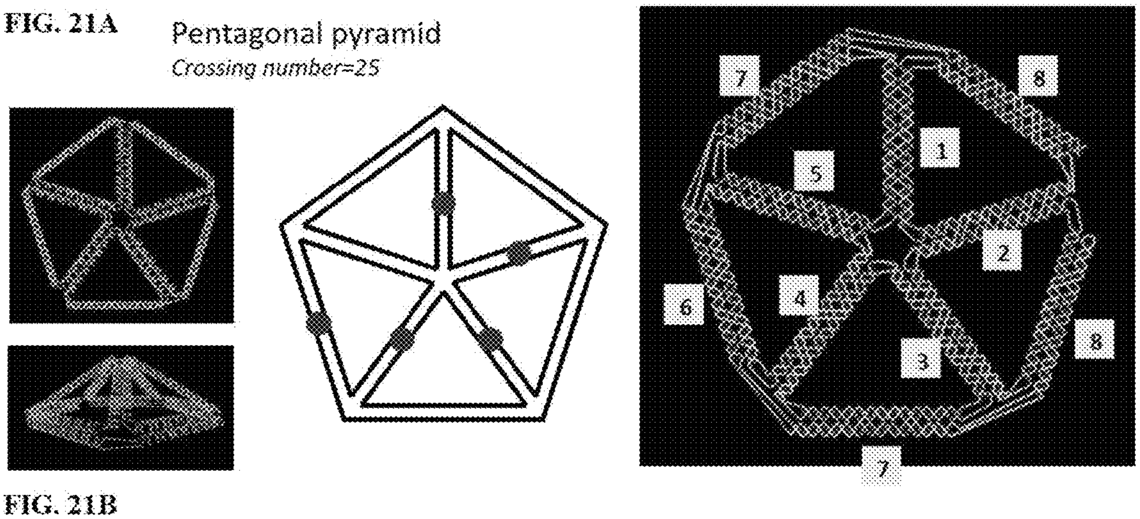
FIG. 21B
| Step | 1 | 2 | 3 | 4 | 5 | 6 | 7 | 8 |
|---|---|---|---|---|---|---|---|---|
| Cross number | 3 | 3 | 3 | 3 | 2 | 3 | 2 | 2 |
| length | 666 | 664 | 644 | 644 | 66 | 444 | 46 | 44 |
| bp | 36 | 32 | 28 | 28 | 24 | 24 | 20 | 16 |
FIG. 21C
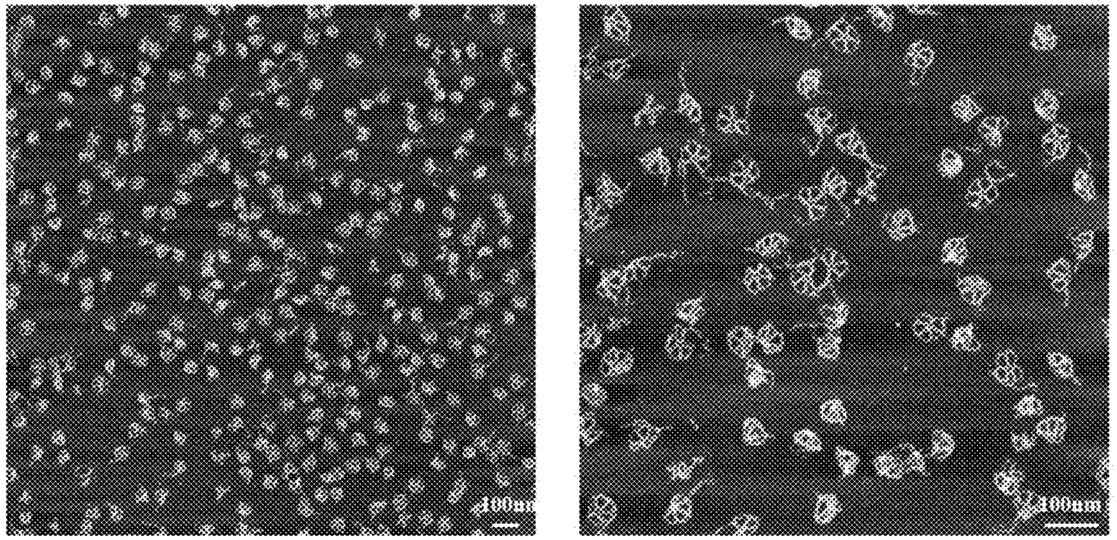

ssRNA tetrahedron with crossing numbers

With Crossing Number

Crossing number=15

| Step | 1 | 2 | 3 | 4 | 5 |
|---|---|---|---|---|---|
| Cross number | 3 | 3 | 2 | 3 | 2 |
| Bases | 888 | 888 | 88 | 888 | 88 |
| Bases | 24 | 24 | 16 | 24 | 16 |

ssRNA tetrahedron without crossing numbers

Zero Crossing Number

AFM Images

DNA as A Nanoscale Building Block

Structures with High Crossing Number

3D Knots

Production of ssRNA

SEQUENCE LISTING

<160> NUMBER OF SEQ ID NOS: 30

<210> SEQ ID NO 1
<211> LENGTH: 1673
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 1
atccaggaag ggctatggtt ttcatcgaag atagacaaat agacagcatg ccaatgatga 60
tcagaagagg acgagttttg gccatatctg gcatgttttt catgccgatt ctatctgagt 120
tcgccaacct actttttgta ggtcgaggag agcttttagc tcatcgaact cttaccagtc 180
atcttatttc ccagcaataa cgaggttggg ttttaggact tgcttcgact aggaacggga 240
gggagaaggg aacgagatac tcgtagattt tgttgaccga aacaaaccaa accgcagcta 300
cgacgcacca tgatggtatc tcgattttag ctcagggcac tagtggtagg tagtggtggg 360
gtggcgaact acctgtctat cttttcctca agactagaat cctcatcgtg atgagtacag 420
gaacagtagg acagctgatt ttggattccc agagtgactt tttgtcacta ggcacctcag 480
cgaaatctat ctcggttttt ccgagaacag taccagtttt aggctcgcgg ttcttggaac 540
cttggcagta gacaaccttt ccagggaacg tgcttttgac ctaacttgga tgctttttgc 600
atcctgttag tagcggcctc cgtgacgtag tttttctacg tagctgatgg attttgtacc 660
gctgcagtct gctacatcag ggacggactg attcacctct agctcacatt ttctagcggg 720
tggtgagctt tttgctcacg agtggaattc aacggccctt tcaatctttt tgattgaagc 780
atccgttgtt ttaattccac tcgcagtaca tctatgtgct cagtctccgt ttttcggagt 840
agtcgcacat agatgtactg ccacccgcta gtgtgagcta gatcatgatc agtccgtccc 900
tgatgtaggt ttgtgcagcg gtactccatc agctagtaac acgcaagtgg tacctcctgg 960
ctttttgcca ggctaagcca cttgcgtgtt actcacggag gccttttgct actaacagct 1020
tcgtttttcg aagcaagtta ggtcgcacgt tccctctcgt ggttgtctac tgccaaggtt 1080
cagtcgaccg cgagcctctg gtactgttga aactttttgt ttcatagatt tcgctttttg 1140
aggtgcctac acgatctcat caacgctaag gccacttttt gtggctacct cgttgatgag 1200
atcgtgtctg ggaatcctca gctgtcctta ttgtcctgta ctcagatgaa tgaggattct 1260
tcgattgagg gatagacagg tctgatgcca ccccaccact acctaccttg tctgccctga 1320
gcttcgagat accaggtgag tgcgtcgtag ctgcggtttg cagactttcg gtcaactcta 1380
cgagtatgga aatcccttct ccctcccgtt cctcaagaaa gcaagtcctc ccaacctcgt 1440
actgtctggg aaataatcac gctggtaaga gtagtctgag ctgctctcct cgagtagctc 1500
gtcgactcta gtcggtgtgt ttttcacacc tcagtgagtc gacgagctac ttggcgaact 1560
cttttagata gaatcgctct ctttttgaga gcagatatgg ccctcgtcct cttagttcca 1620
tcattggcat gctgtctata ctagtatctt cgatgccata gatgctcctg gat 1673

<210> SEQ ID NO 2
<211> LENGTH: 3561
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 2

```
atcacccttg gtctcagacg gatcaatcgc tgtgttactc gtacgggcga ttacagattc    60
actgcgacac ctgggagatg ccgactccca tgaccaactt tttttccacgt catggtcttg   120
ttttcaccat acgtcccctg ttttttgtcg agacgtttag actcaacgcc cggcactcac   180
gacgtgagaa tgggcctcta cgtcctgctc gtcgtctaca catgtgctac accgtgttta   240
gttttttgga ggcacggtgc agcttttagt acatgtgccc agagtctttt gccgtcgttg   300
tagcagcaat catgttgtca agcatgtagc ttttacggag agatccgttc ttttttcggt   360
cgatctgttt ccgtacctgc gctaggccga tgtgatgcct ggctcgttac tttgcactgt   420
ccgacaggtt attccgagtt cggtttacat gttttttgcc tgaaaccgac tcgttttagt   480
aacacgaata ggcttttttg cgctttcgtc aggaggcagt ctatgaactg ctttgggac    540
ctaccatgcg gctcctgaag ctgaacgaca cggaccttcg gtcggtgtag attgtctcgg   600
ttgtcatcca tatggcacgg aaagacagcg tgttacccac cgatcgttcg agcagctcaa   660
ccggattgga ggatcagctc gctggagttc tggcgacgca cgacgcacct tttaggacaa   720
caccgattag gccttaaagc tacttacggt atctgggcat tgtggtctac ttccaggtgt   780
aggtccctaa tcccggcgtg ctacaagccc atgaacaggg ccttaggcgt ccaccttccc   840
tttgaaagat ttccagcgca gcgacacagc gatcccgtgg ttagtaggtg atctgttgtc   900
cgtgagacgt acaaggtatt accactcgac gaaagtgaca tatccccaga aatgttctgc   960
atttagtatc cctggatgct tgctgtcttc catgtgcaat gtaaaaccgc tggagttggc  1020
tttggtgtcg tcaggtaagc gtttggcaga ggcaagagag caaattcgcc ataagagaga  1080
tctcgcgagg tatgagggta ccttgcgctc ttagccatgg tgcacctcac acttcactct  1140
ctggtggttc gcagaggcct gagctgttcg cacgtccgct gcacctcgtg accacacttg  1200
ttaggaatcg aatgggacga ctaatgagcc tttgaaactg gttgacgtct ccagaggacg  1260
tgtctaaggc tgaggcaatg ctggctgaca cggacaacct ggtcacttgc gctccgtcgt  1320
cacgactctt ggggccatga ggttgacgag ttttttgcct ccaacctgca gcttttcaag  1380
ttaagtgaga cctttttttca cagcacttca tcgccaactc gccaatgcga caagctgtct  1440
ctggaaaacg cacatacgtt ggagtggatg gagattccgt agacgtatga ctgttttttc  1500
agtgatacgt gatacttta tgggtaggag aagtggttga gttcgtacca tttgccagtc  1560
tcgtcttcct ccagacccta cgttttcata tgacgtcagt acttttttcg tgtgacgtgg  1620
tttccccgac actggagtcg ctttggcaag gggttgtggc aaatcgttaa cggtttgcac  1680
gcaacatctg catcatggca accttttttc ggttccatga aagagttttc tgagtgacca  1740
gtctagtttt tctagacgaa ctactcagct cttgctctta accgtttttt ggttgaagag  1800
ctgcagtttt atgttgcgtg caaacccggg acgatttgcc acaacccctt gccaaagccc  1860
aaccagtgtc gggttttgaa acctgccaac acgttttttg tacttggcac atatgcgtag  1920
ggtctgactc aagacgagac tggcaaatgg tacgaactca acgaggagtc ctacccatgt  1980
atcccctcac actgtttttt cagtctgagg gctacgtttt gaatctccat acgctgcaac  2040
gtatgtgcgt tttccagaga cacgagaccg cattggcgag ttgttttgcg atggcccact  2100
gtgttttttg gtcttgggca acttggctgc gaaagcgagg cttttttctc gtgctttcca  2160
tggttttccc caagagttcg ttcgacggag cgcaccgcac caggttgtcc gtgtccagta  2220
gcattgcctc ttttagcctt agacgtcgga tctggagacg tcaaccagtt tcaaagacat  2280
```

-continued

```
cgtagtcgtc ccattcgttt tattcctaac agccagagtc acgaggtgca gctcctccgc    2340

gaacagctcg ctgctctgcg aaccttttac cagagagtct cctctgaggt gcaccatggc    2400

taagagcgca aggtacgagt atacctcgcg attttgatct ctcttccctg taatttgctc    2460

tcttgcacgc cgcaaacgct tacctgaacc tggcaaagtt ttccaactcc agacgacgta    2520

cattgcacat ggaagacagc aagcatccag agtgactaaa tgcagtttta acatttctgg    2580

ggatacgcaa ctttcgtcga gtggtaatac cttgtaccac acacggacaa cattttgatc    2640

acctactaac cagttaatcg ctgtgtcgct gcgctggaaa tcttgactag ggaaggtggt    2700

tttacgccta aggatggcgt catgggcttg tagcctctgc ggattaggga cctaccgaca    2760

caagtatttt gaccacaatg tgcgattacc gtaagtagct ttaaggccta atcggtgaca    2820

gcctaaaagg tgcttttgtc gtgcgtcagt gtgactccag cgagctgagg acgtaatccg    2880

gttgaaggcc tcgaacgatc ttttggtggg taacccactc tctttccgtg ccatatggat    2940

gacaacgctt gtaatctaca ccgaccgttt taaggtccgt gcgtgacagc ttcaggagag    3000

tgatggtagg tcccaaagca gcctcataga ctgcttttct cctggagcca gcgcttttt     3060

gcctaggctc gttactcgag taatacccag gcttttttca tgtggtatta actcttttgg    3120

aataacctac gtcccagtgc aaagtaacga gccaggcatc gctcatgcct agcgcaggta    3180

cttttggaaa cttagtgacc gttttttgaa cgactaactc cgtgctacat gcttgctgtc    3240

atgattgctg ctacaacgac ggcaaaagac atcgcacaca tgtactgctg cacccctcct    3300

ccttttttct aaaaggtgtg tagcttttac atgtgtagcg gtttagcagg acgtagaggc    3360

ccattctcac gtcgtgggat ccgggcgttg attttgtcta actccgtcga cttttttcag    3420

ggcggagatg gtgcaagaat ccctcgtggt ttttgttgg   agggatgagt cttttggcat    3480

ctcccaggtg ttgtcgtgaa tctgtaatcg cccgtacgag taagtctgcg attgatcctt    3540

ttgtctgaag ttcagggtga t                                              3561
```

<210> SEQ ID NO 3
<211> LENGTH: 3561
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 3

```
atcacccttg gtctcagacc aactcgccaa tgcgacaagc tgtctctgga aaacgcacat      60

acgttggagt ggatggagat tcgactccca tgaccaactt ttttccacgt catggtcttg     120

ttttcaccat acgtcccctg ttttttgtcg agacgtttag acgctacatg cttgctgtca    180

tgattgctgc tacaacgacg gcaaaagaca tcgcacacat gtactgctac accgtgttta    240

gttttttgga ggcacggtgc agcttttaga actgaagcgg tttagcagga cgtagaggcc    300

cattctcacg tcgtgggatc cgggcgttga ttttacggag agatccgttc ttttttcggt    360

cgatctgttt ccgtacctgc gcttggccga tgtgatgcct ggctcgttac tttgcactct    420

ccgacaggtt attccgagtt cggtttacat gttttttgcc tgaaaccgac tcgttttagt    480

aacacgaata ggcttttttg cgctttcgtc aggagtactt ccaggtgtag gtccctaatc    540

ccggcgtgct acaagcccat gaacagggcc ttaggcgttg ttgtccgtga gacgtacaag    600

gtattaccac tcgacgaaag tgacatatcc ccagaaatgt tgatcgttcg agcagctcaa    660

ccggattgga ggatcagctc gctggagttc tggcgacgca cgacctgcat ttagtatccc    720
```

-continued

```
tggatgcttg ctgtcttcca tgtgcaatgt aaaaccgctg gagttgggca gtctatgaac    780
tggctttggg acctaccatg cggctcctga agctgaacga cacggacctt tcgcgaggta    840
tgagggtacc ttgcgctctt agccatggtg cacctcacac ttcactctca gctgaggcgg    900
tgtagattgt ctcggttgtc atccatatgg cacggaaaga cagcgtgtta cccaccgcac    960
cttttaggac aacaccgatt aggccttaaa gctacttacg gtatctgggc attgtggtcg   1020
aggcaatgct ggctgacacg gacaacctgg tcacttgcgc tccgtcgtca cgactcttgg   1080
ggccaccttc cctttggaag atttccagcg cagcgacaca gcgatcccgt ggttagtagg   1140
tgatcggttc gcagaggcct gagctgttcg cacgtccgct gcacctcgtg accacacttg   1200
ttaggaatcg aatgggacga ctaatgagcc tttgaaactg gttgacgtct ccagaggacg   1260
tgtctaaggc tctttggtgt cgtcaggtaa gcgtttggca gaggcaagag agcaaattcg   1320
ccataagaga gatcccatga ggttgacgag ttttttgcct ccaacctgca gcttttcaag   1380
ttaagtgaga cctttttca cagcacttca tcgcggatca atcgctgtgt tactcgtacg   1440
ggcgattaca gattcactgc gacacctggg agatgcccgt agacgtatga ctgtttttc    1500
agtgatacgt gatactttta tgttgcgtgc aaacccggga cgatttgcca caacccttg    1560
ccaaagccca accagtgtcg ggttttcata tgacgtcagt actttttcg tgtgacgtgg    1620
tttccgtagg gtctgactca agacgagact ggcaaatggt acgaactcaa cgaggagtcc   1680
tacccatctg catcatggca accttttttc ggttccatga aagagttttc tgagtgacca   1740
gtctagtttt tctagacgaa ctactcagct cttgctctta accgtttttt ggttgaagag   1800
ctgcagtttt atgggtagga gaagtggttg agttcgtacc atttgccagt ctcgtcttcc   1860
tccagaccct acgttttgaa acctgccaac acgtttttg tacttggcac atatgcccga    1920
cactggagtc gctttggcaa ggggttgtgg caaatcgtta acggtttgca cgcaacatgt   1980
atcccctcac actgtttttt cagtctgagg gctacgtttt ggcatctccc aggtgttgtc   2040
gtgaatctgt aatcgcccgt acgagtaagt ctgcgattga tccttttgcg atggcccact   2100
gtgtttttg gtcttgggca acttggctgc gaaagcgagg ctttttctc gtgctttcca     2160
tggttttgat ctctcttccc tgtaatttgc tctcttgcac gccgcaaacg cttacctgaa   2220
cctggcaaag ttttagcctt agacacgtcc gagtgagacg tcaaccagtt tcaaaggctc   2280
atgccacgtc ccattcgttt tattcctaac agccagagtc acgaggtgca gctcctccgc   2340
gaacagctcg ctgctctgcg aacctttga tcacctacta accagttaat cgctgtgtcg    2400
ctgcgctgga aatcttgact agggaaggtg gttttcccca agagttcgtt cgacggagcg   2460
caccgcacca ggttgtccgt gtccagtagc attgcctctt ttgaccacaa tgtgcgatta   2520
ccgtaagtag ctttaaggcc taatcggtga cagcctaaaa ggtgcttttg gtgggtaacc   2580
cactctcttt ccgtgccata tggatgacaa cgcttgtaat ctacaccgcc tcttttagct   2640
gagagtctcc tctgaggtgc accatggcta agagcgcaag gtacgagtat acctcgcgat   2700
tttaaggtcc gtgcgtgaca gcttcaggag agtgatggta ggtcccaaag cagcctcata   2760
gactgctttt ccaactccag acgacgtaca ttgcacatgg aagacagcaa gcatccagag   2820
tgactaaatg cagttttgtc gtgcgtcagt gtgactccag cgagctgagg acgtaatccg   2880
gttgaaggcc tcgaacgatc ttttaacatt tctggggata cgcaactttc gtcgagtggt   2940
aataccttgt accacacacg gacaacattt tacgcctaag gatggcgtca tgggcttgta   3000
gcctctgcgg attagggacc taccgacaca agtattttct cctggagcca gcgctttttt   3060
```

-continued

```
gcctaggctc gttactcgag taatacccag gctttttca tgtggtatta actcttttgg   3120

aataacctgt cggatctggc aaagtaacga gccaggcatc acatcgtagt agcgcaggta   3180

cttttggaaa cttagtgacc gtttttgaa cgactaactc cgttcaacgc ccggcactca   3240

cgacgtgaga atgggcctct acgtcctgct cgtcgtcttc agttctgctg cacacctcct   3300

cctttttct aaaaggtgtg tagcttttag tacatgtgcc cagagtcttt tgccgtcgtt   3360

gtagcagcaa tcatgttgtc aagcatgtag cttttgtcta actccgtcga ctttttcag   3420

ggcggagatg gtgcaagaat ccctcgtggt tttttgttgg agggatgagt cttttgaatc   3480

tccatacgct gcaacgtatg tgcgttttcc agagacacga gaccgcattg gcgagttgtt   3540

ttgtctgaag ttcagggtga t                                             3561
```

<210> SEQ ID NO 4
<211> LENGTH: 6552
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 4

```
caactcctcg attcccgctt gtttgcactt gtatgtacat agtgtcagat cgcttacgct     60

tgcgtggcga tcatctagtc gtcgtttttt gttccactag atagtatttt caggcgttga    120

ctaggcgccc gaggtatttc aagaagacaa ctgattaagt gtgttttcaa gtccaactac    180

tactttttg cggaagttgt cccttctcta ccgtcttgct cagtgttcag agactttgct    240

ggtgaagtgc cgcaccgcct gctgttaaga gagctttttt gggagcttaa cgcaaatttt    300

ccacgtaaac tgttggtttt ttgactcagt ttaggactga gtcaagcatg gtcggtccca    360

cagaatccgg aagcccagtc agaaaacatg gtagcgcttc ccctgggttt tttcagaagg    420

gaagcgccat tttgcatatt taccactcgt gactcgtagg gaggacgcct agtgaagcgc    480

gtctcatttt ctcgaggagt gagggctttt ttccaggcac tctgtgtcgt cccgttaagg    540

atgtgagtgt catggcgagc accagacaga ggccgtgaac gcttgaagcg agagccgttt    600

tttgacatct cgctggtgct tttcacctag caactatcgt tttttcatga gttgcctctg    660

cttgagcatc aagtcgtaat cgtccatgtt aggtgcgctt ctagaagacc ggtgtccagt    720

atgggtgtga tctcctgtct tgcctggtac cgctttccag gatcgggtac gggactcgtg    780

cccggaacat cagggcaaat cgcggtctca tataggactg tacccacaca cttgtcttcg    840

ccgttcggaa ctttcggagt atacacagtc ttgttgcgct ttaacagatc atctgtcata    900

agtaaggggt tgcacatatc caagatggga ttgcaacggt caaccggata ttacgtattt    960

tcctgggcta gcgtcggatt tcggcttcct tgggactgaa cagggatcgt ttggtgctag   1020

gcgctggcct ttcacacggg cgtgtgcagc acagatcatc taatcatatg taacttgacc   1080

ccgtttgcct catcagtcct catgatgagt aagtagccat cttcagtaaa tcttcgtcta   1140

acatagggta catactcatc atggacactt tcttccgaat gcctgctacc cgcacctcaa   1200

ccgccctaag actattggtg cttcttcact tcgtctgagt cagcctctcc atctgtcact   1260

ccaagggata gcggacgacc ccgagtgtct tgaattgcat ctacgaaaac gttcggacta   1320

cttttctacg tctgttatct cagtccttgc cgacgtcgta ggtcgtgata acgtccaagt   1380

cgggttgcga ccaaggccag acggaaggtg gattagttgt tacttcgcca gtgagagttt   1440

gcctagcttg gatcactgac gtctgatgtt agcgtaatct agatcactgg ggttctgcca   1500
```

-continued

```
cagtccggtg agtacagcac agatcgtata catcacgaac gtttgtccag tcgcggaaca   1560
ctgaaatgaa ctaacgctga catgtatgac aaccaacatg attacacacg cttgtgagcg   1620
agtctctgca tgaggagtgc tccacagtga gtgactacgc tgccagctgc agcgcgcgtt   1680
tgtttcgggt cccttcagca tcgaactgat ccgctaaacg tcttcacagg caagacgtcg   1740
cgaatagcgg aacgatgcag gtatcttagt catgcgcaac caaccaccac aggtgtgcta   1800
ctacgattcg tccgtcggca tttaacgctc cgccgttgga tcgataaatg gtttctggaa   1860
ttatatagcc ggtagatcgg ccgagacact tacgtataat gagcccactt atcctcttct   1920
tgtgaacact gcttgctata ctcttgcaca cctcggtcgc agacggtaaa gactactgaa   1980
tacggcgata gcgtatgtgc gcatgacgcg cggtgaacac atggtgccaa acactttctt   2040
cgtgacccga attgaataat cgcttataca acctgaaagt gccgtacgca ttcgccgtgg   2100
gctaaagcgc gatcaagtct caccccttggt agtcgagttg tcgggcgtag cagctctctg   2160
tcctcgtccc attactttgc ttagtgaatg gaagactgtg gtaatgctcc tcacgaggat   2220
agtcaactga ccgtcatgca gctgacgacg tttaacgatc ctgcatctct cccaagatag   2280
tcagatccgt aacgagactt gcaggactcg aataccctct aactatccgc actagagtgc   2340
cggaggcagt tcgcccttgt aggatcggag gtagtcagtt gatagaaggg ctgatggctc   2400
gtcctcgaag ttgaactccc tcagccacac ttggttccta cagcagttgc atctgaagaa   2460
tctgtcgaca cagacatgcc ttcggcgctc gtcccactta tgcaagcgca ttcgtcgagg   2520
caaggagctc acttagagcg tctgatggtt tagtactgag tgagatatcg tcccttctaa   2580
tggactttgg tcctgcggtt attttgggag cggcacatga cgcgccaagc actcatactt   2640
ttttcgatca gtgctcgtac ttttcttatg cttcgagcca cgttgccgcg catatcaatt   2700
ctacctaggc atacctgttt tcttaacagc cactgtgttt tttgcggctg gctggtcagg   2760
gcgactctga gaatagaaag gtgcgtgtaa tcatagagtg agagcgggtg tctgtggtct   2820
ccgatatctt ttttgagcgc ggagagttta ttttatgcct cgtggggctc tttttttgtag   2880
cccacgtcag attgctgaca gatcacgttg atttcgttcc agtaaagtga aatgaactct   2940
gaccgggagt gccaacgata cttttttgta atgttggcgc atattttaag cgcgtgactg   3000
catatcagat gagatgttag ggaggtgaga agtactcacc ttttggcgtg cacgccgtgg   3060
ttttttgatt agcgtggtcg ggtggccgga atggtatgcc taaacaccag acatctgaac   3120
tgtctggttc ataatgtgac acttgtctgg ctttttttcgt gaacaagttt gtattttact   3180
agggaggatg ggctttttgc ccacggatcc tagttacaat gatcgtcacg ttttttgcca   3240
gcgatcagtc acttttatta tgaaccgtaa tcttcagatg tctggtgttt aggagcgtca   3300
ttccggccat tttcccgacg gacttaatct tttttccacg agtcccacgc cggtgagtac   3360
ttaagctctc cctaacatct catctgattg tccatcacgc gctttatgca gtatgattac   3420
ttttttgtat ccatactact ccttttcggt cagagtagcc cacactttac tggaacgaaa   3480
tcatgaccat ctgtcagcat tttatctgaa agttgctact tttttgagcc aacttaggca   3540
ttaaacgacc gtcgctcttt tttgatatac ggtcccacat tttgacaccc gcttgtgcac   3600
tatgattaca cgcacctttc atctgtcaga gtcgcctttt ctgacctagg cgccgctttt   3660
ttcacaggcc tagttaagca ggtatgcctg acgtgaattg atatgcgcgg caacgactgt   3720
agaagcataa ggtacgtcta tcgatcgttt tttgtatgga tagatggcgt tttcgtcatt   3780
cttcgctccc aaaacctaac caggaccaaa acgacttaga agggactttt gatatctcac   3840
```

-continued

```
ctctgtctaa accatcagac gctctaaaca tcctccttgc ctcttttgac gaatgcgacg   3900
aagtaagtgg gacgagcgcc gaagagggct ctgtgtcgac ttttagattc cctggatgca   3960
actgccaggc aaaccaagtg ttcacaaggg agttcaattt tcttcgagga ctacagttca   4020
gcccttctat caactgacac gtcccgatcc tacattttag ggcgtgtggc ctccggcaca   4080
gttccgcgga tagttgacaa gtattcgagt cttttctgca acagccgtta cggatcaacg   4140
attcttggga gatcccaagg atcgttaatt ttacgtcgtc agtggacaga cggtcagttg   4200
actatcctca gcttgagcat taccattttc agtcttccag actggaagca aagtaatggg   4260
acgagggatc tgagctgcta cgttttcccg acgtcacgac taccaagatt agaacttgat   4320
cgctgcacag cccacggcgt tttaatgcgt acgtgagact caggttgtat aagcgattat   4380
gggcatcggg tcacgatttt agaaagcagg tggcaccatg taagtgtcgc gcgtcattat   4440
gtcatacgct atcttttgcc gtaactggta gtctttacgt agaacgaccg aggtaacgta   4500
gagtatagca ttttagcagt gttctgactg agaggataag tgggctcatt acgaccaagt   4560
gtctcggttt tccgatctac cacttcaata attccagaaa ccatttatga gcacaacggc   4620
ggagttttcg ttaagcctcg acggacgaac gactttagca cacctacgac ggttggttgc   4680
gttttcatga ctaagtactg agcatcgttc cgctattcgc gagaggatgc ctgtgaagtt   4740
ttacgtttct gtgatcagtt cgaagtgata gggacccgac taacacgcgc gctgctttta   4800
gctggcagcc gtaagactca ctgtggagca ctcctccaag tgagactcgc tcttttacaa   4860
gcgtgtagac agatgttggt tgtcatacat gtccatacta gttcatttct tttagtgttc   4920
cgcttcacta caaacgttcg tgatgtatac acagagtgct gtactctttt accggaagcg   4980
ggcagaaccc ctgctgacta gattacgaac aaatcagacg tcattttgtg atccaaggtc   5040
ctaaaactct cactggcgaa gtaatggtca atccaccttc ttttcgtctg atgctggtcg   5100
caacctcgta gggacgttat cgtggtctac gacgtcgttt tgcaaggttc aagataacag   5160
accgtctgaa gtagtccggt gcatttcgta gatgttttca attcaagaat acgtgggtcg   5220
tccgctatcc cttggcaacg cagatggaga gttttgctga ctcagcttgc atgaagaagc   5280
accaatagtc ttgcatgggt tgaggtgctt ttgggtagtg ttcattcgga agagttcacc   5340
catgatgagg cgcaacccta tgttattttg acgaagatta tacctagatg gctacttact   5400
catcatcgtc tctgatgagg cattttaacg ggaactagtt acatatgggt gagtgatctg   5460
tgcgctttac gcccgtgtgt tttaaaggcg tctgcctagc accatgacta ccctgttcag   5520
gatgcaggaa gccgaatttt atccgacgct tcatttggaa aatacgtaat atccggtacg   5580
tggttgcaat ccccttttatc ttggatactc actacccctt acttatgaca gatgtattct   5640
taaagcgcaa ttttcaagac aacttatact ccgaatctag tgaacggcga aagagggtgt   5700
gtgggtattt tcagtcctat agcacttcgc gatttgccct gatgttcctc aatcgagtcc   5760
cgtattttcc cgatttcaga aagcggtact gtaggagaca ggagaggctg cccatactgg   5820
attttcaccg ggtgcctaga agcgcataac cgatggacga ttgtccattg atgctcaatt   5880
ttgcagagtt tcttcatgtt ttttcgataa gaaataggtg gcaccgtggt catgtctttt   5940
ttcggctgac cactcaagtt ttcgttcacg gctcagtact ggtgctcgcc atgacactcg   6000
tgagcttaac gggacttttg acacatccgt cctggttttt tgccctacgg actcgagtga   6060
gacgcgctcg ttgaggcgtc ctccctacga gtcaacgtat gtaaatatgc tggcgaacaa   6120
gttctgtttt ttcccagctt gttcgctatt ttccatgttt tcacaagagg cttccggatt   6180
ctgtgggact acgtatgctt gactctttta gtcctgagga gagtcttttt tccaactcct   6240
```

-continued cacgtggttt gctacatcct cccttttttg ctctgatgta agcagttttg cggtgcggcg 6300
gctatccagc aaagtctctg aacactcgat cagacggtag agttttaagg gagcctatcc 6360 gctttttgt agttaggcga cttgcacact taatcgacca tcttcttgaa atacctcggg 6420
ctaggactca acgcctgtac tactgcaggg aactttttc gacgctgcag tgatcttttg 6480
ccacgcaagg tagtccgatc tgacactatg tacataatgc agcaaacaag cgttttggaa 6540
tcatccggtt gg 6552

<210> SEQ ID NO 5
<211> LENGTH: 7521
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 5
atcacgacgc tgtttcacgg ttaactcctc acgctccaca gaccagtact tccgactttt 60
caaccttgta ccactaggag tgtttcctcg agttaacctt ttttctccaa ctcgatggta 120
ttttaagatt ggtgtctggc acatagctgc tcctagtacc aaaccttaga ttcctacgtt 180
ctataggttt tcagaggcca agatcggttt tttgggagct tggcaccacg ctcatgtgtc 240
gggatcatag gctgacgatt actcggtact tgcgatcatg acatagagat tgttgtgatt 300
cgctgtcctt ttttgttggg cgaatacagg ttttatacca ctgacgaagg tttttttcgtg 360 tgtcaggcat aggtcgttcg tagggtcccc tatgcgttga tagaatttgg tgttcggaac 420
gtcagaacaa ttcgggagca gcgtcatgga cttttttcga agtgacgcat gacttttgcg 480
tactgttccc tcgcaaatat gccaggagtg tgaacacatc ctggtcaccc tcagggacca 540
ttttacgatg tcctcaattc ttttttgtcc cgaggagctc cccttgctca atggtgacga 600
aagtcatacc gtccagagcc gtgtggatgg ctacggtcag aggagggatc tctgtcctgg 660
tatgggtgga agtcctcgtg agagttgggt gcgcgtacat tgccagactt cggcaagttt 720
agccttaact cgtcaggtgc cagacatcct ctattgtccg acaactgtag tctcaaaggc 780
gtctggctgc acggcttatt acgacgactc cgtcaatgga ctgccttgac agtcggtggc 840
atagcggtgt tatgagtcag cgtgaggtta ctacgatact acgagggaca gatgttctct 900
gtacatgtgc aagtgggtgc catttaagct agtagcagag tgcgatgtgc actgtggact 960
tcttcatgct tggacttgta aaccgagagc tcacgacacc attcaatcgg cgacagagca 1020
caccgtcgaa tgcataggac cttggctttt gtatcctacg gtgcataaat gccagagatg 1080
atgtagctct ccgatatgcg atgtgacacc gtaccagcac gtacgtatcc catgtacgga 1140
ccttgatcgc gcgcataacc gtccgcccac tatgtcggct gctgctactc cctcgattat 1200
gtaccctaaa aggcacgtag cgtgaagggg catcatttgg tccacaatgt gctaatgttt 1260
gaagccatag cagggcgggt gtatgtatgc cgtggtgaaa gcgtcacgct gggtagcagc 1320
gatggccacc aagcagcgtg catcaggtcc agaatagcct cgcaaagcca gaatagacac 1380
accaagtcca tgtccagtct cgcaaaagta gtgaaggctt ttgctgggtt tcgaccttag 1440
ttactggcag catggatagc acatgacgcc aacgtgtgaa agtaccaatg tcgactgcgc 1500
gagagttaga ctgaacggca gtacgtgcta tctcctgcag cggtgattca atctcggagg 1560
agtaggcaga gcgtcgagga atagtcactg gcgataatct tgtattcgag cgctgccgca 1620

-continued

```
tgcgaattag tcaccgtggg tgtatctacg ttggctgcag ctcgcacgtc ggctgactcc   1680
gtaccgctct tccgaactat cgaccataac ctgccggcga actcctttgc taggctccgg   1740
aagcatagac aatagcttcg agtacccatg gccttgtagc tgaaagatga cttgccacaa   1800
ttggaggctc gttccaatct gtctgcgatt caaacctctt cccaaatcta tacggttacc   1860
tcgcagggct cctcatttcc atgattcatt ctacccgcta accgtccttg cctggaaata   1920
acctgtccgt agcaggtaga ccgcttgcca tcgtcagcgt cctccgtgcg gtaaacttgt   1980
cactgagggt tacctttggt caagtttctg accgatcagt gacacccaga cctttccaca   2040
ccccgaaggc taggcaagac tgtggtatgg aagtgtgggt gtccctgcct acgcctcatg   2100
tggacgcact cattgaccga ctcgtggtgc tctacatgtt ccacagcaac ggaaggggac   2160
tcgatggtgc gtgctagaga gttcatgtac ggaatccatg tctatcctag gtcgattagg   2220
cgttgacggt tgctcgggag tcctcaagtt ctatctatat cggggcatct gagatacggt   2280
gtctatccat atactccggt accgattaac aggttcgata tgccctcaag actgggttgt   2340
acagagcagg ctggtccatc taggctagtt attgcgtccg gatggctgca ggccacgcat   2400
gcctacgctt agtatgcctg cagtctaaat gttttgtccg gtcagtgaca cttgacgaag   2460
aatgagtgga ttgtgctatt aacacgtcgg ctacctcaca ttctgtctac cctttactgc   2520
ctcgagctcc gagccggaac gactacacag tttctgaaaa cttcgaaact ccatttgaaa   2580
ctgcgagacg cttgcacgtc tacgcatggc tgttcgtaac ggagtgaccg tcacactaca   2640
gggatacagc aagccattcg cgttgccaac agcgtctaac atgtattaga ggagtcggat   2700
ttcttatgtg tcgcgtgcgg actctcgatc tcgttccact ctctggaaaa catttgtctt   2760
aggggtgttg acccgttcgg ttgtcattga aatgacccga ctcgcactaa ctgcgtattg   2820
gtttctccaa aatgttgggg tcactccaag gtgacgtctc gtgccgtgtt gcgcaccatt   2880
tccttcacgt tagtaccact ttctctgggg tagctgaggg tacaataggt tttttgtagc   2940
tgtaccatac gttttcatga ctgtgaatgt ctttttttcct gatcacatga cggtgctgaa   3000
ccgagccttc atcaacgtcc tgagtactgc ctacaacaag ttctggtctg ctggattacc   3060
tgggagagta ggtttttttgc cactctccct cgacttttgt tatcttgact aggaagcgaa   3120
cgcctgggtt ggtcgtcgat agcaccacgc taccagacct cttttgaggt agctcctacc   3180
ctttttttgaa ctggagccaa ttgcaacatg cttccgactc atggtcatca ttgatgggtc   3240
atcaatacgt gttggacagt agatgcgtac ctgcagcacg agttttttgc aaggctgcag   3300
acacttttat tcccatctca ggactttttt gtaccgagat aattgtctca ttggtgccac   3360
catcaccgtc caccaatggc ccagatgcga ttccaaagct gtgctgtccg actattgtcg   3420
tacacttttt tatactcgac aaggcagttt tcgaacggaa ctcagggtcg gaaccattat   3480
ccgtgcggat acacgcaatg tgacactacc aggattttcc tctacctagc ctagtttttt   3540
cccttctagg tgacacggca tgtgactgag gcaaaagcgg tttctgcgat ggctaatttc   3600
gtcgaagccg atcaactatt ttccagagag gtaccttttt tgtgagctct ctcttgcttt   3660
tgagactaca gcctctagtt tttctagaga tcccagtctc gcaagcatct cctcactttt   3720
ttggtacgag atgggaaatt ttatagttga tcggcttcac tcaaattagc catcgcagaa   3780
accgcttttg agcaagtcac atgccttttg tgtcaagcca aagggttttt tctaggtggc   3840
ttagaggtcc tggtagtgcg tgattgcgtg tatccgcacg gataatggtt gtgcccctga   3900
gttccgttcg ctgcccagga tagtattttt ttgtgtaatc ctgtagtctt ttggacagca   3960
cacgttcaga atcgcatctg ggccattggt ggacggtgat tcacgcacca atgagtttta   4020
```

-continued caattgacgt ggtacttttt tgtcctacgt cgggaatgtg tccgtctact tgcttttttc 4080
tcgttagacg ggtacttttg catctactgc atgctacgta ttgatgaccc atcaatgatg 4140
accatgactt cgaagcatgt tgttttcaat tgagcagagt tctttttggg gtactgctta 4200
cctcgaggtc tggtagtcgg gtgctatcga cgaccaaccc aggcgttcgc tgtagcatca 4260
agataacgtc gacatctggt ggcttttttc ctaccagatg aggtatttta tccagcagag 4320
tacgccttgt tgtaggcagt actcaggacg ttgatgacca gtcggttcag cattttccgt 4380
cactcactca ggtttttga catgtgaggt catgcgtata tactggctac tttttcccta 4440
tcagtatctc agttttctac cctgacgaaa gtggtactaa cgtctctgaa atggtgcgca 4500
acactcaccg agacgtcact tttcttggac aagccccaac attttggaga tcgtaatacg 4560
cagttagtgc gccaggggtc atttcatttt atgacaaccg gcttcatcaa cacccctaag 4620
acaaatgttt tcatgcccgt ggaacgagat cgattttgag tcccagtgcg acacataaga 4680
aatcactatc ctctaataca tgttattgcc tgttggcaac ttttgcgaat ggctctgacg 4740
atccctgtag tgtgacggtc actccgttac gagaccccat gcgtagattt tcgtgcaagc 4800
ggtcatgagt ttcaaatgga gtttcgaagt tttcagaaat cccgtagtcg ttccttttgg 4860
ctcgtctgtc gaggcagtaa agggttcgta gaatgtgagg tagccggtcc gttaatagca 4920
cttttaatcc agggtttctt cgtcaagtgt cagcagccgg acaaaacatt tagggaccag 4980
gcatactatt ttagcgtagg caacacccgc ctgcagccat ccggacgcaa taacgctcga 5040
agatggacca gcctgttttc tctgtacaat ggccacttga gggcatcagc aacctgttaa 5100
tcggtacgca tgtatatgga tattttgaca ccgtattcgg actgccccga tatagataga 5160
acttgagggt taaggagcaa ccgtcaacgt tttcctaatc gactgctact agacatggat 5220
tccgtacatg aactctctag ccgacaccat cgagtctttt cccttccgtt atggacgaac 5280
atgtagagca ctggctttcg gtcaatgatc tggtccacat gagttttgcg taggcagtcc 5340
tcgccacact tccataccct ccgattgcct agcctcgctg gtgtggaaag ttttgtctgg 5400
gtgtcactga gcactcagaa acttgaccaa aggtaaccct cacacgcaag tttaccgttt 5460
tcacggagga ctggtcggat ggcaagcggt ctggtacgta cggacaggtt attcgagctc 5520
aaggttttac ggttagcgcc gtacatgaat catggaaatg aggagccctg gtcacaaacc 5580
gtatagattt gttttggaag aggtttgaat caggtacaga ttggaacgag cctccaattg 5640
tgggcgttca tctttcagtt ttctacaagg ccatgggtga cggaagctat tgtctatgct 5700
tccggagcct cctcaaggag ttcgcttttc ggcaggttag ctgacatagt tcggaagagc 5760
acctgcgagt cagccgacgt gtccagggca gcttttcaac gtagattgcg tgacggtgac 5820
taattcgcat gcggcagcta gcctatacaa gattatcgct tttcagtgac tatggacaca 5880
cgctctgcct actcacagtc gattgaatca ctcgggcagg agatagtttt cacgtactgc 5940
gctttggtct aactctcgcg cagtcgacat tggtacttgg tgacgttggc gtcttttatg 6000
tgctatctcc aacgccagta actaaggtcg aaacccagca aaagcgtcga ctacttttgc 6060
ttttgagact ggacgctgtg ttggtgtgtc tattccacga gtgcgaggct atgtgcgacc 6120
tgatgcattt tcgctgcttg gcccagttcg ctgctaccat cggtgacgct ttcaccacgc 6180
ggaacataca cccgttttcc ctgctatgaa cgggaacatt agcacattgt ggaccaaatg 6240
cagagacttc acgctacgtg cttttctttt actcaacata atcgagggag tactgacagc 6300
cgacatagtg ggcactgggt tatgcgcgtt ttcgatcaag gtggtagaat gggatacgta 6360

```
cgtgctggta cggtcgaggt tcgcatatcg gagagttttc tacatcatcg atcagattta   6420

tgcaccgtag gatacaaaag ccaaggtgag ctgcattcga cgttttgtgt gcgagctcgc   6480

cgattgaatg gtgagacgag ctctcggttt acaaacgtaa gcatgaagat tttagtccag   6540

cacgcacatc gcactctgct cgacgcttaa atggcaccca cgacgacatg tacagatttt   6600

gaacatctgt tgtcgatagt atcgtagtaa cctcacgctg actcataagt tggctatgcc   6660

acctttgac tgtgtgagca gtccattgac ggagaacccg taataagccg tgcagagtca   6720

cgcctttgag ttttactaca gttgctcaga aatagaggat gtctggcacc tgacgaactc   6780

ccgctaaact tgccgaattt tgtctggcaa tccagaagca cccaactctc acgaggactt   6840

ccacccataa ggcgacagag atccttttct cctccagacg tagccatcca cacgggaagg   6900

gacggtatga ctttcgggca cattgagcaa gttttgggag cagcgtggga ctttttttgaa   6960

ttacgctcat cgttggtccc tgagcaacac caggatgtgt tcacactcct ggcatatttg   7020

tcgacaaaca gtacgcgtca tcacatgctt cgttttttgt ccacatgtgt gctcttttcc   7080

gaattgtttg ctgtttccga acaccaaatt ctatcaacgc atagggacag ctacgaacga   7140

cttttctatg cagtcgacac gtttttttcct tccgacttgg tatcctgttc gtcaccaact   7200

tttttggaca tgacgacaca attttcaatc tctattctcg catcgcaagt accgagtaat   7260

cgtcagccta tgactgtgac acatgagctt ttgtggtggt ctcctccctt ttttccgatg   7320

agaccctctg cctatagaac ggctcaatct aaggtttggt actaggagca gctatgtctg   7380

atccaccaat ctttaccaca ccagtggagt tttttggtta ctggtgggaa attttcactc   7440

ctagtggtac agcagtgaaa agtcggaagt actggtctgt ggacaaggag gagttaactt   7500

ttcgtgaagg gatgtcgtga t                                                7521
```

<210> SEQ ID NO 6
<211> LENGTH: 7051
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 6

```
atccagggag tggcgtaccg acacaagagt acgcccctaa tgcatggagc ctcgtctagg     60

atattttctt ccccaggcct attcacagtt ttttggtctc ataggcagct agcactgcta    120

gtgggatgag ctggacacac ttgtggtgag gcagtgcgtc aacctaggct tacgggacta    180

cctacctccc tgggaggctg tcttcacgga tgctgctttg gtctaagcct tttttcctgt    240

cgaccaatga atcgcacttg gccatgcttt ctgcatttgg gctaggataa ggaccatgct    300

cgtgcacgta cagagaagac tctttttttgt ccattctctt agtccggtat gagcttatgg    360

acgaagccct aggatctgta aggagcatcg agtaaatcgt tcgtgtgtgg catagcgacg    420

tcaagcaggt gtacctgttc gagttttcct ggaagagttc ccgttttttg gaccactctt    480

atggcgcaac catcgaaatg gggctgtaat cgcctggatg gagcgattcc ctttaggacc    540

gtccactgca gtggactttt ttcgagtctg cagtccgaca aaggcaggtc tgttggtctt    600

cggtatgagc atccgcaacc acatgtgccc agaaagtagg atcacttctc tgcatgtacg    660

tctcagccaa gaggaagaag ccagagacac tcatgtcttt tttgtatgca gtgtcaacga    720

caagcggttc attgggattg agtgtctatg attcgttcat ctaggctcga ccgagagtaa    780

gccagatgcc ttttttctta ggtggctttg tcgcaaatca cggaaccaaa ggatgcatga    840
```

```
ttagcggaga ctctcttccg atttgcaatc ggaggttctg atcgtaccac atgccgactt    900
acaaccatgg taacatgttt ctcgccaggt agatcttcgt acttatcccg atagagttct    960
tcgtttgagc ctctcatgag ttctacactc ttgtcacttc ggtacagaag tcgtggatac   1020
ctgattggtt aagatcttcc acatggcacg acaacagagg cttgcgtgcc tggaatcgtt   1080
agtgatattc ctacattgcc ccattcctcc gctaagggta cggtacacca gtaggcatgt   1140
caactcacac acactggagt ttggaacaac gagaaattgt aggcagccat ggtaacgttt   1200
ataatgtaac atttcggagg aacagacagc tcatcgcctt cacacggtac catgtcctca   1260
atcctgggga catcctgaca tgctaggata aatcgggctc tacgacgaac ttggcctagg   1320
tttataacgc gtctatatat ctcggaaaat gagataccta ggggacccta cactttctct   1380
acaccaagca tctggcccta catgagtttc acatgggttg gaatctaatg gttggcaatc   1440
gcagaacgtg cctttaacct gggagtaaca gacctacgat tagccattat cccctaatct   1500
gccaaccatt tgacacgcta gggatagatg cttagcccga atcttgcact tgtgtttcca   1560
tatggcggat cttcgaaact catggccacc tttcccaacg catttggatc tttgtgcaac   1620
tcgaagggac aaaggttcct atcaatcagt gtaaaccggt cgctcatttc cgcctggtgc   1680
tcgtgcgttg cttacctaat acactctaag gaatttggaa caagctggtg acggacggct   1740
gaggtcgtcc tgtttcgggt aactgcacac tagcgtcgta tcgtagggta agtggctcag   1800
gggacgcatt tgctgacggt cagaatatcg cgtttaatcc agttgtctcg acgatttgca   1860
ggaccttaat acgctgcatg tcaacggcta cgttgatagt gcttcttacg tttcactctc   1920
cagtagctac agctcgtgaa tccccaacac tgagcattta acgcagaccg ttagatgtac   1980
tcacacagtc caacgcttca ctagaaaaca attttctagg taacgcgcga gactctaatc   2040
ttgtccacac gatcggatta atgccggaac tgctgatact agccgtccct ctcgatgtgt   2100
gacttcggac gatccttatt ggatgctatg gactccgact gcgtaggata gaagataccg   2160
gctacatcca gagccatatg aagtgtccgt tgtgtcggtt acggtgtcct aacggtcttg   2220
ggacccgtat cctgcttgca acacagcttc tttcaaggtt gctcgtttga gtggtctccc   2280
cagggttatc aagacagtgg ccatactagc gttccactcg gtaaaatccg acctcggaca   2340
ctcagcctga gacgcagaga gaactaggtc ggctgaagcc tttggtgagt aacgaccctt   2400
actcggagcg tgtgttcgaa ggaaagtcat tgacagaagg cacgttttct caggacctag   2460
tgttaggtta cgggctatca catgaactgg cttattgaat ctttcaccat acaacagatg   2520
tgtatgtgca tcctatctaa agcactgttt gtccaagatg aggatctagt atcggttcct   2580
cctcacacac tgggacactt ctgtttgacc cagactggtc cgaatgctac atgtaagctc   2640
ttcatagtct tttccagcgg cactactgta ggagcccaga gtcacaaccg ccacatggac   2700
acccgctgtt gtactccacg attggcatgg taagtgaagt tctaggtcag agggtcctat   2760
tcacgtgcga tactaagtga tacgatagcc atcgtgactt gtttgtgact accaaccacc   2820
acgtcctact cttgaggaaa ggatcacttt cctaccgtag cgatctacta cccagaccac   2880
accgaaggca agatcccttc ttgtttgatt ggctagccat actacgtgaa gttgtgcgaa   2940
agtgggacgt ctacctaccg tctcatattg tatcataacc gagcctgacg ttctgtggta   3000
gacacttcga aaccttgcct tttttggttg tgtttctcgt ctgtcgacca tctacgaaga   3060
cttcgtcgca tgctgttcaa gatgaaagtc ggaacggaca accacagtgt ccttttttct   3120
gtgatgtggt agtacgtagc tgcagctgtc aactatcgga ttctaagcgc gagtgtgctg   3180
```

-continued

```
ctgaggtaga cgttgacacc acccgccaca ccatagtctc tggatgaatg accccgtggg   3240
aagtgtgacg tggtttttc tcttgcacac tagccgtata gcccaaatcc tacagtcttt   3300
gtctggctat atgccaattg cgacgaatgc tatcacaaca tggatgtttt ttgagtggtg   3360
ttggatgcgt gaacatttct acacacgtag agaaggacgt gcacggagca gtcttgcact   3420
gggcacatgt gtgtagtctt gctatccaac acgggatgac ttgtgctgca tcgtggcact   3480
cgtctagttt ttctagactc cacccacgat gcagtttcac aagagccacc gtgttggata   3540
gcaagactaa gtgtgtgtgc tttccagtgc aagtgatggc cgtgcacgtc cttctctacg   3600
gaccaagaaa tgttcatttc gcatcatgac ccactctttt ttcatccagt cattgatagc   3660
attctttgtc gcacgacaca tatagccaga caaagactga ccacgttggg tttctatacg   3720
gctttccacc aagagttttt tccacgtgtg gaatcccatt tcggggtcat tgcaaacgag   3780
actatggtgt ggcgggtgtc acaaacgtct accttttcag caggttggtc gcgcttagaa   3840
tccgatagta agatcctgca tttgctacgt acttgagact cacagttttt tggacacgtc   3900
tcatgtcctt tgttccgact tgtgcaatga acagcatgcg acgaagtccc tagagatggt   3960
cgactttaga cgacctctac aaccttttt ggcaagagag ggaagtgtct actttcacag   4020
attaggaggc tcggttatga tacaatactg ttaggtagtt tgtagacgtc cagagagcgc   4080
acaacttcca tgagtatgtt ggtccaatcc aagaagggat agatgcttcg gtgtggtctg   4140
ggtagtccca atctacggta gggtgatttg gctctcaaga gtaggacgtg gtgggatcca   4200
gtcaccaagt cacgattctg ttcgtatgtg atagtatcgc acaactcaag gactttcctc   4260
tgacctgctg tatcacttac catgccaatc gtgcgaacca acagcgggtt ttgtccataa   4320
acgggttgtt ggcctgggct cctatctcgt tgccgctgga gactaatgct cgcttacatg   4380
tagcattcgg actccattgg gtccagaagt gtccgtcctt gtgaggagga accgatacta   4440
agcatgcatc ttggaccagt ggacagcata ggatgcacat acacatctcc gtaatggtgg   4500
attcaataag agctgtcatg tgatagcccg taaccttagc tgaggtcctg agacgtgtgg   4560
tacgtcaatg acttgatgtc gaacctgttc tccgagtaag tttggtcgtg ttcgaccaaa   4620
ggcttcagcc gaccttacag cctctgtttc gtctcaggca actcttccga ggtcggattt   4680
taccgatacc tacgctagta tgtttgccac tccagagata acgtgtggga gaccactagg   4740
gtcagcaacc ttggaagcca ctgagcaagc aggatctttg tcccatcgag gttaggacac   4800
ctttgtaacc tgtgaaacgg acacttcata tggctcgttt gctagccttt ggtatcttct   4860
cgtggtcgca gtcggagtcc atagcattgt cgaaggatcg tcctttgaag tctggtctcg   4920
agagggacgg ctagtatccc atcatccggt ttcattaatc cgcgaccttg gacaagattc   4980
acctctcgct tccaacctag attgttttct aagcccgcgt tggactgtgt gagtacaatg   5040
tccggtctgc gtttgctcca gctaggggat tcacgagctg tagctcagct agagtgcgta   5100
agaagcatgc ctaacgtagc cgttgacatg cagatcccaa aggtcctgct cgtctcctag   5160
actggattaa acgcgatatt cgcgtagtca gctgcgtccc ctgtcatcct taccctacga   5220
tacgacgctc acacacagtt acccgcagga atcgtgcagc cgtccgtaga gagcttggcg   5280
ttaattcctt agatttgtgt atcccaaaag caacgcacga gcaccaggac ctcgtgagct   5340
ttgaccggtt tatgtgtttt gataggaaca cgggtcccta gaccttgcac gatccaaatg   5400
ccacacgaaa ggtggccatg agtttcgtga cagcgccata tggcacaatc atctgattcg   5460
ggctaagcat ctatcttcgt cgtgtctggt tggcagaacg tcggataatg gctaatcgta   5520
ggttgagacc tcccaggttg gcactgtagc cgattgccaa ccattagatt cgctatcatg   5580
```

tgctcatgta ggggtctttg cttgcctgag agaaagtgtc aaacgcccta tttggtatct 5640
catcgaggta gatatataga cgcgttataa ttgggggcca agttcgtttt cgtaggtgaa 5700
gatttatcct agcatgtcag gtctaaccca ggtttattga ggacaccttc tcgtgtgaag 5760
gctcctagct gtacacgcct ccgtgttaca ttatgtggct taccagactt gcctacaatt 5820
cagtagtgtt ctttcaaact ccagatccgt tgagttgaca tgcctactgg ttctgagtac 5880
ccttagcttt ggaggatcct agcaatgtag gaatatcact aatccacaca ggctttacgc 5940
aagcctgaca gttcgtgcca tgtggaagat cttcgaagat caggtatcct ttacgactgg 6000
ctaaccgaac actcaagagt gtaggtgaat tgagaggctc cgaagtgagt gatcgggata 6060
agtacgaaga tcgtggaggc gagcatgtta ccatatagct aagtcggcat gtggtacgat 6120
gctacactcc gattgctcgg acacttttct ccgctaatac gtcatcctgc tagtccgtga 6180
tttgtttcga caacagaccc taagtttttt ggcatcgtct gtactctcgg tctttgagcc 6240
tcttgcaacg aatcatagac actcaataga tcggaacctt tgcttgtcgt tcctcaggca 6300 tactttttttg acatgctgag gtctggtttc ttcttcctcc ctttcgagac gtacatgcag 6360
agaagtttgg ttactttctg ggtttcacat gcttcggcgg atgctcatac cgaagacact 6420
gtcacctgtt tcctttgtcg gtacctcgac tcgttttttg tccacgaggt aggacgtttg 6480
tcctaaaggt gtggactcca tccaggcgat tacagctagg attcgatggt tgtttcgcca 6540
tctccttggt cctttttcg ggaaaggagc caggaaaact tttcgaacat cagaacctgc 6600
ttgacgtcgc tatgcacgga tcgaactttg atttactcgt gaagacttac agatcctagg 6660
gcttcgcagt caagctcata cctttggact agttccatgg actttttga gtctggaacg 6720 tacgtgcacg tttagcatgc agtgtatcct agcccaaatg cagaagatcc tgccaatttg 6780
tgcgattcag actgtgacag gtttttggc ttaacagtca gcagtttcat ccgtgaactt 6840
tagctcccag ggaggtaggt agtcgttgta gcctaggttg tttacgcacc tatccaccac 6900
aagtgtgtcc agctccgtat tctagcttta gtgctagctt gagtggagac cttttttctg 6960
tgacactcac tgggtttgaa gaaaatagag acaacgaggc tccatgcatt agggtgaccc 7020
tcttgtgtcg tttgtacgcg tggacctgga t 7051

<210> SEQ ID NO 7
<211> LENGTH: 1779
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 7
gggagaggau ccagaugaug ucucuauggc caaaaguuga agguccgacu acacguugcg 60
uaacgguaag cacucauaug aguaugacag gucauagcag uaaaacgucu auaguccagc 120
aggaaacugc uggauagguu gggcagugca acuaggucga cgaaagucga guugccuagu 180
augaaaagaa cagucgucuc gugaugucca gcgaguagca guaucuuaga gagucgauuc 240
ucgcacuggg uugaaaaucc aaguaacacu uugcgaaagc aaagugggua acucaagguu 300
ucaucuccac cacgaaagug guaugugucu gccuuaaaau ugcggugcuu cauaagugau 360
cgaucguuac ugucagcucc agaccuuuac cacuguguca gacagaaaau ggauacgggu 420
cguuacucac cgcuuuagua gugaucagua cuucuacuua agaccacuag augcuaaaau 480
cuggcccaaa agauuuggau uugacccaug uccuuacuga uuacucauuc ucgucauccg 540
aguucaaaac uacguaggaa ugcaucaugc agaacuacug agcgauccaa uaaugguuca 600
ggagugugua uaucuaaaag cgugucuagc aggugugcu ggguacacgu cucgaauaga 660
cgagcgacgu ugggcacuau acgguaaaac ugugacacug uugucggaaa cgacaacaga 720
ccucaagaga uuagcaacgu gcacggaaac gugcgucgca aagcuacaaa aucuagugca 780
ccuuaggaau ggucauaaua gaugccgucc agcugucaug acaccuaggg ucacuccaaa 840
acucucuaac ugguacgaga aaucguacca cugaccaagg gaacuagaga caguguccuu 900
cuagaaauag aaggacacac augaacguuc caaaacuugg ucagucucca gcgaaagcug 960
gagaguuaga gagggaguga cccuagguua aguagaagcu ggacggcauc uauuaugacc 1020
aaguaacgag ugcacuagag uagcuuugcg acaacgggaa accguuacgu ugcuaaucua 1080
aaacuugagg uccauguauc gaaagauaca uggugucaca gaccgcugac acaccaacgu 1140
cgcucgugag cugacgacgu guacccagca cuuaugacua gacacgcaga uauacacacu 1200
ccaucgacuc uauuggaucg cucaguaguu cugcaaucac gaguccuacg uaggaacucg 1260
gaugacgaca uacucaaauc aguaaggaca ugggucaaau cuguagucgu ugggccagaa 1320
gcaucuagug gucugucaug acaguacuga ucacuacuaa agcgguguuc cuaagcccgu 1380
auccacuguu auagugcgug guaaaggucu gcuauucgaa guaacgaucg auccacaccu 1440
gagcaccgca aaaggcagac acaugugcag aaaugcacgg agaugaaacc uaaaaugagu 1500
uaccccaacg aagaaauucg uugguuacuu ggacaaccca gugcgagaug aaccauucua 1560
agauacugcu acucgcugga cugaugcaua cgacuguucc auacuaggca accguucgaa 1620
agaacgccua guugcacuga aaacccaacc uagccguaga gaaaucuacg gccuauagac 1680
gacugcuaug accugugaau gaguuaugag ugcuuaccgu uacgcaacgc aaaucuugac 1740
cuucaacggc caguucaugu ucaucuggau cuucucgag 1779

<210> SEQ ID NO 8
<211> LENGTH: 1808
<212> TYPE: DNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 8
atcggacctt acatcagaac acacgaggtc ctaatgtggt gcttcgtgtg gagccagatt 60
aggcctaaaa tcttgaacac gggtctcagt aattgatgat gctgtctgag agcatgccac 120
aactacggga gggtaggccc cttgacatcc tttctgggtt caccaaatag gggatgtgtt 180
aggatgtctc ggttcttaag ctattggtct tcttgattgt cagcctgtcg ttcataacag 240
acgagtaact gtgttggcac ggcacgtctg ttgtcggaat cctgcacaac attctgttga 300
ctttcccaag acgaccttcc agtgctgcta aatgtatcta gcctcaactt gcaaggcgcg 360
taccgcgaat cgaatgcgtt ttccatctgg aaaattgtgt gaaacgttat gactattgcg 420
cacgaaatgt agagctcaga cctcacgtgc gttcgtttga caataggtgg tcgtagttgc 480
catgacgtgg cactgtccga atcggacgtg cagcctgcat tagctggctt atttagattt 540
ctgaagccgg ctgttggcag ttctcccgat tacaatagcc caacagtgca cgtgggcacg 600
gcctctggta gggcatgtgc gattgtcgaa agtgggacca agctctctcg tcggtccgcc 660
tggaggtttg gacccataag tttgcgagaa atcactgagc tctctttctc aacacccaga 720

```
catccaacgt tacgtacgac aagtcttgca gccatagttt cgtggatctc agggagccat    780
tcaaatccga ctactgggat agagtctggt tctattagac gtagaccggt gatgcctata    840
aagcaggggt agttgcggcg actggaaggc tcgaagtgcc aattgatttt caggctgatc    900
tagtttttct agatcagcct gaaaatcaac gttaccttcg agccttccag tcgccgggtg    960
taccccctgct ttataggcat catttccggt ctacgtctaa taccgtcaga ctctatccca  1020
gtaagacgat ttgaatggct ccctagactc cacgctatgg ctgcaagact tgtcgtacgt   1080
ggtcggggat gtctgggtgt tgagaaagag aacctcatga tttctcgcct tatgggtcca   1140
aacgaagacg cggaccgacg agagcgagac gtcccacttt ctcccatcgc acatgcccta   1200
ccagaggttt ccgtgcccac gtgcactcac cggctattgt aatcgggaga acgtaacgca   1260
gccggcttca gaaatctaaa taagtttcca gctaatgcgc aggacacgtc cgattcggat   1320
gccgtcacgt catggcaact cgtctgacct attgtccgaa cgcacgtgag gttgaggttc   1380
tacatttcgt gcgcaatagt catccgacct cacacaattt tccagatgga cgcattcgat   1440
tcgcggtacg cgccttcaca cgtgaggcta gatacattta gcatgtgtgg aaggtcgtct   1500
tggggtcaac agaatgttgt aggctgttcc gacaacagac gcagtgcgcc aacacagtta   1560
ctacgacctt atgaacgaca ggcttttgac aatcaactcc agcaatagct taagaacagc   1620
ttgatcctaa cacagacact atttggtgaa cccagggatg tcaaggggcc taccctcgaa   1680
cagttgtggc atgctctcgt cgagcatcat caattactgg agaccgtgtt caagtttatt   1740
ttaggcctaa tctggctcgc aagtaagcac cacattagga cctcggcact tctgatgtaa   1800
ggtccgat                                                            1808
```

<210> SEQ ID NO 9
<211> LENGTH: 2418
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 9

```
atcttgactg gaataacttg tcgatcctcg tgtggcgttt gtcagggtag tacaggtgcg     60
gactcaggaa cgatgtatcg ccatacacca agctacagtc tccaaaggaa aagcgttgct    120
tagtcacccc gacgttcgga ccatgatgcg ggtgaaaatg caacgttctc cgtagtgatc    180
tcggtgagct tggtacgcca gtgaagtgcg acggactagt cggatcgttt gtatccactt    240
accagcaata acaaagtgac gacatcaaaa cgtgcgaccg cacagaccag tgttctgtcc    300
gctaattgac gtaccactac ctaatcgaaa catacctgct cgtatgtgct cgtggatgct    360
tgcggaactg ttatgggctt tctctttagc ggcgatgtct cggctatgga gttttggagt    420
tctgcaccgg ccggtgtggt gtggcaaaga tcccatttac ttctctgccc agtggctgtt    480
atcaagccga gcgtcaaccc aaacttaact ggcagtgcta actgcactgg gttctctcac    540
ttaaatggac ctcggctcgg gcagctgggc cactcgaatc tgcgctccca gataaactcg    600
acccatcact tgcataggtg ggctgtcgtg actagcatgt tatcctcaag ctcggactcg    660
ggatcccgtg ttccgcacaa ttcgggcttg agggcacgtg tcccataggt acctacgctg    720
gagaaaacag atctgcgaag gacaggctat tagctttaga tctctgtggc acaacgggtt    780
gccattggag ctggtataag catagctcgc atctaggccc aagtctcttc taggttcttc    840
```

```
ctcgcgtcga gagaagtata aatcgcaccc aatccataat acccaacccg gcataaagtc    900

ctcaaaggat tactgcaact gttactgctg attctcggaa atgtgacggt agttacgtac    960

ggtaccagac ccttgacaat ttcgattggg tccgggttct tatcttgatc acacttttca   1020

tgatacctat gtgtacacag cctgagcctt aactagtttg acgggaaaac acaatagacg   1080

cactgttttc agcgaaatag gacctgagag gactttgtca agcatggctg ctttgagccg   1140

ttgggaatca gtgtttatgg acggatcttg cacctgacgt ctctcaccta aaggttatct   1200

agtttttcta gataaccttt aggtactcga cgtcaggtgc aagatccgtt cgttgacact   1260

gattcccaac ggctcaaagc atttgccatg gtccacaaag tcctctcagg ttacctttcg   1320

ctgaaaacag tgtacgtatt gtgttttccc gtcctagtta aggctcaggt gggagacaca   1380

taggtatcat gaaaagtgtg cgagccataa gaacccggac ccaatcgttg tcaagggtct   1440

ggtaccgtat gcgactaccg tcacatttcc cgtcatcagc agtaagctgg tcagtaatcc   1500

tttgagtttg actttatgcc gggttgggta caacgaattg ggtgcgattt atacttcgag   1560

tgacgcgagg aagaacctag aagtttagac ttgggcctag atgtccacta tgcttataga   1620

gcagccaatg gcaacccgtg tagtgacaga gatctgctaa tagcctgtcc tactgccatc   1680

tgttttctcc aggacgctta cctatgggac acgcactggc aagcccgaat tgtgtttcgg   1740

aacacgggat cccgcaggcg agcttgagga taacatgctc tgtgtgacag cccacctatg   1800

caagtgatgg gttttcgagt ttatcctgtg tcgcagattc gagtggccca gctgccatca   1860

aggaggtcca tttaagtgag agaacccatt tgtgcagtta gctcgcagag ttaagtttgg   1920

gttcgtaggc ggcttgataa cagctgccct gcagagaagt tgggatcttt gccacaccac   1980

acacctcggt gcagaactcc aaaactccat agcgatcaca tcgccgctaa agaggcccat   2040

aacagttccg caagcacgag cgagcacata cccagctgta tgtttcgatt agtgtgccgt   2100

acgtcaatta gcgtttgaca gaacactggt ctgcgtagtc gcacgttttg atgtgagaac   2160

tttgttattc agttgaagtg gataccgatc cgactacttg gtcgcacttc actggcgcct   2220

aaagctcacc gagatcaccg tcgagaacgt tgcattttca cccgtttcat catggtccga   2280

acgtcgggac acagaagcaa cgcttttcct ttggacctgg tagcttggtg tatggcgata   2340

ctttatcgtt cctgagtccg ccggcgtact accctgacaa acgccacacg agcgaggaca   2400

agttattcca gtcaagat                                                 2418
```

<210> SEQ ID NO 10
<211> LENGTH: 2720
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 10

```
atccacagta gatgcgcttt ccgctgtcga agcgactaga atcgataacc tcgtcgccta     60

aattctagcg atctttctcg tgggtatgta agcaaggacc gagtccatag ttgaaatcgg    120

acacttctag tcctctgggc ataaacagag tcgactggtc tcgtacatac tgtcaaacga    180

atgcctgtag aggatacctc cacctacgat accataagga tagacatttt ctgttacacc    240

tattcatcac cggtttggct acgtccgtgc agccgttcgt gagtaagacc acatctgacg    300

cgggagaaag cgcatgtgcc aagtacagac ctagcaagcc ggacggatgt aattctgcct    360

aggagcacca ggctacgatc gattcgcgtt tatagcctct tatctcgagc tcgtctcgtc    420
```

-continued

```
tgccacgtac ttccgcgcgg gtatatagac actttgccaa cgtgctgagc gtttccataa    480
ctaggatata tgtgggttcc agtagagagg gacaagtcct ggttgatggt tttatcgcca    540
ctgggtccag cgaaccaccg atcagcagga tcacatctgc agtagacgcg aaagaggtcg    600
ggactcccgt ataagtgcta ggcaccaaac gcatttaaga atccggacgg tctgccggat    660
actcgttcac cgtagccaaa atggcacctg aggctcaaaa ccacgaccgc gaacataaga    720
atacttacgc tgccatggga cgggtatccc tgacacttag gaggcagtcg ataaagaagt    780
gcagtgactg cctatcaccc ttggtctgcc cgtctgttag actctatatt ctgactaccc    840
agtggtcacg ataccggtgc cagcctacgg gtctgaagcc aggagtcgat gctgaattgt    900
cctttgcgat acagatatga acgacgtgct aggcgctgtg gagtcctact gtactacggg    960
atgtatacgt gtgcctagac aataaaggta agctatgcta ccatcgcagg actattcact   1020
aacgtctttc ctgagctaca taccgatcga tagagttgcc ttttagttta gatgaacgtc   1080
acctaaatat cttccagaca ggccgagaac tggcacgcat cttcgtattt agtcgacgga   1140
tgggctcctt tgatcctgtt ggattacgac tatggtacca aagaacgatc tctatgagat   1200
ccactttctc cgtgaagaaa caatcccgca cgaggcaact acgtttaccc tgttggagag   1260
cacttgctgc ctgcgcgtca aaccgtcaga gggtggcatc tgagacgttg taccggattg   1320
atgggagagt agcgcccagc cgagttctag tttttctaga actcggctgg gccacgctct   1380
cccatcaatc cggtacagtt tggcagatgc caccctctga cggtttgact ttgcgcaggc   1440
agcaagtgca ggtcaacagg gtaaacgtag gcatctcgtg cgggattgtt tcgagacgga   1500
ggtggatctc atagagacca tggtttggta ccatagtcgt aatccaacgt cgtgaaagga   1560
gcccatccgt cgacttacga agatgctgtg cagttctcgg cctgtctctg cgatatttag   1620
gtgacgttgg tgtaaactaa aaggcaactc tatctttgat cggtatgtag ctcaggaacc   1680
aaactagtga atagtcctgc gatggcgtga tagcttacct ttattgtcta gtttgcacac   1740
gtatcgcgga cgtagtacag taggaagacg aagcgcctag cagagggttc atatctgtat   1800
cgcggacaat tcagcatctc gcgttggctt cagacccgtt cctgcgcacc ggtatcgtga   1860
tggaccggta gtcagaatat agtttagtct aacagacggg catgataagg gtgataggca   1920
gtcactgtcc cagtttatcg actgcctcct aagtgtcagt ttggataccc gtctcgttcc   1980
agcgtaagta ttcttatgtt cgcgaggatc gttttgagcc tcaggtgcca ttttggtttc   2040
tacggtgaac gagtatccgg acacgggtcc ggattcttaa atgcgtttgg taggagccac   2100
ttatacggga gtctttccga cctcttgact ccctactgca gatgtgaagg ctgtgatcgg   2160
tggttcgccc actgcagtgg cgataccatc aaccaggact tgtccctgcg aactggaacc   2220
cacatatatc ctagttatca gcacgctcag cacgttggcg tgtctatata cccgacatcc   2280
agtacgtggc agacgctcca cgctcgagat aacgtcctat aaacgcgaat cgatcgtatt   2340
tgcctggtgc tcgctcctag aattacatcc gtccggcttg ctaccgtgtt acttggcaca   2400
tgcgctttct cccgctttgt cagagtgcgt cttactcacg aacggggaaa cggacgtagc   2460
caaacccatc atgaataggt gtaacagatg tctatcctta tggtatcgtt ctcggaggta   2520
tcctctacag ttgctcgttt gacagtatgt acttcaccag tcgacttttc tgtttatgcc   2580
cagaggacta ctgggatccg atttcaacta tggactcatc acttgcttac atacccacga   2640
gaatttagat cgctagaatt tagctctcga ggttatcgat tctagtcgct tcgaggaagg   2700
aaagcgcatc tactgtggat                                               2720
```

<210> SEQ ID NO 11
<211> LENGTH: 3022
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11
atcatgcgtg agccggactc ctgtactcat tgctaatgta cctatggcta aggagtcggg 60
tacacatatc tctttcccga taaacacatc tgcgattcgg aagcccgtca gctttcgatc 120
gctctgatca caccggagtt ggctcttgct tcgtatagtg cagaaagtgc gaattgagta 180
acctctctca cgaatgagaa gacactactg cgtgtcgtca gttgggattt ccgctgggta 240
cacagcttcg ggtacgctct attcactgcc catacgcggc tagtgcctgg aaagcaattc 300
aaacgtcacg gagtctcctc acgtgggatg agcacccacg tgactaacga accactggga 360
cgcggctcga ctttgaagtt tcatctttaa gcccagtaaa ccgcagcttc aaacgaaatg 420
ttacacgaca catccatcgc tcatgaacaa acgcatttgt actccactag accggatcct 480
tacttttccg acggtttcca attgcctgcc aagacacaat ctaacgtcct cggaaccctt 540
agcgacgcac ataggtccct cgtgggacca acccgaaagg agtatggaga gtgtcttttg 600
gtgggattta ggacctcgcg tccacacatc tgcatttgta ccgcgggtgt aagtcacagg 660
gcttttcggg atcacttgct aacttttccc tattgctatt acgaacaggc agacatatga 720
aaggccacca gtcggcatcc ggttgctgca cgtcacttgc tttccggttg ttctcctggt 780
aacaacatgt tggctcgtga gtatgcaact gtccaactgt ccagtaaaga tcttctgatg 840
ccaaatcgtt cctggacttc attcagttgt atcagtactt acctggtacg tttgttgaaa 900
acaagcctta tgcacacttt acccagttac gaacggtcat gactctccgt taagagagaa 960
gagtgatttg catcggaaat ggacgtttaa ggaccttaga gtagtaagcc ataagacaga 1020
gaacgagagg aatggagctg agccgacata ttccactgac aagcaatgcc agccgtgtgc 1080
tgcggcaata gttaactcag ctcatgctac actggcctct tgattaaacc tctgacaaaa 1140
gccgcacgga ctgggcacag tagccgtagc gtgtgatgtt cgactgtgca ccagagcttt 1200
tggtaacgct tttaggtaga cgggaaccgg gaaaactgtg tgacatgtta accaatctgc 1260
catatacgag gaacgtcccg aagtgacttt gcagaacatc atacagctcc atgactggca 1320
cgtccgcgaa gtcggttcga cgcaccttgg ttggtttccg tcccttataa tgtggtggag 1380
taccagtagc aataagtcgg gttcctaggc tcgcagagtt ctatccatgt gccgactatg 1440
ggaccgtctc agcagggagt aggtacgaga ccctgaccct cgggcagtgg gaatctgcgt 1500
tctctagttt ttctagagaa cgcagattca tgttgcccga gggtcagggt ctcgtaccta 1560
ggttctgctg agacggtccc atagtctttg gcacatggat agaactagtg gagcctagga 1620
acccgactta tgatccatgg tactccacca cattataagg gactttggaa accaaccaag 1680
gtggtgtgaa ccgacttcgc ggacaggtca gtcatggagc tgtatctgct tctgcgtcac 1740
ttcgggacgt tcctcgtata tcactggttg gttaacatgt cacacagttt tcgttgcacc 1800
cgtctaccta gcgttaccaa aagccaggca gcacagtcga atgggacacg ctacggctac 1860
tgccgacagt ccgtgcggct tttgtcagtt taggtttaat caagaggcca gttggatctg 1920
agctgagtta actattgccc actcacacgg ctggcattgc ttgtctttag tggaatatgt 1980
cggctagtgt ccattcctct acgtggctgt cttatggctt agaggagtaa ggtccttcgt 2040

```
ccatttccga tgcaaatcag gcatctctct taacaccgtc tcatgaccgt tcgtacggtc   2100

ttaaagtgtg cataagtttg cttgttttca acaaaccgct caggtaagta ctgatacaac   2160

tgaatgactt gcaggaacga tttggcatca gaatttgatc tttactctct ccttggacag   2220

ttgcatatgg tccagccaac atgttgtttg cgtcagaaca accgggcaag tgacgtgcag   2280

ctgcaacatg ccgactggtg gcctttcata tgccagtgtg ttcgtaatag caatagggag   2340

ttagcaagtg atcccgaaaa gcccttcaga gtacacccgc ggtacaaatg caccgatgtg   2400

gacgcgaggt ccttcccacc aaaagacagg acagatactc ctttcgggtc tcacgcacga   2460

gggacctatg accagggcta agggttccga ggtttacgtt agattgtgtc ttctctggca   2520

attggaagga gagggaaaag taaggatcac tgggagtgga gtactgcgtt tgttcatgag   2580

cgatggccac gtcgtgtaac atttcgtttg aagctgcctc ctactgggct taaagatgct   2640

tcaaagtcga gccgcgtccc cagcgttcgt tagtccgttc tgtgctcatc ccacgtctac   2700

tcactccgtg acgtttgttt aattgctttc tctggtctag ccgcgtacat ccagtgaata   2760

gagcgtactg ccagctgtgt acccagcggt cccaactgac gacacgcagt acgtccttct   2820

cattcgtgag aggtgctact caattcgcac tttgatgact atacgaagtt tcaagagcca   2880

actccggtgt gagtgactcg atcgaaagct gacgggcttg atgatcgcag atgtgtttat   2940

cgggatttaa gagatatgtg taccccaagc cttagccata ggtacattag caatgaagcg   3000

aggagtccgg ctcacgcatg at                                             3022
```

<210> SEQ ID NO 12
<211> LENGTH: 588
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
gaacaggtga gctcataatg gcgtacgttc gtacccattt tcgtagacac tcctcagttt     60

tttcaagaga gtgggcgtgt tgagactaca acaggttttt tgtcactgta gtagatcttt    120

tcctggctta aatcaggtcg ccggcatctg atactggcat caggctgtga cggacaaaat    180

caacttttga caaagagcac agggtttttt gatactgctc gagctctcgg gaagcgagtt    240

ggtttttga agttcgcttt cgggttttgc aagataagag gcaccctagc ctcagcgcag    300

caattattcg ttgttgacga aacgcagtcc gttttctcca aggtacatag gtttttgca    360

acgtacccat ggtccttgac atgtttaggt tttttgcgtg acatgtgtcg gttttaagag    420

tggtggacac ggacgtcacc ttgaagtctg atgcacaact ctggacccat gtgtatcatt    480

ttagatacga gcaatccgtt ttttgagggt gctcgcccgt ggaagagaca gtgcggtttt    540

ttctctcctg tcttggcatt ttggacttct cgtgcttcca caatgacc                 588
```

<210> SEQ ID NO 13
<211> LENGTH: 572
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 13

-continued

```
cacctgttcg gtcattgtga cacgtcgaga agtcctgcca ctgtacgaga gtttttttccg      60

cagtacagct tccttttacg ggccttctcc ctcttttttc ggatagaagg tatcttgata      120

cacatgggtc gttcgatgtg catcagactt caaggtgacg tcgaattgca ccactcttcc      180

gactacacgc acgctttttt cctaacgtgt acaaggtttt accatgccag ggttgctttt      240

ttcctatcct ggttggagcg gactgcgttt cgtgctggcc gaataattgc tgcgctgagg      300

ctaggcgttg gcttatcttg ccccgatgga taacttcttt tttccaacta tccacccgat      360

tttgagctct ctgcgtatct tttttccctg gcagatttgt cgttgatttt gtccgtagtc      420

cgctgatgcc agtatcagat gccggcgagt cacgttaagc cagggatctc gattggtgac      480

ttttttcctg tcaatcgctc aattttcacg ccaccagtct tgttttttct gagctggttc      540

tacgtgggta cgaacgtaca gacagatgag ct                                    572
```

<210> SEQ ID NO 14
<211> LENGTH: 268
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 14

```
catgacggag attacctcga actccagctc ggataggttt tgaggactac aacgtgtaat      60

attttgccta agggttagca atcctgtcta gctaaaacac gtagttttcg agctctgacg      120

tgacgccatc gatacctcag cgtatcgcct cggactctac cacagagggt attttcctta      180

tgcgcccaac ggtgtgtggc tccgtgcacc aattcctgcc agcgttgctt acagcgactt      240

ttgcgctcga ctcaattctc cactgatc                                         268
```

<210> SEQ ID NO 15
<211> LENGTH: 252
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 15

```
tccgtcatgg atcagtggac gtgtcagtcg agcgcgtcgc tgtaagcaac caacaaagga      60

attggtgcac ggagccacac acgtgcctgc gcataaggta ccctctgtgg tagcacagca      120

ggcgatacgc tgaggtatcg atggccctga ttcagagctc gctacgtgtt ttagctgcca      180

ttgattgcta acccttaggc aaaatattga agcatgtagt cctccctatc cgagctggac      240

agagtggtaa tc                                                          252
```

<210> SEQ ID NO 16
<211> LENGTH: 1896
<212> TYPE: RNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
gggagaguug cgaagaaucu aacacuagug uacaagggcu ucuccuuauc agagaucaug      60

augacaacag gugaauggag ggucuaacau aagaguaauc caaugcuucg aacuaaccuu      120
```

```
ccccuugugg uuauccuagc cuagcauaua cguucugaga aaacuucccu cuacucacca    180

ucugcagcaa uacucuacua caggucucuu uucacucuag gggaugcagc uaacgaccua    240

cguguuauga agguccuaga uuugaguagc uccacucucg ugcauggggu ggacgguaac    300

gcccuucugg guuucucaaa aggggugug ccagcugaac uauggcuuug gcguuucuuu    360

cggaagcgaa gcugaugcuu gcugaggcag auccacugaa aacccuugcc uccagacucg    420

agcuucgcga cagcguggcc ggaucaugcu ccccuuaguc agagucuuac ugacguaaca    480

aaacaggcaa auggucucug ucaagaugcc ccuuugugac cgucgggaug uauguaacuu    540

augcgugauu ucaccggcca uacucugguc gucauucgcu gauuguaggg augccagcgg    600

ccucaacuac uaguggaugu acaaccccgg uaaugcucug ccauaccggu aaggggacua    660

uaagacccac guguuacucg cgcguuauau gauggcucau cagccauguu auccaaaagu    720

ccaguuaccu cugacuccuc gccgugcugg gacuaucucg agucgcgaac uacaauacga    780

gcaauucccgc aucccaaaag uccauaacuu guauucgauc cgcaugcuag augacaguuu    840

cuugucggcu gugaacuggu ugcgacguga gcucuagcgc ccuguguaac cugaagaagu    900

aguugugcua uugaacucuu gugcuagaac cgaaugacuc gaagucuaga aauagacuuc    960

gacauguacu guucuagcac aagaguucaa uagcaaucag gucucuucag guuacacagg   1020

gcgcuagaga aaacucacgu cgccuaggcu acacagccga caagaggaag guuucuagca   1080

ugcggaugau uacucaguua uggacgggau gcggaauugc ucguauugua gggaucaugu   1140

cgagauaguc ccagcacggc gaggugggcu ucguaacugg acggauaaca uggcugaauc   1200

cccuacauau aacgcgcgac uguaguaugg gucuuauagu cauggugagg guauggcaga   1260

gcauaaaaua ccgggguugu acauccacug accugauagg ccgcuggcau cccuacaauc   1320

agaguacaug gaccagagua uggccaaaag gugaaaucag cguuaccuua cauacauccc   1380

gcgagaguga aaggggcauc uuguaggacc ucauuugccu gguuacguca guaagagaag   1440

cccaaagggg agcaugaucc ggccacgcuc augauccgcu cgagucugga ggcaagggca   1500

guggaucugc cucaugucau cucagcuucg cuuccgaaag aaacgcugua cacuaaguuc   1560

agcuggcaac accccgagaa acccagaagg cgcauaaggu ccacccccaug caacggucac   1620

gagcuacuca aaucacagag acucauaaca cguagguaaa acguuagcug cugagccaug   1680

agugaaaaga gacguaacac ggaguauugc ugcagcccuu accuagaggg aagcucagaa   1740

cguauaugaa ccaguuggau aaccacaagg aacugucaag uucgaagcau ugcgaauaca   1800

uuauguuaga cccucaaaac auucaccugu gcaagcaaug aucucugaua aggagaagcc   1860

cucaaagcca uguguuagau ucuucgcaac ucuccc                             1896
```

<210> SEQ ID NO 17
<211> LENGTH: 1684
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic polynucleotide"

<400> SEQUENCE: 17

```
gggagauuac ucauaagggc uggcuugguu cacuaggagc uaguugggua gcccgucacc     60

agugcguaca gcccguucau ccgcuuugcg auugcucaca caacgcuucg aguuuacccg    120

uucugcgauu gaucgaaaga ucaggacauc gacgggugaa cucgaguugg gaagugagcg    180
```

```
aucgcaagcg aucgaaacgg aaaacucgcu gcuuaccgua ugaauaggag guaccuucug    240

ccgguagucg uucguucagu aagcugagcu cgaaagagcu guaguaguug aacggacgac    300

uaacuuagau cguagagacc gaggcauacg guuccuugaa aaggacgca augaccucgg    360

uuucuacggu cuaaguaaau caauaucacc acuacuaccu augccacgaa aacccauugc    420

cgaggaucca caauggugcu cacgcguuua uguagcauuu ugagcgggau cgguugagag    480

aaaucucaug gaguuacgcu caagaugcua gcacacgccg agccuauaga gauggauccu    540

gcuucgaaag aagcuccuac ggucucuaug ggcucggugu gugccuagcu cguagcucua    600

acuccaauca ugguggaaaa ugaguagucc aucgcagagu auucggccug ugagcguugu    660

uacggauuug cugcagcgga uggaguuuau gcgaaagcau agacucucga ucgcgcagca    720

gauccguauu cccaaccaca ggucgaauac cgauguccgg acugcucaaa aagagcgggg    780

uuagcaugcg uugccaucuc aacaucuccg uacugcacuc uacaugacaa guacgagggu    840

aucuuguucg ugagaucguu caugguagca cgcagcuucg gcugaggagc gauccacaac    900

gcucuagaaa uagagcuggu gacaucgcuc uucagccgcu ccuaggugcu aucaugaacc    960

cuuaugagaa caaaaagucg cgugggcccc aaugccuaga gcuaaaugcg aaaggugcaa   1020

gcuacgcaca gcgucugaua aggcgaguga aaacucgucu uaguucgucu ugugcguggc   1080

uugccgcgau uccauuuagu ucuaggucgu cuaucccaug cgacaaaaag auauccuccc   1140

ucugaccaug uagcgugcag ugcggagaag aggugugaga cgcgcaugcu gcguugaaaa   1200

acgcucgaaa accgucucau accucucucc gugauaucag uaggauucgu cagaggcgca   1260

ugaaaaugcg guacuuguga auccugcuga uauuacggag uguugaggug gcaaguuuuc   1320

gaaaccucgc ucccaccgug auaccgaucc gagcuaugag cuagcauaaa ugcgugagua   1380

ccauugccgu aggacggcga uggguugccu cagacgcagc ccuaguuauc uaccuuucga   1440

uccuuggcca cuucauuggg gacuucgaaa gaaguauaga cgaaaguggc uaaggaugaa   1500

ucgcgagaua auuagggcua gacgaacggc aaaaaacgug guauagcagc uuacggugau   1560

guugauuucc ggcaggaggu acuuccuauu ucauugcgaa gcggcgagaa aagcugugcg   1620

cacguugugg gggcuacuca acuagaagcu gcugaaccga gccagcgauc ucacguaauc   1680

uccc                                                                1684
```

<210> SEQ ID NO 18
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 18

```
ggtggtggtg gttgtggtgg tggtggtcta aagttttgtc gtgaattgcg              50
```

<210> SEQ ID NO 19
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 19

```
gtaaagcttt ttttttttta caaccaccac cacc                               34
```

-continued

<210> SEQ ID NO 20
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 20
ggtggtggtg gttgtggtgg tggtggtaga gcttgacggg gaaatcaaaa 50

<210> SEQ ID NO 21
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 21
tgtagcattt ttttttttta caaccaccac cacc 34

<210> SEQ ID NO 22
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 22
ggtggtggtg gttgtggtgg tggtggcgag aaaggaaggg aacaaactat 50

<210> SEQ ID NO 23
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 23
tgagtttctt ttttttttta caaccaccac cacc 34

<210> SEQ ID NO 24
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 24
ggtggtggtg gttgtggtgg tggtggatag gaacccatgt acaaacagtt 50

<210> SEQ ID NO 25
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 25
caagcccatt ttttttttt acaaccacca ccacc                35

<210> SEQ ID NO 26
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
ggtggtggtg gttgtggtgg tggtggcacc accctcattt cctattatt        50

<210> SEQ ID NO 27
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
ccgccagctt ttttttttta caaccaccac cacc                34

<210> SEQ ID NO 28
<211> LENGTH: 50
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
ggtggtggtg gttgtggtgg tggtggctac attttgacgc tcacctgaaa        50

<210> SEQ ID NO 29
<211> LENGTH: 34
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
ccctcagttt ttttttttta caaccaccac cacc                34

<210> SEQ ID NO 30
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 30
ggtggtggtg gttgtggtgg tggtgg                26

HIGHLY KNOTTED MOLECULAR TOPOLOGIES FROM SINGLE-STRANDED NUCLEIC ACIDS

RELATED APPLICATIONS

This application claims the benefit of priority to U.S. Provisional Application No. 62/663,678, filed on Apr. 27, 2018, the entire disclosure of which is incorporated herein by reference.

GOVERNMENT FUNDING

This invention was made with government support under N00014-15-1-2689 awarded by the Office of Naval Research and 1360635, 1563799, 1334109 awarded by the National Science Foundation. The government has certain rights in the invention.

SEQUENCE LISTING

The instant application contains a Sequence Listing which has been submitted electronically in ASCII format and is hereby incorporated by reference in its entirety. Said ASCII copy, created on Jul. 6, 2020, is named G8118-01301_SL.txt and is about 68,525 bytes in size.

BACKGROUND

Topological knots are complex structures which are formed from continuous loops with a number of crossover events. Molecular knots are present in biopolymers such as DNA and proteins. (M. L. Mansfield, *Nat Struct Biol* 1, 213-214 (1994); F. Takusagawa, et al., *J Am Chem Soc* 118, 8945-8946 (1996); W. R. Taylor, *Nature* 406, 916-919 (2000); J. R. Wagner, et al., *Nature* 438, 325-331 (2005); J. J. Champoux, *Annu Rev Biochem* 70, 369-413 (2001); L. F. Liu, et al., *Nucleic Acids Res* 9, 3979-3989 (1981)). During protein folding, the protein molecules occasionally exhibit small amounts of strand-crossing structures. DNA knots can be formed during DNA replication and are eventually resolved by DNA topoisomerases. While DNA knots are present in some bacterial phage genomes during DNA packing, the DNA knots are not predictable or well organized (L. F. Liu, et al., *P Natl Acad Sci-Biol* 78, 5498-5502 (1981)).

Constructing synthetic molecular knots presents an extraordinarily high level of control over the objects and their assembly behaviors at nanometer scales. (R. S. Forgan, et al., *Chem Rev* 111, 5434-5464 (2011)). It is challenging to design and construct highly knotted nanostructures with well-defined geometries. DNA synthesis technologies allows for the programmability of nucleic acid sequences imparting both information and function. The programmability of nucleic acids makes them suitable candidates for creating arbitrary knots at the molecular level. A diversity of design techniques and approaches for DNA self-assembly have been exploited, resulting in a wide variety of nanostructures that exhibit geometric complexity that is comparable to or even more complex than that found in nature.

SUMMARY

In some aspects, this disclosure provides for a knotted, self-assembled single-stranded nucleic acid (ssNA) nanostructure comprising a crossing number from 1 to 1200 and comprising at least one paranemic cohesion crossover. In some aspects, the nanostructure comprises a crossing number from 2 to 100 crossings. In some aspects, the nanostructure comprises a crossing number from 9 to 67 crossings. In some aspects, the nucleic acid is selected from DNA, RNA, or combinations thereof.

In some aspects, the ssNA nanostructure comprises an NA sequence of about 1000 to about 10,000 nucleotides in length. In some aspects, the NA sequence is about 1800 to about 7500 nucleotides in length. In some aspects, the NA sequence is about 6500 to about 7500 nucleotides in length.

In some aspects, the knotted ssNA nanostructure self-assembles into a 3-dimensional shape. In some aspects, the nanostructure self-assembles by means of paranemic cohesion into knots comprising four ssNA regions.

In some aspects, the knotted ssNA nanostructure further comprises a plurality of paranemic adhesion crossovers which occur in one or a plurality of periodic frequencies. In some aspects, the one or a plurality of periodic frequencies is selected from every 6, 7, 8, 9, 10, 11, 12, 13, 14, 15, 16, 17, 18, 19, or 20 bp.

In some aspects, the folding efficiency of the nanostructure is greater than 50%. In some aspects, the folding efficiency of the nanostructure is greater than 85%. In some aspects, the folding efficiency of the nanostructure is greater than 90%. In some aspects, the folding efficiency of the nanostructure is greater than 91%, 92%, 93%, 94%, 95%, or higher.

In some aspects, the knotted ssNA nanostructure comprises at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In some aspects, the knotted ssNA nanostructure comprises at least about 85% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In some aspects, the knotted ssNA nanostructure comprises at least about 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In some aspects, the knotted ssNA nanostructure comprises at least about 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In some aspects, the knotted ssNA nanostructure comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16 or SEQ ID NO:17.

In some aspects, the knotted ssNA nanostructure comprises DNA having 9 crossings forming a square knotted DNA.

In some aspects, the knotted ssNA nanostructure comprises a nucleic acid having the sequence of SEQ ID NO:1.

In some aspects, the knotted ssNA nanostructure consists of a nucleic acid having the sequence of SEQ ID NO:1.

In some aspects, the knotted ssNA nanostructure comprises DNA having 23 crossings forming a 3-square knotted DNA before hierarchical design.

In some aspects, the knotted ssNA nanostructure comprises a nucleic acid having the sequence of SEQ ID NO:2 or SEQ ID NO: 3. In some aspects, the knotted ssNA nanostructure consists of a nucleic acid having the sequence of SEQ ID NO:2 or SEQ ID NO: 3.

In some aspects, the knotted ssNA nanostructure comprises DNA having 57 crossings forming a 9-square knotted DNA before hierarchical design.

In some aspects, the knotted ssNA nanostructure comprises a nucleic acid having the sequence of SEQ ID NO:4. In some aspects, the knotted ssNA nanostructure consists of a nucleic acid having the sequence of SEQ ID NO:4.

In some aspects, the knotted ssNA nanostructure comprises DNA having 57 crossings forming a 9-square knotted DNA after hierarchical design.

In some aspects, the knotted ssNA nanostructure comprises a nucleic acid having the sequence of SEQ ID NO:5. In some aspects, the knotted ssNA nanostructure consists of a nucleic acid having the sequence of SEQ ID NO:5.

In some aspects, the knotted ssNA nanostructure comprises DNA having 67 crossings forming a hexagonal knotted DNA.

In some aspects, the knotted ssNA nanostructure comprises a nucleic acid having the sequence of SEQ ID NO:6. In some aspects, the knotted ssNA nanostructure consists of a nucleic acid having the sequence of SEQ ID NO:6.

In some aspects, the knotted ssNA nanostructure comprises RNA having 9 crossings forming a square knotted RNA. In some aspects, the knotted ssNA nanostructure comprises a sequence encoded by or complementary to a nucleic acid having the sequence of SEQ ID NO:7. In some aspects, the knotted ssNA nanostructure consists of a sequence encoded by or complementary to a nucleic acid having the sequence of SEQ ID NO:7.

In some aspects, the knotted ssNA nanostructure comprises DNA having 15 crossings forming a tetrahedron. In some aspects, the knotted ssNA nanostructure comprises a nucleic acid having the sequence of SEQ ID NO:8 or SEQ ID NO:17. In some aspects, the knotted ssNA nanostructure consists of a nucleic acid having the sequence of SEQ ID NO:8 or SEQ ID NO:17.

In some aspects, the knotted ssNA nanostructure comprises DNA having 20 crossings forming a pyramid. In some aspects, the knotted ssNA nanostructure comprises a nucleic acid having the sequence of SEQ ID NO:9. In some aspects, the knotted ssNA nanostructure consists of a nucleic acid having the sequence of SEQ ID NO:9.

In some aspects, the knotted ssNA nanostructure comprises DNA having 22 crossings forming a triangular prism. In some aspects, the knotted ssNA nanostructure comprises a nucleic acid having the sequence of SEQ ID NO:10. In some aspects, the knotted ssNA nanostructure consists of a nucleic acid having the sequence of SEQ ID NO:10.

In some aspects, the knotted ssNA nanostructure comprises DNA having 25 crossings forming a pentagonal pyramid. In some aspects, the knotted ssNA nanostructure comprises a nucleic acid having the sequence of SEQ ID NO:11. In some aspects, the knotted ssNA nanostructure consists of a nucleic acid having the sequence of SEQ ID NO:11.

In some aspects, the knotted ssNA nanostructure further comprises a topological control strand comprising a sequence selected from a nucleic acid having the sequence of SEQ ID NO:12, SEQ ID NO:13, SEQ ID NO:14 or SEQ ID NO:15. In some aspects, the knotted ssNA nanostructure further comprises a topological control strand consisting of a sequence selected from a nucleic acid having the sequence of SEQ ID NO:12, SEQ ID NO:13, SEQ ID NO:14 or SEQ ID NO:15.

In some aspects, the knotted ssNA nanostructure further comprises a 5'-end and a 3'-end, wherein the 5'-end and/or the 3'-end further comprises 1-5 nucleotide terminal extensions. In some aspects, both the 5'-end and the 3'-end of the knotted ssNA nanostructure comprise terminal extensions and the terminal extensions hybridize to form a single strand of nucleic acid.

In some aspects, the knotted ssNA nanostructure further comprises at least one diagnostic agent operably linked to said nanostructure.

In some aspects, the knotted ssNA nanostructure further comprises at least one therapeutic agent operably linked to said nanostructure. In some aspects, at least one therapeutic agent is an anti-tumor agent. In some aspects, the at least one therapeutic agent is a chemotherapeutic drug.

In some aspects, the nanostructure is replicable. In some aspects, the replication occurs in a transformed cell.

In some aspects, this disclosure relates to a pharmaceutical composition comprising a knotted, self-assembled single-stranded nucleic acid (ssNA) nanostructure comprising a plurality of crossings and comprising at least one paranemic cohesion crossover, and a pharmaceutically acceptable carrier.

In some aspects, this disclosure relates to a method of inducing an immune response in a subject, comprising administering to the subject an effective amount of a knotted ssNA nanostructure described herein. In some aspects, the knotted ssNA nanostructure comprises a knotted, self-assembled single-stranded nucleic acid (ssNA) nanostructure comprising a plurality of crossings and comprising at least one paranemic cohesion crossover.

In some aspects, this disclosure relates to a method of treating a disease or disorder in a subject, comprising administering to the subject a therapeutically effective amount of a knotted ssNA nanostructure as described herein or a pharmaceutical composition as described herein. In some aspects, the knotted ssNA nanostructure comprises a knotted, self-assembled single-stranded nucleic acid (ssNA) nanostructure comprising a plurality of crossings and comprising at least one paranemic cohesion crossover. In some aspects, the disease or disorder is cancer. In some aspects, the cancer is breast cancer.

In some aspects, the method further comprises administering at least one therapeutic agent to the subject. In some aspects, the at least one therapeutic agent is a tumor targeting agent. In some aspects, the tumor targeting agent is selected from a monoclonal tumor-specific antibody or an aptamer.

In some aspects, this disclosure relates to the use of a knotted ssNA nanostructure as described herein or a composition as described herein for the manufacture of a medicament for inducing an immune response in a subject.

In some aspects, this disclosure relates to a nanostructure for inducing an immune response in a subject.

In some aspects, this disclosure relates to a use of a knotted ssNA nanostructure as described herein or a composition as described herein for the manufacture of a medicament for treating a disease or disorder in a subject.

In some aspects, this disclosure relates to a knotted ssNA nanostructure as described herein or a composition as described herein for the prophylactic or therapeutic treatment of a disease or disorder in a subject.

In some aspects, this disclosure relates to a kit comprising a knotted ssNA nanostructure as described herein or a composition as described herein and instructions for administering the nanostructure/composition to a subject to induce an immune response or to treat a disease or disorder. In some aspects, the kit further comprises at least one therapeutic agent.

In some aspects, this disclosure provides a single-stranded nucleic acid (ssNA) nanostructure comprising from 9 to 67 crossings and comprising at least one paranemic cohesion crossover, wherein the nanostructure is self-assembled. In some aspects, the nanostructure is replicable. In some aspects, the nanostructure is a topological knot.

In some aspects, the nucleic acid is DNA

In some aspects, the nucleic acid is RNA.

In some aspects, the nanostructure comprises an NA sequence of about 1000 to about 10,000 nucleotides in length.

In some aspects, the NA sequence is about 1800 to about 7500 nucleotides in length.

In some aspects, the nanostructure comprises at least about 75% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In some aspects, the nanostructure comprises at least about 85% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In some aspects, the nanostructure comprises at least about 95% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In some aspects, the nanostructure comprises at least about 99% sequence identity to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In some aspects, the nanostructure comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, or SEQ ID NO:17.

In some aspects, the nanostructure comprises DNA having 9 crossings forming a square knotted DNA.

In some aspects, the nanostructure comprises SEQ ID NO:1.

In some aspects, the nanostructure consists of SEQ ID NO:1.

In some aspects, the nanostructure comprises DNA having 23 crossings forming a 3-square knotted before hierarchical design.

In some aspects, the nanostructure comprises SEQ ID NO:2.

In some aspects, the nanostructure consists of SEQ ID NO:2.

In some aspects, the nanostructure comprises SEQ ID NO:3.

In some aspects, the nanostructure consists of SEQ ID NO:3.

In some aspects, the nanostructure comprises DNA having 57 crossings forming a 9-square knotted DNA before hierarchical design.

In some aspects, the nanostructure comprises SEQ ID NO:4.

In some aspects, the nanostructure consists of SEQ ID NO:4.

In some aspects, the nanostructure comprises DNA having 57 crossings forming a 9-square knotted DNA after hierarchical design.

In some aspects, the nanostructure comprises SEQ ID NO:5.

In some aspects, the nanostructure consists of SEQ ID NO:5.

In some aspects, the nanostructure comprises DNA having 67 crossings forming a hexagonal knotted DNA.

In some aspects, the nanostructure comprises SEQ ID NO:6.

In some aspects, the nanostructure consists of SEQ ID NO:6.

In some aspects, the nanostructure comprises RNA having 9 crossings forming a square knotted RNA.

In some aspects, the nanostructure comprises a sequence encoded by or complementary to SEQ ID NO:7.

In some aspects, the nanostructure consists of a sequence encoded by or complementary to SEQ ID NO:7.

In some aspects, the nanostructure comprises DNA having 15 crossings forming a tetrahedron.

In some aspects, the nanostructure comprises SEQ ID NO:8.

In some aspects, the nanostructure consists of SEQ ID NO:8.

In some aspects, the nanostructure comprises DNA having 20 crossings forming a pyramid.

In some aspects, the nanostructure comprises (SEQ ID NO:9).

In some aspects, the nanostructure consists of (SEQ ID NO:9).

In some aspects, the nanostructure comprises DNA having 22 crossings forming a triangular prism.

In some aspects, the nanostructure comprises (SEQ ID NO:10).

In some aspects, the nanostructure consists of (SEQ ID NO:10).

In some aspects, the nanostructure comprises DNA having 25 crossings forming a pentagonal pyramid In some aspects, the nanostructure comprises SEQ ID NO:11.

In some aspects, the nanostructure consists of SEQ ID NO:11.

In some aspects, the nanostructure comprises topological control strand SEQ ID NO:12, SEQ ID NO:13, SEQ ID NO:14 or SEQ ID NO:15.

In some aspects, the nanostructure consists of topological control strand SEQ ID NO:12, SEQ ID NO:13, SEQ ID NO:14 or SEQ ID NO:15.

In some aspects, the nanostructure has a 5'-end and a 3'-end, wherein the 5'-end and/or the 3'-end further comprise 1-5 nucleotide terminal extension.

In some aspects, both the 5'-end and the 3'-end comprise terminal extensions and the terminal extension hybridize to form a single strand of nucleic acid.

In some aspects, at least one diagnostic agent operably linked to the nanostructure.

In some aspects, at least one therapeutic agent is operably linked to the nanostructure.

In some aspects, the at least one therapeutic agent is a tumor antigen peptide.

In some aspects, this disclosure provides a pharmaceutical composition comprising the nanostructure described herein and a pharmaceutically acceptable carrier.

In some aspects, the pharmaceutical composition further comprising at least one therapeutic agent.

In some aspects, the at least one therapeutic agent is a chemotherapeutic drug (e.g., doxorubicin).

In some aspects, this disclosure provides a method of inducing an immune response a subject (e.g., a mammal, which can include or exclude a human), comprising administering to the subject an effective amount of a nanostructure or a composition as described herein.

In some aspects, this disclosure provides a method of treating a disease or disorder in a subject, comprising administering to the subject a therapeutically effective amount of a nanostructure or a composition as described herein.

In some aspects, the disease or disorder is cancer.

In some aspects, the cancer is breast cancer.

In some aspects, the method further comprises administering at least one therapeutic agent to the subject.

In some aspects, the at least one therapeutic agent is a tumor targeting agent (e.g., a monoclonal tumor-specific antibody, antibody fragment or an aptamer).

In some aspects, this disclosure provides a use of a nanostructure or composition as described herein for the manufacture of a medicament for inducing an immune response in a subject (e.g., a mammal, which can include or exclude a human).

In some aspects, this disclosure provides a nanostructure or composition as described herein for inducing an immune response.

In some aspects, this disclosure provides the use of a nanostructure or composition as described herein for the manufacture of a medicament for treating a disease or disorder in a subject.

In some aspects, this disclosure provides a nanostructure or composition as described herein for the prophylactic or therapeutic treatment a disease or disorder.

In some aspects, this disclosure provides a kit comprising a nanostructure or composition as described herein and instructions for administering the nanostructure/composition to a subject to induce an immune response or to treat a disease or disorder.

In some embodiments, the kit further comprises at least one therapeutic agent.

BRIEF DESCRIPTION OF DRAWINGS

FIG. 1A depicts the first method which is to assemble with preformed individual X-nodes that are linked together with specific sticky ends associations and ligation. FIG. 1B depicts the second method where a single chain is threaded and knotted into the target topology. FIG. 1C depicts paranemic crossover motifs which were introduced as the building blocks for the knotted nucleic acid nanostructures. FIG. 1D A schematic diagram that shows the design and folding pathway of a single-stranded DNA to form knot $9_1$ as an example. A single chain DNA was assigned with partially paired regions to first form a large loop-stem hairpin structure. Then, the unpaired loop regions were designed to interact with each other through paranemic cohesions to form the target knot. The formation of the knot involved the threading of the two ends of the loop-stem structure by following a pathway similar to that shown in FIG. 1B.

FIG. 2A shows a 9 crossing DNA square, FIG. 2B shows a 9 crossing RNA square, FIG. 2C shows a 23 crossing DNA rectangle with 3 square cavities, FIG. 2D shows a 57 crossing DNA 3×3 square lattice, and FIG. 2E shows a 67 crossing DNA hexagonal lattice.

(FIG. 3A) A designed model shows the best folding pathway for the three-square structure with 23 crossings, by following the optimization rules. The red to gray color scale represent the order of the paranemic cohesion interaction strengths on the edges based on the number and length of the paranemic cohesions involved. FIG. 3B shows the paranemic interaction regions are designed with lengths of 4 bp or 6 bp with distinct expected binding strengths (6 bp>4 bp). The folding order of the knot structure is guided by controlling the sequences and lengths of the paranemic interactions in each individual edge. FIG. 3C shows that the folding efficiency of the various structures was compared by using different folding pathways before and after optimization. FIG. 3D shows that the AFM images revealed a dramatic increase in the folding yield of well-form structures from 0.9% (N=221) to 57.9% (N=214).

FIG. 4A shows a DNA link structure with linking number of 8 was designed and constructed from four linear ssDNA (top row and bottom left image). As used herein, the term "linking number" refers to the number of links within a knotted NA nanostructure. High resolution AFM images confirmed the successful formation of the target structures (bottom right images). FIG. 4B shows that the four linear ssDNA strands were first ligated into two closed circles, and the assembled final structures from the two circles showed obvious defects under AFM imaging.

FIG. 6A. The schematics show how to assign 9 crosses on a square geometry. As each edge has the same length, well-distributed crosses are preferred to maintain the stability of the DNA knotted nanostructure. FIG. 6B. Paranemic cohesion interaction, each contains two parallel crossovers with 4 bp or 6 bp. These base pairs represent the cross in the knot design schematics. The distance between the adjacent paranemic cohesion crosses are designed as integer multiples of one DNA helical turn (10, 11, 21 or 32 bp). A linking structure comprised of two ssDNA loops and one crossover was designed to connect DNA strands in each outer corner. FIG. 6C. An arrangement of each of the edges of the square with the corresponding DNA knotted nanostructures. FIG. 6D. Adding small linking structures at the vertexes finishes the design of the structure. The DNA strands in the inner corners are connected directly using poly T loops ($T_4$ is used for a 90 degree turn in the square). The outer corners are linked with the linking structure containing one paranemic cohesion interaction.

FIG. 7A. An edge with an odd numbers of crosses enables the two loops that form the edge to connect into one large loop, i.e. to form a knot structure, while an edge with even numbers of crosses produces a link between two separate loops. The schematics show an edge with 3 crosses that formed a knot of $3_1$, and an edge of 2 crosses that resulted in a link structure called a Hopf link. FIG. 7B. To form a knot structure instead of a link, an odd number of crossings among the individual loops was required and different orders of connections to link the loops (a, b, c, c) was selected to produce the target knot. The loops are designated according to their geometric relationships, and the two c loops are the same due to their symmetry. The largest loop a is connected with either loops b or c, while c is only connected with loops a or b, not with the other loop c. All of the possible orders of connections among the loops is listed, which represents different folding pathways that could form the target knot structures. Pathways 1 and 3 are branched and pathways 2,4, and 5-8 are linear.

FIGS. 9A-9D. The sequence design for the hierarchical folding based on the selected best pathway. FIG. 9A. A schematic of the cross section of the c-b-c-a folding path (as shown in FIGS. 7A-7B, 8A-8B). The ends of the partially folded dsDNA are located at the upper left corner. The gradual color change from red to grey represents the order of the looping. FIG. 9B. The folding order of all of the edges are labeled as steps 1 to 7. The edges that are marked as 1-3 are the 3-cross edges while 4-7 are the 2-cross edges. FIG. 9C. A knotted DNA nanostructure that represents the target topological geometry. The white numbers are the length (bp) of each paranemic cohesion interaction. FIG. 9D. A summary table of the design parameters for the structure, including the number of bases in each paranemic cohesion, and the GC content of the paranemic cohesions in each edge.

FIG. 11A. The ssDNA replication process. First, the two halves of the ssDNA gene (red and blue), were obtained by restriction enzyme digestion from a commercially synthesized plasmid. Then, the custom synthesized ssDNA gene was ligated into a phagemid vector pGEM-7zf(−) (black) by T4 DNA ligase (New England Biolabs) and co-transformed into *E. coli* DH5α competent cells (New England Biolabs) with the helper plasmid pSB4423 (orange). During the phage replication, the ssDNA sequence (red and blue) was packed into the phage capsid as its genome. Recombinant phages were then harvested from the *E. coli* medium and the recombinant phage genomic DNA was isolated and purified. The EcoRV restriction sites were initially designed at the ends of the ssDNA and the phage DNA digestion by EcoRV restriction enzyme produced the ssDNA molecule (partially paired and folded into a hairpin, with the 5' and 3' ends meeting each other and the unpaired bubbles as paranemic cohesion sites). FIG. 11B. An example of the 1800 nt ssDNA purification by gel electrophoresis. Lane 1 represents the 1 kb dsDNA ladder. Lane 2 contains the purified phage DNA without EcoRV cleavage. After EcoRV digestion, the 1800 nt ssDNA molecule (lower band) is separated from the vector DNA (upper band) in lane 3. The 1800 nt ssDNA molecule runs slightly faster than the 1 kb dsDNA (2000 nt).

FIG. 12A shows the design schematic of the square knotted DNA nanostructure $9_1$. FIG. 12B shows representative AFM images of the square knotted DNA nanostructure $9_1$.

FIG. 13A shows the design schematic of the 9-square knotted DNA nanostructure. FIG. 13B shows representative AFM images of the 9-square knotted DNA nanostructure.

FIG. 14A shows the design schematic of the hexagonally knotted DNA nanostructure. FIG. 14B shows representative AFM images of knotted DNA nanostructures of the hexagonally knotted DNA nanostructure.

FIGS. 15A-15C. The design and characterization of the 9-square knotted DNA nanostructure with hierarchical folding. FIG. 15A depicts the folding pathway design. The numbers on the edges mark the anticipated order of the formation of the crosses on the edges, based on the designed sequences. FIG. 15B depicts the sequence design. The length of the paranemic cohesion, the number of the base pairs involved, and the GC content of the base pairs are all tuned to make the expected strength of the paranemic cohesion interactions follow the anticipated folding order. FIG. 15C shows representative AFM images of the folded knot structure (with 57 crossings). A majority (if not all) of the structures formed show some degree of errors. It seems that if the crossings in some of the earlier steps did not form properly, the crossings in the later steps could still form, but that the errors would be permanently trapped and there would be no chance of correcting the errors. Since each crossing may have a certain rate of error, with 57 crossings, the final product is expected to have a low yield. Nevertheless, the stepwise yield is quite high (>90%) with the overall structures having a high resemblance to the expected design. Most of the structures have more than half of their edges properly formed.

FIG. 16A shows two linearly annealed and partially paired dsDNAs, (with internal loops for paranemic cohesions between the two DNA), can self-assemble into the designed structure with a high yield, as shown in the AFM images of the self-assembled knotted NA nanostructures. A small number of the final structures show mild defects. FIG. 16B shows that after circularization, the two circular dsDNA molecules cannot form the nanostructure. The AFM images show that all of the final structures contain moderate to extensive defects.

FIG. 17A shows the design schematics of the square knotted RNA nanostructure $9_1$. In some embodiments, an a-form double helix is the structural model. FIG. 17B shows an RNA paranemic cohesion design that was based on A-form double helices. 8 bp was chosen as the length of the paranemic cohension for RNA; 33 bp was chosen as the length of the repeating unit (3 full turns). FIG. 17C shows representative AFM images of the self-assembled knotted NA nanostructures, illustrating a high folding yield (~60%) of the expected structure.

FIGS. 18A-18D. The design and characterization of the tetrahedron knotted DNA nanostructure. FIG. 18A. The design schematics of the folding pathway. In the middle 2D diagram, the red dots mark the edges of the tetrahedron that have the 3 crossing numbers. The number on the edges mark the anticipated order of formation of the edges. FIG. 18B shows the vertexes all show the illustrated chirality. FIG. 18C shows the sequence design parameters that facilitate the folding order. FIG. 18D shows a representative AFM image of the self-assembled knotted NA nanostructures. Most of the structures in the image display the expected structure. However, some of the structures shown are missing one or two edges.

FIGS. 19A-19C. The design and characterization of a pyramid knotted DNA nanostructure (crossing number=20). FIG. 19A shows the design schematics of the folding pathway. FIG. 19B shows the sequence design parameters that facilitate the folding order. FIG. 19C shows representative AFM images. However, although many of the structures that are shown are distorted or broken, due to interactions with the substrate surface, a majority of the edges shown are well formed.

FIGS. 20A-20C. The design and characterization of the triangular prism with the knotted DNA nanostructure (crossing number=22). FIG. 20A shows the design schematic that includes the folding pathway. FIG. 20B shows the sequence design parameters that facilitate the folding order. FIG. 20C shows representative AFM images of the self-assembled knotted NA nanostructures.

FIGS. 21A-21C. Design and characterization of a pentagonal pyramid that has a knotted DNA nanostructure (crossing number=25). FIG. 21A shows the design schematics of the folding pathway. FIG. 21B shows the sequence design parameters that facilitate the folding order. FIG. 21C shows representative AFM images of the self-assembled knotted NA nanostructures.

FIG. 22A shows a raw cryo-EM micrograph with visible nanostructures. FIG. 22B show the reference-free 2D class averages and projections of the final 3D reconstruction. FIG. 22C is a graph depicting a gold-standard FSC plot for the final 3D reconstruction of the nanostructures. FIG. 22D shows the tilt-pair validation result. The grey circle shows nanostructure pairs that cluster around the experimental tilt geometry.

DETAILED DESCRIPTION

This disclosure provides a method to create self-assembled ssDNA/ssRNA knotted nanostructures with high crossing numbers. These knotted nanostructures are self-assembled from a replicable single stranded nucleic acid and the knotted nanostructures are well organized with relative high yields. Various two-dimensional (2D) ssDNA knotted nanostructures are designed and characterized with high crossing numbers. The self-assembly is optimized with hierarchical folding, which significantly increases the yield. In some embodiments, the knotted nanostructure method creates ssRNA and three-dimensional (3D) ssDNA knotted nanostructures. In some embodiments, the crossover points occur in a periodic manner. This disclosure further provides for a method for constructing nucleic acids nanostructures with complex molecular topologies.

In some embodiments, this disclosure provides for a method of designing and constructing highly knotted nucleic acid nanostructures, each weaved from a single-stranded DNA and/or RNA chain by hierarchical folding in a prescribed order. In some embodiments, sets of DNA and/or RNA knotted nanostructures of two- or three-dimensional shapes are designed and constructed from NA sequences ranging from 1800 to 7500 nucleotides in length. The shapes of the nanostructures of this disclosure exhibit an unprecedented amount of complicated topological features, with high crossing numbers. Each step of the folding/threading process formed one crossing node and resulted in a surprisingly high yield of well-formed one crossing (~96%). In some embodiments, the single-stranded DNA and/or RNA knots are replicated and amplified enzymatically in vitro or in vivo, and offers many potential transformative applications. In some embodiments, the ssDNA and/or ssRNA knotted nanostructures with high crossing numbers are self-assembled from a replicable single stranded nucleic acid and are well organized with relatively high folding yields compared to randomly designed NA sequences.

Complex molecular knots with high crossing numbers are achieved by folding, following a prescribed folding order, single-stranded DNA and/or RNA of customized sequences into target shapes.

Programming Highly Knotted Molecular Topologies from Single-stranded Nucleic Acids Molecular knots represent some of the most extraordinary topological structures. Knotted DNA structures are often formed during genomic DNA replication and transcription. However, natural DNA knots are not predictable and do not have well-formed geometric shapes, nor periodic crossover events. The inventors have designed rules for programming synthetic nucleic acid sequences which self-assemble into highly knotted nanostructures with well-defined geometries and topologies.

Figure 29:
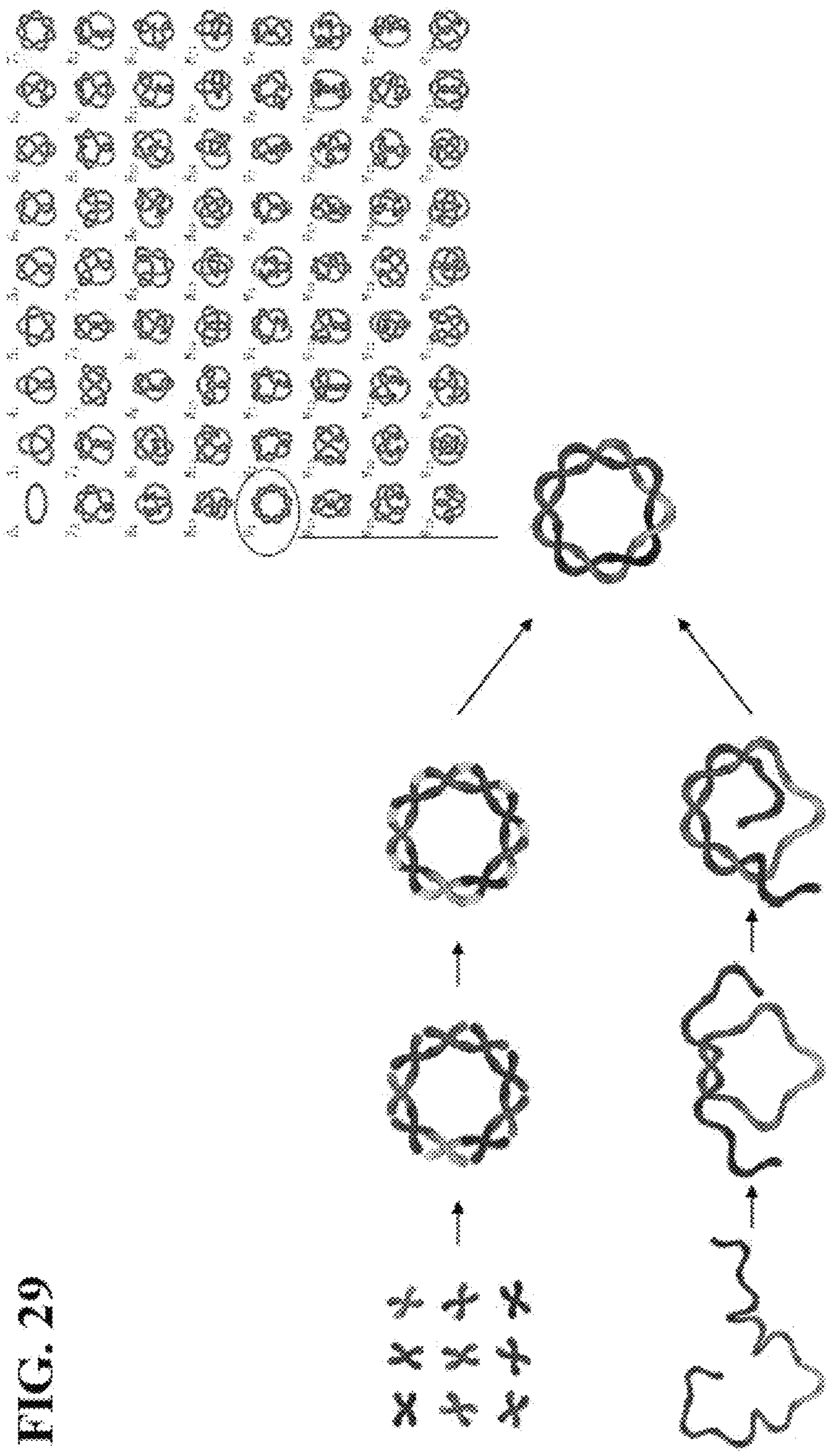
FIG. 29 shows two methods for creating DNA knotted nanostructures.
Figure 30:
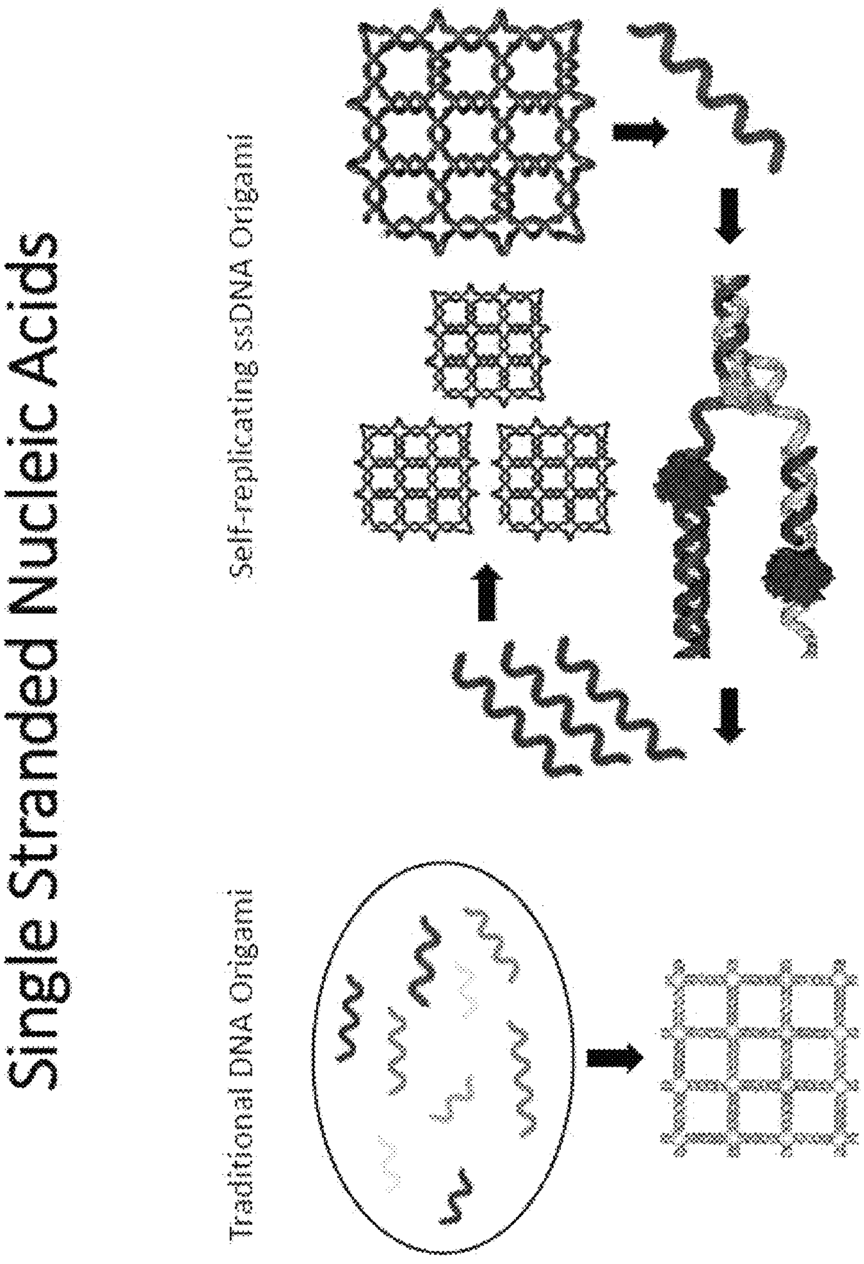
FIG. 30 shows single stranded nucleic acids: traditional DNA nanostructures and self-replicating ssDNA nanostructures.

In some embodiments, the nucleic acid (DNA and/or RNA) knotted nanostructure is constructed by a "granular build-up method." In some embodiments of the granular build-up method, as summarized in FIG. 29, a knot is assembled by connecting nine right-handed X-shaped junction tiles together. In some embodiments, the nucleic acid knot is constructed by a "single threading method." In some embodiments of the singular threading method, a single chain polynucleotide sequence is threaded through itself nine times. This disclosure includes a method for creating topological knots of single-stranded DNA and/or RNA with high crossing numbers. In some embodiments, the method comprises the use of single-stranded nucleic acids and high crossing numbers periodically throughout the nanostructure.

Both multi-stranded DNA and/or RNA sequences designed for NA knotted nanostructures and single-stranded DNA and/or RNA sequences designed for NA knotted nanostructures self-assemble via self-folding. There are advantages to the nucleic acids being single-stranded nucleic acids. As shown in FIG. 11, a ssDNA knotted nanostructure can be a self-replicating system, which enables cost-efficient, large-scale production using enzymatic and biological replication. The ssDNA knotted nanostructure also involves a unimolecular folding process which is independent of the reactant concentration, and offers higher folding yield and more robust folding kinetics than multi-stranded structures produced via concentration-dependent intermolecular self-assembly methods.

Figure 31:
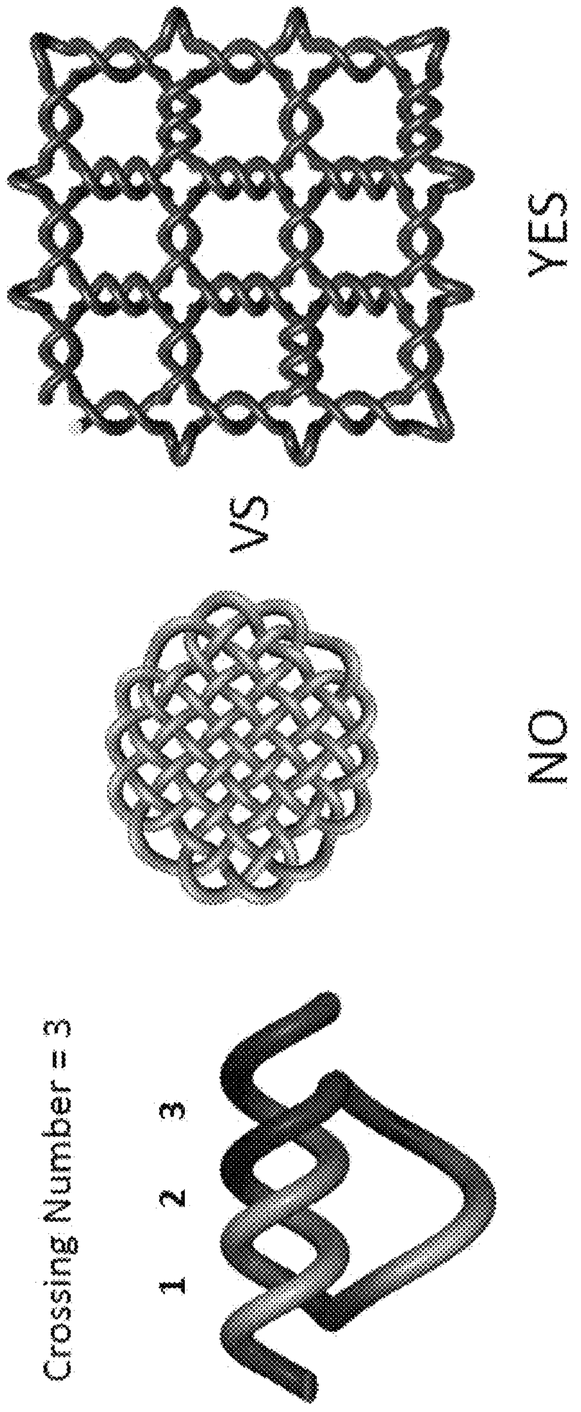
FIG. 31 shows knotted nanostructures with high numbers of crossings.
Figure 32A:
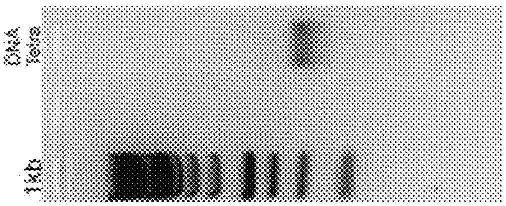
FIGS. 32A-32B shows a depiction of 3D knots.
Figure 32B:
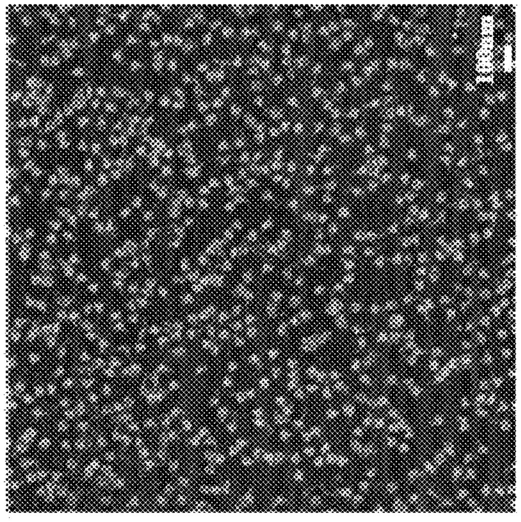
Figure 33:
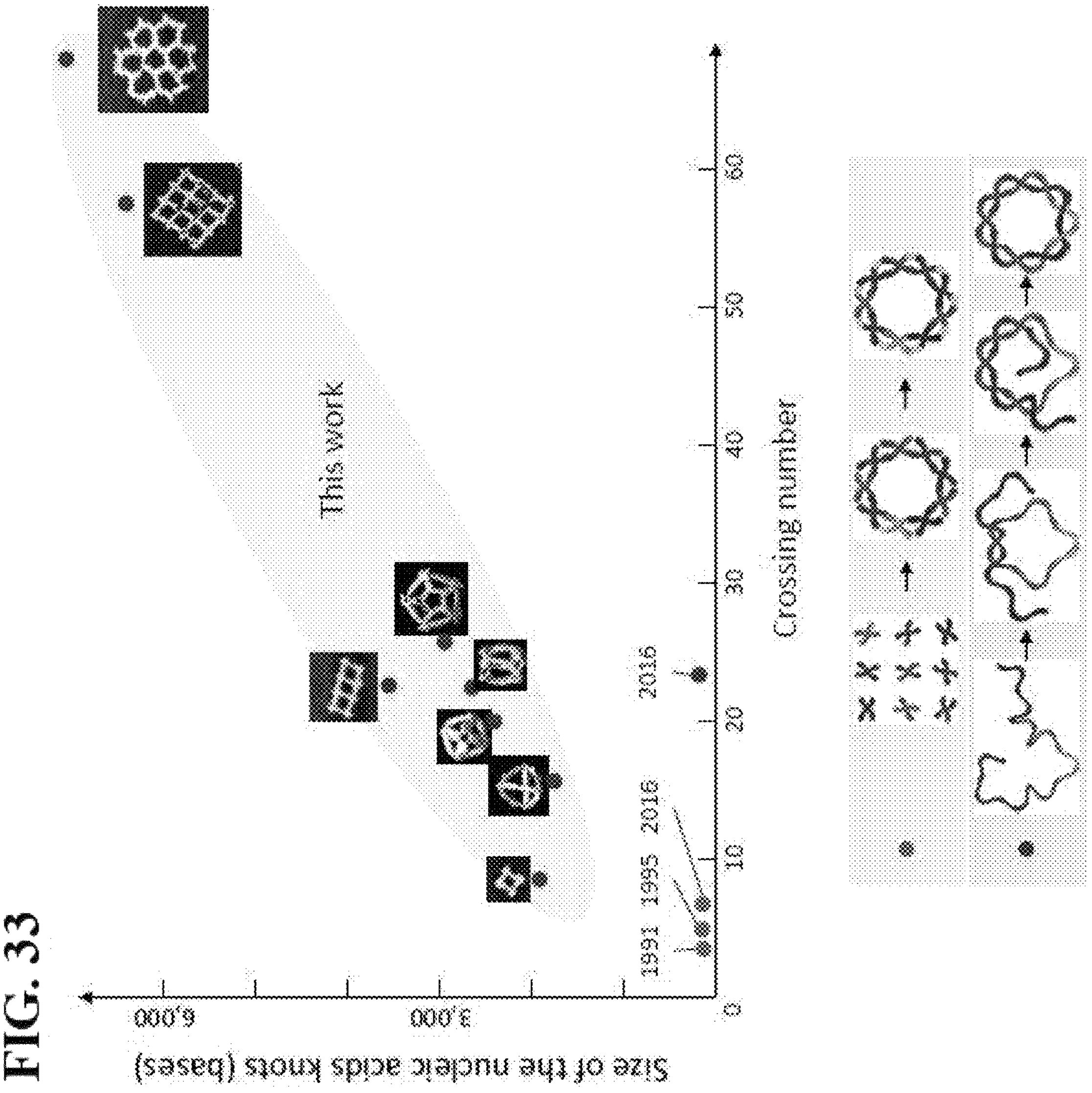
FIG. 33 shows the size of nucleic acid knotted nanostructures of some embodiments of this disclosure.
Figure 34:
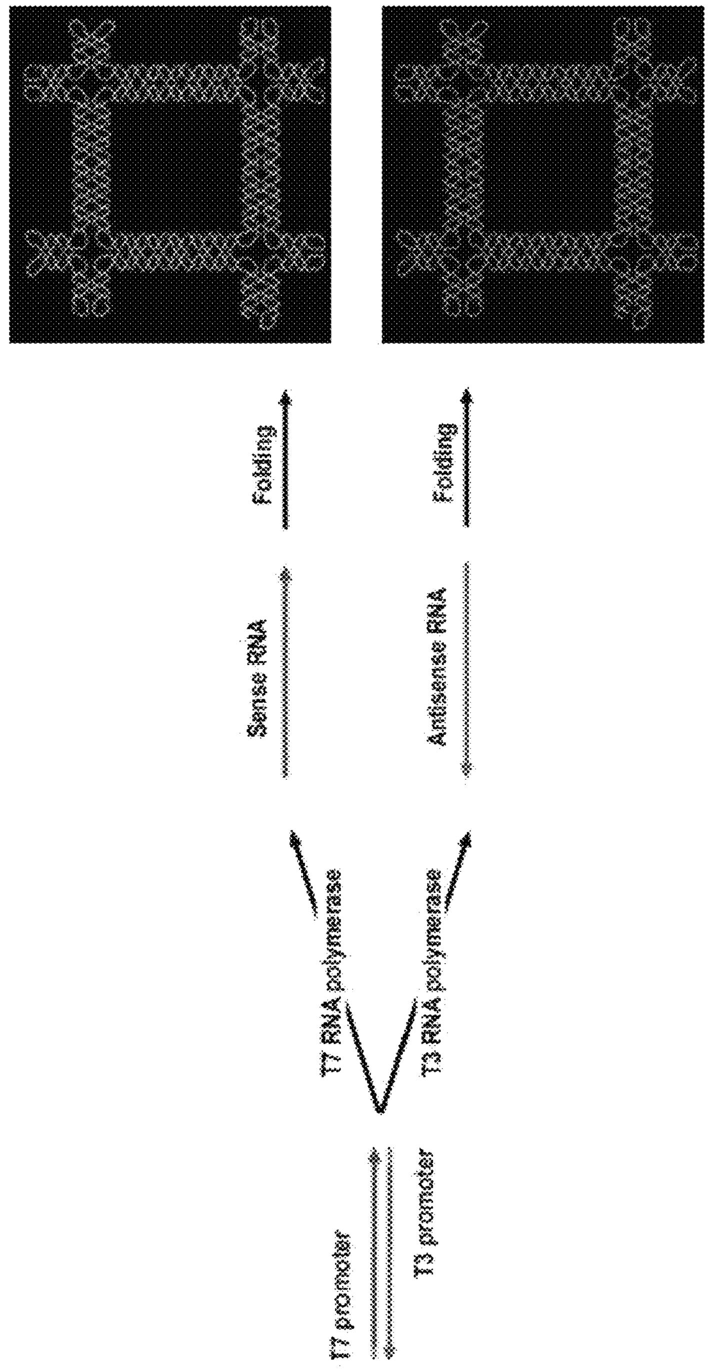
FIG. 34 depicts the production of ssRNA which creates knotted ssRNA nanostructures of some embodiments of this disclosure.

As used herein, the term "crossing" refers to a knot invariant that shows the smallest number of crossings in any diagram of the knot, representing the topological complexity of a knot. In some embodiments, the knots described herein can comprise 2 to 100 crossings. In some embodiments, the knots described herein can comprise from 9 to 67 crossings. In some embodiments, the crossing number of the knots described herein can comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 crossings. In one embodiment, as shown in the left panel of FIG. 31, a knot consists essentially of a crossing number of 3. Compact structures do not facilitate the correct folding of DNA. To create high crossing number knots, "wireframe" networks are better candidates for constructing knotted structures because they offer more space for DNA chains to thread through the structures. A wireframe network is defined by the construction of 2D or 3D structures in which only vertices and edges/lines are used to define the outline of the structures. For DNA wireframe networks, the vertices are represented by multi-arm junctions and the edges are DNA tiles which can include or exclude: dsDNA helices, DX (double crossover) tiles, paranemic cohesion tiles, and multi-helical bundles.

In some embodiments, the method for creating knotted NA nanostructures comprises using crossover motifs as the modular building blocks and a node-edge network as the geometric blueprint for arbitrary nanostructures. In some embodiments, as shown in, FIGS. 1A-1D two parallel crossovers are separated by 4 or 6 base pairs to form an X-shape. The nine X-shaped DNA tiles were arranged into a square with 2, 2, 2, and 3 crossings on the four edges respectively, and the adjacent paranemic cohesion junctions separated by 1 or 2 turns of the double stranded DNA. After connecting the nearest DNA strands and adding small linking structures at the four vertexes, the resulting design consisted of only one long contiguous ssDNA. The overall routing of the ssDNA could be treated as a two-step process. First, half of the DNA chain folded back to partially pair with the other half of the DNA, leaving several unpaired single-stranded regions in between the perfectly paired regions. Then, the unpaired regions matched to each other by paranemic cohesive interactions and finally knotted into the target topology.

Figures 3A, 3B, 3C, 3D:
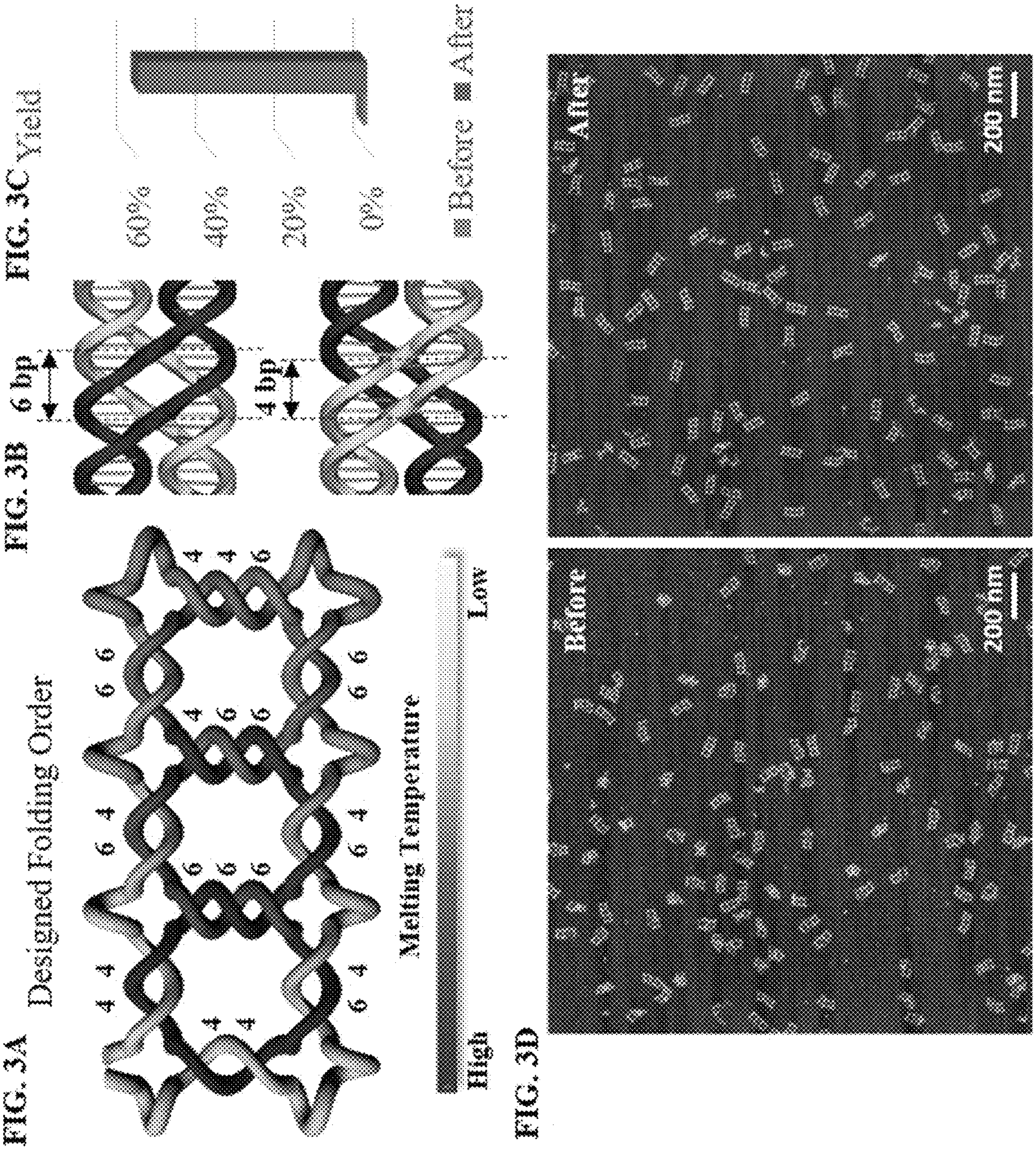
FIGS. 3A-3D. Optimization of the folding pathway for ssDNA knots.

In some embodiments, this disclosure includes a topologically- and kinetically-favorable folding method to create knotted DNA and/or RNA nanostructures with high crossing numbers. In some embodiments, the crossings occur in a periodic manner. In some embodiments, the method involves a hierarchical folding strategy to guide the knotting process in a prescribed order. In some embodiments, as discussed in Example 1, the method comprises several essential rules for optimizing the folding pathway. The optimized folding path for a three-column grid structure with 23 crossings is shown in FIGS. 3A, 3B, and 9D. As shown in the foregoing figures, the folding order of the edges is guided and controlled by changing the number (2 or 3), the length (6 or 4 bp), and the sequence (GC percentage) of paranamic cohesion regions. The folding yield of the two types of scaffold routings were compared by AFM imaging as shown in FIGS. 3C, and 3D. The selected best folding pathway as shown in FIGS. 3A, 3B, 9D produced about 60% well-formed structures, while a control random other folding pathway showed a yield as low as 1%.

In some embodiments, the method comprises design procedures to create highly complex DNA knots with increasing crossing numbers occurring in a periodic manner. In some embodiments, as shown in FIGS. 2A-2E, a 3 by 3 square grid of DNA knots with 57 crossed nodes in a periodic manner was designed with an optimized folding pathway. Other geometric layouts also follow similar design principles. A large molecular knot with 67 crossings in a hexagonal lattice was also designed and constructed. In some embodiments, the design strategies for ssDNA knotted nanostructures is adapted to create ssRNA knots by adjusting selected design parameters and experimental conditions as described herein. Each of these ssDNA and/or ssRNA knots are folded from a replicable single-stranded nucleic acid molecule with sizes ranging from 1800 to 7500 nucleotides. High-resolution AFM images confirm the successful formation of the target nanostructures, as shown in FIGS. 2A-2E.

Figure 4A:
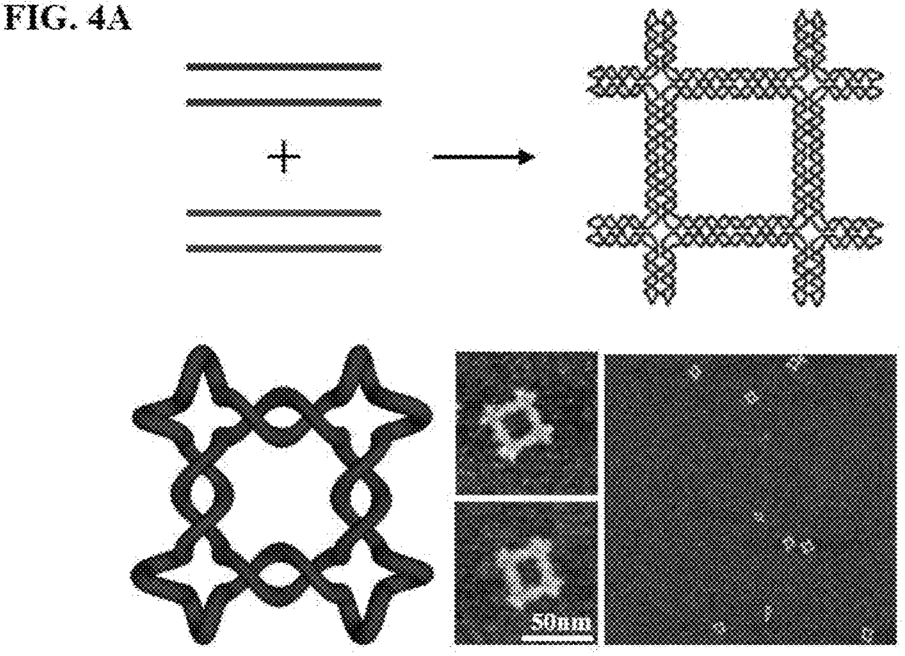
FIGS. 4A-4B. Topological control experiments.
Figure 4B:
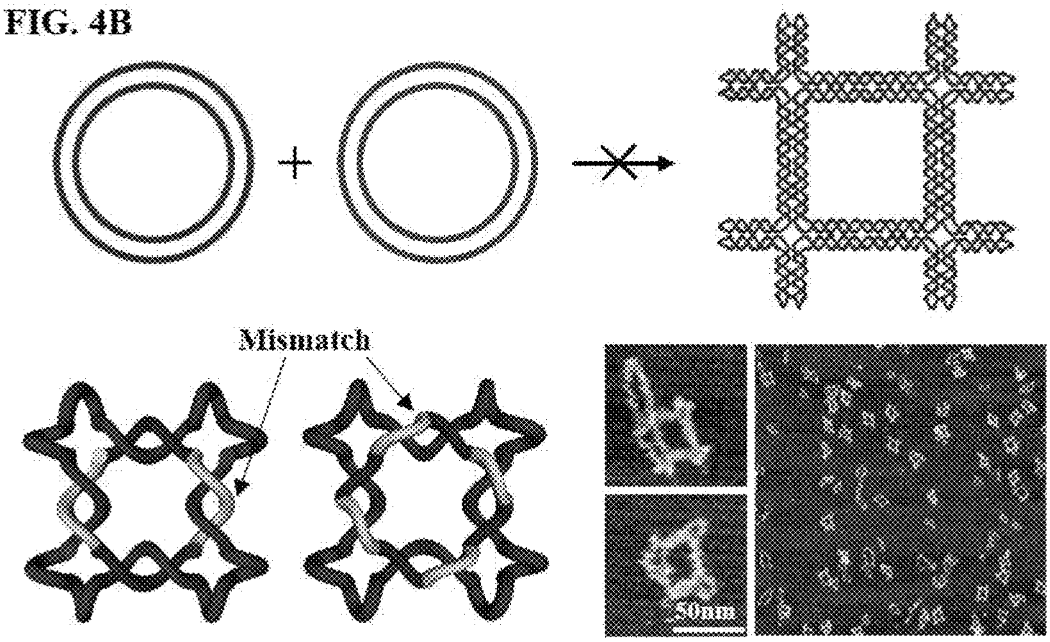
Figures 5A, 5B, 5C, 5D:
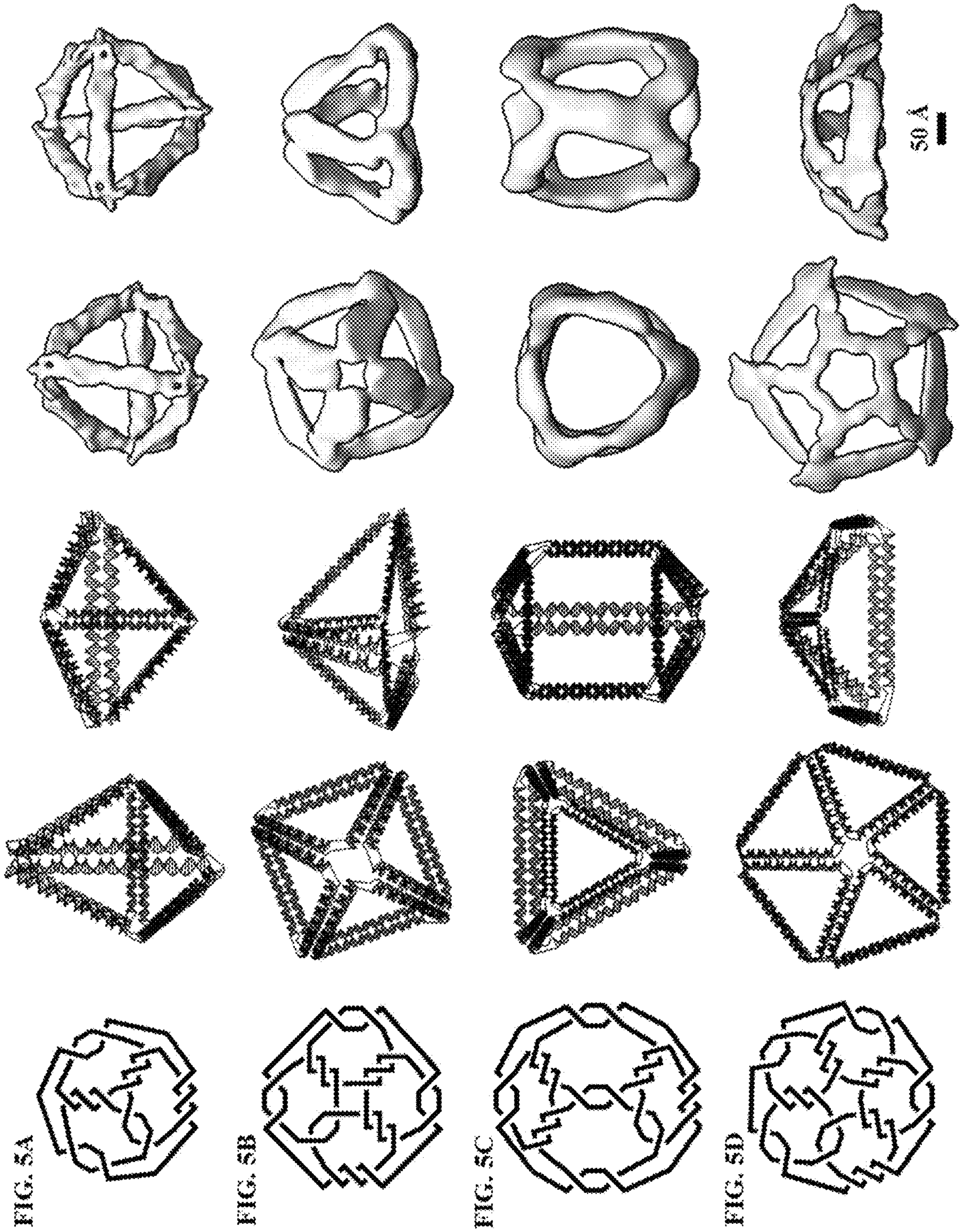
FIGS. 5A-5D. Design topologies and cryo-EM reconstruction of three-dimensional single-stranded DNA knots. A schlegel diagram (left panel) transforms a three-dimensional object into a two-dimensional diagram. By following the same design rules of two-dimensional knots, several three-dimensional DNA knot frameworks were designed (middle panels of two different view angles for each structure). The cryo-EM reconstruction (right panel) revealed the correct formations of a tetrahedron with crossing number 15 (FIG. 5A), a square pyramid with crossing number 20 (FIG. 5B), a triangular prism with crossing number 22 (FIG. 5C), and a pentagonal pyramid with crossing number 25 (FIG. 5D).
Figure 6A:
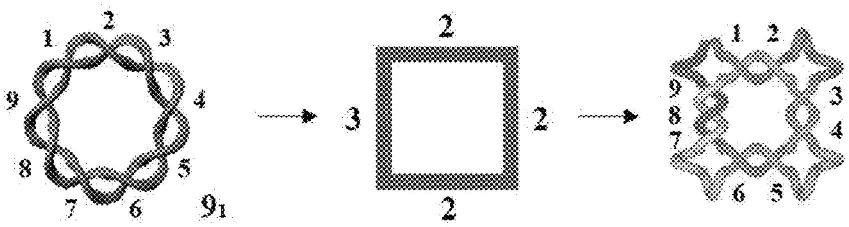
FIGS. 6A-6D. The design of a DNA knot $9_1$.
Figure 6B:
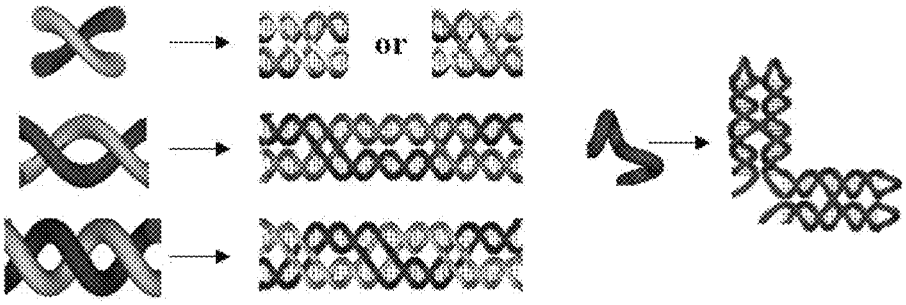
Figure 6C:
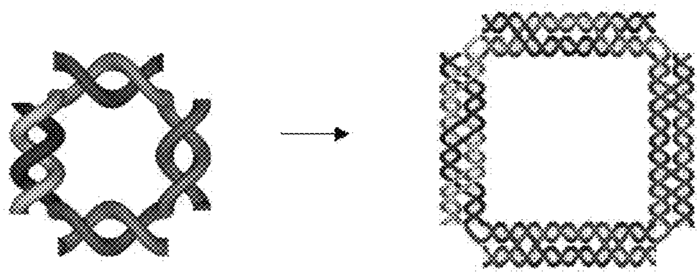
Figure 6D:
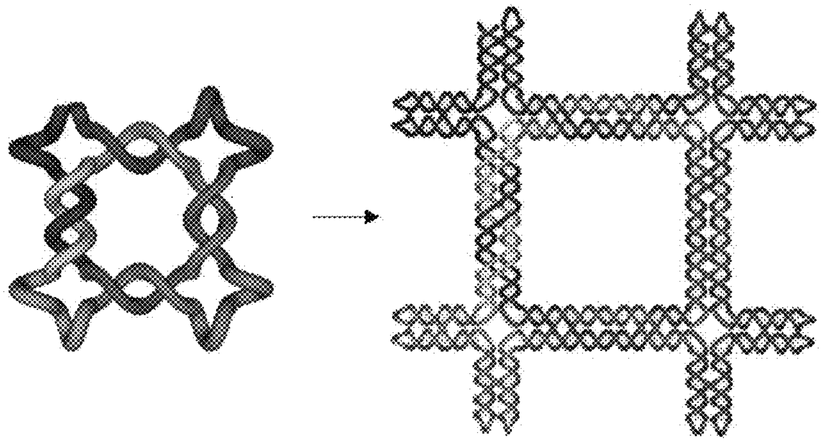

AFM imaging confirms the formation of the defected nodes in the final knotted NA nanostructure comprising perfect-match or mis-matched links. Topological control experiments were conducted to validate the use of AFM imaging as a method to detect the formation of defected nodes. As shown in FIGS. 4A-4B, a link structure was designed with a linking number of 8 as the topological control. As used herein, the term "linking number" refers to the number of links within a knotted NA nanostructure. A link is a sub-structure comprising two dsDNA rings, which connected to each other through 8 paranemic cohesions. This particular link structure was constructed by annealing two linear dsDNAs with 8 unpaired bubbles. These unpaired regions within these two linear dsDNAs interact with their counterparts to form the stable paranemic cohesions. Sticky ends closed the two rings after the formation of the nanostructure. This particular link structure assembled well as compact conformations, and the nanostructures were characterized by high resolution AFM images, as shown in FIGS. 4A-4B. If, however, the two linear dsDNAs were first ligated to form closed rings before interaction, these two dsDNA rings would not be able to interweave into the fully inter-locked loop structure. As expected, although the two dsDNA rings could still bind with each other partially through some of the paranemic cohesion interactions, extensive defects were observed in all of the structures under high resolution AFM. This experiment confirmed that the AFM imaging method can confirm the formation of the inter-lock topology.

In some embodiments, this disclosure provides for a method to create 3D architectures with arbitrary geometries comprising knotted NA nanostructures as described herein. The versatility of the method was demonstrated by constructing four ssDNA polyhedral meshes as shown in FIGS. 5A-5D: a tetrahedron, a pyramid, a triangular prism, and a pentagonal pyramid with crossing numbers 15, 20, 22, and 25, respectively. A schlegel diagram transfers the 3D objects to their topologically equivalent 2D nets. Optimized folding pathways were designed carefully for step-wise hierarchical assembly and the corresponding ssDNA strands were designed, synthesized, and assembled. AFM images showed an abundance of well-folded 3D nanoparticles with the expected sizes. Single particle cryo-EM 3D reconstruction revealed that the overall conformations matched the designed geometries well. The vertex design for the ssDNA knots was different from the multi-arm junction design based on the double crossover motif, as shown in FIGS. 5A, 18B, 32A, and 32B. There is a 5 bp difference in length between the two parallel dsDNAs that form each edge, leading to chiral vertices and inclined edges in the ssDNA knots. This unique geometric feature identifies conformational diastereomers, which is when the structure is turned inside out, while satisfying all programmed Watson-Crick base pairing with the same network. The 3D reconstruction data indicated that the ssDNA knots preferred to point the major grooves inwards at the vertices.

It has been a long-standing challenge to construct molecular knots with increasing size and complexity in a programmable and controllable way. In some embodiments, this disclosure provides for methods of folding single-stranded nucleic acids with completely custom-designed sequences, to create ssDNA and/or ssRNA nanostructures with highly complex topologies that are programmable, replicable, and scalable. This disclosure further provides for various 2D nanostructures which are designed, constructed, and characterized using high resolution AFM imaging. The folding yield of the knots is optimized by following a set of design rules to select the best folding pathway and programming the step-wise hierarchical folding pathway through sequence design in the paranemic cohesion regions. In some embodiments, the method is applied to construct ssRNA knotted nanostructures and/or three-dimensional (3D) ssDNA knotted nanostructures. The 3D knotted nanostructures are characterized by cryogenic transmission electronic microscopy (cryo-EM) single particle reconstruction, which confirmed that the nanostructures had assumed the designated geometry. The present ssDNA knotted nanostructures are much larger than structures made by other methods (up to 7.5 k bases, compared to only up to 30 bases for other methods) and can exhibit complex topology structures (with as high as 67 crossing numbers, compared to only 1 crossing for other methods).

Design Principles for ssRNA Knotted Nanostructures

Figures 17A, 17B, 17C:
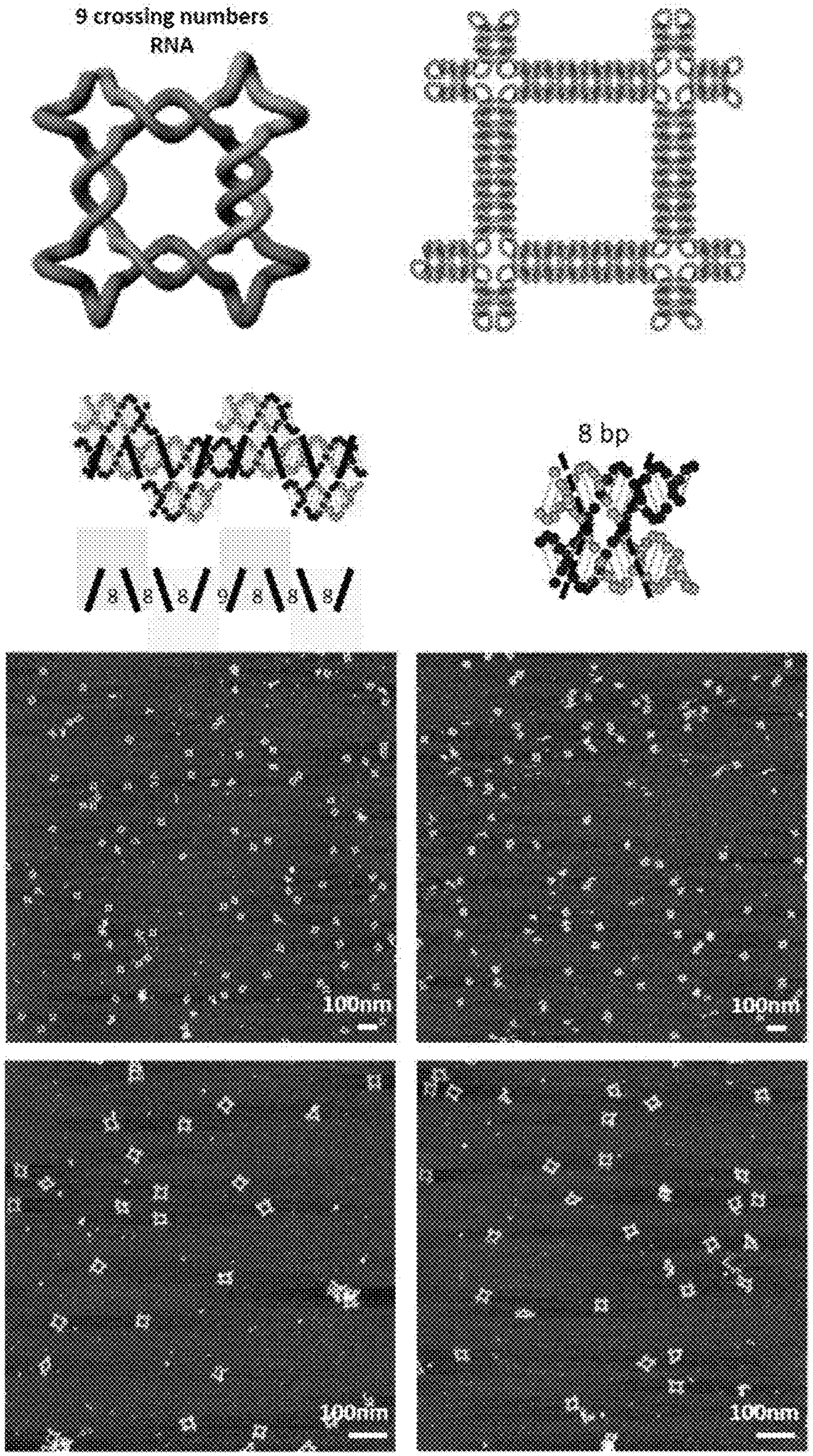
FIGS. 17A-17C. The design and characterization of the square knotted RNA nanostructure $9_1$.
Figure 22A:
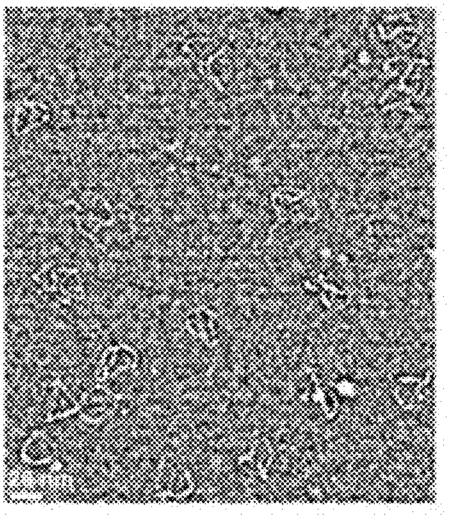
FIGS. 22A-22D. Cryo-EM characterization of a single stranded DNA tetrahedron.
Figure 22C:
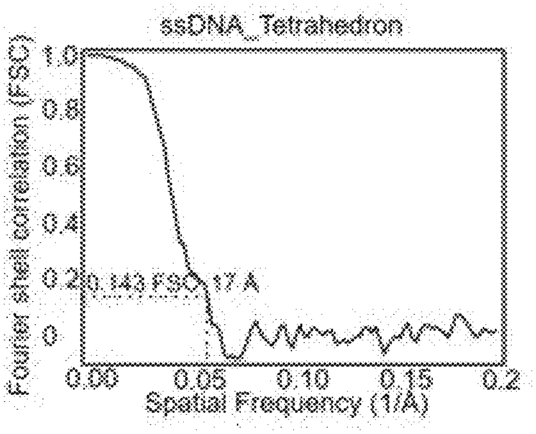
Figure 22B:
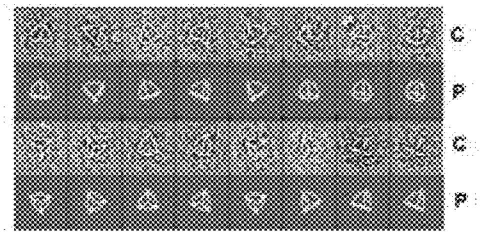
Figure 22D:
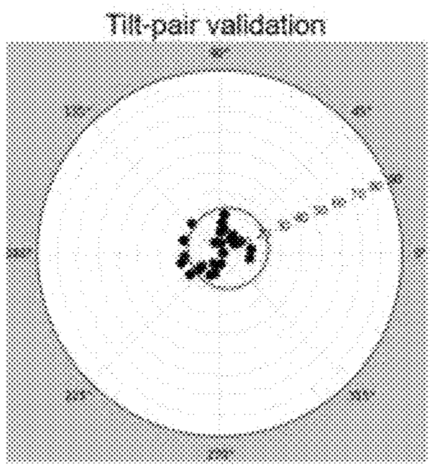
Figure 23A:
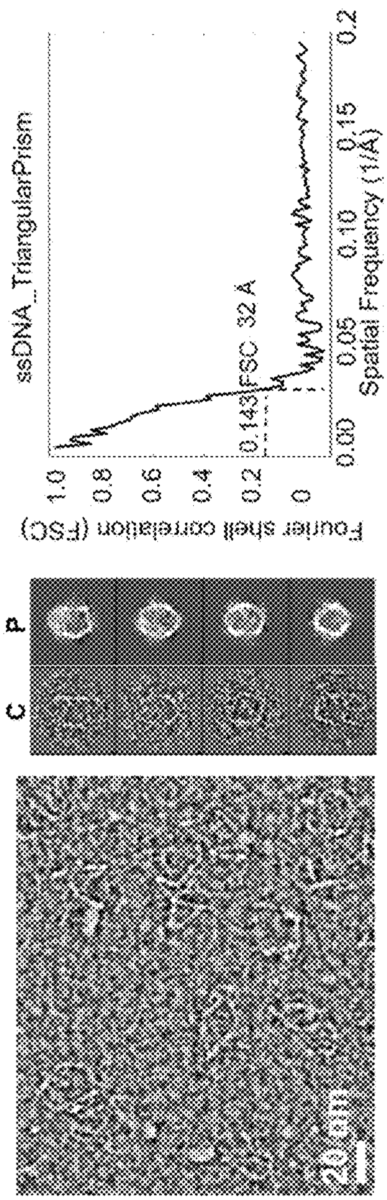
FIGS. 23A-23C. Cryo-EM characterization of an ssDNA triangular prism (FIG. 23A), pyramid (FIG. 23B) and pentagonal pyramid (FIG. 23C). For each structure, a raw cryo-EM micrograph is shown with visible particles. There are also images on the right in smaller boxes, showing the raw particles. Furthermore, a Gold-standard FSC plot is also shown for the 3D reconstruction of these particles.
Figure 23B:
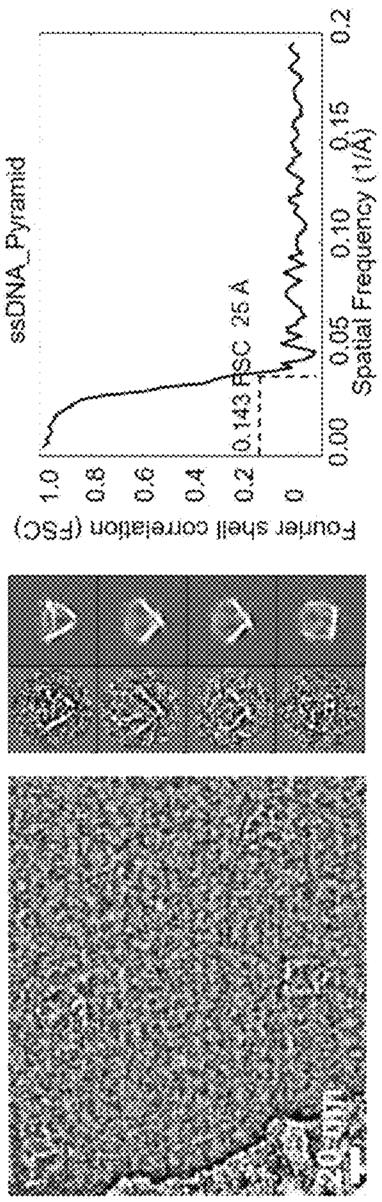
Figure 23C:
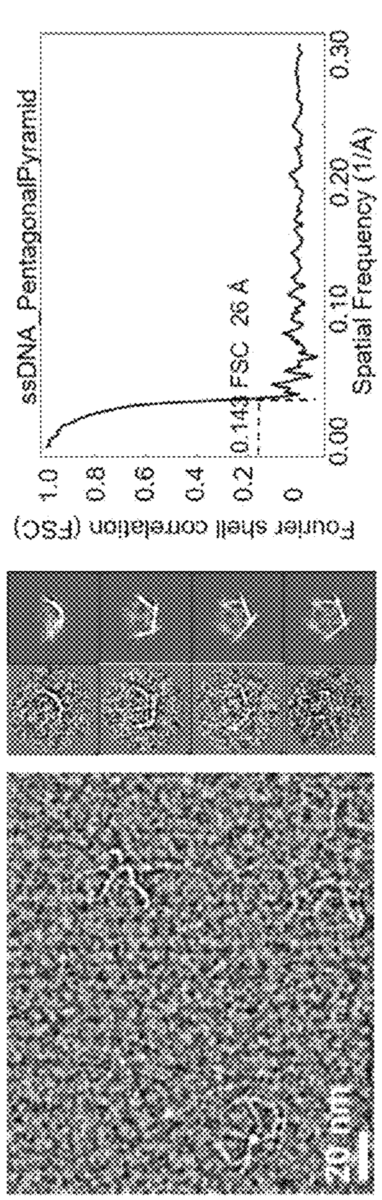

In some embodiments, this disclosure provides for methods of designing and creating ssRNA knotted nanostructures. An X-shaped RNA modular building block is designed that was similar to the paranemic cohesion structures of DNA. The same steps are followed for constructing the ssRNA knotted nanostructures as the steps for constructing ssDNA knotted nanostructures. First, based on the 3D modeling of an A-form dsRNA helix (11 bp per helical turn, 19 degree inclination of base pairs) and the best geometric fitting, 8 (instead of 4 or 6) base pairs were chosen for the length of a paranemic crossover, as shown in FIG. 17B. For an 8 base-pair paranemic cohesion, a total of $4^8=65536$ possible sequences provided an adequate sequence space for the selection of unique complementarity to sufficiently avoid undesired interactions between the paranemic cohesion motifs. Second, given the 11 base pairs per turn of an A-form dsRNA, the lengths of the inter-motif stems were assigned as alternating between 8 and 9 bp, as shown in FIGS. 17A-17C) to achieve a structural repeating unit of 33 bps for three full helical turns (i.e. 8 bp+8 bp stem+8 bp+9 bp stem=33 bp=3 full turns). In this design, the neighboring structural units were in line with each other without accumulating helical twist, and the final assembled knotted NA nanostructure was expected to stay in 2D. Like the ssDNA $9_1$ knot, 2, 2, 2, and 3 crossings were assigned on the four edges of a square, respectively, and looped the vertices to form one single-stranded RNA. After generating the appropriate sequences by following the same sequence design rules as the ssDNA nanostructures, the dsDNA gene coding for the long RNA strand was synthesized, and the ssRNA molecule was obtained by an in vitro transcription reaction. After an annealing step, the ssRNA knotted nanostructures comprising $9_1$ knots were confirmed by AFM images.

Figure 24:
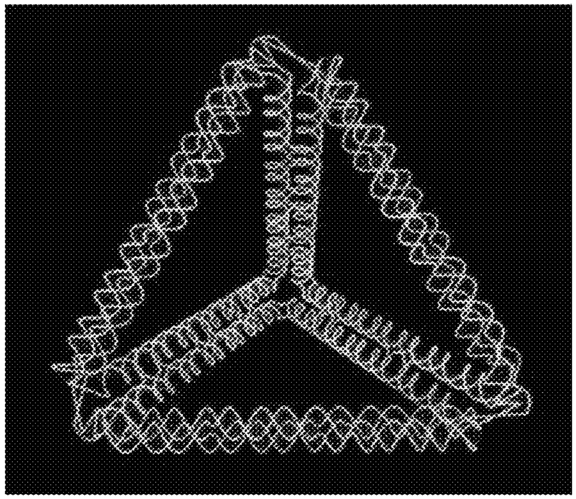
FIG. 24 shows one embodiment of a ssRNA knotted nanostructure in the form of a tetrahedron with crossing numbers.
Figure 24:
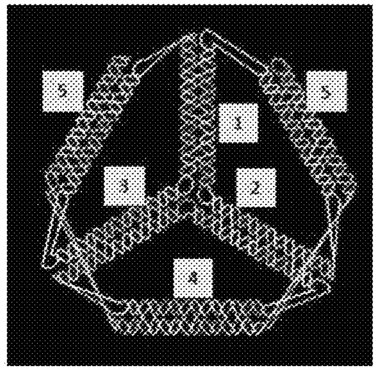
Figure 25:
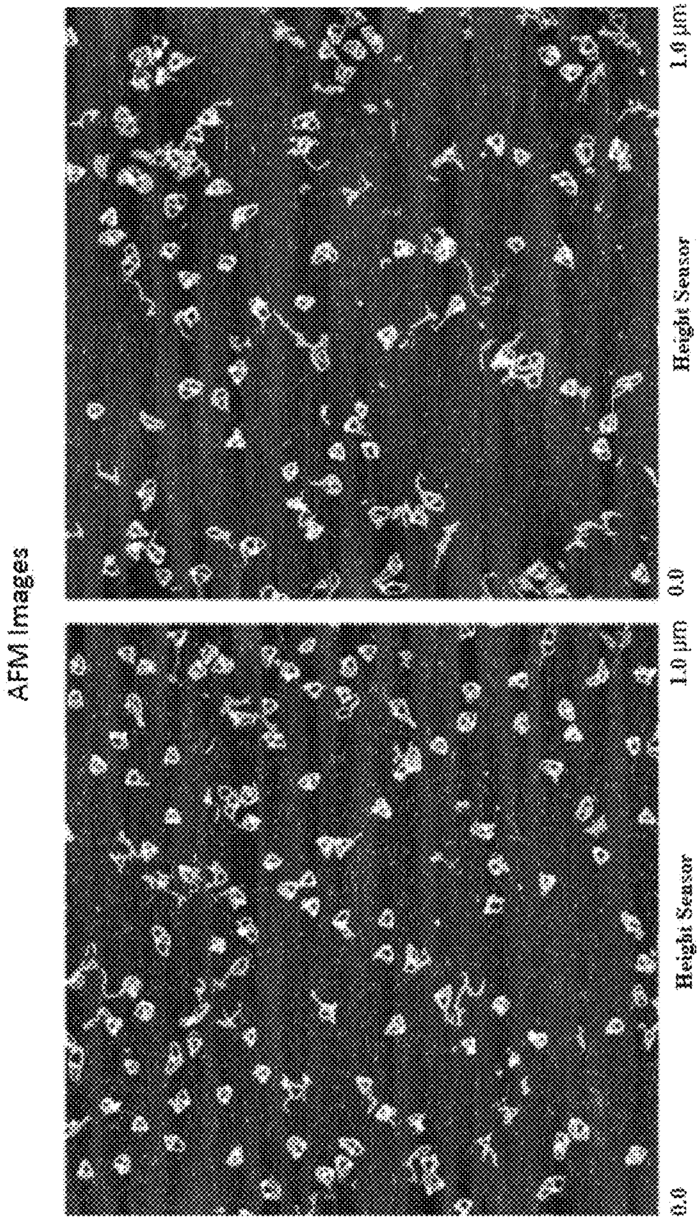
FIG. 25 shows AFM images of ssRNA knotted nanostructures in the form of tetrahedrons with crossing numbers.
Figure 26:
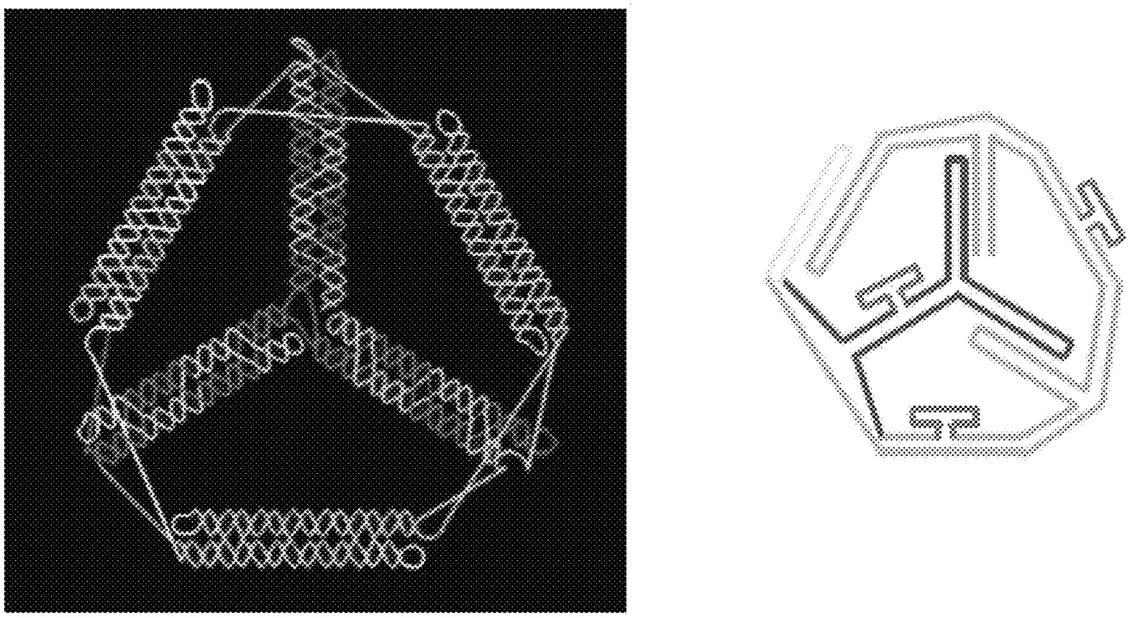
FIG. 26 shows ssRNA knotted nanostructures in the form of tetrahedron without crossing numbers.
Figure 27:
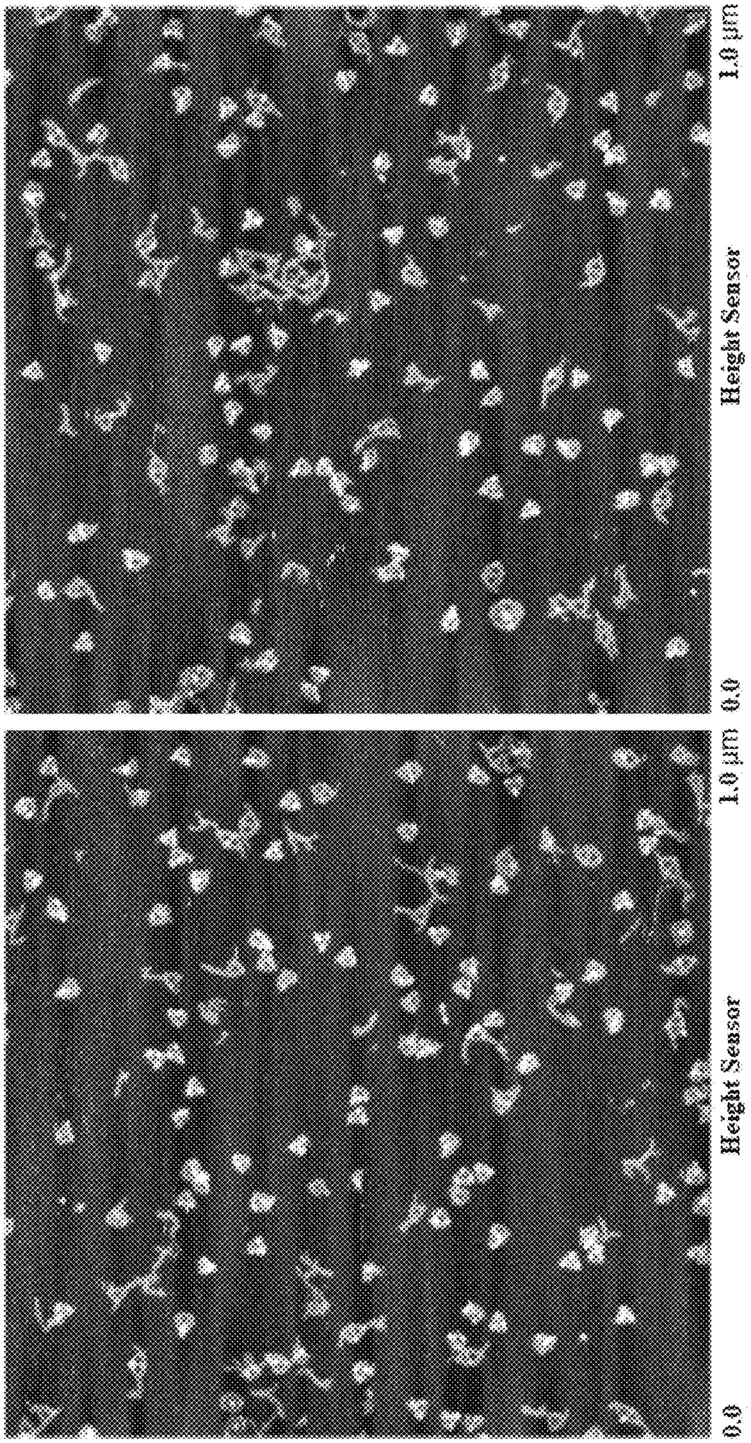
FIG. 27 shows AFM images of ssRNA knotted nanostructures in the form of tetrahedrons without crossing numbers.
Figure 28:
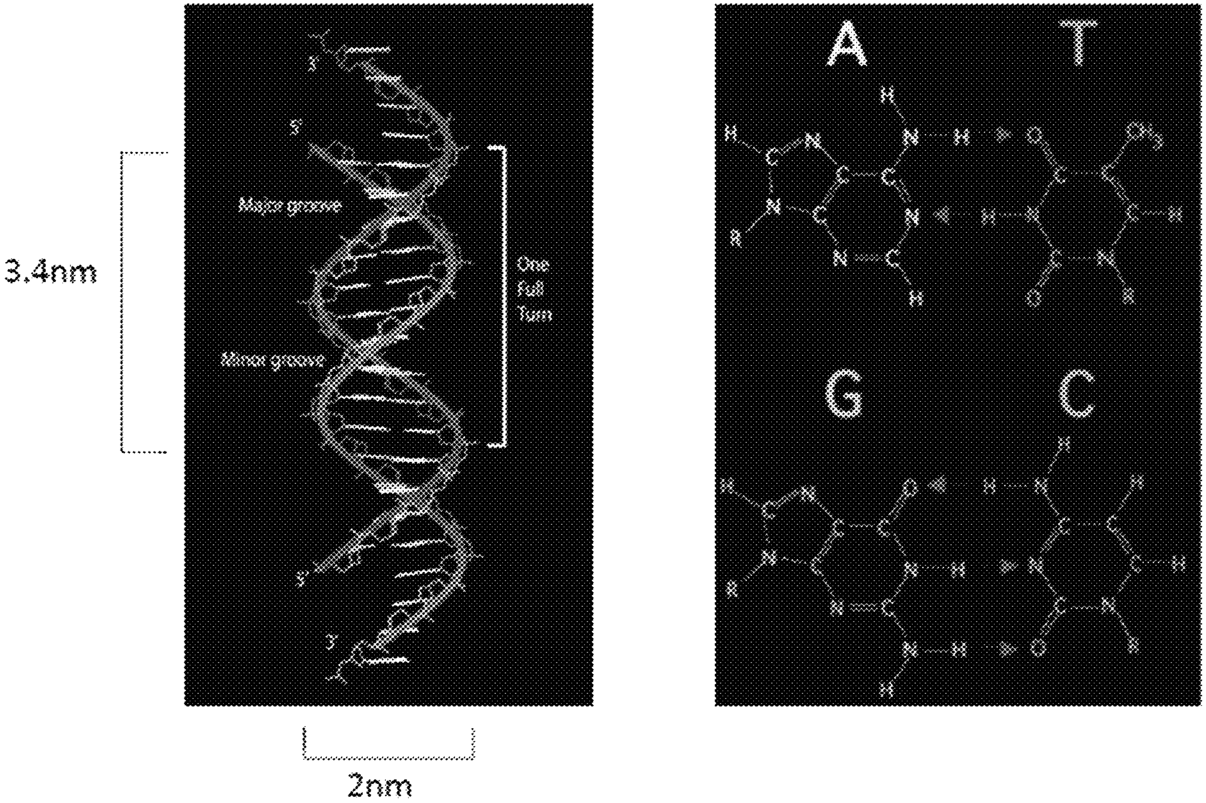
FIG. 28 shows DNA as a nanoscale building block.

Both the chemical and enzymatic synthesis of long ssDNA molecules is technically challenging because the chain possesses a large portion of self-complementarity. As shown in the folding pathway depicted in FIG. 11A, the ssDNA molecule first forms a long hairpin structure with the 5' and 3' ends meeting each other. The full-length ssDNA strand was first split into two equal halves, with each strand lacking significant secondary structures. Each of the halves were then inserted into plasmids as double stranded genes and amplified by cloning. The two dsDNA genes were obtained separately from the plasmids by restriction enzymes digestion (EcoRI+XbaI and XbaI+HindIII respectively) and were then ligated together with a linearized phagemid vector, pGEM-7zf(−). In order to obtain the full-length ssDNA molecule, the recombinant M13 phage was replicated in *E. coli* with the assistance of a helper plasmid, pSB4423. Because the helper plasmid, pSB4423, does not contain a phage replication origin, only the phagemid vector containing the full-length ssDNA gene was able to act as a template for the phage DNA replication. After the extraction and purification of the recombinant phage DNA, EcoRV digestion was performed to cut out the target ssDNA. Native agarose gel electrophoresis was used to separate the target ssDNA from the phagemid vector ssDNA. Using this method, all of the long ssDNA strands were synthesized and amplified at a nanomole quantity (with 1 L scale of *E. coli* culture) and high purity. The ssDNA strand was obtained, then self-assembled (folded) in a 1×TAE-Mg buffer with a 12 hour or 24 hour annealing ramp from 65° C. to 25° C., as shown in FIGS. 22A-22D and 23A-23C. The folded products were then characterized by using AFM imaging, gel electrophoresis and/or cryo-EM imaging. ssRNA knotted nanostructures were similarly produced, as shown in FIG. 24.

Nucleic Acid Knotted Nanostructures and Compositions Thereof

As used herein, the term "nucleic acid nanostructure" refers to a nanoscale structure comprising nucleic acid (NA), wherein the nucleic acid acts both as a structural and function element. In some embodiments, the nucleic acid nanostructure is DNA. In some embodiments, the nucleic acid nanostructure is RNA. In some embodiments, the nucleic acid nanostructure comprises both DNA and RNA. In some embodiments, NA nanostructures can also serve as a scaffold for the formation of other structures. The nucleic acid nanostructures are prepared based on the concept of base-pairing. While no specific sequence is required, the sequences of each oligonucleotide segment must be partially complementary to certain other sequences within the oligonucleotide segment to enable hybridization and assembly of the nanostructure. In certain embodiments, the nucleic acid nanostructure is a nucleic acid rectangle nanostructure, self-assembled from one single-stranded nucleic acid molecule through paranemic cohesion crossover.

In some embodiments, the length of each nucleic acid strand is variable and depends on the type of nanostructure to be created. In some embodiments, the nucleic acid nanostructure is comprised of a single oligonucleotide strand. In some embodiments, the NA strand is about 100 nucleotides in length to about 20,000 nucleotides in length, or any length there-between. In some embodiments, the NA strand is about 100 nucleotides in length to about 10,000 nucleotides in length, 1000 nucleotides in length to about 10,000 nucleotides in length, 1200 nucleotides in length to about 10,000 nucleotides in length, about 1200 to about 7500 nucleotides in length, about 1500 to about 8000 nucleotides in length, about 1800 to about 7500 nucleotides in length. In some embodiments, the nucleic acid strand is about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, about 5100, about 5200, about 5300, about 5400, about 5500, about 5600, about 5700, about 5800, about 5900, about 6000, about 6100, about 6200, about 6300, about 6400, about 6500, about 6600, about 6700, about 6800, about 6900, about 7000, about 7100, about 7200, about 7300, about 7400, about 7500, about 7600, about 7700, about 7800, about 7900, about 8000, about 8100, about 8200, about 8300, about 8400, about 8500, about 8600, about 8700, about 8800, about 8900, about 9000, about 9100, about 9200, about 9300, about 9400, about 9500, about 9600, about 9700, about 9800, about 9900, or about 10000 nucleotides in length, or between any of the aforementioned lengths.

In some embodiments, the NAs are synthesized de novo using oligonucleotide synthesis methods. In some embodiments, the oligonucleotide synthesis methods are selected from the cyanoethyl phosphoramidite method (Beaucage, S. L., and Caruthers, M. H., Tet. Let. 22:1859,1981); nucleoside H-phosphonate method (Garegg et al., Tet. Let. 27:4051-4054,1986; Froehler et al., Nucl. Acid. Res. 14:5399-5407, 1986; Garegg et al., Tet. Let. 27:4055-4058, 1986, Gaffney et al., Tet. Let. 29:2619-2622, 1988). These chemistries can be performed by a variety of automated oligonucleotide synthesizers available in the market, including the use of an in vitro transcription method. In some embodiments, the oligonucleotide synthesis methods are selected from enzymatic step-wise addition methods. The enzymatic step-wise addition methods can include or exclude the method described in: WO 2016/034807, WO 2015/159023, WO 2019/030149, US 2014/0363852, US 2018/0274001, and US 2016/0108382, each of which are herein incorporated by reference.

In some embodiments, the NA nanostructure exhibits increased nuclease resistance compared to a control. In some embodiments, the control is an unfolded single-stranded nucleic acid molecule comprising the same nucleic acid sequence as the NA nanostructure. In some embodiments, nuclease resistance of the NA nanostructure is 10%, 20%, 30%, 40%, 50%, 60%, 70%, 80%, 90%, 95% or more than a control NA sequence.

In some embodiments, the NA nanostructure is assembled using a single stranded NA molecule. In some embodiments, the NA nanostructure comprises both single stranded and double stranded regions. In some embodiments, the single-stranded regions are at the 3' terminus, the 5' terminus, or both the 3'- and 5'-terminus of the nanostructure sequence.

In some embodiments, the NA nanostructure is comprised of one ssNA molecule that self-assembles into a nanostructure. In some embodiments, the NA nanostructure is assembled from one ssNA molecule through paranemic cohesion crossovers. As used herein, the term "paranemic cohesion crossover" refers to a four-stranded nucleic acid complex containing a central dyad axis that relates two flanking parallel double helices. In some embodiments, paranemic cohesion crossovers form when bases outside a hairpin structure pair with bases within the hairpin or internal loop. In some embodiments, the paranemic adhesion crossovers occur in a periodic manner throughout the nanostructure. The periodicity can be a single phase or multiple phases. In some embodiments, the number of multiple phases of periodicity are 2, 3, 4, 5, 6, 7, 8, 9, or 10. In some embodiments, the length of each phase is independently selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more base pairs.

In certain embodiments, the NA nanostructure comprises one single-stranded NA (ssNA) molecule, wherein the ssNA molecule forms at least one paranemic cohesion crossover. In some embodiments the NA nanostructure is a rectangle nanostructure. In some embodiments, the single stranded NA molecule is selected from any one of SEQ ID NO:1-15.

In some embodiments, this disclosure provides for a NA nanostructure comprising a nucleic acid sequence having at least about 60% sequence identity to any one of SEQ ID NO:1-15. In some embodiments, the NA nanostructure comprises a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to any one of SEQ ID NO:1-15. In some embodiments, the NA nanostructure consists of a nucleic acid sequence having at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, $9_1$%, 92%, 93%, 94%, 95%, 96%, 97%, 98%, 99% or 100% sequence identity to any one of SEQ ID NO:1-15. In certain embodiments, the NA nanostructure comprises any sequence comprising any one of SEQ ID NO:1-15. In some embodiments, the NA nanostructure consists of any one of SEQ ID NO:1-15.

In some embodiments, the NA nanostructure comprises one or more modified nucleic acids. In some embodiments, the one or more modified nucleic acids are selected from inosine residues, alkynyl-modified nucleotides, In some embodiments, the alkynyl modified nucleotides are chemically synthesized from a phosphoramidite selected from: 5'-Dimethoxytrityl-5-[(6-oxo-6-(dibenzo[b,f]azacyclooct-4-yn-1-yl)-capramido-N-hex-6-yl)-3-acrylimido]-2'-deoxyUridine,3'-[(2-cyanoethyl)-(N,N-diisopropyl)]-phosphoramidite, 5'-Dimethoxytrityl-5-ethynyl-2'-deoxyUridine, 3'-[(2-cyanoethyl)-(N,N-diisopropyl)]-phosphoramidite, 5'-Hexynyl Phosphoramidite, 5'-Dimethoxytrityl-5-(octa-1,7-diynyl)-2'-deoxyuridine, 3'-[(2-cyanoethyl)-(N,N-diisopropyl)]-phosphoramidite, 10-(6-oxo-6-(dibenzo[b,f]azacyclooct-4-yn-1-yl)-capramido-N-ethyl)-O-triethyleneglycol-1-[(2-cyanoethyl)-(N,N-diisopropyl)]-phosphoramidite, 6-Bromo-hex-1-yl-(2-cyanoethyl)-(N,N-diisopropyl)-phosphoramidite, 3-Dimethoxytrityloxy-2-(3-(5-hexynamido) propanamido)propyl-1-O-[(2-cyanoethyl)-(N,N-diisopropyl)]-phosphoramidite, and 5'-Dimethoxytrityl-3'-propargyl-5-methyl-2'-deoxyCytosine-N-succinoyl-long chain alkylamino-CPG.

In some embodiments, one or more agents (e.g., 1, 2, 3, 4, 5, 6, 7, 8, 9, 10 etc.) are operably linked to the NA nanostructure. The one or more agents can include or exclude diagnostic agents or therapeutic agents. In some embodiments, at least one diagnostic agent is operably linked to the NA nanostructure. In some embodiments, at least one therapeutic agent is operably linked to the NA nanostructure. In some embodiments, at least one diagnostic agent and at least one therapeutic agent are operably linked to the NA nanostructure.

Diagnostic agents can include or exclude fluorophores, radioisotopes, nanoparticles, and colorimetric indicators.

As used herein, the term "therapeutic agent" refers to agents that provide a therapeutically desirable effect when administered to an animal. The animal is a mammal, which can include or exclude a human. The therapeutic agent may be of natural or synthetic origin. In some embodiments, the therapeutic agent can include or exclude a nucleic acid, a polypeptide, a protein, a peptide, a radioisotope, saccharide or polysaccharide or an organic compound, which can include or exclude a small molecule. The term "small molecule" includes organic molecules having a molecular weight of less than about, e.g., 1000 daltons. In one embodiment a small molecule can have a molecular weight of less than about 800 daltons. In another embodiment a small molecule can have a molecular weight of less than about 500 daltons.

In some embodiments, the therapeutic agent is an immuno-stimulatory agent, a radioisotope, a chemotherapeutic drug or an immuno-therapy agent. In some embodiments, the immune-stimulatory agent can include or exclude an antibody or an antibody fragment. In some embodiments, the therapeutic agent is a vaccine. In some embodiments, the vaccine can include or exclude a cancer vaccine. In some embodiments, the therapeutic agent is a tumor targeting agent. In some embodiments, the tumor targeting agent is selected from a monoclonal tumor-specific antibody, a nanobody, a scFv, or an aptamer. In some embodiments, the therapeutic agent is an antibody. In some embodiments, the antibody therapeutic agent is a monoclonal antibody. In some embodiments, the monoclonal antibody is an anti-PD1 antibody. In some embodiments, the therapeutic agent is an antigen. In some embodiments, the antigen is selected from a tumor associated antigen or a tumor specific antigen. In some embodiments, the therapeutic agent is a tumor antigen peptide(s).

The linkage between the agent(s) and the NA nanostructure can include any group that connects the NA nanostructure and the agent, provided that said linkage does not interfere with the function of the agent or the NA nanostructure. In some embodiments, chemistries that link the agent to an oligonucleotide can include or exclude disulfide linkages, amino linkages, and covalent linkages. In some embodiments, the linker can include or exclude aliphatic or ethylene glycol linkers. In some embodiments, the linker can include or exclude phosphodiester, phosphorothioate and/or other modified linkages. In some embodiments, the linker is a binding pair. In some embodiments, the "binding pair" refers to two molecules which interact with each other through any of a variety of molecular forces including or excluding ionic, covalent, hydrophobic, van der Waals, and hydrogen bonding, so that the pair have the property of binding specifically to each other. Specific binding means that the binding pair members exhibit binding to each other under conditions where they do not bind to another molecule. Examples of binding pairs are biotin-avidin, hormone-receptor, receptor-ligand, enzyme-substrate probe, IgG-protein A, antigen-antibody, aptamer-target and the like. In some embodiments, a first member of the binding pair comprises avidin or streptavidin and a second member of the binding pair comprises biotin.

Compositions and Kits

Certain embodiments of the invention also provide a composition comprising an NA nanostructure described herein and a carrier. In some embodiments, the composition comprises a plurality of NA nanostructures.

In some embodiments, the composition further comprises at least one therapeutic agent described herein.

In some embodiments, the composition is pharmaceutical composition and the carrier is a pharmaceutically acceptable carrier.

The present invention further provides kits for practicing the present methods. Certain embodiments of the invention provide a kit comprising an NA nanostructure described herein and instructions for administering the NA nanostructure to induce an immune response or to treat a disease or condition. In some embodiments, the immune response is anti-tumor immunity. In some embodiments, the kit further comprises a therapeutic agent described herein and instructions for administering the therapeutic agent in combination (simultaneously or sequentially) with the NA nanostructure.

Certain Methods

In some embodiments, an NA nanostructure described herein is used as an immuno-adjuvant to boost an immune response. In some embodiments, the immune response induces anti-tumor immunity.

Certain embodiments of the invention provide a method of inducing an immune response a subject. The subject is a mammal, which can include or exclude a human. The method comprises administering to the subject an effective amount of an NA knotted nanostructure or composition as described herein.

In some embodiments, the administration of the NA knotted nanostructure described herein increases an immune response by at least about, e.g., 20%, 30%, 40%, 50%, 60%, 70%, 80%, 90%, or more, compared to a control. Methods of measuring an immune response include using an assay as described in the Examples. As used herein, the phrase "inducing an immune response" refers to the activation of an immune cell. Methods of measuring an immune response include using an assay described in the Examples. As used herein, the phrase "effective amount" refers to an amount of an NA nanostructure described herein that induces an immune response.

Certain embodiments of the invention also provide a method of treating a disease or disorder in a subject, comprising administering to the subject a therapeutically effective amount of an NA nanostructure or a composition as described herein.

In some embodiments, a method of the invention further comprises administering at least one therapeutic agent to the subject.

In some embodiments, the at least one therapeutic agent is administered in combination with the NA nanostructure. As used herein, the phrase "in combination" refers to the simultaneous or sequential administration of the NA nanostructure and the at least one therapeutic agent. For simultaneous administration, the NA nanostructure and the at least one therapeutic agent is present in a single composition or is separate. In some embodiments, when the NA nanostructure and at least one therapeutic agent are administered simultaneously, they are administered by either the same or different routes.

Certain embodiments of the invention provide an NA nanostructure or a composition as described herein for use in medical therapy.

Certain embodiments of the invention provide the use of an NA nanostructure or a composition as described herein for the manufacture of a medicament for inducing an immune response in a subject. In some embodiments, the subject is a mammal, which can include or exclude a human.

Certain embodiments of the invention provide the use of an NA nanostructure or a composition as described herein for the manufacture of a medicament for inducing an immune response in a subject in combination with at least one therapeutic agent. In some embodiments, the subject is a mammal, which can include or exclude a human.

Certain embodiments of the invention provide an NA nanostructure or a composition as described herein for inducing an immune response.

Certain embodiments of the invention provide an NA nanostructure or a composition as described herein for inducing an immune response, in combination with at least one therapeutic agent.

Certain embodiments of the invention provide the use of an NA nanostructure or a composition as described herein for the manufacture of a medicament for treating a disease or disorder in a subject.

Certain embodiments of the invention provide the use of an NA nanostructure or a composition as described herein for the manufacture of a medicament for treating a disease or disorder in a subject, in combination with at least one therapeutic agent.

Certain embodiments of the invention provide an NA nanostructure or a composition as described herein for the prophylactic or therapeutic treatment a disease or disorder.

Certain embodiments of the invention provide an NA nanostructure or a composition as described herein for the prophylactic or therapeutic treatment of a disease or disorder, in combination with at least one therapeutic agent.

In some embodiments, the disease or disorder is a condition that requires a boost of the host immunity. In some embodiments, the disease or disorder is cancer. In some embodiments, the disease or disorder is an infectious disease.

In some embodiments, the cancer is carcinoma, lymphoma, blastoma, sarcoma, or leukemia. In some embodiments, the cancer is a solid tumor cancer.

In some embodiments, the cancer is squamous cell cancer, small-cell lung cancer, non-small cell lung cancer, adenocarcinoma of the lung, squamous carcinoma of the lung, cancer of the peritoneum, hepatocellular cancer, renal cell carcinoma, gastrointestinal cancer, gastric cancer, esophageal cancer, pancreatic cancer, glioma, cervical cancer, ovarian cancer, liver cancer, bladder cancer, hepatoma, breast cancer (which can include or exclude endocrine resistant breast cancer), colon cancer, rectal cancer, lung cancer, endometrial or uterine carcinoma, salivary gland carcinoma, kidney cancer, liver cancer, prostate cancer, vulval cancer, thyroid cancer, hepatic carcinoma, melanoma, leukemia, or head and neck cancer. In some embodiments, the cancer is breast cancer.

In some embodiments, the therapeutic agent is a therapeutic agent described herein. In certain embodiments, the therapeutic agent is selected from an immuno-stimulatory agent, a radioisotope, a chemotherapeutic drug or an immuno-therapy agent. In some embodiments, the immunotherapy agent can include or exclude an antibody or an antibody fragment. In some embodiments, the therapeutic agent is a vaccine, which can include or exclude a cancer vaccine. In some embodiments, the therapeutic agent is a tumor targeting agent, which can include or exclude a monoclonal tumor-specific antibody or an aptamer. In some embodiments, the therapeutic agent is an antibody. In some embodiments, the therapeutic agent is a monoclonal antibody. In some embodiments, the monoclonal antibody is an anti-PD1 antibody. In some embodiments, the therapeutic agent is an antigen. The antigen is selected from a tumor associated antigen or a tumor specific antigen. In some embodiments, the therapeutic agent is a tumor antigen peptide(s).

Administration

As described herein, methods of the invention comprise administering a composition comprising an NA nanostructure described herein, and optionally, a therapeutic agent to a subject. In some embodiments, such compositions are formulated as a pharmaceutical composition and administered to a mammalian host, which can include or exclude a human patient in a variety of forms adapted to the chosen route of administration, i.e., orally or parenterally, by intravenous, intramuscular, intraperitoneal or topical or subcutaneous routes.

In some embodiments, the compositions are systemically administered, e.g., orally, in combination with a pharmaceutically acceptable vehicle which can include or exclude an inert diluent or an assimilable edible carrier. The compositions may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained. The tablets, troches, pills, capsules, and the like may also contain the following: binders which can include or exclude gum tragacanth, acacia, corn starch or gelatin; excipients which can include or exclude dicalcium phosphate; a disintegrating agent which can include or exclude corn starch, potato starch, alginic acid and the like; a lubricant which can include or exclude magnesium stearate; and a sweetening agent which can include or exclude sucrose, fructose, lactose or aspartame or a flavoring agent which can include or exclude peppermint, oil of wintergreen, or cherry flavoring may be added. When the unit dosage form is a capsule, it may contain, in addition to materials of the above type, a liquid carrier, which can include or exclude a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring which can include or exclude cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. In some embodiments, the liquid carrier or vehicle can be a solvent or liquid dispersion medium comprising a liquid which can include or exclude: water, ethanol, a polyol (for example, glycerol, propylene glycol, liquid polyethylene glycols, and the like), vegetable oils, nontoxic glyceryl esters, and suitable mixtures thereof. The proper fluidity can be maintained by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids which can include or exclude talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants which can include or exclude fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners which can include or exclude synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver a compound to the skin can include or exclude: Jacquet et al. (U.S. Pat. No. 4,608,392), Geria (U.S. Pat. No. 4,992,478), Smith et al. (U.S. Pat. No.

4,559,157) and Wortzman (U.S. Pat. No. 4,820,508), each of which are herein incorporated by reference in their entirety.

Useful dosages of compounds can be determined by comparing their in vitro activity, and in vivo activity in animal models. Methods for the extrapolation of effective dosages in mice, and other animals, to humans can include U.S. Pat. No. 4,938,949, herein incorporated by reference.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The compound may be conveniently formulated in unit dosage form. In one embodiment, the invention provides a composition comprising a compound formulated in such a unit dosage form. The desired dose may conveniently be presented in a single dose or as divided doses administered at appropriate intervals. In some embodiments, the dose interval is selected from two, three, four or more sub-doses per day. The sub-dose itself may be further divided, e.g., into a number of discrete loosely spaced administrations; which can include or exclude multiple inhalations from an insufflator or by application of a plurality of drops into the eye.

Nucleic Acid Nanostructure

In some embodiments, single-stranded nucleic acid (ssNA) nanostructure described herein is a component in a nanostructure and functions as a molecular payload carrier, including inducing anti-tumor vascularization effects.

In some embodiments, the ssNA nanostructure further comprises NA targeting strands, wherein each targeting strand is operably linked to a targeting moiety. In some embodiments, the targeting moiety is an aptamer. In some embodiments, the aptamer is specific for nucleolin.

In some embodiments, the ssNA nanostructure further comprises NA imaging strands, wherein each imaging strand is operably linked to an imaging agent. In some embodiments, the imaging agent is fluorescent dye.

As used herein, the term "ssNA nanostructure" refers to a nanoscale structure comprising a NA, wherein the NA acts both as a structural and functional element. In some embodiments, ssNA nanostructures also serve as a scaffold for the formation of other structures. In some embodiments, ssNA nanostructures are prepared from one or more nucleic acid oligonucleotides. In some embodiments, the ssNA nanostructure is an ssNA rectangle knotted nanostructure, self-assembled from single-stranded DNA or RNA molecules. In some embodiments, the ssNA nanostructure further comprises one or more fastener strands of DNA, wherein the one or more fastener strands of DNA fastens the rectangular sheet into a tube-shaped knotted NA nanostructure. In some embodiments, the rectangular sheet is about 10 to about 150 nm in length (e.g., 10, 20, 30, 40, 50, 60, 70, 80, 90, 100, 110, 120, 130, 140, or 150 nm), and about 10 to about 150 nm width. In some embodiments, the dimension of the rectangular sheet is about 90 nm×about 60 nm×2 nm.

In some embodiments, the tube-shaped knotted NA nanostructure has a diameter of about 10-50 nm. In some embodiments, the tube-shaped knotted NA nanostructure has a diameter of about 19 nm.

In some embodiments, the ssNA nanostructures comprises one or more DNA capture strands, wherein each capture strand is operably linked to a therapeutic agent.

In some embodiments, the ssNA nanostructure further comprises NA targeting strands, wherein each targeting strand is operably linked to a targeting moiety. In some embodiments, the targeting moiety is an aptamer.

In some embodiments, the fastener strand is a Y-shaped structure. In some embodiments, the Y-shaped structure comprises an F50 AS1411 aptamer sequence that specifically binds to nucleolin, and a Comp15 DNA strand partially complementary to the AS1411 sequence, wherein the F50 and the Comp15 sequences form a 14- to 16-base pair duplex.

In some embodiments, the Y-shaped structure comprises F50 and Comp15; F50-48 and Comp15-48; F50-73 and Comp15-73; F50-97 and Comp15-97; F50-120 and Comp15-120; F50-144 and, Comp15-144; or F50-169 and Comp15-169. In some embodiments, the Y-shaped structure sequences can include or exclude a fluorophore or quencher at the 3' or 5' (or both) terminae of the sequences. In some embodiments, the fluorophore is FITC. In some embodiments, the quencher is BHQ.

In some embodiments, the fastener strands comprise a nucleic acid sequence comprising the sequence of:

```
F50:
                                          (SEQ ID NO: 18)
5'-
GGTGGTGGTGGTTGTGGTGGTGGTGGTCTAAAGTTTTGTCGTGAATTGC
G-3';

Comp15:
                                          (SEQ ID NO: 19)
5'-GTAAAGCTTTTTTTTTTTTACAACCACCACCACC-3';

F50-48:
                                          (SEQ ID NO: 18)
5'-GGTGGTGGTGGTTGTGGTGGTGGTGGTCTAAAGTTTTGTCGTGAAT
TGCG-3';

Comp15-48:
                                          (SEQ ID NO: 19)
5'-GTAAAGCTTTTTTTTTTTTACAACCACCACCACC-3';

F50-73
                                          (SEQ ID NO: 20)
5'-GGTGGTGGTGGTTGTGGTGGTGGTGGTAGAGCTTGACGGGGAAATC
AAAA-3';

Comp15-73:
                                          (SEQ ID NO: 21)
5'-TGTAGCATTTTTTTTTTTTACAACCACCACCACC-3';

F50-97:
                                          (SEQ ID NO: 22)
5'-GGTGGTGGTGGTTGTGGTGGTGGTGGCGAGAAAGGAAGGGAACAAA
CTAT-3';

Comp15-97:
                                          (SEQ ID NO: 23)
5'-TGAGTTTCTTTTTTTTTTTACAACCACCACCACC-3';

F50-120:
                                          (SEQ ID NO: 24)
5'-GGTGGTGGTGGTTGTGGTGGTGGTGGATAGGAACCCATGTACAAAC
AGTT-3';

Comp15-120:
                                          (SEQ ID NO: 25)
5'-CAAGCCCATTTTTTTTTTTTACAACCACCACCACC-3';

F50-144:
                                          (SEQ ID NO: 26)
5'-GGTGGTGGTGGTTGTGGTGGTGGTGGCACCACCCTCATTTTCCTAT
TATT-3;

Comp15-144:
                                          (SEQ ID NO: 27)
5'-CCGCCAGCTTTTTTTTTTTACAACCACCACCACC-3';
```

-continued

```
F50-169:
(SEQ ID NO: 28)
5'-GGTGGTGGTGGTTGTGGTGGTGGTGGCTACATTTTGACGCTCACCT
GAAA-3';
or

Comp15-169:
                                    (SEQ ID NO: 29)
5'-CCCTCAGTTTTTTTTTTTTACAACCACCACCACC-3'.
```

In some embodiments, the capture strand is extended with ssNA comprising four binding sites to form a complex with thrombin-NA molecules.

In some embodiments, ssNA nanostructure further comprises one or more functional strand of NA operably linked to an aptamer for targeting delivery of the nanostructure forming a targeting strand.

In some embodiments, the aptamer is specific for nucleolin. In some embodiments, the aptamer that is specific for nucleolin is an F50 AS1411 aptamer having the sequence: 5'-GGTGGTGGTGGTTGTGGTGGTGGTGG-3' (SEQ ID NO: 30). In some aspects, the targeting strand comprises a domain comprising a polynucleotide sequence for attaching to a therapeutic agent described herein. In some embodiments, when the nucleolin-specific aptamer is presented to nucleolin on a tumor cell surface, the aptamer will competitively bind to the surface-bound nucleolin. In some embodiments, when the RNA nanostructure scaffold is in the form of a tube comprising a fastener strand wherein the fastener strand is a nucleolin-specific aptamer, when the aptamer competitively binds to the tumor cell surface-bound nucleolin, the fastener strand will release from one or all of the RNA nanostructure scaffolds wherein the scaffold will change shape from a tube to an open rectangular sheet.

In some embodiments, one or more targeting strands are positioned at one or more corners of the rectangular sheet.

In some embodiments, one or more capture strands is operably linked to a fluorescent dye to form an imaging strand.

In some embodiments, the therapeutic agent is operably linked to the top surface of the rectangular sheet.

In some embodiments, the therapeutic agent is operably linked to the bottom surface of the rectangular sheet.

In some embodiments, the therapeutic agent is operably linked to an imaging agent. In some embodiments, the imaging agent is a fluorescent dye.

In some embodiments, the therapeutic agent is a protein.

In some embodiments, the therapeutic agent is thrombin.

In some embodiments, the therapeutic agent is siRNA, a chemotherapeutic agent or a peptide therapeutic agent.

In some embodiments, the thrombin is operably linked to the functional strand of ssNA by means of a sulfosuccinimidyl-4-(N-maleimidomethyl) cyclohexane-1-carboxylate (sulfo-SMCC) as a bifunctional crosslinker.

In some embodiments, the nanostructure comprises four thrombin molecules.

In some embodiments, the target molecule is nucleolin.

In some embodiments, the thrombin is operably linked to an imaging agent. In some embodiments, the imaging agent is a fluorescent dye.

Certain embodiments of the invention provide a pharmaceutical composition comprising the DNA nanostructure described herein.

In some embodiments, the composition further comprises at least one therapeutic agent.

In some embodiments, the at least one therapeutic agent is a chemotherapeutic drug (e.g., doxorubicin).

Certain embodiments of the invention provide a method of treating a disease or disorder in a subject, comprising administering to the subject a therapeutically effective amount of the NA nanostructure or pharmaceutical composition as described herein.

In some embodiments, the disease or disorder is cancer.

In some embodiments, the cancer is breast cancer, ovarian cancer, melanoma or lung cancer.

Certain embodiments of the invention provide a use of the ssNA nanostructure or a composition as described herein for the manufacture of a medicament for inducing a tumor necrosis response in a subject (e.g., a mammal, which can include or exclude a human).

Certain embodiments of the invention provide a ssNA nanostructure or a composition as described herein for the prophylactic or therapeutic treatment a disease or disorder.

Certain embodiments of the invention provide a kit comprising the ssNA nanostructure or a composition as described herein and instructions for administering the ssNA nanostructure/composition to a subject to induce an immune response or to treat a disease or disorder. In some embodiments, the kit further comprises at least one therapeutic agent.

The invention also provides processes disclosed herein that are useful for preparing a ssNA nanostructure described herein.

In some embodiments, one or more agents (e.g., 1, 2, 3, 4, 5, 6, 7, 8, 9, 10, or more) are operably linked to the ssNA nanostructure. The agents are selected from diagnostic agents or therapeutic agents. In some embodiments, at least one diagnostic agent is operably linked to the ssNA nanostructure. In some embodiments, at least one therapeutic agent is operably linked to the ssNA nanostructure. In some embodiments, at least one diagnostic agent and at least one therapeutic agent are operably linked to the ssNA nanostructure.

As used herein, the term “therapeutic agent” includes agents that provide a therapeutically desirable effect when administered to an animal. In some embodiments, the subject is a mammal, which can include or exclude a human. The agent is of natural or synthetic origin. In some embodiments, the therapeutic agent can include or exclude a nucleic acid, a polypeptide, a protein, a peptide, a radioisotope, saccharide or polysaccharide or an organic compound. In some embodiments, the organic compound can include or exclude a small molecule. The term “small molecule” includes organic molecules having a molecular weight of less than about, e.g., 1000 daltons. In one embodiment, a small molecule can have a molecular weight of less than about 800 daltons. In another embodiment, a small molecule can have a molecular weight of less than about 500 daltons.

In some embodiments, the therapeutic agent is an immuno-stimulatory agent, a radioisotope, a chemotherapeutic drug or an immuno-therapy agent. In some embodiments, the immune-stimulatory agent is selected from an antibody or an antibody fragment. In some embodiments, the antibody fragment is a nanobody, scFv, or camelid antibody. In some embodiments, the therapeutic agent is a vaccine, which can include or exclude a cancer vaccine. In some embodiments, the therapeutic agent is a tumor targeting agent, which can include or exclude a monoclonal tumor-specific antibody or an aptamer. In some embodiments, the therapeutic agent is an antibody. In some embodiments, the antibody is a monoclonal antibody. In some embodiments, the monoclonal antibody is an anti-PD1 antibody. In some embodiments, the therapeutic agent is an antigen. In some embodiments, the antigen is selected from a tumor associated antigen or a tumor specific antigen. In some embodiments, the therapeutic agent is a tumor antigen peptide(s). In some embodiments, the therapeutic agent is an RNAi molecule. In some embodiments, the RNAi molecule is selected from siRNA, shRNA, or miRNA. In some embodiments, the therapeutic agent is a small molecule drug. In some embodiments, the therapeutic agent is thrombin.

In some embodiments, the therapeutic agent is a chemotherapeutic agent. In some embodiments, the chemotherapeutic agent is selected from: Abraxane (chemical name: albumin-bound or nab-paclitaxel), Adriamycin (chemical name: doxorubicin), carboplatin (brand name: Paraplatin), Cytoxan (chemical name: cyclophosphamide), daunorubicin (brand names: Cerubidine, DaunoXome), Doxil (chemical name: doxorubicin), Ellence (chemical name: epirubicin), fluorouracil (also called 5-fluorouracil or 5-FU; brand name: Adrucil), Gemzar (chemical name: gemcitabine), Halaven (chemical name: eribulin), Ixempra (chemical name: ixabepilone), methotrexate (brand names: Amethopterin, Mexate, Folex), Mitomycin (chemical name: mutamycin), mitoxantrone (brand name: Novantrone), Navelbine (chemical name: vinorelbine), Taxol (chemical name: paclitaxel), Taxotere (chemical name: docetaxel), thiotepa (brand name: Thioplex), vincristine (brand names: Oncovin, Vincasar PES, Vincrex), and Xeloda (chemical name: capecitabine). In some embodiments, the chemotherapeutic agent is selected from: Abraxane (Paclitaxel (with albumin) Injection), Adriamycin (Doxorubicin), Afinitor (Everolimus), Alecensa (Alectinib), Alimta (PEMETREXED), Aliqopa (Copanlisib), Alkeran Injection (Melphalan), Alunbrig (Brigatinib), Aredia (Pamidronate), Arimidex (Anastrozole), Aromasin (Exemestane), Arranon (Nelarabine), Arzerra (Ofatumumab), Avastin (Bevacizumab), Bavencio (Avelumab), Beleodaq (Belinostat), Besponsa (Inotuzumab Ozogamicin), Bexxar (Tositumomab), BiCNU (Carmustine), Blenoxane (Bleomycin), Blincyto (Blinatumomab), Bosulif (Bosutinib), Braftovi (Encorafenib), Busulfex (Busulfan), Cabometyx (Cabozantinib), Calquence (Acalabrutinib), Campath (Alemtuzumab), Camptosar (Irinotecan), Caprelsa (Vandetanib), Casodex (Bicalutamide), CeeNU (Lomustine), CeeNU Dose Pack (Lomustine), Cerubidine (Daunorubicin), Cinqair (Reslizumab), Clolar (Clofarabine), Cometriq (Cabozantinib), Copiktra (Duvelisib), Cosmegen (Dactinomycin), Cotellic (Cobimetinib), Cyramza (Ramucirumab), CytosarU (Cytarabine), Cytoxan (Cytoxan), Cyclophosphamide, Dacogen (Decitabine), Darzalex (Daratumumab), DaunoXome (Daunorubicin Lipid Complex), Daurismo (Glasdegib), Decadron (Dexamethasone), DepoCyt (Cytarabine Lipid Complex), Dexamethasone Intensol (Dexamethasone), Dexpak Taperpak (Dexamethasone), Docefrez (Docetaxel), Doxil (Doxorubicin Lipid Complex), DTIC (Decarbazine), Eligard (Leuprolide), Ellence (Ellence (epirubicin)), Eloxatin (Eloxatin (oxaliplatin)), Elspar (Asparaginase), Emcyt (Estramustine), Emend (Fosaprepitant), Empliciti (Elotzumab), Erbitux (Cetuximab), Erivedge (Vismodegib), Erleada (Apalutamide), Erwinaze (Asparaginase *Erwinia chrysanthemi*), Ethyol (Amifostine), Etopophos (Etoposide), Eulexin (Flutamide), Fareston (Toremifene), Farydak (Panobinostat), Faslodex (Fulvestrant), Femara (Letrozole), Firmagon (Degarelix), FloPred (Prednisolone), Fludara (Fludarabine), Folex (Methotrexate), Folotyn (Pralatrexate), FUDR (FUDR (floxuridine)), Gazyva (Obinutuzumab), Gemzar (Gemcitabine), Gilotrif (Afatinib), Gleevec (Imatinib Mesylate), Halaven (Eribulin), Herceptin (Trastuzumab), Hexalen (Altretamine), Hycamtin (Topotecan), Hycamtin (Topotecan), Hydrea (Hydroxyurea), Ibrance (Palbociclib), Iclusig (Ponatinib), Idamycin PFS (Idarubicin), Idhifa (Enasidenib), Ifex (Ifosfamide), Imbruvica (Ibrutinib), Imfinzi (Durvalumab), Imlygic (Talimogene Laherparepvec), Inlyta (Axitinib), Intron A alfab (Interferon alfa-2a), Iressa (Gefitinib), Istodax (Romidepsin), Ixempra (Ixabepilone), Jakafi (Ruxolitinib), Jevtana (Cabazitaxel), Kadcyla (Ado-trastuzumab Emtansine), Keytruda (Pembrolizumab), Kisqali (Ribociclib), Kyprolis (Carfilzomib), Lanvima (Lenvatinib), Leukeran (Chlorambucil), Leukine (Sargramostim), Leustatin (Cladribine), Lorbrena (Lorlatinib), Lupron (Leuprolide), Lynparza (Olaparib), Lysodren (Mitotane), Matulane (Procarbazine), Megace (Megestrol), Mekinist (Trametinib), Mektovi (Binimetinib), Mesnex (Mesna), Mustargen (Mechlorethamine), Mutamycin (Mitomycin), Myleran (Busulfan), Mylotarg (Gemtuzumab Ozogamicin), Navelbine (Vinorelbine), Nerlynx (Neratinib), Neulasta (filgrastim), Neulasta (pegfilgrastim), Neupogen (filgrastim), Nexavar (Sorafenib), Nilandron (Nilandron (nilutamide)), Ninlaro (Ixazomib), Nipent (Pentostatin), Nolvadex (Tamoxifen), Odomzo (Sonidegib), Oncaspar (Pegaspargase), Oncovin (Vincristine), Opdivo (Nivolumab), Panretin (Alitretinoin), Paraplatin (Carboplatin), Perjeta (Pertuzumab), Platinol (Cisplatin), PlatinolAQ (Cisplatin), Pomalyst (Pomalidomide), Portrazza (Necitumumab), Proleukin (Aldesleukin), Purinethol (Mercaptopurine), Reclast (Zoledronic acid), Revlimid (Lenalidomide), Rituxan (Rituximab), RoferonA alfaa (Interferon alfa-2a), Rubex (Doxorubicin), Rubraca (Rucaparib), Rydapt (Midostaurin), Sandostatin (Octreotide), Soltamox (Tamoxifen), Sprycel (Dasatinib), Stivarga (Regorafenib), Sutent (Sunitinib), Sylvant (Siltuximab), Synribo (Omacetaxine), Tabloid (Thioguanine), Taflinar (Dabrafenib), Tagrisso (Osimertinib), Talzenna (Talazoparib), Tarceva (Erlotinib), Targretin Capsules (Bexarotene), Tasigna (Decarbazine), Taxol (Paclitaxel), Taxotere (Docetaxel), Tecentriq (Atezolizumab), Temodar (Temozolomide), Tepadina (Thiotepa), Thioplex (Thiotepa), Tibsovo (Ivosidenib), Toposar (Etoposide), Torisel (Temsirolimus), Treanda (Bendamustine hydrochloride), Trelstar (Triptorelin), Tykerb (lapatinib), Unituxin (Dinutuximab), Valstar (Valrubicin), Varubi (Rolapitant), Vectibix (Panitumumab), Velban (Vinblastine), Velcade (Bortezomib), Venclexta (Venetoclax), Vepesid (Etoposide), Vepesid (Etoposide Injection), Verzenio (Abemaciclib), Vesanoid (Tretinoin), Vidaza (Azacitidine), Vincasar PFS (Vincristine), Vincrex (Vincristine), Vistogard (Uridine Triacetate), VitrakvI (Larotrectinib), Vizimpro (Dacomitinib), Votrient (Pazopanib), Vumon (Teniposide), Wellcovorin IV (Leucovorin), Xalkori (Crizotinib), Xeloda (Capecitabine), Xospata (Gilteritinib), Xtandi (Enzalutamide), Yervoy (Ipilimumab), Yescarta (Axicabtagene), Yondelis (Trabectedin), Zaltrap (Ziv-aflibercept), Zanosar (Streptozocin), Zejula (Niraparib), Zelboraf (Vemurafenib), Zevalin (Ibritumomab Tiuxetan), Zoladex (Goserelin), Zolinza (Vorinostat), Zometa (Zoledronic acid) Zortress (Everolimus), Zydelig (Idelalisib), Zykadia (Ceritinib), and Zytiga (Abiraterone).

Linkages

The linkage between the agent(s) and the ssNA nanostructure connects the ssNA nanostructure and the agent and does not interfere with the function of the agent or the ssNA nanostructure. In some embodiments, chemistries that link the agent to an oligonucleotide can include or exclude disulfide linkages, amino linkages, and covalent linkages. In some embodiments, the linker can include or exclude aliphatic or ethylene glycol linkers. In some embodiments the linker can include or exclude phosphodiester, phosphorothioate and/or other modified linkages. In some embodiments, the linker is a binding pair. As used herein, the term "binding pair" refers to two molecules which interact with each other through any of a variety of molecular forces which can include or exclude ionic, covalent, hydrophobic, van der Waals, and hydrogen bonding, so that the pair have the property of binding specifically to each other. Specific binding means that the binding pair members exhibit binding to each other under conditions where they do not bind to another molecule. Binding pairs can include or exclude biotin-avidin, hormone-receptor, receptor-ligand, enzyme-substrate probe, IgG-protein A, antigen-antibody, aptamer-target and the like. In some embodiments, a first member of the binding pair comprises avidin or streptavidin and a second member of the binding pair comprises biotin. In some embodiments, a first member of the binding pair comprises nickel and a second member of the binding pair comprises a His-tag. In some embodiments, the binding pair is another affinity ligand interaction.

Therapeutic Agents to be Administered

In some embodiments, the therapeutic agent is thrombin. In some embodiments, the therapeutic agent is a tumor targeting agent. In some embodiments, the therapeutic agent is an RNAi molecule. In some embodiments, the RNAi molecule is selected from e.g. siRNA, shRNA, and miRNA.

Certain Definitions

As used herein, the term "about" means±10%.

As used herein, the term "knot" refers to a continuous or near-continuous double-stranded nucleic acid sequence embedded in 3-dimensional Euclidian space comprising a crossing number larger than zero. A crossing number is a knot invariant that shows the smallest number of crossings in any diagram of the knot, representing the topological complexity of a knot. The knot can be closed or open. An open knot comprises nucleic acid strands which are not fully ligated. In some embodiments, an open knot is also referred to as a "pseudoknot." An open knot comprises one or a plurality of 3' terminae and one or a plurality of 5' terminae. A closed knot comprises nucleic acid strands which are continuous. The nucleic acids can be selected from: DNA, RNA, or mixtures thereof. In some embodiments, the DNA comprises natural or unnatural DNA base-pairs. In some embodiments, the knots of this disclosure exclude compact structures wherein a first double-stranded nucleic acid strand is parallel to a second double-stranded nucleic acid strand because the compact structures will not facilitate the correct folding of DNA. In some embodiments, knots of this disclosure are constructed to exhibit wireframe networks which are better candidates for constructing knotted structures, because they offer more space for ssNA chains to thread through the structures. In some embodiments, the knot further comprises a plurality of hairpins with an extended quasi-continuous double-helical stem region.

As used herein, the term "knotted nanostructure" refers to a nanostructure comprising knots and a series of crossover events occurring in periodic order. In some embodiments, the periodic order is a single phase (e.g., ever 8 bp). In some embodiments, the periodic order comprises a plurality of phases (e.g., every 8 bp, and every 3 bp). In some embodiments, the periodic order comprises one, two, three, four, five, six, seven, eight, nine, or ten phases. In some embodiments, the phase is every 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or more basepairs (bp) in length. In some embodiments, the knotted nanostructure comprises a crossing number equal to zero, which is topologically equivalent to an unknotted circle.

In some embodiments, the knotted nanostructures are greater than 10 nm along any given axis of the nanostructure. In some embodiments, the knotted nanostructures are greater than 10, 20, 30, 40, 50, 60, 70, 80, 90, 100, 110, 120, 130, 140, 150, 160, 170, 180, 190, 200, 210, 22, 230, 240, 250, or higher nm along any given axis of the nanostructure.

As used herein, the term "operably-linked" refers to the association two chemical moieties so that the function of one is affected by the other, e.g., an arrangement of elements wherein the components so described are configured so as to perform their usual function.

As used herein, the term "nucleic acid" refers to deoxyribonucleotides or ribonucleotides and polymers thereof in either single- or double-stranded form, comprising monomers (nucleotides) containing a sugar, phosphate and a base that is either a purine or pyrimidine. Unless specifically limited, the term encompasses nucleic acids containing analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

As used herein, the terms "nucleotide sequence" and "nucleic acid sequence" refer to a sequence of bases (purines and/or pyrimidines) in a polymer of DNA or RNA, which can be single-stranded or double-stranded. In some embodiments, the nucleotide sequence comprises synthetic, non-natural or altered nucleotide bases, and/or backbone modifications (e.g., a modified oligomer, which can include or exclude a morpholino oligomer, phosphorodiamate morpholino oligomer or vivo-mopholino). The terms "oligo", "oligonucleotide" and "oligomer" may be used interchangeably and refer to such sequences of purines and/or pyrimidines. The terms "modified oligos", "modified oligonucleotides" or "modified oligomers" may be similarly used interchangeably, and refer to such sequences that contain synthetic, non-natural or altered bases and/or backbone modifications (e.g., chemical modifications to the internucleotide phosphate linkages and/or to the backbone sugar).

Modified nucleotides can include or exclude alkylated purines; alkylated pyrimidines; acylated purines; and acylated pyrimidines. These classes of pyrimidines and purines can include or exclude pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2-methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine. Backbone modifications can include or exclude chemical modifications to the phosphate linkage. The chemical modifications to the phosphate linkage can include or exclude e.g. phosphorodiamidate, phosphorothioate (PS), N3'phosphoramidate (NP), boranophosphate, 2',5'phosphodiester, amide-linked, phosphonoacetate (PACE), morpholino, peptide nucleic acid (PNA), inverted linkages (5'-5' and 3'-3' linkages)) and sugar modifications (e.g., 2'-O-Me, UNA, LNA).

The oligonucleotides described herein may be synthesized using solid or solution phase synthesis methods. In some embodiments, the oligonucleotides are synthesized using solid-phase phosphoramidite chemistry (U.S. Pat. No. 6,773,885, herein incorporated by reference) with automated synthesizers, herein incorporated by reference. Chemical synthesis of nucleic acids allows for the production of various forms of the nucleic acids with modified linkages, chimeric compositions, and nonstandard bases or modifying groups attached in chosen places through the nucleic acid's entire length. In some embodiments, the oligonucleotides described herein may be synthesized using enzymatic methods which can include adding single-bases via an enzyme.

Some embodiments of the invention encompass isolated or substantially purified nucleic acid compositions. As used herein an "isolated" or "purified" DNA molecule or RNA molecule refers to a DNA molecule or RNA molecule that exists apart from its native environment and is therefore not a product of nature. An isolated DNA molecule or RNA molecule may exist in a purified form or may exist in a non-native environment. In some embodiments, the non-native environment can include or exclude a transgenic host cell. In some embodiments, the terms "isolated" or "purified" includes a nucleic acid molecule which is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

By "portion" or "fragment," as it relates to a nucleic acid molecule, sequence or segment of the invention, when it is linked to other sequences for expression, is meant a sequence having at least 80 nucleotides, at least 150 nucleotides, or at least 400 nucleotides. If not employed for expressing, a "portion" or "fragment" means at least 9, at least 12, at least 15, or at least 20, consecutive nucleotides, e.g., probes and primers (oligonucleotides), corresponding to the nucleotide sequence of the nucleic acid molecules of the invention.

"Recombinant DNA molecule" is a combination of DNA sequences that are joined together using recombinant DNA technology and procedures to join together DNA sequences as described in Sambrook and Russell, Molecular Cloning: A Laboratory Manual, Cold Spring Harbor, NY: Cold Spring Harbor Laboratory Press ($3^{rd}$ edition, 2001), herein incorporated by reference.

"Homology" refers to the percent identity between two polynucleotides or two polypeptide sequences. Two DNA or polypeptide sequences are "homologous" to each other when the sequences exhibit at least about 75% to 85% (including 75%, 76%, 77%, 78%, 79%, 80%, 81%, 82%, 83%, 84%, and 85%), at least about 90%, or at least about 95% to 99% (including 95%, 96%, 97%, 98%, 99%) contiguous sequence identity over a defined length of the sequences.

The following terms are used to describe the sequence relationships between two or more nucleotide sequences: (a) "reference sequence," (b) "comparison window," (c) "sequence identity" (d) "percentage of sequence identity," (e) "substantial identity" and (f) "complementarity".

(a) As used herein, "reference sequence" is a defined sequence used as a basis for sequence comparison. A reference sequence may be a subset or the entirety of a specified sequence. In some embodiments, the specified sequence can include or exclude a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally is 30 contiguous nucleotides, 40 contiguous nucleotides, 50 contiguous nucleotides, 100 contiguous nucleotides, or longer. Those of skill in the art understand that to avoid a high similarity to a reference sequence due to inclusion of gaps in the polynucleotide sequence a gap penalty is typically introduced and is subtracted from the number of matches.

In some embodiments, methods of alignment of sequences for comparison are determined by mathematical algorithm. In some embodiments, the determination of percent identity, including sequence complementarity, between any two sequences is accomplished using a mathematical algorithm. In some embodiments, such mathematical algorithms can include or exclude the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993), all of which are herein incorporated by reference.

In some embodiments, computer implementations of these mathematical algorithms are utilized for comparison of sequences to determine sequence identity or complementarity. Such implementations can include or exclude: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al. (Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. A test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

Comparison of nucleotide sequences for determination of percent sequence identity may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, the terms "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. In some embodiments, the identity between any two nucletic acid sequences is 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, 95%, 96%, 97%, 98%, or 99%.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described herein using standard parameters.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. As used herein, the term "bind(s) substantially" refers to complementary hybridization between a probe nucleic acid and a target nucleic acid and embraces minor mismatches that in some embodiments is accommodated by reducing the stringency of the hybridization media to achieve the desired detection of the target nucleic acid sequence.

(f) The term "complementary" as used herein refers to the broad concept of complementary base pairing between two nucleic acids aligned in an antisense position in relation to each other. When a nucleotide position in both of the molecules is occupied by nucleotides normally capable of base pairing with each other, then the nucleic acids are considered to be complementary to each other at this position. Two nucleic acids are substantially complementary to each other when at least about 50%, at least about 60%, or at least about 80% of corresponding positions in each of the molecules are occupied by nucleotides which normally base pair with each other (e.g., A:T (A:U for RNA) and G:C nucleotide pairs).

As used herein, the term "derived" or "directed to" with respect to a nucleotide molecule means that the molecule has complementary sequence identity to a particular molecule of interest.

The term "subject" as used herein refers to humans, higher non-human primates, rodents, domestic, cows, horses, pigs, sheep, dogs and cats. In one embodiment, the subject is a human.

The term "therapeutically effective amount," in reference to treating a disease state/condition, refers to an amount of a therapeutic agent that is capable of having any detectable, positive effect on any symptom, aspect, or characteristics of a disease state/condition when administered as a single dose or in multiple doses. Such effect need not be absolute to be beneficial.

The terms "treat' and "treatment" refer to both therapeutic treatment and prophylactic or preventative measures, wherein the object is to prevent or decrease an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The invention will now be illustrated by the following non-limiting Example.

Example 1

Synthetic topological DNA nanostructures have previously been constructed by creating topological nodes based on B-form/Z-form double-stranded DNA (dsDNA) helices (J. E. Mueller, et al. *J Am Chem Soc* 113, 6306-6308 (1991); S. M. Du, et al. *J Am Chem Soc* 114, 9652-9655 (1992); S. M. Du, et al. *J Am Chem Soc* 117, 1194-1200 (1995); C. D. Mao, et al. *Nature* 386, 137-138 (1997)), paranemic crossovers (Y. P. Ohayon et al., *ACS Nano* 9, 10296-10303 (2015); Y. R. Ohayon et al., *ACS Nano* 9, 10304-10312 (2015)), and DNA four-way junctions (D. Liu, et al. *Nat Chem* 8, 907-914 (2016)). In contrast to the strategies that rely on the design of individual topological nodes and finding the appropriate DNA motifs/interactions with which to assemble such nodes, a completely different approach is to fold one long single-stranded DNA (ssDNA) chain into programmable topologies with periodic crossover events.

This disclosure includes a method for creating topological knots comprising single-stranded DNA (ssDNA) and/or single-stranded RNA (ssRNA) with high crossing numbers at periodic intervals. As used herein, the term "crossing" refers to a knot invariant that shows the smallest number of crossings in any diagram of the knot, representing the topological complexity of a knot (J. W. Alexander, *T Am Math Soc* 30, 275-306 (1928)). A crossing applied to ssDNA or ssRNA knots is the cross-hybridization of two separate strands resulting in a pair of double-helix structures. The number of "crossings" in a NA nanostructure is the "crossing number," Each of the ssDNA or ssRNA knots are folded and then self-assembled from a replicable single-stranded nucleic acid molecule with sizes ranging from 1800 to 7500 nucleotides (nt). In some embodiments, this disclosure includes the design, construction, and characterization of various ssDNA knotted nanostructures that had different crossing numbers and that displayed two-dimensional (2D) patterns. The folding yield of the knotted nanostructures was optimized by programming a step-wise hierarchical folding pathway through sequence design in the paranemic cohesion regions. In some embodiments, the method further comprises a series of design rules to significantly improve the yield of well-formed target nanostructures. In some embodiments, the target nanostructures can include or exclude ssRNA knotted nanostructures and three-dimensional (3D) ssDNA knotted nanostructures. In some embodiments, the 3D knotted nanostructures were characterized by cryogenic transmission electronic microscopy (cryo-EM) single particle reconstruction, which confirmed that the nanostructures had assumed the designated geometry.

Enzymatically transcribed and replicatable knotted nanostructures, comprising single-stranded nucleic acids that can self-fold into molecular knots of customized shapes, enables significant reduction in the cost of production of a multi-stranded DNA nanostructure system created from synthetic DNA. In some embodiments, the single-stranded topology enables for the selection and generation of knotted nanostructures with designed functions by using in vitro evolution. This disclosure further provides for a fundamental and general platform for constructing nucleic acids nanostructures with unprecedented complex molecular topologies.

DNA parallel crossover motifs were used as the modular building blocks with a node-edge network as the geometric blueprint to create ssDNA knotted nanostructures. Unlike DNA antiparallel double crossover motifs that contained localized ssDNA, all of the strands of a parallel crossover motif have both 5' and 3' ends that are extended to the terminals, which in some embodiments can be readily connected with other motifs into one long single strand. The use of a parallel crossover motif as the structural building block provides a basic geometric foundation that enables single-stranded routing.

Figure 1A:
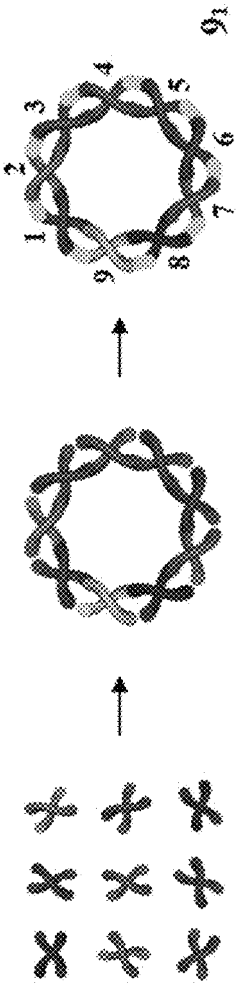
FIGS. 1A-1D. Design of single-stranded DNA/RNA knots. A knot with a crossing number of 9 is constructed via one of two methods.
Figure 1B:
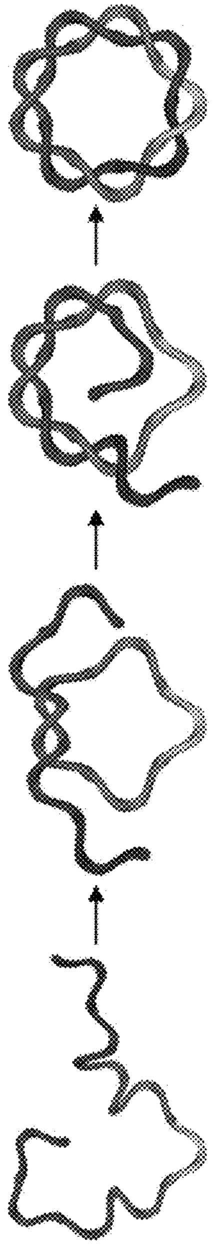
Figure 1C:
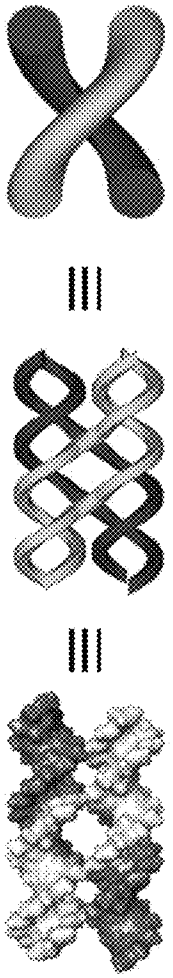
Figure 1D:
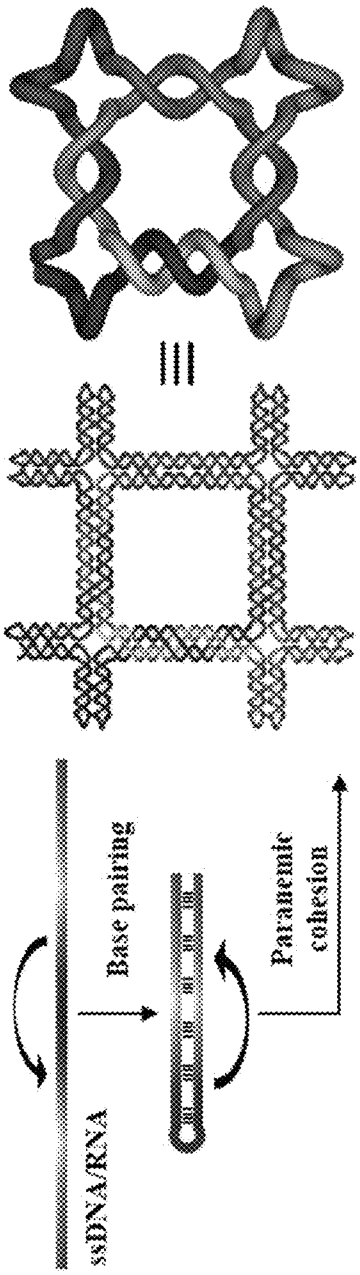

In comparison with the compact parallel or antiparallel helical arrangements, wireframe networks are better candidates for constructing knotted nanostructures, as they offer more space for DNA chains to thread through during the early formation of partial structures. In some embodiments, knot $9_1$ (Alexander-Briggs notation) is assembled by either connecting 9 right-handed X-shaped junction tiles together, as shown in FIG. 1A or by threading a single chain through itself 9 times, as shown in FIG. 1B. Two parallel crossovers were separated by 4 or 6 base pairs to form an X-shaped topology, which represented one cross node in a knot, as shown in FIG. 1C. The 9 X-shaped DNA tiles were configured to be in the pattern of a square with 2, 2, 2, and 3 crossings on the four edges, respectively, as shown in FIG. 1D, and separated the adjacent junctions by 1 turn (10 or 11 bp) or 2 turns (21 bp) of the double stranded DNA. After connecting the nearest DNA strands and adding small linking structures at the four vertexes, the resulting design consisted of only one long ssDNA, as shown in FIGS. 6A-6D and FIG. 1D. The overall routing of the ssDNA was configured as a two-step process. First, half of the DNA chain folded back to partially pair with the other half of the DNA, leaving several unpaired single-stranded regions (~4-6 nts) in between the perfectly paired regions (~10, 11 or 21 bps). Then, the unpaired regions matched to each other by paranemic cohesive interactions and finally knotted into the target topology, as shown in FIG. 1D.

Figures 2A, 2B, 2C, 2D, 2E:
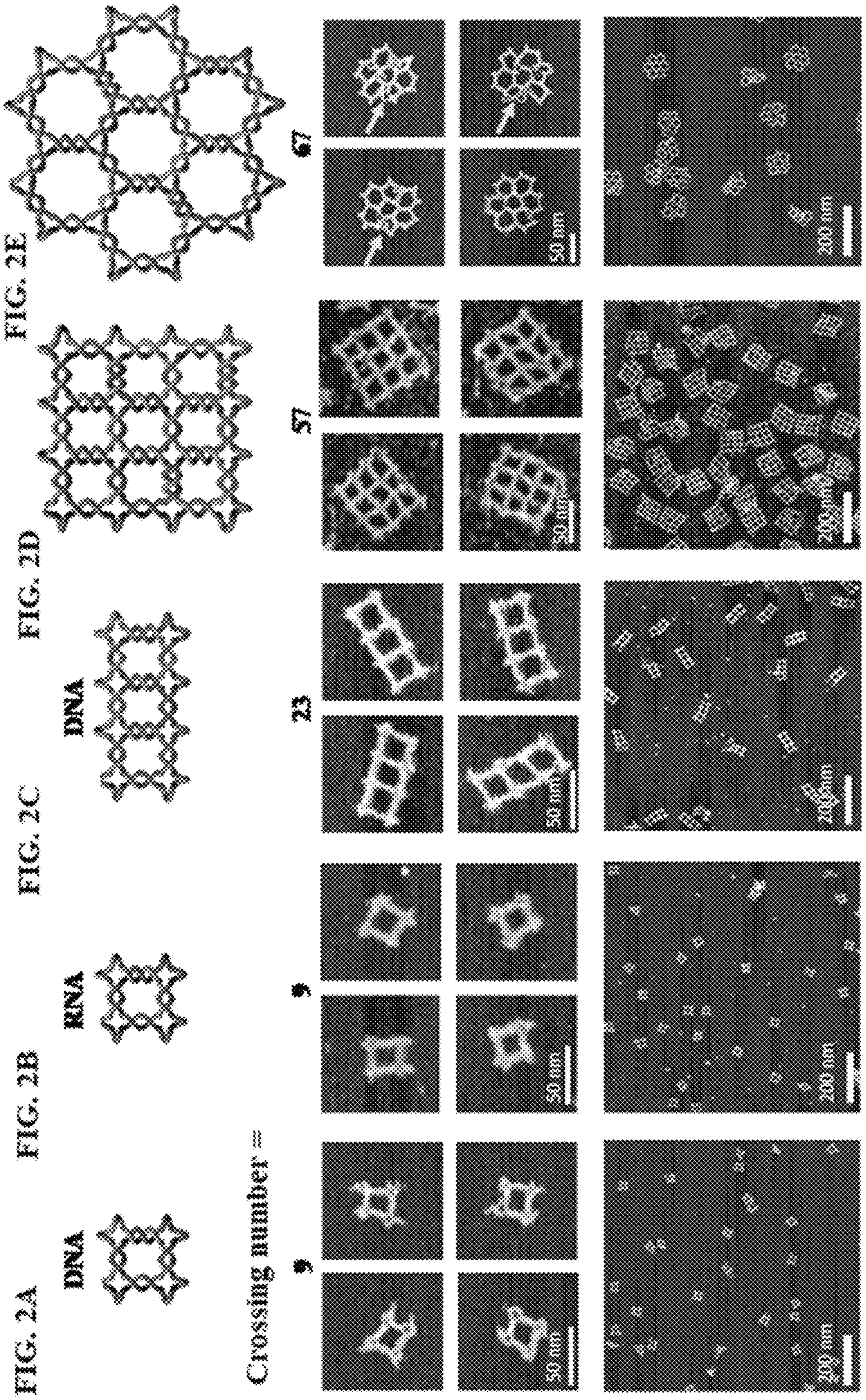
FIGS. 2A-2E. Design and AFM characterization of two-dimensional single-stranded DNA and/or RNA knots. Designer models (top row) for the 2D nanostructures and their corresponding AFM images (middle row shows the zoomed-in images and bottom row shows the zoomed-out images) with increasing crossing numbers.
Figure 7A:
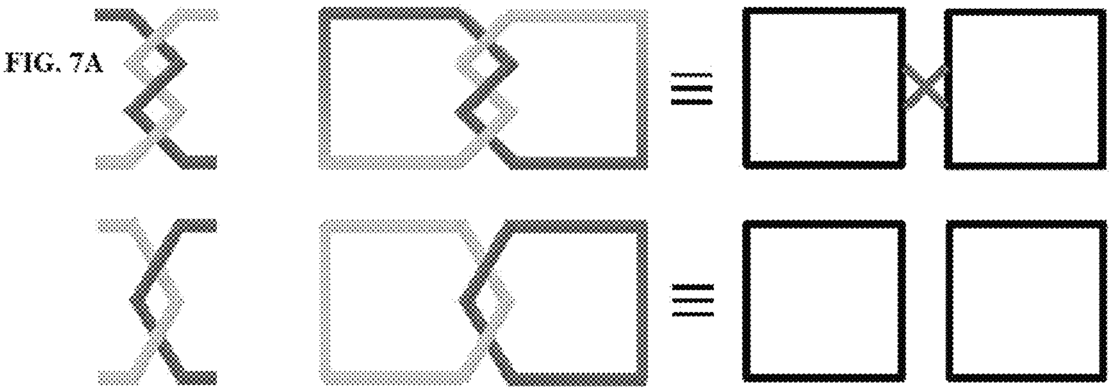
FIGS. 7A-7B. A schematic of the folding pathway design.
Figure 7B:
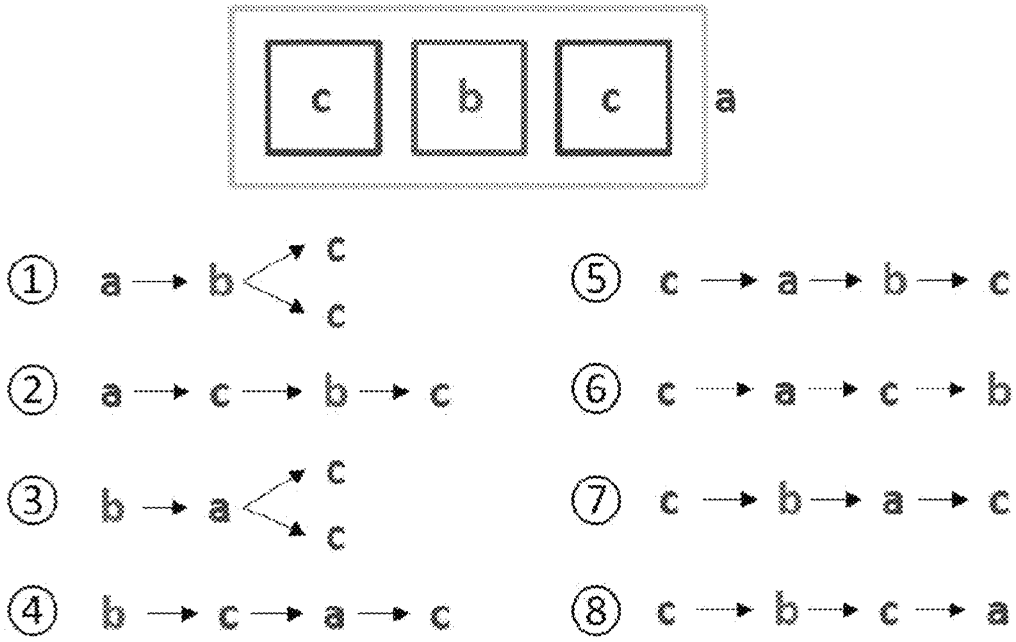

In some embodiments, the method comprises designing a topologically and kinetically favorable folding pathway for the successful formation of complex structures with high crossing numbers, optionally with periodic crossings. The inventors designed a hierarchical folding strategy to guide the knotting process in a prescribed order. In some embodiments, a knot with 23 crossings was assigned to a location on a three-column grid that is represented by a rectangle with three square cavities, as shown in FIG. 2C. To maintain the structural stability and rigidity of each edge, the length and number of crossings on each edge was limited: in any six turns (63 bp) of a double helical DNA, only two or three crossings were allowed. In total, 23 crossings were assigned on the 10 edges, in which seven edges had two crossings and three edges had three crossings, as shown in FIG. 2C. In some embodiments, the folding pathway order was varied as shown in FIGS. 7A-7B. All of the possible combinations for the formation order of the crossings in the knot are listed and compared for their routing pathways, as shown in FIGS. 7A-7B.

Figure 8A:
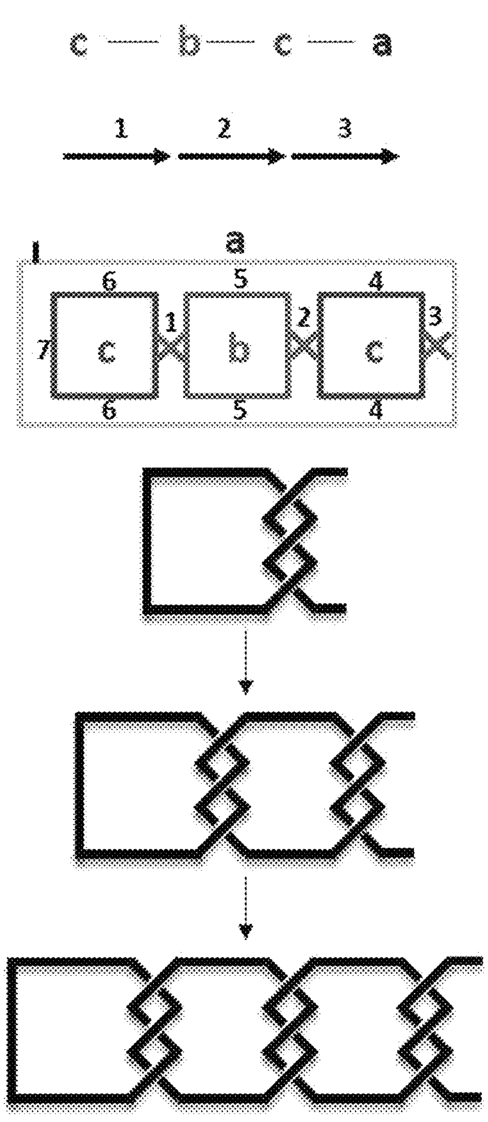
FIGS. 8A-8B. A comparison between a linear folding pathway (FIG. 8A) and a branched folding pathway (FIG. 8B). According to the connection relationship between the loops, a to c, the edges were designed with either 3 crosses or 2 crosses, (with the total number of the crosses being an odd number), to form the knot. The edges with 3 crosses are marked with an X. These edges form earlier than the edges with 2 crosses, due to the annealing step and the difference in the strength of the paranemic cohesions involved. The pathways represent the order of the formation of the three cross edges, i.e. the formation of the corresponding loops. The direction of the linear pathway c-b-c-a (FIG. 8A) is reversed as a-c-b-c without changing the relationships of loop connection. However, these two linear pathways are not equivalent. The loop sequence c-b-c-a was identified as a preferred direction because the two ends will not need to thread into any preformed loops during the early steps, which is when the unfolded strand is still long. For the branched pathway (FIG. 8B), the two ends need to be separated after forming the first 3-cross edges. Each end then travels individually and threads through a preformed loop (the central one) to create the 2-cross edges to form the loops on the sides. The branched path is expected to be less favorable than the linear one because the formation of the 2-cross edges is expected to occur later than the 3-cross edges due to thermodynamic reasons. Among the linear paths, the path should avoid threading through pre-formed structures when the unfolded strand is long. Due to these reasons, path 5 (depicted in FIG. 8A) is more efficient at forming self-assembled knotted nanostructures better than paths 3 or 4 shown in FIGS. 7A-7B.
Figure 8B:
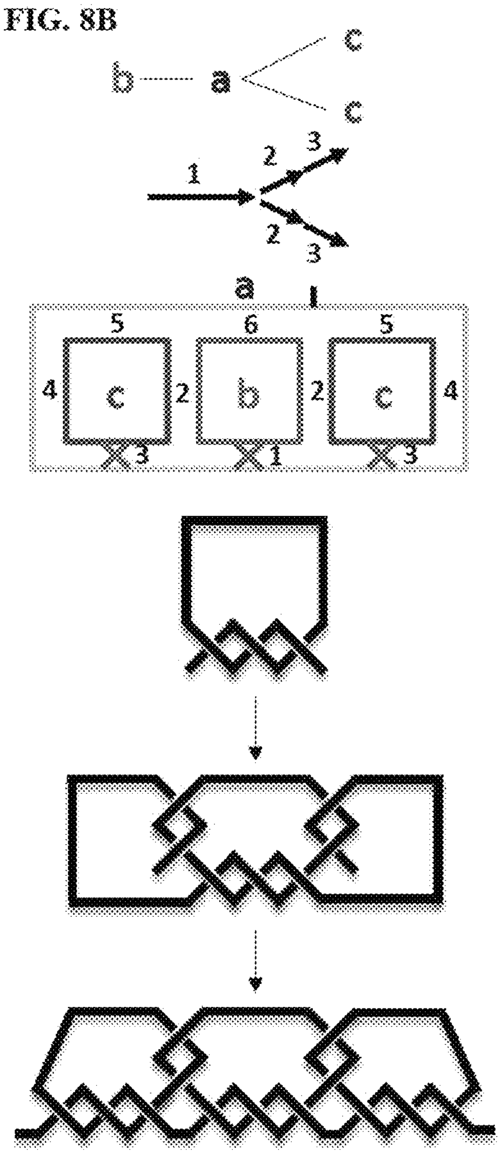
Figure 10A:
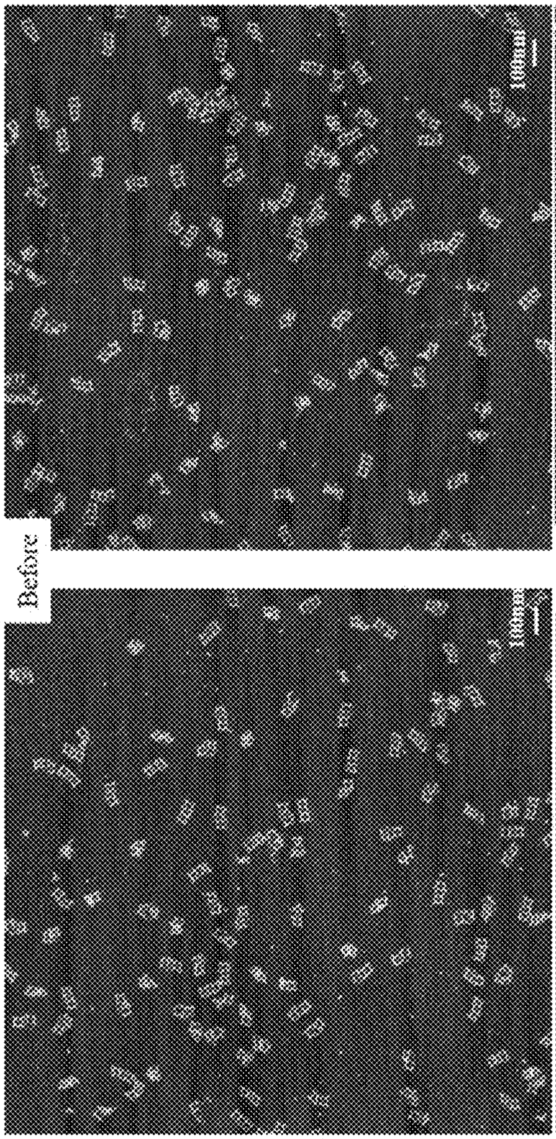
FIGS. 10A-10B. A comparison between the yield of the three-square knot structure 91 and the different folding pathways, via the use of AFM imaging. With an unfavorable folding pathway (FIG. 10A), the folding yield is only 0.9% (2/221). With the best folding pathway (FIG. 10B), the folding yield is increased to 57.9% (124/214). As used herein, the term "folding yield" refers to the number of nanostructures which have adopted the designed nanostructure compared to the number of nanostructures which have not adopted the designed nanostructure.
Figure 10B:
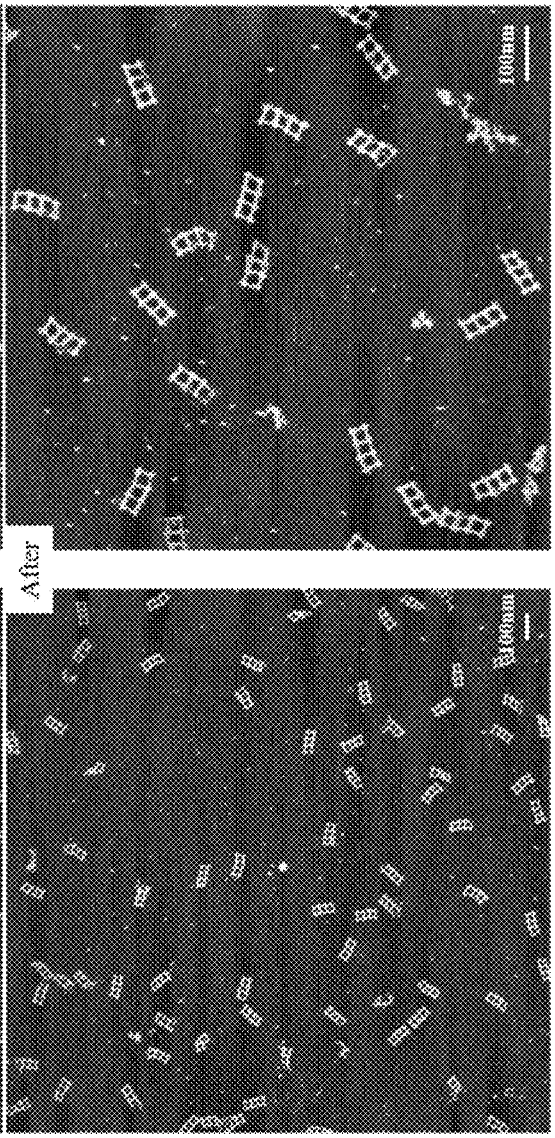

In some embodiments, the method comprises three design rules for optimizing the folding pathway: First, a linear folding path is better than a branched one, because the linear folding pathways involve two free ends that thread to form the loops in a sequentially ordered pathway, while the branched folding pathways have parallel steps that each involves a single free end to thread through the preformed loops. Based on an entropic point of view, the formation of two free ends looping with each other is expected to be easier than one free end threading itself through preformed loops, as shown in FIGS. 8A-8B. Second, a linear folding pathway has two possible folding directions, forwards or backwards. The best folding direction is determined in the early stage of folding when the unfolded portion of the strand is still long, and the strand avoids threading itself through any preformed structures, as shown in FIGS. 8A-8B. Third, it is expected that the edges with three crossings should fold before the edges with two crossings, since the cohesion force provided by three paranemic interactions (totally 12-18 bp) is expected to be stronger than that from two paranemic interactions (totally 8-12 bp). From the crossing positions and the grid layouts, the route for the chain threading is determined by specifying the order in which the chain visits each vertex and knots on each edge. FIG. 3A and FIGS. 9A-9D show the selected folding pathway for the three column grid knots. The folding yield of the two types of scaffold routings were compared by AFM imaging as shown in FIGS. 10A-10B. The selected linear folding pathway produced 57.9% (N=214) well-formed knotted NA nanostructures, while the branched pathway showed a yield as low as 0.9% (N=221).

The next step in the design procedure was to assign an appropriate sequence to enable the long ssDNA to create the structural and topological complexity. The inventors surprisingly discovered several criteria for generating a valid raw sequence: First, the ideal percentage of GC content in all regions of the DNA sequences was determined to be between 30% and 70%, since any GC content outside of this range would adversely affect the DNA synthesis. Second, depending on the size of the ssDNA, every segment that was 6-8 bases long was treated as one unit, to evaluate the uniqueness of the DNA sequence. The specificity of recognition between the designed base pairings rely on the uniqueness of the DNA sequences. Third, the repeating length of G was limited to 4 nt. A raw sequence was obtained by using the inherent algorithm of the Tiamat software, and in adherence with these rules. Then, the raw sequence was inspected manually and several modifications were made: The local sequences that form the paranemic crossovers were checked to make sure that each of the crossovers were stable; the GC content in each of the paranemic cohesion regions were designed individually and inter-dependently as they needed to be compared with one another. It was necessary that all of the paranemic cohesions would have a sequentially decreasing melting temperature, ordered according to the predetermined folding pathway. Lastly, the uniqueness of the paranemic cohesions was optimized independently, such that mismatches and cross-talking in the second step of the folding were minimized.

Figure 11A:
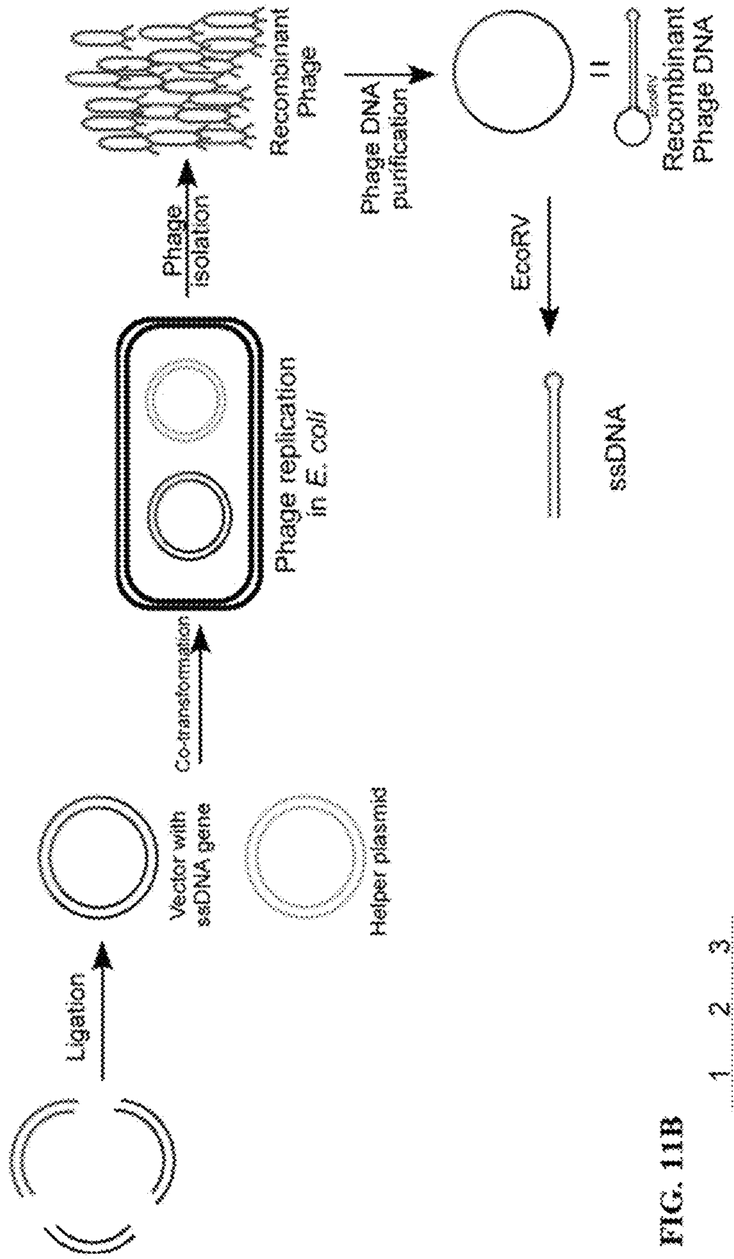
FIGS. 11A-11B. The replication and production of an ssDNA by using a recombinant M13 phage.
Figure 11B:
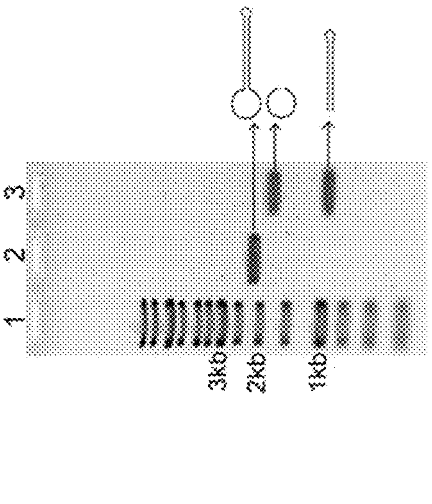
Figure 12A:
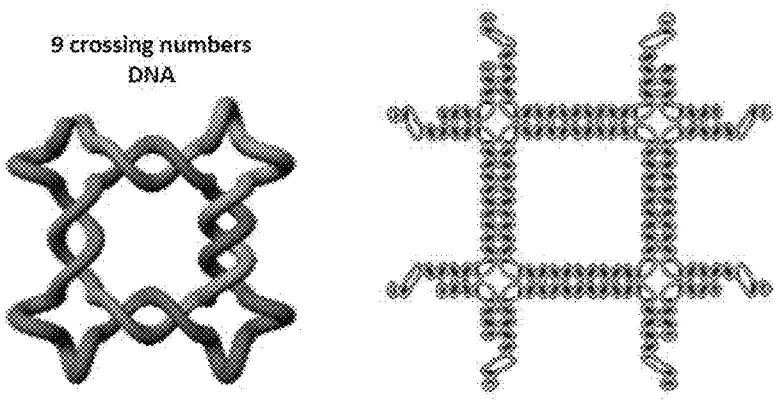
FIGS. 12A-12B. The design and characterization of the square knotted DNA nanostructure $9_1$.
Figure 12B:
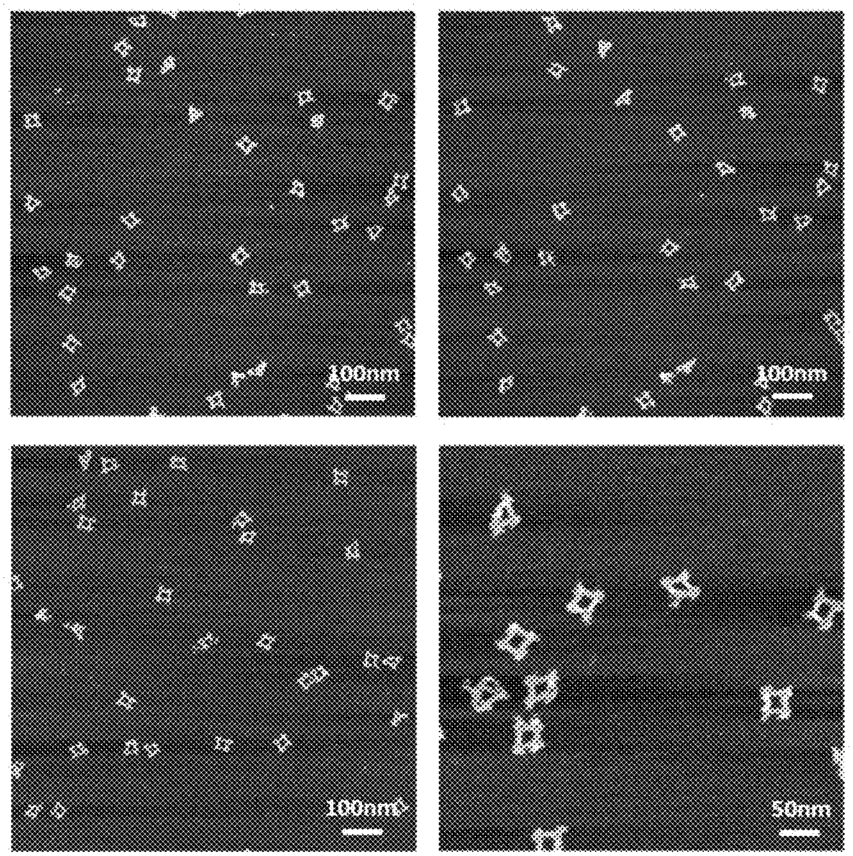

Both the chemical and enzymatic synthesis of long ssDNA molecules are technically challenging, because the chain possesses a large portion of self-complementarity. As shown in the folding pathway, the ssDNA molecule will first form a long hairpin structure with the 5' and 3' ends meeting each other. The full-length ssDNA strand was divided into two equal halves, with each strand lacking significant secondary structures. Each half was then inserted into plasmids as double stranded genes, and then amplified them by cloning. The two dsDNA genes were obtained separately from the plasmids by restriction enzymes digestion (EcoRI+XbaI and XbaI+HindIII respectively) and were then ligated together with a linearized phagemid vector, pGEM-7zf(−), as depicted in FIG. 11A. To obtain the full-length ssDNA molecule, the recombinant M13 phage was replicated in *E. coli* with the assistance of a helper plasmid, pSB4423 (A. N. Marchi, et al., *Nano Lett* 14, 5740-5747 (2014), herein incorporated by reference). Because the helper plasmid, pSB4423, does not contain a phage replication origin, only the phagemid vector containing the full-length ssDNA gene was able to act as a template for the phage DNA replication. After the extraction and purification of the recombinant phage DNA, EcoRV digestion was performed to cut out the target ssDNA, as shown in FIG. 11A. Native agarose gel electrophoresis was used to separate the target ssDNA from the phagemid vector ssDNA, as shown in FIG. 11B. The long ssDNA strands were synthesized and amplified at a nanomole quantity (with 1 L scale of *E. coli* culture) and high purity using the aforementioned method. The ssDNA strand was obtained, then self-assembled (folded) in a 1×TAE-Mg buffer with a 12 hour or 24 hour annealing ramp from 65° C. to 25° C.). The folded products were then characterized by using AFM imaging, gel electrophoresis and/or cryo-EM imaging.

Figure 13A:
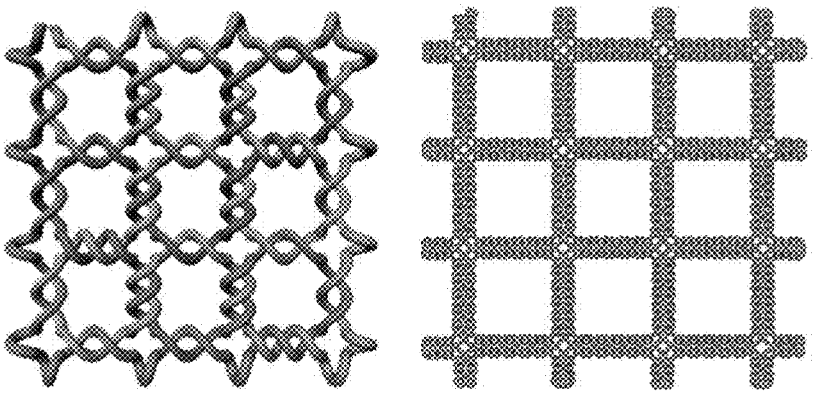
FIGS. 13A-13B. The design and characterization of the 9-square knotted DNA nanostructure.
Figure 13B:
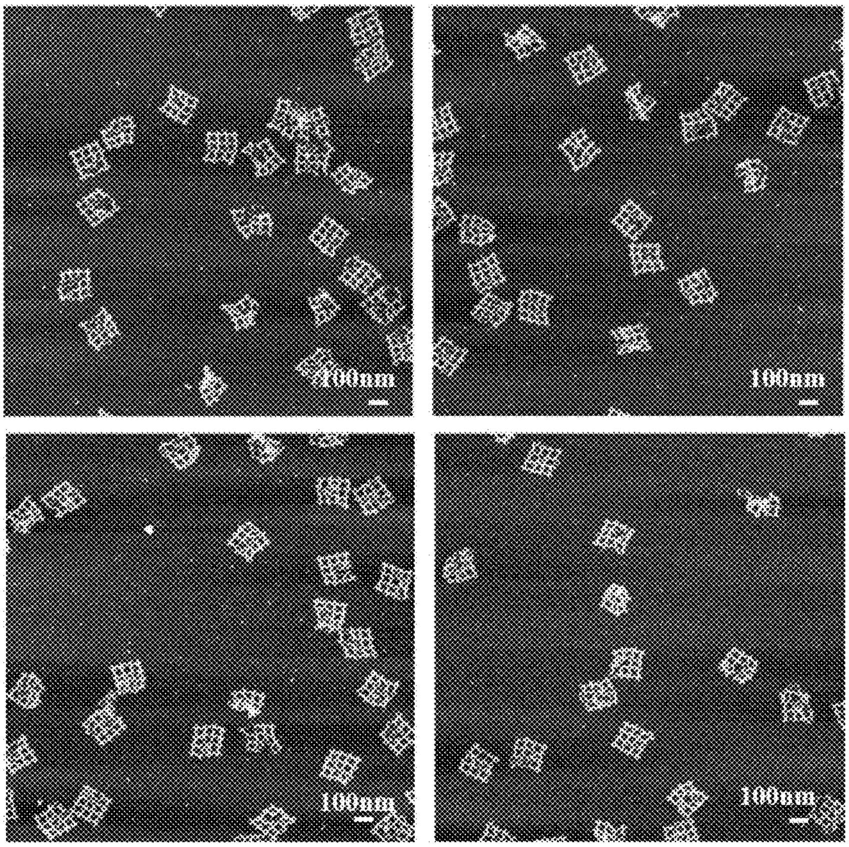
Figure 14A:
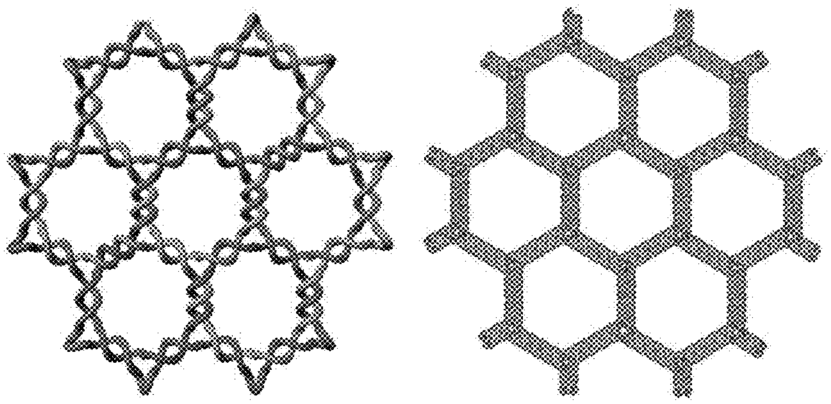
FIGS. 14A-14B. The design and characterization of the hexagonally knotted DNA nanostructure.
Figure 14B:
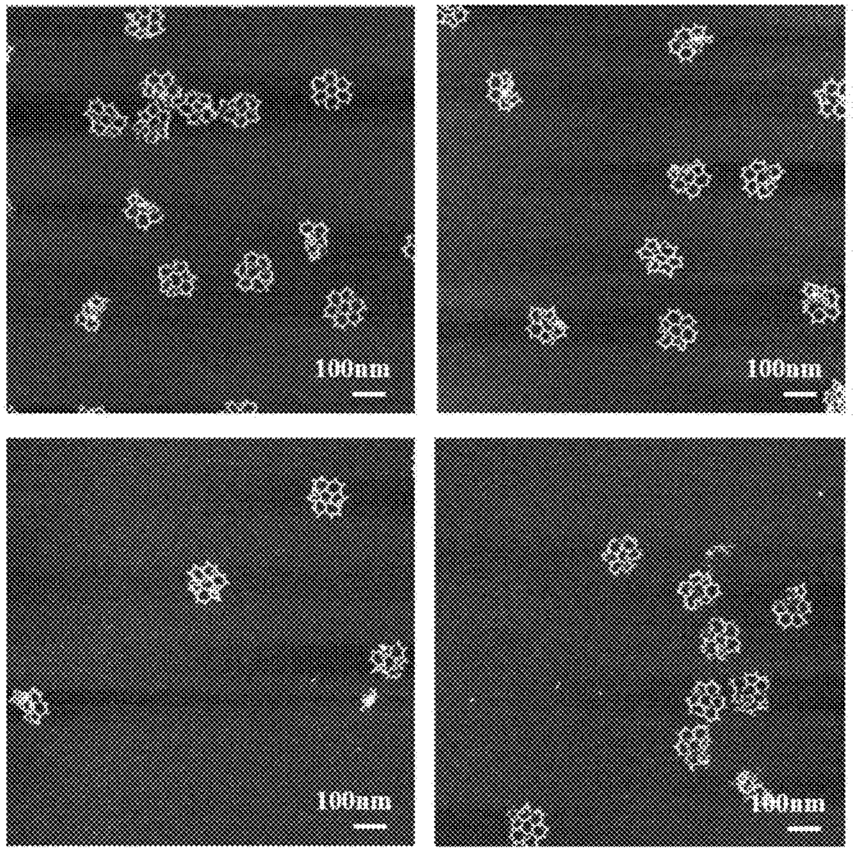

In some embodiments, this disclosure provides for methods of creating complex DNA knotted nanostructures with increasing crossing numbers. A 3 by 3 square grid of DNA knots with 57 crossed nodes was designed with an optimized linear folding pathway, as shown in FIG. 2D and FIG. 13B. Other geometric layouts were also used following similar design principles. A large molecular knot with 67 crossings in a hexagonal lattice was also designed and constructed. High resolution AFM images confirmed the successful formation of the target nanostructures, as shown in FIG. 2E and FIG. 14A-14B.

Smaller knot nanostructures with crossing numbers 9 and 23 folded well with yields as high as 69% (N=103) and 58% (N=214), respectively, as shown in FIGS. 2A& C, 12A-12B and 10A-10B. However, as the crossing number of the knot increased to 57 or 67, the folding yield dropped significantly and in the images, only 1.2% of the resulting nanostructures were perfectly formed with the 57 crossing number (N=327) and none of the resulting nanostructures were perfectly formed with the 67 crossing numbers (N=58) based on single molecule analysis by high-resolution AFM imaging, as shown in FIGS. 2D&E, 13A-13B and 14A-14B. Most of the formed nanostructures examined exhibited some degree of various folding defects, as shown in FIGS. 2D-2E. With such a high complexity, even the hierarchical folding optimization did not significantly increase the overall yield, as shown in FIGS. 15A-15C. The folding behaviors in the ssDNA knotted nanostructures were remarkably different than that of the classic DNA nanostructures. To make the target knotted nanostructure, the ssDNA chain needed to fold following an exactly defined order. If one crossing was misfolded in an earlier stage, it would be impossible (or at least extremely difficult) for it to correct itself afterwards. The yields of those knotted nanostructures were not surprisingly low when compared to the yields of the chemical synthesis reactions that contained multiple steps. The average yield for each knotting step (crossing step) was at least 90%, and in the low crossing number cases, the single step yield was as high as ~96%.

Figure 16A:
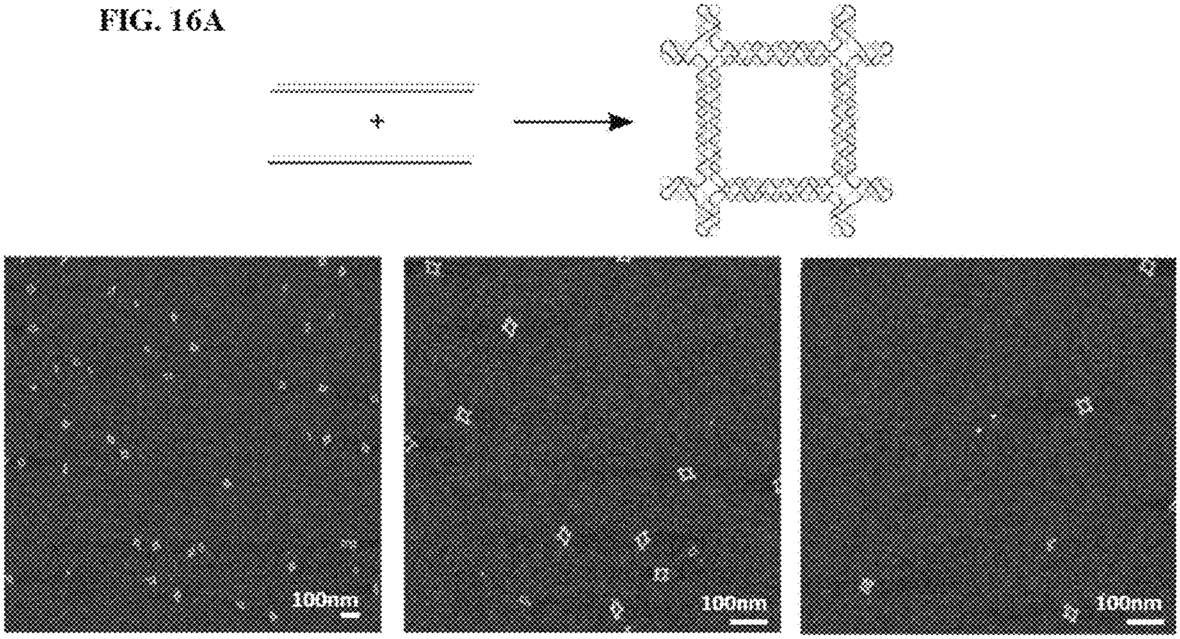
FIGS. 16A-16B. Topological control with linear and circular DNA.
Figure 16B:
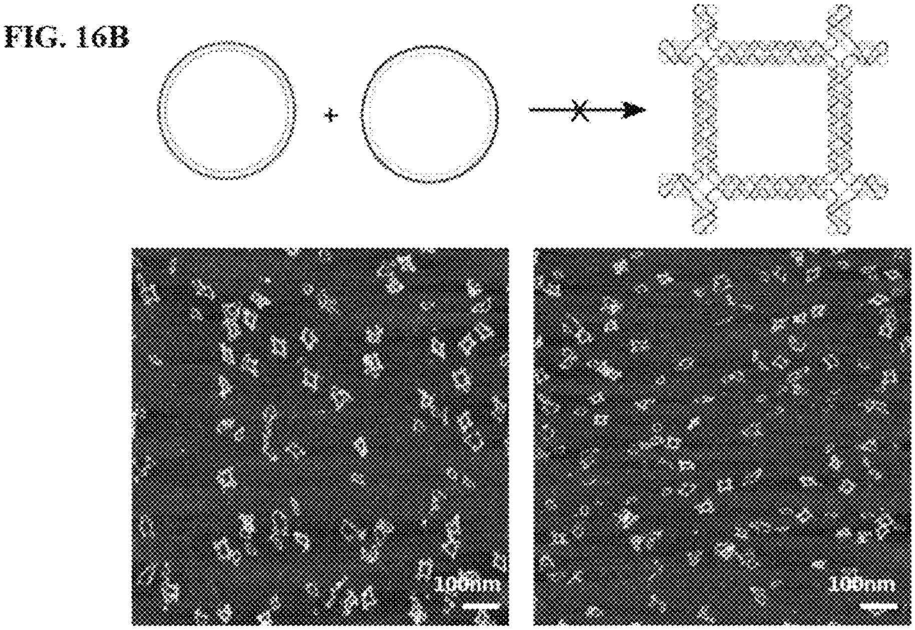

As most of the high crossing number (57 and 67) ssDNA knotted nanostructures were characterized by high resolution AFM imaging, as shown in FIGS. 2A-2E, one question was raised: whether or not the formation of the defected nodes in the final knotted nanostructure could be truly and completely identified with AFM imaging. A link structure was designed with 8 nodes as a topological control, as shown in FIGS. 4A-4B. The aforementioned link structure contained 2 dsDNA rings (each only partially complementary), which connected to each other through 8 paranemic cohesions. The aforementioned structure was formed by annealing two linear dsDNAs (each pre-formed from two ssDNAs) with 8 stretches of mismatches (bubbles) 6 nt each, as shown in FIGS. 4A-4B and FIGS. 16A-16B. The mismatches within these two linear dsDNAs would interact with their counterparts to form the stable paranemic cohesions. 9-bp sticky ends that extended from both ends of the dsDNAs closed the two rings after the formation of the correct structure. This link structure assembled well, as characterized by high resolution AFM imaging, as shown in FIG. 4A. On the contrary, if the two linear dsDNAs were first ligated to form closed ring structures, these two dsDNA rings would not be able to assemble into the fully interlocked loop nanostructure. As expected, although the two dsDNA rings could still bind with each other partially through some of the paranemic cohesion interactions, as shown in FIGS. 4B and 16A-16B, extensive defects were observed in all of the nanostructures, as shown in FIGS. 3A-3D and 16A-16B, which resembled those observed in FIGS. 2C and D with high crossing numbers. This experiment confirmed that the defects observed for the NA knotted nanostructures with high crossing numbers under high resolution AFM imaging were real defects that were due to mis-formed crossings, but not due to the scratching or damaging of the nanostructures by the AFM tip.

In some embodiments, this disclosure provides for methods of creating ssRNA knotted nanostructures. An X-shaped RNA modular building block was designed, which was similar to the structures of DNA. Then, based on the 3D modeling of an A-form dsRNA helix (11 bp per helical turn, 19 degree inclination of base pairs) and the best geometric fitting, 8 (instead of 4 or 6) base pairs were chosen for the length of a paranemic crossover, as shown in FIGS. 17A-17C. For an 8 base-pair paranemic cohesion, a total of $4^8$=65536 possible sequences provided an adequate sequence space for the selection of unique complementarity to sufficiently avoid undesired interactions between the paranemic cohesion motifs. Second, given the 11 base pairs per turn of an A-form dsRNA, the lengths of the inter-motif stems were designed as alternating between 8 and 9 bp, as shown in FIGS. 17A-17C to achieve a structural repeating unit of 33 bps for three full helical turns (i.e. 8 bp+8 bp stem+8 bp+9 bp stem=33 bp=3 full turns). In this design the neighboring structural units were in line with each other without accumulating helical twist, and the final assembled nanostructure was expected to stay in 2D. Like the ssDNA $9_1$ knot, 2, 2, 2, and 3 crossings on the four edges of a square were designed and the vertexes were looped to form one single-stranded RNA, as shown in FIG. 2B. After generating the appropriate sequences by following the same sequence design rules as the ssDNA knotted nanostructures, the dsDNA gene coding for the long RNA strand was first synthesized, and then the ssRNA molecule was obtained by an in vitro transcription reaction. After annealing, the AFM images revealed the successful formation of the ssRNA $9_1$ knots, as shown in FIG. 2B and FIGS. 17A-17C.

In some embodiments, this disclosure provides for methods of creating 4 ssDNA polyhedral meshes as knotted NA nanostructures: a tetrahedron, a pyramid, a triangular prism, and a pentagonal pyramid with crossing numbers 15, 20, 22, and 25, respectively, as shown in FIGS. 5A-5D. A schlegel diagram was used to transfer the 3D objects to their topologically equivalent 2D nets. Optimized folding pathways were designed carefully for step-wise hierarchical assembly and the corresponding ssDNA strands were designed, synthesized, and assembled. AFM images showed an abundance of well-folded 3D nanoparticles with the expected sizes, as shown in FIGS. 18A-18D, 19A-19C, 20A-20B, and 21A-21C. Single particle cryo-EM 3D reconstruction revealed that the overall conformations matched the designed geometries well, as shown in FIGS. 5A-5D and FIGS. 22A-22D and 23A-23C. The vertex design for the ssDNA knotted nanostructures was different from the multi-arm junction design based on the double crossover (DX) motif. There is a 5 bp difference in length between the two parallel dsDNAs that form each edge, leading to chiral vertices and inclined edges in the ssDNA knotted nanostructures, as shown in FIGS. 5A-5D. In some embodiments, the foregoing unique geometric feature can identify conformational diastereomers, which is when the structure is turned inside out, while satisfying all programmed Watson-Crick base pairing with the same network connectivity. The 3D reconstruction data indicated that the ssDNA knots preferred to point the major grooves inwards at the vertices.

In some embodiments, this disclosure provides for a method of folding single-stranded nucleic acids with completely custom-designed sequences to create ssDNA/ssRNA knotted nanostructures with highly complex topologies that are programmable, potentially replicable, and scalable. In some embodiments, the ssDNA knots described herein comprise one single routing strand that has high crossing numbers without the help of any auxiliary DNA. Various 2D and 3D shapes have been designed and successfully constructed with a surprisingly high yield (~96%) of crossing steps. The same strategy has also been adapted for the design and construction of complex ssRNA knotted nanostructures. The ssDNA knotted nanostructures described herein comprise large DNA sequences (up to 7.5 k bases) and highly complicated topology (as high as 67 crossing number).

In some embodiments, the method comprises the single-stranded folding process of nucleic acids. In some embodiments, the folding process is replicated and amplified in biological systems for cost-efficient, large scale production. In some embodiments, the single-stranded folding process is programmed in nucleic acid synthesis in target cells to produce nanostructures that harness functions in vivo.

In some embodiments, this disclosure provides for methods of using programmable ssDNA and ssRNA knots that enable the construction of engineered molecular devices and multivalent aptamers to use in directed evolution methods.

Materials and Methods

DNA/RNA Sequence Design

DNA and/or RNA nanostructures and sequences were designed using the Tiamat software (Yanlab.asu.edu/Tiamat.exe) (S. Williams et al., Tiamat: A Three-Dimensional Editing Tool for Complex DNA Structures. 5347, 90-101 (2009)).

DNA and/or RNA sequences were generated by using the following criteria in the Tiamat software: (1) Unique sequence limit: 8 nt; (2) Repetition limit: 6-8 nt; (3) G repetition limit: 4 nt; (4) GC content: 0.45-0.55. Once sequences were generated, a few nucleotides were adjusted to eliminate the restriction enzyme targeting sequences (e.g. by EcoRI, EcoRV, HindIII and XbaI) for cloning purposes. Then, the raw sequences of the paranemic cohesion regions were inspected manually and several modifications were made: the local sequences that form the paranemic crossovers were checked to make sure that each of the crossovers were stable; the GC content in each paranemic cohesion region were designed individually and inter-dependently as they needed to be compared with one another so that all of the paranemic cohesions would have a strength that was ordered sequentially according to a predetermined folding pathway; lastly, the uniqueness of the paranemic cohesions was optimized independently, so that the occurrence of mismatches and cross-talking in the second step of the folding process were minimized. For ssRNA sequences, a T7 promoter sequence was followed by two or three consecutive Gs that were manually incorporated onto the 5' end of the strand to facilitate efficient in vitro transcription reactions during gene synthesis.

ssDNA/RNA Synthesis

The ssDNA sequences described herein were divided into two fragments with restriction sites added onto both ends. The first fragment contained EcoRI and XbaI restriction sites and the second one contained XbaI and HindIII restriction sites. The EcoRV sites were also manually added to both ends of the full-length sequence to facilitate the production of the final ssDNA. The two DNA fragments that were ordered as double stranded genes in plasmids were from Biobasic Company (Biobasic.com) with sequences that were verified through Sanger sequencing. The two DNA fragments that were cleaved from the plasmids by the restriction enzymes were then subcloned into an EcoRI and a HindIII linearized pGEM-7zf(−) vector (Promega). After sequencing verification, the pGEM-7zf(−) vector that contained the full ssDNA genes was co-transformed into *E. coli* DH5u competent cells along with a helper plasmid pSB4423, a kind gift from Dr. Stanley Brown (Niels Bohr Institute, Denmark). *E. coli* colonies were formed after overnight incubation at 37° C., and a single colony was inoculated into the 2xYT medium that had been supplemented with 2 mM $MgSO_4$ (Sigma-Aldrich) and grown at 37° C. overnight with shaking at 250 rpm. During the overnight growth, the recombinant M13 phages were continuously produced and secreted into the medium. During the next day, the culture was centrifuged at 5,000 g for 15 min to pellet down the *E. coli* cells. The recombinant M13 phage was precipitated from the recovered supernatant with the addition of NaCl (to 30 g per liter) and PEG8000 (to 40 g per liter), and incubated in the 4° C. cold room for 1 hour. The precipitated phage was then collected by centrifugation at 4,500 g and 4° C. for 15 min. The recombinant phage DNA was isolated from the harvested phage. The phage ssDNA was digested by EcoRV enzyme (New England Biolabs) and resolved on a 1% agarose gel. The correct bands were sliced and purified by using a Monarch DNA Gel Extraction Kit (New England Biolabs).

For the ssRNA molecule synthesis, the DNA sequence with a T7 promoter at the 5' end was first cloned into a pUC19 vector by using the same method as the ssDNA gene cloning process that was described above. The plasmid containing the ssRNA gene was linearized by using a HindIII enzyme (New England Biolabs) and the plasmid was purified by using a Phenol/chloroform extraction and ethanol precipitation. The in vitro transcription reaction was carried out by using the T7 RiboMAX Express Large Scale RNA Production System (Promega), following the manufacturer's instructions. The RNA molecules were then purified via a RNA Clean & Concentrator-25 kit (Zymo Research).

ssDNA/RNA Nanostructure Assembly

The purified DNA and/or RNA molecules were diluted to 5-10 nM in 1×TAE-Mg buffer (40 mM Tris, 20 mM Acetic Acid, 2 mM EDTA and 12.5 mM Magnesium acetate, pH 8.0). The resulting solution was annealed from 65° C. to 25° C. with a cooling ramp of 1° C. per 20 minutes to form the NA nanostructures.

AFM Characterization

All samples were imaged in "ScanAsyst mode in fluid," using a Dimension FastScan microscope with PEAKFORCE-HiRs-F-A tips (Bruker Corporation). After annealing, 2 μl of each sample was deposited onto a freshly cleaved mica surface (Ted Pella, Inc.), and left to adsorb for 1 minute. Then, 80 μl of 1×TAE-Mg buffer and 2 μl 100 mM of a $NiCl_2$ solution was added onto the mica, and 40 μl of the same buffer was deposited onto the microscope tip. The samples were then scanned by following the manufacturer's instructions.

Topological Control Experiments

Four single-stranded DNAs with customized sequences were synthesized by The Biobasic company (Biobasic.com) and then cloned into a pBluescript SK(+) vector (Biobasic), with the gene sequences flanked by two BtsCI restriction sites. The final plasmids were then co-transformed with pSB4423 to produce recombinant M13 phages. The phage particles and phage DNAs were then purified by using the same methods as described in the ssDNA synthesis section. The ssDNAs were cleaved off from the recombinant phage DNAs by using a BtsCI restriction enzyme (New England Biolabs) and were gel purified by using a 4% urea denaturing PAGE gel. The four ssDNAs were annealed into two sets of dsDNAs (partially hybridized) in the 1× annealing buffer (50 mM Tris-HCl pH8.0 and 100 mM NaCl). The two linear dsDNAs were mixed in a 20 nM concentration in a 1×TAE-Mg buffer, annealed from 65° C. to 25° C. at 1° C. per 20 minutes to form the paranemic cohesion interactions, and were then characterized by AFM imaging. The sticky ends on the two sets of the dsDNAs were able to close the ring structure without ligation. In the second control experiment, the two linear dsDNAs were ligated separately with T4 DNA ligase in a 1× ligation buffer (Thermo Fisher Scientific) at room temperature for 1 hour to enable them to form the two circular dsDNAs. The ligation products were treated with exonuclease I and exonuclease III (New England Biolabs) to remove any linear DNA. The solution was further purified using a Monarch PCR & DNA Cleanup Kit (New England Biolabs). The two circular dsDNAs were then mixed at 20 nM in a 1×TAE-Mg buffer, annealed from 65° C. to 25° C. at 1° C. per 20 minutes and characterized by AFM imaging.

CryoEM Specimen Preparation and Data Acquisition

In the cryo-EM portion of the experiment, 2 μL of the aforementioned single stranded DNA nanostructure samples (concentrated to ~0.3 μM using Amicon 100 kDa centrifugal filters) were applied onto a 200 mesh R1.2/1.3 holey carbon Quantifoil grid (Quantifoil Micro Tools GmbH) that was cleaned with acetone (Sigma-Aldrich) for 12 hours and glow discharged for 40 seconds before use. The grid was blotted for 3.5 seconds and immediately frozen in liquid ethane by using a Vitrobot Mark IV (FEI) with a constant temperature of 6° C. and with humidity levels at 100%. The grid was stored in liquid nitrogen until the imaging session. All of the grids were examined on a JEM2200FS (field emission gun) cryo-electron microscope (JEOL) that was operated under the following parameters: 200 kV, spot size 2, condenser aperture 70 μm, objective aperture 60 μm. The images were recorded under a low-dose condition on a direct detection device (DDD) (DE-20 4 k×5 k camera, Direct Electron, LP) while operating in movie mode at a recording rate of 24 raw frames per second. Other conditions included a 30,000× microscope magnification (corresponding to a calibrated sampling of 1.59 Å/pixel) and a dose of 40 electrons/$Å^2$ with a defocus ranging from 1.5 to 3 μm.

For the ssDNA tetrahedron sample, a total of 47 images were recorded on the DE-20 detector. Motion correction was performed by running the averages of 3 consecutive frames with the use of the DE_process_frames.py script (Direct Electron, LP). A total of 533 particle images were manually boxed, contrast transfer function corrected, and extracted with the use of EMAN2 (Tang, G., Peng, L., Baldwin, P. R., Mann, D. S., Jiang, W., Rees, I., and Ludtke, S. J. (2007) EMAN2: an extensible image processing suite for electron microscopy, Journal of structural biology 157, 38-46.) Approximately 50 particles were used to generate a de novo initial model in the EMAN2. The final 3D reconstruction, in the EMAN2, with a tetrahedron symmetry applied, resulted in a density map with resolution at 17 Å. This density map was calculated via the use of the 0.143 criterion of the Fourier shell correlation (FSC) curve with a mask. A Gaussian low-pass filter was applied to the final 3D maps that had been displayed in the Chimera UCSF software package.

Tilt-pair validation for the cryo-EM map was performed by collecting data at two goniometer angles, 0° and 10°, for each region of the grid. The test was performed using the e2tiltvalidate.py program in EMAN2. Additional details on the tilt-pair validation is provided in Table 1.

TABLE 1

Tilt-pair validation of single stranded DNA tetrahedron

| | |
|---|---|
| # Total particle pairs | 49 |
| # Particle pairs in cluster | 15 |
| Fraction in cluster (%) | 30.6 |
| Mean tilt angle (°) | 9.47 |
| RMSD tilt angle (°) | 4.00 |
| Mean tilt axis (°) | 42.4 |
| RMSD tilt axis (°) | 54.9 |
| Experimental tilt angel (°) | 9.9 |

A total of 53, 75, and 46 micrographs of ssDNAs that folded into triangular prisms, pyramids, and pentagonal pyramids, respectively, were collected. Subsequently, 226, 330, and 238 particles were extracted, respectively. The initial models were generated as mentioned above and the final reconstructions were applied with corresponding C3, C4, and C5 symmetries that yielded EM density maps at resolutions of 32, 25, and 26 Å. These resolutions were calculated with the use of the 0.143 criterion of the Fourier shell correlation (FSC) curve with mask, respectively.

Sequences:

9 crossing number square knotted DNA (SEQ ID NO:1):

```
ATCCAGGAAGGGCTATGGTTTTCATCGAAGATAGACAAATAGACAGCAT
GCCAATGATGATCAGAAGAGGACGAGTTTTGGCCATATCTGGCATGTTT
TTCATGCCGATTCTATCTGAGTTCGCCAACCTACTTTTTGTAGGTCGAG
GAGAGCTTTTAGCTCATCGAACTCTTACCAGTCATCTTATTTCCCAGCA
ATAACGAGGTTGGGTTTTAGGACTTGCTTCGACTAGGAACGGGAGGGAG
AAGGGAACGAGATACTCGTAGATTTTGTTGACCGAAACAAACCAAACCG
CAGCTACGACGCACCATGATGGTATCTCGATTTTAGCTCAGGGCACTAG
TGGTAGGTAGTGGTGGGGTGGCGAACTACCTGTCTATCTTTTCCTCAAG
ACTAGAATCCTCATCGTGATGAGTACAGGAACAGTAGGACAGCTGATTT
TGGATTCCCAGAGTGACTTTTTGTCACTAGGCACCTCAGCGAAATCTAT
CTCGGTTTTTCCGAGAACAGTACCAGTTTTAGGCTCGCGGTTCTTGGAA
CCTTGGCAGTAGACAACCTTTCCAGGGAACGTGCTTTTGACCTAACTTG
GATGCTTTTTGCATCCTGTTAGTAGCGGCCTCCGTGACGTAGTTTTTCT
ACGTAGCTGATGGATTTTGTACCGCTGCAGTCTGCTACATCAGGGACGG
ACTGATTCACCTCTAGCTCACATTTTCTAGCGGGTGGTGAGCTTTTTGC
TCACGAGTGGAATTCAACGGCCCTTTCAATCTTTTTGATTGAAGCATCC
GTTGTTTTAATTCCACTCGCAGTACATCTATGTGCTCAGTCTCCGTTTT
TCGGAGTAGTCGCACATAGATGTACTGCCACCCGCTAGTGTGAGCTAGA
TCATGATCAGTCCGTCCCTGATGTAGGTTTGTGCAGCGGTACTCCATCA
GCTAGTAACACGCAAGTGGTACCTCCTGGCTTTTTGCCAGGCTAAGCCA
CTTGCGTGTTACTCACGGAGGCCTTTTGCTACTAACAGCTTCGTTTTTC
GAAGCAAGTTAGGTCGCACGTTCCCTCTCGTGGTTGTCTACTGCCAAGG
TTCAGTCGACCGCGAGCCTCTGGTACTGTTGAAACTTTTTGTTTCATAG
ATTTCGCTTTTTGAGGTGCCTACACGATCTCATCAACGCTAAGGCCACT
TTTTGTGGCTACCTCGTTGATGAGATCGTGTCTGGGAATCCTCAGCTGT
CCTTATTGTCCTGTACTCAGATGAATGAGGATTCTTCGATTGAGGGATA
GACAGGTCTGATGCCACCCCACCACTACCTACCTTGTCTGCCCTGAGCT
TCGAGATACCAGGTGAGTGCGTCGTAGCTGCGGTTTGCAGACTTTCGGT
CAACTCTACGAGTATGGAAATCCCTTCTCCCTCCCGTTCCTCAAGAAAG
CAAGTCCTCCCAACCTCGTACTGTCTGGGAAATAATCACGCTGGTAAGA
GTAGTCTGAGCTGCTCTCCTCGAGTAGCTCGTCGACTCTAGTCGGTGTG
TTTTTCACACCTCAGTGAGTCGACGAGCTACTTGGCGAACTCTTTTAGA
TAGAATCGCTCTCTTTTTGAGAGCAGATATGGCCCTCGTCCTCTTAGTT
```

-continued

CCATCATTGGCATGCTGTCTATACTAGTATCTTCGATGCCATAGATGCT

CCTGGAT 23 crossing number 3-square knotted DNA before hierarchical design (SEQ ID NO:2):

ATCACCCTTGGTCTCAGACGGATCAATCGCTGTGTTACTCGTACGGGCG

ATTACAGATTCACTGCGACACCTGGGAGATGCCGACTCCCATGACCAAC

TTTTTTCCACGTCATGGTCTTGTTTTCACCATACGTCCCCTGTTTTTG

TCGAGACGTTTAGACTCAACGCCCGGCACTCACGACGTGAGAATGGGCC

TCTACGTCCTGCTCGTCGTCTACACATGTGCTACACCGTGTTTAGTTTT

TTGGAGGCACGGTGCAGCTTTTAGTACATGTGCCCAGAGTCTTTTGCCG

TCGTTGTAGCAGCAATCATGTTGTCAAGCATGTAGCTTTTACGGAGAGA

TCCGTTCTTTTTTCGGTCGATCTGTTTCCGTACCTGCGCTAGGCCGATG

TGATGCCTGGCTCGTTACTTTGCACTGTCCGACAGGTTATTCCGAGTTC

GGTTTACATGTTTTTTGCCTGAAACCGACTCGTTTTAGTAACACGAATA

GGCTTTTTTGCGCTTTCGTCAGGAGGCAGTCTATGAACTGGCTTTGGGA

CCTACCATGCGGCTCCTGAAGCTGAACGACACGGACCTTCGGTCGGTGT

AGATTGTCTCGGTTGTCATCCATATGGCACGGAAAGACAGCGTGTTACC

CACCGATCGTTCGAGCAGCTCAACCGGATTGGAGGATCAGCTCGCTGGA

GTTCTGGCGACGCACGACGCACCTTTTAGGACAACACCGATTAGGCCTT

AAAGCTACTTACGGTATCTGGGCATTGTGGTCTACTTCCAGGTGTAGGT

CCCTAATCCCGGCGTGCTACAAGCCCATGAACAGGGCCTTAGGCGTCCA

CCTTCCCTTTGGAAGATTTCCAGCGCAGCGACACAGCGATCCCGTGGTT

AGTAGGTGATCTGTTGTCCGTGAGACGTACAAGGTATTACCACTCGACG

AAAGTGACATATCCCCAGAAATGTTCTGCATTTAGTATCCCTGGATGCT

TGCTGTCTTCCATGTGCAATGTAAAACCGCTGGAGTTGGCTTTGGTGTC

GTCAGGTAAGCGTTTGGCAGAGGCAAGAGAGCAAATTCGCCATAAGAGA

GATCTCGCGAGGTATGAGGGTACCTTGCGCTCTTAGCCATGGTGCACCT

CACACTTCACTCTCTGGTGGTTCGCAGAGGCCTGAGCTGTTCGCACGTC

CGCTGCACCTCGTGACCACACTTGTTAGGAATCGAATGGGACGACTAAT

GAGCCTTTGAAACTGGTTGACGTCTCCAGAGGACGTGTCTAAGGCTGAG

GCAATGCTGGCTGACACGGACAACCTGGTCACTTGCGCTCCGTCGTCAC

GACTCTTGGGGCCATGAGGTTGACGAGTTTTTTGCCTCCAACCTGCAGC

TTTTCAAGTTAAGTGAGACCTTTTTTCACAGCACTTCATCGCCAACTCG

CCAATGCGACAAGCTGTCTCTGGAAAACGCACATACGTTGGAGTGGATG

GAGATTCCGTAGACGTATGACTGTTTTTTCAGTGATACGTGATACTTTT

ATGGGTAGGAGAAGTGGTTGAGTTCGTACCATTTGCCAGTCTCGTCTTC

CTCCAGACCCTACGTTTTCATATGACGTCAGTACTTTTTTCGTGTGACG

TGGTTTCCCCGACACTGGAGTCGCTTTGGCAAGGGGTTGTGGCAAATCG

TTAACGGTTTGCACGCAACATCTGCATCATGGCAACCTTTTTTCGGTTC

CATGAAAGAGTTTTCTGAGTGACCAGTCTAGTTTTTCTAGACGAACTAC

-continued

TCAGCTCTTGCTCTTAACCGTTTTTTGGTTGAAGAGCTGCAGTTTTATG

TTGCGTGCAAACCCGGGACGATTTGCCACAACCCCTTGCCAAAGCCCAA

CCAGTGTCGGGTTTTGAAACCTGCCAACACGTTTTTTGTACTTGGCACA

TATGCGTAGGGTCTGACTCAAGACGAGACTGGCAAATGGTACGAACTCA

ACGAGGAGTCCTACCCATGTATCCCCTCACACTGTTTTTTCAGTCTGAG

GGCTACGTTTTGAATCTCCATACGCTGCAACGTATGTGCGTTTTCCAGA

GACACGAGACCGCATTGGCGAGTTGTTTTGCGATGGCCCACTGTGTTTT

TTGGTCTTGGGCAACTTGGCTGCGAAAGCGAGGCTTTTTTCTCGTGCTT

TCCATGGTTTTCCCCAAGAGTTCGTTCGACGGAGCGCACCGCACCAGGT

TGTCCGTGTCCAGTAGCATTGCCTCTTTTAGCCTTAGACGTCGGATCTG

GAGACGTCAACCAGTTTCAAAGACATCGTAGTCGTCCCATTCGTTTTAT

TCCTAACAGCCAGAGTCACGAGGTGCAGCTCCTCCGCGAACAGCTCGCT

GCTCTGCGAACCTTTTACCAGAGAGTCTCCTCTGAGGTGCACCATGGCT

AAGAGCGCAAGGTACGAGTATACCTCGCGATTTTGATCTCTCTTCCCTG

TAATTTGCTCTCTTGCACGCCGCAAACGCTTACCTGAACCTGGCAAAGT

TTTCCAACTCCAGACGACGTACATTGCACATGGAAGACAGCAAGCATCC

AGAGTGACTAAATGCAGTTTTAACATTTCTGGGGATACGCAACTTTCGT

CGAGTGGTAATACCTTGTACCACACACGGACAACATTTTGATCACCTAC

TAACCAGTTAATCGCTGTGTCGCTGCGCTGGAAATCTTGACTAGGGAAG

GTGGTTTTACGCCTAAGGATGGCGTCATGGGCTTGTAGCCTCTGCGGAT

TAGGGACCTACCGACACAAGTATTTTGACCACAATGTGCGATTACCGTA

AGTAGCTTTAAGGCCTAATCGGTGACAGCCTAAAAGGTGCTTTTGTCGT

GCGTCAGTGTGACTCCAGCGAGCTGAGGACGTAATCCGGTTGAAGGCCT

CGAACGATCTTTTGGTGGGTAACCCACTCTCTTTCCGTGCCATATGGAT

GACAACGCTTGTAATCTACACCGACCGTTTTAAGGTCCGTGCGTGACAG

CTTCAGGAGAGTGATGGTAGGTCCCAAAGCAGCCTCATAGACTGCTTTT

CTCCTGGAGCCAGCGCTTTTTTGCCTAGGCTCGTTACTCGAGTAATACC

CAGGCTTTTTTCATGTGGTATTAACTCTTTTGGAATAACCTACGTCCCA

GTGCAAAGTAACGAGCCAGGCATCGCTCATGCCTAGCGCAGGTACTTTT

GGAAACTTAGTGACCGTTTTTTGAACGACTAACTCCGTGCTACATGCTT

GCTGTCATGATTGCTGCTACAACGACGGCAAAAGACATCGCACACATGT

ACTGCTGCACACCTCCTCCTTTTTTCTAAAAGGTGTGTAGCTTTTACAT

GTGTAGCGGTTTAGCAGGACGTAGAGGCCCATTCTCACGTCGTGGGATC

CGGGCGTTGATTTTGTCTAACTCCGTCGACTTTTTTCAGGGCGGAGATG

GTGCAAGAATCCCTCGTGGTTTTTTGTTGGAGGGATGAGTCTTTTGGCA

TCTCCCAGGTGTTGTCGTGAATCTGTAATCGCCCGTACGAGTAAGTCTG

CGATTGATCCTTTTGTCTGAAGTTCAGGGTGAT 23 crossing number 3-square knotted DNA after hierarchical design (SEQ ID NO:3):

ATCACCCTTGGTCTCAGACCAACTCGCCAATGCGACAAGCTGTCTCTGG

AAAACGCACATACGTTGGAGTGGATGGAGATTCGACTCCCATGACCAAC

TTTTTTCCACGTCATGGTCTTGTTTTCACCATACGTCCCCTGTTTTTG

TCGAGACGTTTAGACGCTACATGCTTGCTGTCATGATTGCTGCTACAAC

GACGGCAAAAGACATCGCACACATGTACTGCTACACCGTGTTTAGTTTT

TTGGAGGCACGGTGCAGCTTTTAGAACTGAAGCGGTTTAGCAGGACGTA

GAGGCCCATTCTCACGTCGTGGGATCCGGGCGTTGATTTTACGGAGAGA

TCCGTTCTTTTTTCGGTCGATCTGTTTCCGTACCTGCGCTTGGCCGATG

TGATGCCTGGCTCGTTACTTTGCACTCTCCGACAGGTTATTCCGAGTTC

GGTTTACATGTTTTTTGCCTGAAACCGACTCGTTTTAGTAACACGAATA

GGCTTTTTTGCGCTTTCGTCAGGAGTACTTCCAGGTGTAGGTCCCTAAT

CCCGGCGTGCTACAAGCCCATGAACAGGGCCTTAGGCGTTGTTGTCCGT

GAGACGTACAAGGTATTACCACTCGACGAAAGTGACATATCCCCAGAAA

TGTTGATCGTTCGAGCAGCTCAACCGGATTGGAGGATCAGCTCGCTGGA

GTTCTGGCGACGCACGACCTGCATTTAGTATCCCTGGATGCTTGCTGTC

TTCCATGTGCAATGTAAAACCGCTGGAGTTGGGCAGTCTATGAACTGGC

TTTGGGACCTACCATGCGGCTCCTGAAGCTGAACGACACGGACCTTTCG

CGAGGTATGAGGGTACCTTGCGCTCTTAGCCATGGTGCACCTCACACTT

CACTCTCAGCTGAGGCGGTGTAGATTGTCTCGGTTGTCATCCATATGGC

ACGGAAAGACAGCGTGTTACCCACCGCACCTTTTAGGACAACACCGATT

AGGCCTTAAAGCTACTTACGGTATCTGGGCATTGTGGTCGAGGCAATGC

TGGCTGACACGGACAACCTGGTCACTTGCGCTCCGTCGTCACGACTCTT

GGGGCCACCTTCCCTTTGGAAGATTTCCAGCGCAGCGACACAGCGATCC

CGTGGTTAGTAGGTGATCGGTTCGCAGAGGCCTGAGCTGTTCGCACGTC

CGCTGCACCTCGTGACCACACTTGTTAGGAATCGAATGGGACGACTAAT

GAGCCTTTGAAACTGGTTGACGTCTCCAGAGGACGTGTCTAAGGCTCTT

TGGTGTCGTCAGGTAAGCGTTTGGCAGAGGCAAGAGAGCAAATTCGCCA

TAAGAGAGATCCCATGAGGTTGACGAGTTTTTTGCCTCCAACCTGCAGC

TTTTCAAGTTAAGTGAGACCTTTTTTCACAGCACTTCATCGCGGATCAA

TCGCTGTGTTACTCGTACGGGCGATTACAGATTCACTGCGACACCTGGG

AGATGCCCGTAGACGTATGACTGTTTTTTCAGTGATACGTGATACTTTT

ATGTTGCGTGCAAACCCGGGACGATTTGCCACAACCCCTTGCCAAAGCC

CAACCAGTGTCGGGTTTTCATATGACGTCAGTACTTTTTTCGTGTGACG

TGGTTTCCGTAGGGTCTGACTCAAGACGAGACTGGCAAATGGTACGAAC

TCAACGAGGAGTCCTACCCATCTGCATCATGGCAACCTTTTTTCGGTTC

CATGAAAGAGTTTTCTGAGTGACCAGTCTAGTTTTTCTAGACGAACTAC

TCAGCTCTTGCTCTTAACCGTTTTTTGGTTGAAGAGCTGCAGTTTTATG

GGTAGGAGAAGTGGTTGAGTTCGTACCATTTGCCAGTCTCGTCTTCCTC

CAGACCCTACGTTTTGAAACCTGCCAACACGTTTTTTGTACTTGGCACA

-continued

TATGCCCGACACTGGAGTCGCTTTGGCAAGGGGTTGTGGCAAATCGTTA

ACGGTTTGCACGCAACATGTATCCCCTCACACTGTTTTTTCAGTCTGAG

GGCTACGTTTTGGCATCTCCCAGGTGTTGTCGTGAATCTGTAATCGCCC

GTACGAGTAAGTCTGCGATTGATCCTTTTGCGATGGCCCACTGTGTTTT

TTGGTCTTGGGCAACTTGGCTGCGAAAGCGAGGCTTTTTTCTCGTGCTT

TCCATGGTTTTGATCTCTCTTCCCTGTAATTTGCTCTCTTGCACGCCGC

AAACGCTTACCTGAACCTGGCAAAGTTTTAGCCTTAGACACGTCCGAGT

GAGACGTCAACCAGTTTCAAAGGCTCATGCCACGTCCCATTCGTTTTAT

TCCTAACAGCCAGAGTCACGAGGTGCAGCTCCTCCGCGAACAGCTCGCT

GCTCTGCGAACCTTTTGATCACCTACTAACCAGTTAATCGCTGTGTCGC

TGCGCTGGAAATCTTGACTAGGGAAGGTGGTTTTCCCCAAGAGTTCGTT

CGACGGAGCGCACCGCACCAGGTTGTCCGTGTCCAGTAGCATTGCCTCT

TTTGACCACAATGTGCGATTACCGTAAGTAGCTTTAAGGCCTAATCGGT

GACAGCCTAAAAGGTGCTTTTGGTGGGTAACCCACTCTCTTTCCGTGCC

ATATGGATGACAACGCTTGTAATCTACACCGCCTCTTTTAGCTGAGAGT

CTCCTCTGAGGTGCACCATGGCTAAGAGCGCAAGGTACGAGTATACCTC

GCGATTTTAAGGTCCGTGCGTGACAGCTTCAGGAGAGTGATGGTAGGTC

CCAAAGCAGCCTCATAGACTGCTTTTCCAACTCCAGACGACGTACATTG

CACATGGAAGACAGCAAGCATCCAGAGTGACTAAATGCAGTTTTGTCGT

GCGTCAGTGTGACTCCAGCGAGCTGAGGACGTAATCCGGTTGAAGGCCT

CGAACGATCTTTTAACATTTCTGGGGATACGCAACTTTCGTCGAGTGGT

AATACCTTGTACCACACACGGACAACATTTTACGCCTAAGGATGGCGTC

ATGGGCTTGTAGCCTCTGCGGATTAGGGACCTACCGACACAAGTATTTT

CTCCTGGAGCCAGCGCTTTTTTGCCTAGGCTCGTTACTCGAGTAATACC

CAGGCTTTTTTCATGTGGTATTAACTCTTTTGGAATAACCTGTCGGATC

TGGCAAAGTAACGAGCCAGGCATCACATCGTAGTAGCGCAGGTACTTTT

GGAAACTTAGTGACCGTTTTTTGAACGACTAACTCCGTTCAACGCCCGG

CACTCACGACGTGAGAATGGGCCTCTACGTCCTGCTCGTCGTCTTCAGT

TCTGCTGCACACCTCCTCCTTTTTTCTAAAAGGTGTGTAGCTTTTAGTA

CATGTGCCCAGAGTCTTTTGCCGTCGTTGTAGCAGCAATCATGTTGTCA

AGCATGTAGCTTTTGTCTAACTCCGTCGACTTTTTTCAGGGCGGAGATG

GTGCAAGAATCCCTCGTGGTTTTTTGTTGGAGGGATGAGTCTTTTGAAT

CTCCATACGCTGCAACGTATGTGCGTTTTCCAGAGACACGAGACCGCAT

TGGCGAGTTGTTTTGTCTGAAGTTCAGGGTGAT 57 crossing number 9-square knotted DNA before hierarchical design (SEQ ID NO:4):

CAACTCCTCGATTCCCGCTTGTTTGCACTTGTATGTACATAGTGTCAGA

TCGCTTACGCTTGCGTGGCGATCATCTAGTCGTCGTTTTTTGTTCCACT

AGATAGTATTTTCAGGCGTTGACTAGGCGCCCGAGGTATTTCAAGAAGA

CAACTGATTAAGTGTGTTTTCAAGTCCAACTACTACTTTTTTGCGGAAG

-continued

TTGTCCCTTCTCTACCGTCTTGCTCAGTGTTCAGAGACTTTGCTGGTGA
AGTGCCGCACCGCCTGCTGTTAAGAGAGCTTTTTTGGGAGCTTAACGCA
AATTTTCCACGTAAACTGTTGGTTTTTTGACTCAGTTTAGGACTGAGTC
AAGCATGGTCGGTCCCACAGAATCCGGAAGCCCAGTCAGAAAACATGGT
AGCGCTTCCCCTGGGTTTTTTCAGAAGGGAAGCGCCATTTTGCATATTT
ACCACTCGTGACTCGTAGGGAGGACGCCTAGTGAAGCGCGTCTCATTTT
CTCGAGGAGTGAGGGCTTTTTTCCAGGCACTCTGTGTCGTCCCGTTAAG
GATGTGAGTGTCATGGCGAGCACCAGACAGAGGCCGTGAACGCTTGAAG
CGAGAGCCGTTTTTTGACATCTCGCTGGTGCTTTTCACCTAGCAACTAT
CGTTTTTTCATGAGTTGCCTCTGCTTGAGCATCAAGTCGTAATCGTCCA
TGTTAGGTGCGCTTCTAGAAGACCGGTGTCCAGTATGGGTGTGATCTCC
TGTCTTGCCTGGTACCGCTTTCCAGGATCGGGTACGGACTCGTGCCCG
GAACATCAGGGCAAATCGCGGTCTCATATAGGACTGTACCCACACACTT
GTCTTCGCCGTTCGGAACTTTCGGAGTATACACAGTCTTGTTGCGCTTT
AACAGATCATCTGTCATAAGTAAGGGGTTGCACATATCCAAGATGGGAT
TGCAACGGTCAACCGGATATTACGTATTTTCCTGGGCTAGCGTCGGATT
TCGGCTTCCTTGGGACTGAACAGGGATCGTTTGGTGCTAGGCGCTGGCC
TTTCACACGGGCGTGTGCAGCACAGATCATCTAATCATATGTAACTTGA
CCCCGTTTGCCTCATCAGTCCTCATGATGAGTAAGTAGCCATCTTCAGT
AAATCTTCGTCTAACATAGGGTACATACTCATCATGGACACTTTCTTCC
GAATGCCTGCTACCCGCACCTCAACCGCCCTAAGACTATTGGTGCTTCT
TCACTTCGTCTGAGTCAGCCTCTCCATCTGTCACTCCAAGGGATAGCGG
ACGACCCCGAGTGTCTTGAATTGCATCTACGAAAACGTTCGGACTACTT
TTCTACGTCTGTTATCTCAGTCCTTGCCGACGTCGTAGGTCGTGATAAC
GTCCAAGTCGGGTTGCGACCAAGGCCAGACGGAAGGTGGATTAGTTGTT
ACTTCGCCAGTGAGAGTTTGCCTAGCTTGGATCACTGACGTCTGATGTT
AGCGTAATCTAGATCACTGGGGTTCTGCCACAGTCCGGTGAGTACAGCA
CAGATCGTATACATCACGAACGTTTGTCCAGTCGCGGAACACTGAAATG
AACTAACGCTGACATGTATGACAACCAACATGATTACACACGCTTGTGA
GCGAGTCTCTGCATGAGGAGTGCTCCACAGTGAGTGACTACGCTGCCAG
CTGCAGCGCGCGTTTGTTTCGGGTCCCTTCAGCATCGAACTGATCCGCT
AAACGTCTTCACAGGCAAGACGTCGCGAATAGCGGAACGATGCAGGTAT
CTTAGTCATGCGCAACCAACCACCACAGGTGTGCTACTACGATTCGTCC
GTCGGCATTTAACGCTCCGCCGTTGGATCGATAAATGGTTTCTGGAATT
ATATAGCCGGTAGATCGGCCGAGACACTTACGTATAATGAGCCCACTTA
TCCTCTTCTTGTGAACACTGCTTGCTATACTCTTGCACACCTCGGTCGC
AGACGGTAAAGACTACTGAATACGGCGATAGCGTATGTGCGCATGACGC
GCGGTGAACACATGGTGCCAAACACTTTCTTCGTGACCCGAATTGAATA
ATCGCTTATACAACCTGAAAGTGCCGTACGCATTCGCCGTGGGCTAAAG
CGCGATCAAGTCTCACCCTTGGTAGTCGAGTTGTCGGGCGTAGCAGCTC

-continued

TCTGTCCTCGTCCCATTACTTTGCTTAGTGAATGGAAGACTGTGGTAAT
GCTCCTCACGAGGATAGTCAACTGACCGTCATGCAGCTGACGACGTTTA
ACGATCCTGCATCTCTCCCAAGATAGTCAGATCCGTAACGAGACTTGCA
GGACTCGAATACCCTCTAACTATCCGCACTAGAGTGCCGGAGGCAGTTC
GCCCTTGTAGGATCGGAGGTAGTCAGTTGATAGAAGGGCTGATGGCTCG
TCCTCGAAGTTGAACTCCCTCAGCCACACTTGGTTCCTACAGCAGTTGC
ATCTGAAGAATCTGTCGACACAGACATGCCTTCGGCGCTCGTCCCACTT
ATGCAAGCGCATTCGTCGAGGCAAGGAGCTCACTTAGAGCGTCTGATGG
TTTAGTACTGAGTGAGATATCGTCCCTTCTAATGGACTTTGGTCCTGCG
GTTATTTTGGGAGCGGCACATGACGCGCCAAGCACTCATACTTTTTTCG
ATCAGTGCTCGTACTTTTCTTATGCTTCGAGCCACGTTGCCGCGCATAT
CAATTCTACCTAGGCATACCTGTTTTCTTAACAGCCACTGTGTTTTTTG
CGGCTGGCTGGTCAGGGCGACTCTGAGAATAGAAAGGTGCGTGTAATCA
TAGAGTGAGAGCGGGTGTCTGTGGTCTCCGATATCTTTTTTGAGCGCGG
AGAGTTTATTTTATGCCTCGTGGGGCTCTTTTTTGTAGCCCACGTCAGA
TTGCTGACAGATCACGTTGATTTCGTTCCAGTAAAGTGAAATGAACTCT
GACCGGGAGTGCCAACGATACTTTTTTGTAATGTTGGCGCATATTTTAA
GCGCGTGACTGCATATCAGATGAGATGTTAGGGAGGTGAGAAGTACTCA
CCTTTTGGCGTGCACGCCGTGGTTTTTTGATTAGCGTGGTCGGGTGGCC
GGAATGGTATGCCTAAACACCAGACATCTGAACTGTCTGGTTCATAATG
TGACACTTGTCTGGCTTTTTTCGTGAACAAGTTTGTATTTTACTAGGGA
GGATGGGCTTTTTGCCCACGGATCCTAGTTACAATGATCGTCACGTTTT
TTGCCAGCGATCAGTCACTTTTATTATGAACCGTAATCTTCAGATGTCT
GGTGTTTAGGAGCGTCATTCCGGCCATTTTCCCGACGGACTTAATCTTT
TTTCCACGAGTCCCACGCCGGTGAGTACTTAAGCTCTCCCTAACATCTC
ATCTGATTGTCCATCACGCGCTTTATGCAGTATGATTACTTTTTTGTAT
CCATACTACTCCTTTTCGGTCAGAGTAGCCCACACTTTACTGGAACGAA
ATCATGACCATCTGTCAGCATTTTATCTGAAAGTTGCTACTTTTTTGAG
CCAACTTAGGCATTAAACGACCGTCGCTCTTTTTTGATATACGGTCCCA
CATTTTGACACCCGCTTGTGCACTATGATTACACGCACCTTTCATCTGT
CAGAGTCGCCTTTTCTGACCTAGGCGCCGCTTTTTTCACAGGCCTAGTT
AAGCAGGTATGCCTGACGTGAATTGATATGCGCGGCAACGACTGTAGAA
GCATAAGGTACGTCTATCGATCGTTTTTTGTATGGATAGATGGCGTTTT
CGTCATTCTTCGCTCCCAAAACCTAACCAGGACCAAAACGACTTAGAAG
GGACTTTTGATATCTCACCTCTGTCTAAACCATCAGACGCTCTAAACAT
CCTCCTTGCCTCTTTTGACGAATGCGACGAAGTAAGTGGGACGAGCGCC
GAAGAGGGCTCTGTGTCGACTTTTAGATTCCCTGGATGCAACTGCCAGG
CAAACCAAGTGTTCACAAGGGAGTTCAATTTTCTTCGAGGACTACAGTT
CAGCCCTTCTATCAACTGACACGTCCCGATCCTACATTTTAGGGCGTGT
GGCCTCCGGCACAGTTCCGCGGATAGTTGACAAGTATTCGAGTCTTTTC
TGCAACAGCCGTTACGGATCAACGATTCTTGGGAGATCCCAAGGATCGT

-continued

TAATTTTACGTCGTCAGTGGACAGACGGTCAGTTGACTATCCTCAGCTT

GAGCATTACCATTTTCAGTCTTCCAGACTGGAAGCAAAGTAATGGGACG

AGGGATCTGAGCTGCTACGTTTTCCCGACGTCACGACTACCAAGATTAG

AACTTGATCGCTGCACAGCCCACGGCGTTTTAATGCGTACGTGAGACTC

AGGTTGTATAAGCGATTATGGGCATCGGGTCACGATTTTAGAAAGCAGG

TGGCACCATGTAAGTGTCGCGCGTCATTATGTCATACGCTATCTTTTGC

CGTAACTGGTAGTCTTTACGTAGAACGACCGAGGTAACGTAGAGTATAG

CATTTTAGCAGTGTTCTGACTGAGAGGATAAGTGGGCTCATTACGACCA

AGTGTCTCGGTTTTCCGATCTACCACTTCAATAATTCCAGAAACCATTT

ATGAGCACAACGGCGGAGTTTTCGTTAAGCCTCGACGGACGAACGACTT

TAGCACACCTACGACGGTTGGTTGCGTTTTCATGACTAAGTACTGAGCA

TCGTTCCGCTATTCGCGAGAGGATGCCTGTGAAGTTTTACGTTTCTGTG

ATCAGTTCGAAGTGATAGGGACCCGACTAACACGCGCGCTGCTTTTAGC

TGGCAGCCGTAAGACTCACTGTGGAGCACTCCTCCAAGTGAGACTCGCT

CTTTTACAAGCGTGTAGACAGATGTTGGTTGTCATACATGTCCATACTA

GTTCATTTCTTTTAGTGTTCCGCTTCACTACAAACGTTCGTGATGTATA

CACAGAGTGCTGTACTCTTTTACCGGAAGCGGGCAGAACCCCTGCTGAC

TAGATTACGAACAAATCAGACGTCATTTTGTGATCCAAGGTCCTAAAAC

TCTCACTGGCGAAGTAATGGTCAATCCACCTTCTTTTCGTCTGATGCTG

GTCGCAACCTCGTAGGGACGTTATCGTGGTCTACGACGTCGTTTTGCAA

GGTTCAAGATAACAGACCGTCTGAAGTAGTCCGGTGCATTTCGTAGATG

TTTTCAATTCAAGAATACGTGGGTCGTCCGCTATCCCTTGGCAACGCAG

ATGGAGAGTTTTGCTGACTCAGCTTGCATGAAGAAGCACCAATAGTCTT

GCATGGGTTGAGGTGCTTTTGGGTAGTGTTCATTCGGAAGAGTTCACCC

ATGATGAGGCGCAACCCTATGTTATTTTGACGAAGATTATACCTAGATG

GCTACTTACTCATCATCGTCTCTGATGAGGCATTTTAACGGGAACTAGT

TACATATGGGTGAGTGATCTGTGCGCTTTACGCCCGTGTGTTTTAAAGG

CGTCTGCCTAGCACCATGACTACCCTGTTCAGGATGCAGGAAGCCGAAT

TTTATCCGACGCTTCATTTGGAAAATACGTAATATCCGGTACGTGGTTG

CAATCCCTTTTATCTTGGATACTCACTACCCCTTACTTATGACAGATGT

ATTCTTAAAGCGCAATTTTCAAGACAACTTATACTCCGAATCTAGTGAA

CGGCGAAAGAGGGTGTGTGGGTATTTTCAGTCCTATAGCACTTCGCGAT

TTGCCCTGATGTTCCTCAATCGAGTCCCGTATTTTCCCGATTTCAGAAA

GCGGTACTGTAGGAGACAGGAGAGGCTGCCCATACTGGATTTTCACCGG

GTGCCTAGAAGCGCATAACCGATGGACGATTGTCCATTGATGCTCAATT

TTGCAGAGTTTCTTCATGTTTTTTCGATAAGAAATAGGTGGCACCGTGG

TCATGTCTTTTTTCGGCTGACCACTCAAGTTTTCGTTCACGGCTCAGTA

CTGGTGCTCGCCATGACACTCGTGAGCTTAACGGGACTTTTGACACATC

CGTCCTGGTTTTTTGCCCTACGGACTCGAGTGAGACGCGCTCGTTGAGG

CGTCCTCCCTACGAGTCAACGTATGTAAATATGCTGGCGAACAAGTTCT

-continued

GTTTTTTCCCAGCTTGTTCGCTATTTTCCATGTTTTCACAAGAGGCTTC

CGGATTCTGTGGGACTACGTATGCTTGACTCTTTTAGTCCTGAGGAGAG

TCTTTTTTCCAACTCCTCACGTGGTTTGCTACATCCTCCCTTTTTTGCT

CTGATGTAAGCAGTTTTGCGGTGCGGCGGCTATCCAGCAAAGTCTCTGA

ACACTCGATCAGACGGTAGAGTTTTAAGGGAGCCTATCCGCTTTTTTGT

AGTTAGGCGACTTGCACACTTAATCGACCATCTTCTTGAAATACCTCGG

GCTAGGACTCAACGCCTGTACTACTGCAGGGAACTTTTTTCGACGCTGC

AGTGATCTTTTGCCACGCAAGGTAGTCCGATCTGACACTATGTACATAA

TGCAGCAAACAAGCGTTTTGGAATCATCCGGTTGG 57 crossing number 9-square knotted DNA after hierarchical design (SEQ ID NO:5):

ATCACGACGCTGTTTCACGGTTAACTCCTCACGCTCCACAGACCAGTAC

TTCCGACTTTTCAACCTTGTACCACTAGGAGTGTTTCCTCGAGTTAACC

TTTTTCTCCAACTCGATGGTATTTTAAGATTGGTGTCTGGCACATAGC

TGCTCCTAGTACCAAACCTTAGATTCCTACGTTCTATAGGTTTTCAGAG

GCCAAGATCGGTTTTTTGGGAGCTTGGCACCACGCTCATGTGTCGGGAT

CATAGGCTGACGATTACTCGGTACTTGCGATCATGACATAGAGATTGTT

GTGATTCGCTGTCCTTTTTTGTTGGGCGAATACAGGTTTTATACCACTG

ACGAAGGTTTTTTCGTGTGTCAGGCATAGGTCGTTCGTAGGGTCCCCTA

TGCGTTGATAGAATTTGGTGTTCGGAACGTCAGAACAATTCGGGAGCAG

CGTCATGGACTTTTTTCGAAGTGACGCATGACTTTTGCGTACTGTTCCC

TCGCAAATATGCCAGGAGTGTGAACACATCCTGGTCACCCTCAGGGACC

ATTTTACGATGTCCTCAATTCTTTTTTGTCCCGAGGAGCTCCCCTTGCT

CAATGGTGACGAAAGTCATACCGTCCAGAGCCGTGTGGATGGCTACGGT

CAGAGGAGGGATCTCTGTCCTGGTATGGGTGGAAGTCCTCGTGAGAGTT

GGGTGCGCGTACATTGCCAGACTTCGGCAAGTTTAGCCTTAACTCGTCA

GGTGCCAGACATCCTCTATTGTCCGACAACTGTAGTCTCAAAGGCGTCT

GGCTGCACGGCTTATTACGACGACTCCGTCAATGGACTGCCTTGACAGT

CGGTGGCATAGCGGTGTTATGAGTCAGCGTGAGGTTACTACGATACTAC

GAGGGACAGATGTTCTCTGTACATGTGCAAGTGGGTGCCATTTAAGCTA

GTAGCAGAGTGCGATGTGCACTGTGGACTTCTTCATGCTTGGACTTGTA

AACCGAGAGCTCACGACACCATTCAATCGGCGACAGAGCACACCGTCGA

ATGCATAGGACCTTGGCTTTTGTATCCTACGGTGCATAAATGCCAGAGA

TGATGTAGCTCTCCGATATGCGATGTGACACCGTACCAGCACGTACGTA

TCCCATGTACGGACCTTGATCGCGCGCATAACCGTCCGCCCACTATGTC

GGCTGCTGCTACTCCCTCGATTATGTACCCTAAAAGGCACGTAGCGTGA

AGGGGCATCATTTGGTCCACAATGTGCTAATGTTTGAAGCCATAGCAGG

GCGGGTGTATGTATGCCGTGGTGAAAGCGTCACGCTGGGTAGCAGCGAT

GGCCACCAAGCAGCGTGCATCAGGTCCAGAATAGCCTCGCAAAGCCAGA

ATAGACACACCAAGTCCATGTCCAGTCTCGCAAAAGTAGTGAAGGCTTT

-continued

TGCTGGGTTTCGACCTTAGTTACTGGCAGCATGGATAGCACATGACGCC
AACGTGTGAAAGTACCAATGTCGACTGCGCGAGAGTTAGACTGAACGGC
AGTACGTGCTATCTCCTGCAGCGGTGATTCAATCTCGGAGGAGTAGGCA
GAGCGTCGAGGAATAGTCACTGGCGATAATCTTGTATTCGAGCGCTGCC
GCATGCGAATTAGTCACCGTGGGTGTATCTACGTTGGCTGCAGCTCGCA
CGTCGGCTGACTCCGTACCGCTCTTCCGAACTATCGACCATAACCTGCC
GGCGAACTCCTTTGCTAGGCTCCGGAAGCATAGACAATAGCTTCGAGTA
CCCATGGCCTTGTAGCTGAAAGATGACTTGCCACAATTGGAGGCTCGTT
CCAATCTGTCTGCGATTCAAACCTCTTCCCAAATCTATACGGTTACCTC
GCAGGGCTCCTCATTTCCATGATTCATTCTACCCGCTAACCGTCCTTGC
CTGGAAATAACCTGTCCGTAGCAGGTAGACCGCTTGCCATCGTCAGCGT
CCTCCGTGCGGTAAACTTGTCACTGAGGGTTACCTTTGGTCAAGTTTCT
GACCGATCAGTGACACCCAGACCTTTCCACACCCCGAAGGCTAGGCAAG
ACTGTGGTATGGAAGTGTGGGTGTCCCTGCCTACGCCTCATGTGGACGC
ACTCATTGACCGACTCGTGGTGCTCTACATGTTCCACAGCAACGGAAGG
GGACTCGATGGTGCGTGCTAGAGAGTTCATGTACGGAATCCATGTCTAT
CCTAGGTCGATTAGGCGTTGACGGTTGCTCGGGAGTCCTCAAGTTCTAT
CTATATCGGGGCATCTGAGATACGGTGTCTATCCATATACTCCGGTACC
GATTAACAGGTTCGATATGCCCTCAAGACTGGGTTGTACAGAGCAGGCT
GGTCCATCTAGGCTAGTTATTGCGTCCGGATGGCTGCAGGCCACGCATG
CCTACGCTTAGTATGCCTGCAGTCTAAATGTTTTGTCCGGTCAGTGACA
CTTGACGAAGAATGAGTGGATTGTGCTATTAACACGTCGGCTACCTCAC
ATTCTGTCTACCCTTTACTGCCTCGAGCTCCGAGCCGGAACGACTACAC
AGTTTCTGAAAACTTCGAAACTCCATTTGAAACTGCGAGACGCTTGCAC
GTCTACGCATGGCTGTTCGTAACGGAGTGACCGTCACACTACAGGGATA
CAGCAAGCCATTCGCGTTGCCAACAGCGTCTAACATGTATTAGAGGAGT
CGGATTTCTTATGTGTCGCGTGCGGACTCTCGATCTCGTTCCACTCTCT
GGAAAACATTTGTCTTAGGGGTGTTGACCCGTTCGGTTGTCATTGAAAT
GACCCGACTCGCACTAACTGCGTATTGGTTTCTCCAAAATGTTGGGGTC
ACTCCAAGGTGACGTCTCGTGCCGTGTTGCGCACCATTTCCTTCACGTT
AGTACCACTTTCTCTGGGGTAGCTGAGGGTACAATAGGTTTTTTGTAGC
TGTACCATACGTTTTCATGACTGTGAATGTCTTTTTTCCTGATCACATG
ACGGTGCTGAACCGAGCCTTCATCAACGTCCTGAGTACTGCCTACAACA
AGTTCTGGTCTGCTGGATTACCTGGGAGAGTAGGTTTTTTGCCACTCTC
CCTCGACTTTTGTTATCTTGACTAGGAAGCGAACGCCTGGGTTGGTCGT
CGATAGCACCACGCTACCAGACCTCTTTTGAGGTAGCTCCTACCCTTTT
TTGAACTGGAGCCAATTGCAACATGCTTCCGACTCATGGTCATCATTGA
TGGGTCATCAATACGTGTTGGACAGTAGATGCGTACCTGCAGCACGAGT
TTTTTGCAAGGCTGCAGACACTTTTATTCCCATCTCAGGACTTTTTTGT
ACCGAGATAATTGTCTCATTGGTGCCACCATCACCGTCCACCAATGGCC
CAGATGCGATTCCAAAGCTGTGCTGTCCGACTATTGTCGTACACTTTTT

-continued

TATACTCGACAAGGCAGTTTTCGAACGGAACTCAGGGTCGGAACCATTA
TCCGTGCGGATACACGCAATGTGACACTACCAGGATTTTCCTCTACCTA
GCCTAGTTTTTTCCCTTCTAGGTGACACGGCATGTGACTGAGGCAAAAG
CGGTTTCTGCGATGGCTAATTTCGTCGAAGCCGATCAACTATTTTCCAG
AGAGGTACCTTTTTTGTGAGCTCTCTCTTGCTTTTGAGACTACAGCCTC
TAGTTTTTCTAGAGATCCCAGTCTCGCAAGCATCTCCTCACTTTTTTGG
TACGAGATGGGAAATTTTATAGTTGATCGGCTTCACTCAAATTAGCCAT
CGCAGAAACCGCTTTTGAGCAAGTCACATGCCTTTTGTGTCAAGCCAAA
GGGTTTTTTCTAGGTGGCTTAGAGGTCCTGGTAGTGCGTGATTGCGTGT
ATCCGCACGGATAATGGTTGTGCCCCTGAGTTCCGTTCGCTGCCCAGGA
TAGTATTTTTTTGTGTAATCCTGTAGTCTTTTGGACAGCACACGTTCAG
AATCGCATCTGGGCCATTGGTGGACGGTGATTCACGCACCAATGAGTTT
TACAATTGACGTGGTACTTTTTTGTCCTACGTCGGGAATGTGTCCGTCT
ACTTGCTTTTTTCTCGTTAGACGGGTACTTTTGCATCTACTGCATGCTA
CGTATTGATGACCCATCAATGATGACCATGACTTCGAAGCATGTTGTTT
TCAATTGAGCAGAGTTCTTTTTTGGGTACTGCTTACCTCGAGGTCTGGT
AGTCGGGTGCTATCGACGACCAACCCAGGCGTTCGCTGTAGCATCAAGA
TAACGTCGACATCTGGTGGCTTTTTTCCTACCAGATGAGGTATTTTATC
CAGCAGAGTACGCCTTGTTGTAGGCAGTACTCAGGACGTTGATGACCAG
TCGGTTCAGCATTTTCCGTCACTCACTCAGGTTTTTTGACATGTGAGGT
CATGCGTATATACTGGCTACTTTTTTCCTATCAGTATCTCAGTTTTCTA
CCCTGACGAAAGTGGTACTAACGTCTCTGAAATGGTGCGCAACACTCAC
CGAGACGTCACTTTTCTTGGACAAGCCCCAACATTTTGGAGATCGTAAT
ACGCAGTTAGTGCGCCAGGGGTCATTTCATTTTATGACAACCGGCTTCA
TCAACACCCCTAAGACAAATGTTTTCATGCCCGTGGAACGAGATCGATT
TTGAGTCCCAGTGCGACACATAAGAAATCACTATCCTCTAATACATGTT
ATTGCCTGTTGGCAACTTTTGCGAATGGCTCTGACGATCCCTGTAGTGT
GACGGTCACTCCGTTACGAGACCCCATGCGTAGATTTCGTGCAAGCGG
TCATGAGTTTCAAATGGAGTTTCGAAGTTTTCAGAAATCCCGTAGTCGT
TCCTTTTGGCTCGTCTGTCGAGGCAGTAAAGGGTTCGTAGAATGTGAGG
TAGCCGGTCCGTTAATAGCACTTTTAATCCAGGGTTTCTTCGTCAAGTG
TCAGCAGCCGGACAAAACATTTAGGGACCAGGCATACTATTTTAGCGTA
GGCAACACCCGCCTGCAGCCATCCGGACGCAATAACGCTCGAAGATGGA
CCAGCCTGTTTTCTCTGTACAATGGCCACTTGAGGGCATCAGCAACCTG
TTAATCGGTACGCATGTATATGGATATTTTGACACCGTATTCGGACTGC
CCCGATATAGATAGAACTTGAGGGTTAAGGAGCAACCGTCAACGTTTTC
CTAATCGACTGCTACTAGACATGGATTCCGTACATGAACTCTCTAGCCG
ACACCATCGAGTCTTTTCCCTTCCGTTATGGACGAACATGTAGAGCACT
GGCTTTCGGTCAATGATCTGGTCCACATGAGTTTTGCGTAGGCAGTCCT
CGCCACACTTCCATACCCTCCGATTGCCTAGCCTCGCTGGTGTGGAAAG

-continued

TTTTGTCTGGGTGTCACTGAGCACTCAGAAACTTGACCAAAGGTAACCC

TCACACGCAAGTTTACCGTTTTCACGGAGGACTGGTCGGATGGCAAGCG

GTCTGGTACGTACGGACAGGTTATTCGAGCTCAAGGTTTTACGGTTAGC

GCCGTACATGAATCATGGAAATGAGGAGCCCTGGTCACAAACCGTATAG

ATTTGTTTTGGAAGAGGTTTGAATCAGGTACAGATTGGAACGAGCCTCC

AATTGTGGGCGTTCATCTTTCAGTTTTCTACAAGGCCATGGGTGACGGA

AGCTATTGTCTATGCTTCCGGAGCCTCCTCAAGGAGTTCGCTTTTCGGC

AGGTTAGCTGACATAGTTCGGAAGAGCACCTGCGAGTCAGCCGACGTGT

CCAGGGCAGCTTTTCAACGTAGATTGCGTGACGGTGACTAATTCGCATG

CGGCAGCTAGCCTATACAAGATTATCGCTTTTCAGTGACTATGGACACA

CGCTCTGCCTACTCACAGTCGATTGAATCACTCGGGCAGGAGATAGTTT

TCACGTACTGCGCTTTGGTCTAACTCTCGCGCAGTCGACATTGGTACTT

GGTGACGTTGGCGTCTTTTATGTGCTATCTCCAACGCCAGTAACTAAGG

TCGAAACCCAGCAAAAGCGTCGACTACTTTTGCTTTTGAGACTGGACGC

TGTGTTGGTGTGTCTATTCCACGAGTGCGAGGCTATGTGCGACCTGATG

CATTTTCGCTGCTTGGCCCAGTTCGCTGCTACCATCGGTGACGCTTTCA

CCACGCGGAACATACACCCGTTTTCCCTGCTATGAACGGGAACATTAGC

ACATTGTGGACCAAATGCAGAGACTTCACGCTACGTGCTTTTCTTTTAC

TCAACATAATCGAGGGAGTACTGACAGCCGACATAGTGGGCACTGGGTT

ATGCGCGTTTTCGATCAAGGTGGTAGAATGGGATACGTACGTGCTGGTA

CGGTCGAGGTTCGCATATCGGAGAGTTTTCTACATCATCGATCAGATTT

ATGCACCGTAGGATACAAAAGCCAAGGTGAGCTGCATTCGACGTTTTGT

GTGCGAGCTCGCCGATTGAATGGTGAGACGAGCTCTCGGTTTACAAACG

TAAGCATGAAGATTTTAGTCCAGCACGCACATCGCACTCTGCTCGACGC

TTAAATGGCACCCACGACGACATGTACAGATTTTGAACATCTGTTGTCG

ATAGTATCGTAGTAACCTCACGCTGACTCATAAGTTGGCTATGCCACCT

TTTGACTGTGTGAGCAGTCCATTGACGGAGAACCCGTAATAAGCCGTGC

AGAGTCACGCCTTTGAGTTTTACTACAGTTGCTCAGAAATAGAGGATGT

CTGGCACCTGACGAACTCCCGCTAAACTTGCCGAATTTTGTCTGGCAAT

CCAGAAGCACCCAACTCTCACGAGGACTTCCACCCATAAGGCGACAGAG

ATCCTTTTCTCCTCCAGACGTAGCCATCCACACGGGAAGGGACGGTATG

ACTTTCGGGCACATTGAGCAAGTTTTGGGAGCAGCGTGGGACTTTTTTG

AATTACGCTCATCGTTGGTCCCTGAGCAACACCAGGATGTGTTCACACT

CCTGGCATATTTGTCGACAAACAGTACGCGTCATCACATGCTTCGTTTT

TTGTCCACATGTGTGCTCTTTTCCGAATTGTTTGCTGTTTCCGAACACC

AAATTCTATCAACGCATAGGGACAGCTACGAACGACTTTTCTATGCAGT

CGACACGTTTTTTCCTTCCGACTTGGTATCCTGTTCGTCACCAACTTTT

TTGGACATGACGACACAATTTTCAATCTCTATTCTCGCATCGCAAGTAC

CGAGTAATCGTCAGCCTATGACTGTGACACATGAGCTTTTGTGGTGGTC

TCCTCCCTTTTTTCCGATGAGACCCTCTGCCTATAGAACGGCTCAATCT

AAGGTTTGGTACTAGGAGCAGCTATGTCTGATCCACCAATCTTTACCAC

-continued

ACCAGTGGAGTTTTTTGGTTACTGGTGGGAAATTTTCACTCCTAGTGGT

ACAGCAGTGAAAAGTCGGAAGTACTGGTCTGTGGACAAGGAGGAGTTAA

CTTTTCGTGAAGGGATGTCGTGAT 67 crossing number hexagonal knotted DNA (SEQ ID NO:6):

ATCCAGGGAGTGGCGTACCGACACAAGAGTACGCCCCTAATGCATGGAG

CCTCGTCTAGGATATTTTCTTCCCCAGGCCTATTCACAGTTTTTTGGTC

TCATAGGCAGCTAGCACTGCTAGTGGGATGAGCTGGACACACTTGTGGT

GAGGCAGTGCGTCAACCTAGGCTTACGGGACTACCTACCTCCCTGGGAG

GCTGTCTTCACGGATGCTGCTTTGGTCTAAGCCTTTTTTCCTGTCGACC

AATGAATCGCACTTGGCCATGCTTTCTGCATTTGGGCTAGGATAAGGAC

CATGCTCGTGCACGTACAGAGAAGACTCTTTTTTGTCCATTCTCTTAGT

CCGGTATGAGCTTATGGACGAAGCCCTAGGATCTGTAAGGAGCATCGAG

TAAATCGTTCGTGTGTGGCATAGCGACGTCAAGCAGGTGTACCTGTTCG

AGTTTTCCTGGAAGAGTTCCCGTTTTTTGGACCACTCTTATGGCGCAAC

CATCGAAATGGGGCTGTAATCGCCTGGATGGAGCGATTCCCTTTAGGAC

CGTCCACTGCAGTGGACTTTTTTCGAGTCTGCAGTCCGACAAAGGCAGG

TCTGTTGGTCTTCGGTATGAGCATCCGCAACCACATGTGCCCAGAAAGT

AGGATCACTTCTCTGCATGTACGTCTCAGCCAAGAGGAAGAAGCCAGAG

ACACTCATGTCTTTTTTGTATGCAGTGTCAACGACAAGCGGTTCATTGG

GATTGAGTGTCTATGATTCGTTCATCTAGGCTCGACCGAGAGTAAGCCA

GATGCCTTTTTTCTTAGGTGGCTTTGTCGCAAATCACGGAACCAAAGGA

TGCATGATTAGCGGAGACTCTCTTCCGATTTGCAATCGGAGGTTCTGAT

CGTACCACATGCCGACTTACAACCATGGTAACATGTTTCTCGCCAGGTA

GATCTTCGTACTTATCCCGATAGAGTTCTTCGTTTGAGCCTCTCATGAG

TTCTACACTCTTGTCACTTCGGTACAGAAGTCGTGGATACCTGATTGGT

TAAGATCTTCCACATGGCACGACAACAGAGGCTTGCGTGCCTGGAATCG

TTAGTGATATTCCTACATTGCCCCATTCCTCCGCTAAGGGTACGGTACA

CCAGTAGGCATGTCAACTCACACACACTGGAGTTTGGAACAACGAGAAA

TTGTAGGCAGCCATGGTAACGTTTATAATGTAACATTTCGGAGGAACAG

ACAGCTCATCGCCTTCACACGGTACCATGTCCTCAATCCTGGGGACATC

CTGACATGCTAGGATAAATCGGGCTCTACGACGAACTTGGCCTAGGTTT

ATAACGCGTCTATATATCTCGGAAAATGAGATACCTAGGGGACCCTACA

CTTTCTCTACACCAAGCATCTGGCCCTACATGAGTTTCACATGGGTTGG

AATCTAATGGTTGGCAATCGCAGAACGTGCCTTTAACCTGGGAGTAACA

GACCTACGATTAGCCATTATCCCCTAATCTGCCAACCATTTGACACGCT

AGGGATAGATGCTTAGCCCGAATCTTGCACTTGTGTTTCCATATGGCGG

ATCTTCGAAACTCATGGCCACCTTTCCCAACGCATTTGGATCTTTGTGC

AACTCGAAGGGACAAAGGTTCCTATCAATCAGTGTAAACCGGTCGCTCA

TTTCCGCCTGGTGCTCGTGCGTTGCTTACCTAATACACTCTAAGGAATT

-continued

TGGAACAAGCTGGTGACGGACGGCTGAGGTCGTCCTGTTTCGGGTAACT

GCACACTAGCGTCGTATCGTAGGGTAAGTGGCTCAGGGGACGCATTTGC

TGACGGTCAGAATATCGCGTTTAATCCAGTTGTCTCGACGATTTGCAGG

ACCTTAATACGCTGCATGTCAACGGCTACGTTGATAGTGCTTCTTACGT

TTCACTCTCCAGTAGCTACAGCTCGTGAATCCCCAACACTGAGCATTTA

ACGCAGACCGTTAGATGTACTCACACAGTCCAACGCTTCACTAGAAAAC

AATTTTCTAGGTAACGCGCGAGACTCTAATCTTGTCCACACGATCGGAT

TAATGCCGGAACTGCTGATACTAGCCGTCCCTCTCGATGTGTGACTTCG

GACGATCCTTATTGGATGCTATGGACTCCGACTGCGTAGGATAGAAGAT

ACCGGCTACATCCAGAGCCATATGAAGTGTCCGTTGTGTCGGTTACGGT

GTCCTAACGGTCTTGGGACCCGTATCCTGCTTGCAACACAGCTTCTTTC

AAGGTTGCTCGTTTGAGTGGTCTCCCCAGGGTTATCAAGACAGTGGCCA

TACTAGCGTTCCACTCGGTAAAATCCGACCTCGGACACTCAGCCTGAGA

CGCAGAGAGAACTAGGTCGGCTGAAGCCTTTGGTGAGTAACGACCCTTA

CTCGGAGCGTGTGTTCGAAGGAAAGTCATTGACAGAAGGCACGTTTTCT

CAGGACCTAGTGTTAGGTTACGGGCTATCACATGAACTGGCTTATTGAA

TCTTTCACCATACAACAGATGTGTATGTGCATCCTATCTAAAGCACTGT

TTGTCCAAGATGAGGATCTAGTATCGGTTCCTCCTCACACACTGGGACA

CTTCTGTTTGACCCAGACTGGTCCGAATGCTACATGTAAGCTCTTCATA

GTCTTTTCCAGCGGCACTACTGTAGGAGCCCAGAGTCACAACCGCCACA

TGGACACCCGCTGTTGTACTCCACGATTGGCATGGTAAGTGAAGTTCTA

GGTCAGAGGGTCCTATTCACGTGCGATACTAAGTGATACGATAGCCATC

GTGACTTGTTTGTGACTACCAACCACCACGTCCTACTCTTGAGGAAAGG

ATCACTTTCCTACCGTAGCGATCTACTACCCAGACCACACCGAAGGCAA

GATCCCTTCTTGTTTGATTGGCTAGCCATACTACGTGAAGTTGTGCGAA

AGTGGGACGTCTACCTACCGTCTCATATTGTATCATAACCGAGCCTGAC

GTTCTGTGGTAGACACTTCGAAACCTTGCCTTTTTTGGTTGTGTTTCTC

GTCTGTCGACCATCTACGAAGACTTCGTCGCATGCTGTTCAAGATGAAA

GTCGGAACGGACAACCACAGTGTCCTTTTTTCTGTGATGTGGTAGTACG

TAGCTGCAGCTGTCAACTATCGGATTCTAAGCGCGAGTGTGCTGCTGAG

GTAGACGTTGACACCACCCGCCACACCATAGTCTCTGGATGAATGACCC

CGTGGGAAGTGTGACGTGGTTTTTTCTCTTGCACACTAGCCGTATAGCC

CAAATCCTACAGTCTTTGTCTGGCTATATGCCAATTGCGACGAATGCTA

TCACAACATGGATGTTTTTTGAGTGGTGTTGGATGCGTGAACATTTCTA

CACACGTAGAGAAGGACGTGCACGGAGCAGTCTTGCACTGGGCACATGT

GTGTAGTCTTGCTATCCAACACGGGATGACTTGTGCTGCATCGTGGCAC

TCGTCTAGTTTTTCTAGACTCCACCCACGATGCAGTTTCACAAGAGCCA

CCGTGTTGGATAGCAAGACTAAGTGTGTGTGCTTTCCAGTGCAAGTGAT

GGCCGTGCACGTCCTTCTCTACGGACCAAGAAATGTTCATTTCGCATCA

TGACCCACTCTTTTTTCATCCAGTCATTGATAGCATTCTTTGTCGCACG

-continued

ACACATATAGCCAGACAAAGACTGACCACGTTGGGTTTCTATACGGCTT

TCCACCAAGAGTTTTTTCCACGTGTGGAATCCCATTTCGGGGTCATTGC

AAACGAGACTATGGTGTGGCGGGTGTCACAAACGTCTACCTTTTCAGCA

GGTTGGTCGCGCTTAGAATCCGATAGTAAGATCCTGCATTTGCTACGTA

CTTGAGACTCACAGTTTTTTGGACACGTCTCATGTCCTTTGTTCCGACT

TGTGCAATGAACAGCATGCGACGAAGTCCCTAGAGATGGTCGACTTTAG

ACGACCTCTACAACCTTTTTTGGCAAGAGAGGGAAGTGTCTACTTTCAC

AGATTAGGAGGCTCGGTTATGATACAATACTGTTAGGTAGTTTGTAGAC

GTCCAGAGAGCGCACAACTTCCATGAGTATGTTGGTCCAATCCAAGAAG

GGATAGATGCTTCGGTGTGGTCTGGGTAGTCCCAATCTACGGTAGGGTG

ATTTGGCTCTCAAGAGTAGGACGTGGTGGGATCCAGTCACCAAGTCACG

ATTCTGTTCGTATGTGATAGTATCGCACAACTCAAGGACTTTCCTCTGA

CCTGCTGTATCACTTACCATGCCAATCGTGCGAACCAACAGCGGGTTTT

GTCCATAAACGGGTTGTTGGCCTGGGCTCCTATCTCGTTGCCGCTGGAG

ACTAATGCTCGCTTACATGTAGCATTCGGACTCCATTGGGTCCAGAAGT

GTCCGTCCTTGTGAGGAGGAACCGATACTAAGCATGCATCTTGGACCAG

TGGACAGCATAGGATGCACATACACATCTCCGTAATGGTGGATTCAATA

AGAGCTGTCATGTGATAGCCCGTAACCTTAGCTGAGGTCCTGAGACGTG

TGGTACGTCAATGACTTGATGTCGAACCTGTTCTCCGAGTAAGTTTGGT

CGTGTTCGACCAAAGGCTTCAGCCGACCTTACAGCCTCTGTTTCGTCTC

AGGCAACTCTTCCGAGGTCGGATTTTACCGATACCTACGCTAGTATGTT

TGCCACTCCAGAGATAACGTGTGGGAGACCACTAGGGTCAGCAACCTTG

GAAGCCACTGAGCAAGCAGGATCTTTGTCCCATCGAGGTTAGGACACCT

TTGTAACCTGTGAAACGGACACTTCATATGGCTCGTTTGCTAGCCTTTG

GTATCTTCTCGTGGTCGCAGTCGGAGTCCATAGCATTGTCGAAGGATCG

TCCTTTGAAGTCTGGTCTCGAGAGGGACGGCTAGTATCCCATCATCCGG

TTTCATTAATCCGCGACCTTGGACAAGATTCACCTCTCGCTTCCAACCT

AGATTGTTTTCTAAGCCCGCGTTGGACTGTGTGAGTACAATGTCCGGTC

TGCGTTTGCTCCAGCTAGGGGATTCACGAGCTGTAGCTCAGCTAGAGTG

CGTAAGAAGCATGCCTAACGTAGCCGTTGACATGCAGATCCCAAAGGTC

CTGCTCGTCTCCTAGACTGGATTAAACGCGATATTCGCGTAGTCAGCTG

CGTCCCCTGTCATCCTTACCCTACGATACGACGCTCACACACAGTTACC

CGCAGGAATCGTGCAGCCGTCCGTAGAGAGCTTGGCGTTAATTCCTTAG

ATTTGTGTATCCCAAAAGCAACGCACGAGCACCAGGACCTCGTGAGCTT

TGACCGGTTTATGTGTTTTGATAGGAACACGGGTCCCTAGACCTTGCAC

GATCCAAATGCCACACGAAAGGTGGCCATGAGTTTCGTGACAGCGCCAT

ATGGCACAATCATCTGATTCGGGCTAAGCATCTATCTTCGTCGTGTCTG

GTTGGCAGAACGTCGGATAATGGCTAATCGTAGGTTGAGACCTCCCAGG

TTGGCACTGTAGCCGATTGCCAACCATTAGATTCGCTATCATGTGCTCA

TGTAGGGGTCTTTGCTTGCCTGAGAGAAAGTGTCAAACGCCCTATTTGG

TATCTCATCGAGGTAGATATATAGACGCGTTATAATTGGGGGCCAAGTT

-continued

CGTTTTCGTAGGTGAAGATTTATCCTAGCATGTCAGGTCTAACCCAGGT
TTATTGAGGACACCTTCTCGTGTGAAGGCTCCTAGCTGTACACGCCTCC
GTGTTACATTATGTGGCTTACCAGACTTGCCTACAATTCAGTAGTGTTC
TTTCAAACTCCAGATCCGTTGAGTTGACATGCCTACTGGTTCTGAGTAC
CCTTAGCTTTGGAGGATCCTAGCAATGTAGGAATATCACTAATCCACAC
AGGCTTTACGCAAGCCTGACAGTTCGTGCCATGTGGAAGATCTTCGAAG
ATCAGGTATCCTTTACGACTGGCTAACCGAACACTCAAGAGTGTAGGTG
AATTGAGAGGCTCCGAAGTGAGTGATCGGGATAAGTACGAAGATCGTGG
AGGCGAGCATGTTACCATATAGCTAAGTCGGCATGTGGTACGATGCTAC
ACTCCGATTGCTCGGACACTTTTCTCCGCTAATACGTCATCCTGCTAGT
CCGTGATTTGTTTCGACAACAGACCCTAAGTTTTTTGGCATCGTCTGTA
CTCTCGGTCTTTGAGCCTCTTGCAACGAATCATAGACACTCAATAGATC
GGAACCTTTGCTTGTCGTTCCTCAGGCATACTTTTTTGACATGCTGAGG
TCTGGTTTCTTCTTCCTCCCTTTCGAGACGTACATGCAGAGAAGTTTGG
TTACTTTCTGGGTTTCACATGCTTCGGCGGATGCTCATACCGAAGACAC
TGTCACCTGTTTCCTTTGTCGGTACCTCGACTCGTTTTTTGTCCACGAG
GTAGGACGTTTGTCCTAAAGGTGTGGACTCCATCCAGGCGATTACAGCT
AGGATTCGATGGTTGTTTCGCCATCTCCTTGGTCCTTTTTTCGGGAAAG
GAGCCAGGAAAACTTTTCGAACATCAGAACCTGCTTGACGTCGCTATGC
ACGGATCGAACTTTGATTTACTCGTGAAGACTTACAGATCCTAGGGCTT
CGCAGTCAAGCTCATACCTTTGGACTAGTTCCATGGACTTTTTTGAGTC
TGGAACGTACGTGCACGTTTAGCATGCAGTGTATCCTAGCCCAAATGCA
GAAGATCCTGCCAATTTGTGCGATTCAGACTGTGACAGGTTTTTTGGCT
TAACAGTCAGCAGTTTCATCCGTGAACTTTAGCTCCCAGGGAGGTAGGT
AGTCGTTGTAGCCTAGGTTGTTTACGCACCTATCCACCACAAGTGTGTC
CAGCTCCGTATTCTAGCTTTAGTGCTAGCTTGAGTGGAGACCTTTTTTC
TGTGACACTCACTGGGTTTGAAGAAAATAGAGACAACGAGGCTCCATGC
ATTAGGGTGACCCTCTTGTGTCGTTTGTACGCGTGGACCTGGAT 9 crossing number square knotted RNA (SEQ ID NO:7):

GGGAGAGGAUCCAGAUGAUGUCUCUAUGGCCAAAAGUUGAAGGUCCGAC
UACACGUUGCGUAACGGUAAGCACUCAUAUGAGUAUGACAGGUCAUAGC
AGUAAAACGUCUAUAGUCCAGCAGGAAACUGCUGGAUAGGUUGGGCAGU
GCAACUAGGUCGACGAAAGUCGAGUUGCCUAGUAUGAAAAGAACAGUCG
UCUCGUGAUGUCCAGCGAGUAGCAGUAUCUUAGAGAGUCGAUUCUCGCA
CUGGGUUGAAAAUCCAAGUAACACUUUGCGAAAGCAAAGUGGGUAACUC
AAGGUUUCAUCUCCACCACGAAAGUGGUAUGUGUCUGCCUUAAAAUUGC
GGUGCUUCAUAAGUGAUCGAUCGUUACUGUCAGCUCCAGACCUUUACCA
CUGUGUCAGACAGAAAAUGGAUACGGGUCGUUACUCACCGCUUUAGUAG
UGAUCAGUACUUCUACUUAAGACCACUAGAUGCUAAAAUCUGGCCCAAA

-continued

AGAUUUGGAUUUGACCCAUGUCCUUACUGAUUACUCAUUCUCGUCAUCC
GAGUUCAAAACUACGUAGGAAUGCAUCAUGCAGAACUACUGAGCGAUCC
AAUAAUGGUUCAGGAGUGUGUAUAUCUAAAAGCGUGUCUAGCAGGUGUG
GCUGGGUACACGUCUCGAAUAGACGAGCGACGUUGGGCACUAUACGGUA
AAACUGUGACACUGUUGUCGGAAACGACAACAGACCUCAAGAGAUUAGC
AACGUGCACGGAAACGUGCGUCGCAAAGCUACAAAAUCUAGUGCACCUU
AGGAAUGGUCAUAAUAGAUGCCGUCCAGCUGUCAUGACACCUAGGGUCA
CUCCAAAACUCUCUAACUGGUACGAGAAAUCGUACCACUGACCAAGGGA
ACUAGAGACAGUGUCCUUCUAGAAAUAGAAGGACACACAUGAACGUUCC
AAAACUUGGUCAGUCUCCAGCGAAAGCUGGAGAGUUAGAGAGGGAGUGA
CCCUAGGUUAAGUAGAAGCUGGACGGCAUCUAUUAUGACCAAGUAACGA
GUGCACUAGAGUAGCUUUGCGACAACGGGAAACCGUUACGUUGCUAAUC
UAAAACUUGAGGUCCAUGUAUCGAAAGAUACAUGGUGUCACAGACCGCU
GACACACCAACGUCGCUCGUGAGCUGACGACGUGUACCCAGCACUUAUG
ACUAGACACGCAGAUAUACACACUCCAUCGACUCUAUUGGAUCGCUCAG
UAGUUCUGCAAUCACGAGUCCUACGUAGGAACUCGGAUGACGACAUACU
CAAAUCAGUAAGGACAUGGGUCAAAUCUGUAGUCGUUGGGCCAGAAGCA
UCUAGUGGUCUGUCAUGACAGUACUGAUCACUACUAAAGCGGUGUUCCU
AAGCCCGUAUCCACUGUUAUAGUGCGUGGUAAAGGUCUGCUAUUCGAAG
UAACGAUCGAUCCACACCUGAGCACCGCAAAAGGCAGACACAUGUGCAG
AAAUGCACGGAGAUGAAACCUAAAAUGAGUUACCCCAACGAAGAAAUUC
GUUGGUUACUUGGACAACCCAGUGCGAGAUGAACCAUUCUAAGAUACUG
CUACUCGCUGGACUGAUGCAUACGACUGUUCCAUACUAGGCAACCGUUC
GAAAGAACGCCUAGUUGCACUGAAAACCCAACCUAGCCGUAGAGAAAUC
UACGGCCUAUAGACGACUGCUAUGACCUGUGAAUGAGUUAUGAGUGCUU
ACCGUUACGCAACGCAAAUCUUGACCUUCAACGGCCAGUUCAUGUUCAU
CUGGAUCUUCUCGAG 15 crossing number DNA tetrahedron (SEQ ID NO:8):

ATCGGACCTTACATCAGAACACACGAGGTCCTAATGTGGTGCTTCGTGT
GGAGCCAGATTAGGCCTAAAATCTTGAACACGGGTCTCAGTAATTGATG
ATGCTGTCTGAGAGCATGCCACAACTACGGGAGGGTAGGCCCCTTGACA
TCCTTTCTGGGTTCACCAAATAGGGGATGTGTTAGGATGTCTCGGTTCT
TAAGCTATTGGTCTTCTTGATTGTCAGCCTGTCGTTCATAACAGACGAG
TAACTGTGTTGGCACGGCACGTCTGTTGTCGGAATCCTGCACAACATTC
TGTTGACTTTCCCAAGACGACCTTCCAGTGCTGCTAAATGTATCTAGCC
TCAACTTGCAAGGCGCGTACCGCGAATCGAATGCGTTTTCCATCTGGAA
AATTGTGTGAAACGTTATGACTATTGCGCACGAAATGTAGAGCTCAGAC
CTCACGTGCGTTCGTTTGACAATAGGTGGTCGTAGTTGCCATGACGTGG
CACTGTCCGAATCGGACGTGCAGCCTGCATTAGCTGGCTTATTTAGATT
TCTGAAGCCGGCTGTTGGCAGTTCTCCCGATTACAATAGCCCAACAGTG

-continued

CACGTGGGCACGGCCTCTGGTAGGGCATGTGCGATTGTCGAAAGTGGGA
CCAAGCTCTCTCGTCGGTCCGCCTGGAGGTTTGGACCCATAAGTTTGCG
AGAAATCACTGAGCTCTCTTTCTCAACACCCAGACATCCAACGTTACGT
ACGACAAGTCTTGCAGCCATAGTTTCGTGGATCTCAGGGAGCCATTCAA
ATCCGACTACTGGGATAGAGTCTGGTTCTATTAGACGTAGACCGGTGAT
GCCTATAAAGCAGGGGTAGTTGCGGCGACTGGAAGGCTCGAAGTGCCAA
TTGATTTTCAGGCTGATCTAGTTTTTCTAGATCAGCCTGAAAATCAACG
TTACCTTCGAGCCTTCCAGTCGCCGGGTGTACCCCTGCTTTATAGGCAT
CATTTCCGGTCTACGTCTAATACCGTCAGACTCTATCCCAGTAAGACGA
TTTGAATGGCTCCCTAGACTCCACGCTATGGCTGCAAGACTTGTCGTAC
GTGGTCGGGGATGTCTGGGTGTTGAGAAAGAGAACCTCATGATTTCTCG
CCTTATGGGTCCAAACGAAGACGCGGACCGACGAGAGCGAGACGTCCCA
CTTTCTCCCATCGCACATGCCCTACCAGAGGTTTCCGTGCCCACGTGCA
CTCACCGGCTATTGTAATCGGGAGAACGTAACGCAGCCGGCTTCAGAAA
TCTAAATAAGTTTCCAGCTAATGCGCAGGACACGTCCGATTCGGATGCC
GTCACGTCATGGCAACTCGTCTGACCTATTGTCCGAACGCACGTGAGGT
TGAGGTTCTACATTTCGTGCGCAATAGTCATCCGACCTCACACAATTTT
CCAGATGGACGCATTCGATTCGCGGTACGCGCCTTCACACGTGAGGCTA
GATACATTTAGCATGTGTGGAAGGTCGTCTTGGGGTCAACAGAATGTTG
TAGGCTGTTCCGACAACAGACGCAGTGCGCCAACACAGTTACTACGACC
TTATGAACGACAGGCTTTTGACAATCAACTCCAGCAATAGCTTAAGAAC
AGCTTGATCCTAACACAGACACTATTTGGTGAACCCAGGGATGTCAAGG
GGCCTACCCTCGAACAGTTGTGGCATGCTCTCGTCGAGCATCATCAATT
ACTGGAGACCGTGTTCAAGTTTATTTTAGGCCTAATCTGGCTCGCAAGT
AAGCACCACATTAGGACCTCGGCACTTCTGATGTAAGGTCCGAT 20 crossing number DNA pyramid (SEQ ID NO:9):

ATCTTGACTGGAATAACTTGTCGATCCTCGTGTGGCGTTTGTCAGGGTA
GTACAGGTGCGGACTCAGGAACGATGTATCGCCATACACCAAGCTACAG
TCTCCAAAGGAAAAGCGTTGCTTAGTCACCCCGACGTTCGGACCATGAT
GCGGGTGAAAATGCAACGTTCTCCGTAGTGATCTCGGTGAGCTTGGTAC
GCCAGTGAAGTGCGACGGACTAGTCGGATCGTTTGTATCCACTTACCAG
CAATAACAAAGTGACGACATCAAAACGTGCGACCGCACAGACCAGTGTT
CTGTCCGCTAATTGACGTACCACTACCTAATCGAAACATACCTGCTCGT
ATGTGCTCGTGGATGCTTGCGGAACTGTTATGGGCTTTCTCTTTAGCGG
CGATGTCTCGGCTATGGAGTTTTGGAGTTCTGCACCGGCCGGTGTGGTG
TGGCAAAGATCCCATTTACTTCTCTGCCCAGTGGCTGTTATCAAGCCGA
GCGTCAACCCAAACTTAACTGGCAGTGCTAACTGCACTGGGTTCTCTCA
CTTAAATGGACCTCGGCTCGGGCAGCTGGGCCACTCGAATCTGCGCTCC
CAGATAAACTCGACCCATCACTTGCATAGGTGGGCTGTCGTGACTAGCA

-continued

TGTTATCCTCAAGCTCGGACTCGGGATCCCGTGTTCCGCACAATTCGGG
CTTGAGGGCACGTGTCCCATAGGTACCTACGCTGGAGAAAACAGATCTG
CGAAGGACAGGCTATTAGCTTTAGATCTCTGTGGCACAACGGGTTGCCA
TTGGAGCTGGTATAAGCATAGCTCGCATCTAGGCCCAAGTCTCTTCTAG
GTTCTTCCTCGCGTCGAGAGAAGTATAAATCGCACCCAATCCATAATAC
CCAACCCGGCATAAAGTCCTCAAAGGATTACTGCAACTGTTACTGCTGA
TTCTCGGAAATGTGACGGTAGTTACGTACGGTACCAGACCCTTGACAAT
TTCGATTGGGTCCGGGTTCTTATCTTGATCACACTTTTCATGATACCTA
TGTGTACACAGCCTGAGCCTTAACTAGTTTGACGGGAAAACACAATAGA
CGCACTGTTTTCAGCGAAATAGGACCTGAGAGGACTTTGTCAAGCATGG
CTGCTTTGAGCCGTTGGGAATCAGTGTTTATGGACGGATCTTGCACCTG
ACGTCTCTCACCTAAAGGTTATCTAGTTTTTCTAGATAACCTTTAGGTA
CTCGACGTCAGGTGCAAGATCCGTTCGTTGACACTGATTCCCAACGGCT
CAAAGCATTTGCCATGGTCCACAAAGTCCTCTCAGGTTACCTTTCGCTG
AAAACAGTGTACGTATTGTGTTTTCCCGTCCTAGTTAAGGCTCAGGTGG
GAGACACATAGGTATCATGAAAAGTGTGCGAGCCATAAGAACCCGGACC
CAATCGTTGTCAAGGGTCTGGTACCGTATGCGACTACCGTCACATTTCC
CGTCATCAGCAGTAAGCTGGTCAGTAATCCTTTGAGTTTGACTTTATGC
CGGGTTGGGTACAACGAATTGGGTGCGATTTATACTTCGAGTGACGCGA
GGAAGAACCTAGAAGTTTAGACTTGGGCCTAGATGTCCACTATGCTTAT
AGAGCAGCCAATGGCAACCCGTGTAGTGACAGAGATCTGCTAATAGCCT
GTCCTACTGCCATCTGTTTTCTCCAGGACGCTTACCTATGGGACACGCA
CTGGCAAGCCCGAATTGTGTTTCGGAACACGGGATCCCGCAGGCGAGCT
TGAGGATAACATGCTCTGTGTGACAGCCCACCTATGCAAGTGATGGGTT
TTCGAGTTTATCCTGTGTCGCAGATTCGAGTGGCCCAGCTGCCATCAAG
GAGGTCCATTTAAGTGAGAGAACCCATTTGTGCAGTTAGCTCGCAGAGT
TAAGTTTGGGTTCGTAGGCGGCTTGATAACAGCTGCCCTGCAGAGAAGT
TGGGATCTTTGCCACACCACACACCTCGGTGCAGAACTCCAAAACTCCA
TAGCGATCACATCGCCGCTAAAGAGGCCCATAACAGTTCCGCAAGCACG
AGCGAGCACATACCCAGCTGTATGTTTCGATTAGTGTGCCGTACGTCAA
TTAGCGTTTGACAGAACACTGGTCTGCGTAGTCGCACGTTTTGATGTGA
GAACTTTGTTATTCAGTTGAAGTGGATACCGATCCGACTACTTGGTCGC
ACTTCACTGGCGCCTAAAGCTCACCGAGATCACCGTCGAGAACGTTGCA
TTTTCACCCGTTTCATCATGGTCCGAACGTCGGGACACAGAAGCAACGC
TTTTCCTTTGGACCTGGTAGCTTGGTGTATGGCGATACTTTATCGTTCC
TGAGTCCGCCGGCGTACTACCCTGACAAACGCCACACGAGCGAGGACAA
GTTATTCCAGTCAAGAT 22 crossing number DNA triangular prism (SEQ ID NO:10):

```
ATCCACAGTAGATGCGCTTTCCGCTGTCGAAGCGACTAGAATCGATAAC
CTCGTCGCCTAAATTCTAGCGATCTTTCTCGTGGGTATGTAAGCAAGGA
CCGAGTCCATAGTTGAAATCGGACACTTCTAGTCCTCTGGGCATAAACA
GAGTCGACTGGTCTCGTACATACTGTCAAACGAATGCCTGTAGAGGATA
CCTCCACCTACGATACCATAAGGATAGACATTTTCTGTTACACCTATTC
ATCACCGGTTTGGCTACGTCCGTGCAGCCGTTCGTGAGTAAGACCACAT
CTGACGCGGGAGAAAGCGCATGTGCCAAGTACAGACCTAGCAAGCCGGA
CGGATGTAATTCTGCCTAGGAGCACCAGGCTACGATCGATTCGCGTTTA
TAGCCTCTTATCTCGAGCTCGTCTCGTCTGCCACGTACTTCCGCGCGGG
TATATAGACACTTTGCCAACGTGCTGAGCGTTTCCATAACTAGGATATA
TGTGGGTTCCAGTAGAGAGGGACAAGTCCTGGTTGATGGTTTTATCGCC
ACTGGGTCCAGCGAACCACCGATCAGCAGGATCACATCTGCAGTAGACG
CGAAAGAGGTCGGGACTCCCGTATAAGTGCTAGGCACCAAACGCATTTA
AGAATCCGGACGGTCTGCCGGATACTCGTTCACCGTAGCCAAAATGGCA
CCTGAGGCTCAAAACCACGACCGCGAACATAAGAATACTTACGCTGCCA
TGGGACGGGTATCCCTGACACTTAGGAGGCAGTCGATAAAGAAGTGCAG
TGACTGCCTATCACCCTTGGTCTGCCCGTCTGTTAGACTCTATATTCTG
ACTACCCAGTGGTCACGATACCGGTGCCAGCCTACGGGTCTGAAGCCAG
GAGTCGATGCTGAATTGTCCTTTGCGATACAGATATGAACGACGTGCTA
GGCGCTGTGGAGTCCTACTGTACTACGGGATGTATACGTGTGCCTAGAC
AATAAAGGTAAGCTATGCTACCATCGCAGGACTATTCACTAACGTCTTT
CCTGAGCTACATACCGATCGATAGAGTTGCCTTTTAGTTTAGATGAACG
TCACCTAAATATCTTCCAGACAGGCCGAGAACTGGCACGCATCTTCGTA
TTTAGTCGACGGATGGGCTCCTTTGATCCTGTTGGATTACGACTATGGT
ACCAAAGAACGATCTCTATGAGATCCACTTTCTCCGTGAAGAAACAATC
CCGCACGAGGCAACTACGTTTACCCTGTTGGAGAGCACTTGCTGCCTGC
GCGTCAAACCGTCAGAGGGTGGCATCTGAGACGTTGTACCGGATTGATG
GGAGAGTAGCGCCCAGCCGAGTTCTAGTTTTTCTAGAACTCGGCTGGGC
CACGCTCTCCCATCAATCCGGTACAGTTTGGCAGATGCCACCCTCTGAC
GGTTTGACTTTGCGCAGGCAGCAAGTGCAGGTCAACAGGGTAAACGTAG
GCATCTCGTGCGGGATTGTTTCGAGACGGAGGTGGATCTCATAGAGACC
ATGGTTTGGTACCATAGTCGTAATCCAACGTCGTGAAAGGAGCCCATCC
GTCGACTTACGAAGATGCTGTGCAGTTCTCGGCCTGTCTCTGCGATATT
TAGGTGACGTTGGTGTAAACTAAAAGGCAACTCTATCTTTGATCGGTAT
GTAGCTCAGGAACCAAACTAGTGAATAGTCCTGCGATGGCGTGATAGCT
TACCTTTATTGTCTAGTTTGCACACGTATCGCGGACGTAGTACAGTAGG
AAGACGAAGCGCCTAGCAGAGGGTTCATATCTGTATCGCGGACAATTCA
GCATCTCGCGTTGGCTTCAGACCCGTTCCTGCGCACCGGTATCGTGATG
GACCGGTAGTCAGAATATAGTTTAGTCTAACAGACGGGCATGATAAGGG
```

-continued

```
TGATAGGCAGTCACTGTCCCAGTTTATCGACTGCCTCCTAAGTGTCAGT
TTGGATACCCGTCTCGTTCCAGCGTAAGTATTCTTATGTTCGCGAGGAT
CGTTTTGAGCCTCAGGTGCCATTTTGGTTTCTACGGTGAACGAGTATCC
GGACACGGGTCCGGATTCTTAAATGCGTTTGGTAGGAGCCACTTATACG
GGAGTCTTTCCGACCTCTTGACTCCCTACTGCAGATGTGAAGGCTGTGA
TCGGTGGTTCGCCCACTGCAGTGGCGATACCATCAACCAGGACTTGTCC
CTGCGAACTGGAACCCACATATATCCTAGTTATCAGCACGCTCAGCACG
TTGGCGTGTCTATATACCCGACATCCAGTACGTGGCAGACGCTCCACGC
TCGAGATAACGTCCTATAAACGCGAATCGATCGTATTTGCCTGGTGCTC
GCTCCTAGAATTACATCCGTCCGGCTTGCTACCGTGTTACTTGGCACAT
GCGCTTTCTCCCGCTTTGTCAGAGTGCGTCTTACTCACGAACGGGGAAA
CGGACGTAGCCAAACCCATCATGAATAGGTGTAACAGATGTCTATCCTT
ATGGTATCGTTCTCGGAGGTATCCTCTACAGTTGCTCGTTTGACAGTAT
GTACTTCACCAGTCGACTTTTCTGTTTATGCCCAGAGGACTACTGGGAT
CCGATTTCAACTATGGACTCATCACTTGCTTACATACCCACGAGAATTT
AGATCGCTAGAATTTAGCTCTCGAGGTTATCGATTCTAGTCGCTTCGAG
GAAGGAAAGCGCATCTACTGTGGAT
```

25 crossing number DNA pentagonal pyramid (SEQ ID NO:11):

```
ATCATGCGTGAGCCGGACTCCTGTACTCATTGCTAATGTACCTATGGCT
AAGGAGTCGGGTACACATATCTCTTTCCCGATAAACACATCTGCGATTC
GGAAGCCCGTCAGCTTTCGATCGCTCTGATCACACCGGAGTTGGCTCTT
GCTTCGTATAGTGCAGAAAGTGCGAATTGAGTAACCTCTCTCACGAATG
AGAAGACACTACTGCGTGTCGTCAGTTGGGATTTCCGCTGGGTACACAG
CTTCGGGTACGCTCTATTCACTGCCCATACGCGGCTAGTGCCTGGAAAG
CAATTCAAACGTCACGGAGTCTCCTCACGTGGGATGAGCACCCACGTGA
CTAACGAACCACTGGGACGCGGCTCGACTTTGAAGTTTCATCTTTAAGC
CCAGTAAACCGCAGCTTCAAACGAAATGTTACACGACACATCCATCGCT
CATGAACAAACGCATTTGTACTCCACTAGACCGGATCCTTACTTTTCCG
ACGGTTTCCAATTGCCTGCCAAGACACAATCTAACGTCCTCGGAACCCT
TAGCGACGCACATAGGTCCCTCGTGGGACCAACCCGAAAGGAGTATGGA
GAGTGTCTTTTGGTGGGATTTAGGACCTCGCGTCCACACATCTGCATTT
GTACCGCGGGTGTAAGTCACAGGGCTTTTCGGGATCACTTGCTAACTTT
TCCCTATTGCTATTACGAACAGGCAGACATATGAAAGGCCACCAGTCGG
CATCCGGTTGCTGCACGTCACTTGCTTTCCGGTTGTTCTCCTGGTAACA
ACATGTTGGCTCGTGAGTATGCAACTGTCCAACTGTCCAGTAAAGATCT
TCTGATGCCAAATCGTTCCTGGACTTCATTCAGTTGTATCAGTACTTAC
CTGGTACGTTTGTTGAAAACAAGCCTTATGCACACTTTACCCAGTTACG
AACGGTCATGACTCTCCGTTAAGAGAGAAGAGTGATTTGCATCGGAAAT
GGACGTTTAAGGACCTTAGAGTAGTAAGCCATAAGACAGAGAACGAGAG
```

-continued

GAATGGAGCTGAGCCGACATATTCCACTGACAAGCAATGCCAGCCGTGT

GCTGCGGCAATAGTTAACTCAGCTCATGCTACACTGGCCTCTTGATTAA

ACCTCTGACAAAAGCCGCACGGACTGGGCACAGTAGCCGTAGCGTGTGA

TGTTCGACTGTGCACCAGAGCTTTTGGTAACGCTTTTAGGTAGACGGGA

ACCGGGAAAACTGTGTGACATGTTAACCAATCTGCCATATACGAGGAAC

GTCCCGAAGTGACTTTGCAGAACATCATACAGCTCCATGACTGGCACGT

CCGCGAAGTCGGTTCGACGCACCTTGGTTGGTTTCCGTCCCTTATAATG

TGGTGGAGTACCAGTAGCAATAAGTCGGGTTCCTAGGCTCGCAGAGTTC

TATCCATGTGCCGACTATGGGACCGTCTCAGCAGGGAGTAGGTACGAGA

CCCTGACCCTCGGGCAGTGGGAATCTGCGTTCTCTAGTTTTTCTAGAGA

ACGCAGATTCATGTTGCCCGAGGGTCAGGGTCTCGTACCTAGGTTCTGC

TGAGACGGTCCCATAGTCTTTGGCACATGGATAGAACTAGTGGAGCCTA

GGAACCCGACTTATGATCCATGGTACTCCACCACATTATAAGGGACTTT

GGAAACCAACCAAGGTGGTGTGAACCGACTTCGCGGACAGGTCAGTCAT

GGAGCTGTATCTGCTTCTGCGTCACTTCGGGACGTTCCTCGTATATCAC

TGGTTGGTTAACATGTCACACAGTTTTCGTTGCACCCGTCTACCTAGCG

TTACCAAAAGCCAGGCAGCACAGTCGAATGGGACACGCTACGGCTACTG

CCGACAGTCCGTGCGGCTTTTGTCAGTTTAGGTTTAATCAAGAGGCCAG

TTGGATCTGAGCTGAGTTAACTATTGCCCACTCACACGGCTGGCATTGC

TTGTCTTTAGTGGAATATGTCGGCTAGTGTCCATTCCTCTACGTGGCTG

TCTTATGGCTTAGAGGAGTAAGGTCCTTCGTCCATTTCCGATGCAAATC

AGGCATCTCTCTTAACACCGTCTCATGACCGTTCGTACGGTCTTAAAGT

GTGCATAAGTTTGCTTGTTTTCAACAAACCGCTCAGGTAAGTACTGATA

CAACTGAATGACTTGCAGGAACGATTTGGCATCAGAATTTGATCTTTAC

TCTCTCCTTGGACAGTTGCATATGGTCCAGCCAACATGTTGTTTGCGTC

AGAACAACCGGGCAAGTGACGTGCAGCTGCAACATGCCGACTGGTGGCC

TTTCATATGCCAGTGTGTTCGTAATAGCAATAGGGAGTTAGCAAGTGAT

CCCGAAAAGCCCTTCAGAGTACACCCGCGGTACAAATGCACCGATGTGG

ACGCGAGGTCCTTCCCACCAAAAGACAGGACAGATACTCCTTTCGGGTC

TCACGCACGAGGGACCTATGACCAGGGCTAAGGGTTCCGAGGTTTACGT

TAGATTGTGTCTTCTCTGGCAATTGGAAGGAGAGGGAAAAGTAAGGATC

ACTGGGAGTGGAGTACTGCGTTTGTTCATGAGCGATGGCCACGTCGTGT

AACATTTCGTTTGAAGCTGCCTCCTACTGGGCTTAAAGATGCTTCAAAG

TCGAGCCGCGTCCCCAGCGTTCGTTAGTCCGTTCTGTGCTCATCCCACG

TCTACTCACTCCGTGACGTTTGTTTAATTGCTTTCTCTGGTCTAGCCGC

GTACATCCAGTGAATAGAGCGTACTGCCAGCTGTGTACCCAGCGGTCCC

AACTGACGACACGCAGTACGTCCTTCTCATTCGTGAGAGGTGCTACTCA

ATTCGCACTTTGATGACTATACGAAGTTTCAAGAGCCAACTCCGGTGTG

-continued

AGTGACTCGATCGAAAGCTGACGGGCTTGATGATCGCAGATGTGTTTAT

CGGGATTTAAGAGATATGTGTACCCCAAGCCTTAGCCATAGGTACATTA

GCAATGAAGCGAGGAGTCCGGCTCACGCATGAT

Topological Control Strands:

1 (SEQ ID NO:12):
GAACAGGTGAGCTCATAATGGCGTACGTTCGTACCCATTTTCGTAGACA
CTCCTCAGTTTTTTCAAGAGAGTGGGCGTGTTGAGACTACAACAGGTTT
TTTGTCACTGTAGTAGATCTTTTCCTGGCTTAAATCAGGTCGCCGGCAT
CTGATACTGGCATCAGGCTGTGACGGACAAAATCAACTTTTGACAAAGA
GCACAGGGTTTTTTGATACTGCTCGAGCTCTCGGGAAGCGAGTTGGTTT
TTTGAAGTTCGCTTTCGGGTTTTGCAAGATAAGAGGCACCCTAGCCTCA
GCGCAGCAATTATTCGTTGTTGACGAAACGCAGTCCGTTTTCTCCAAGG
TACATAGGTTTTTTGCAACGTACCCATGGTCCTTGACATGTTTAGGTTT
TTTGCGTGACATGTGTCGGTTTTAAGAGTGGTGGACACGGACGTCACCT
TGAAGTCTGATGCACAACTCTGGACCCATGTGTATCATTTTAGATACGA
GCAATCCGTTTTTTGAGGGTGCTCGCCCGTGGAAGAGACAGTGCGGTTT
TTTCTCTCCTGTCTTGGCATTTTGGACTTCTCGTGCTTCCACAATGACC 2 (SEQ ID NO:13):
CACCTGTTCGGTCATTGTGACACGTCGAGAAGTCCTGCCACTGTACGAG
AGTTTTTTCCGCAGTACAGCTTCCTTTTACGGGCCTTCTCCCTCTTTTT
TCGGATAGAAGGTATCTTGATACACATGGGTCGTTCGATGTGCATCAGA
CTTCAAGGTGACGTCGAATTGCACCACTCTTCCGACTACACGCACGCTT
TTTTCCTAACGTGTACAAGGTTTTACCATGCCAGGGTTGCTTTTTTCCT
ATCCTGGTTGGAGCGGACTGCGTTTCGTGCTGGCCGAATAATTGCTGCG
CTGAGGCTAGGCGTTGGCTTATCTTGCCCCGATGGATAACTTCTTTTTT
CCAACTATCCACCCGATTTTGAGCTCTCTGCGTATCTTTTTTCCCTGGC
AGATTTGTCGTTGATTTTGTCCGTAGTCCGCTGATGCCAGTATCAGATG
CCGGCGAGTCACGTTAAGCCAGGGATCTCGATTGGTGACTTTTTTCCTG
TCAATCGCTCAATTTTCACGCCACCAGTCTTGTTTTTTCTGAGCTGGTT
CTACGTGGGTACGAACGTACAGACAGATGAGCT 3 (SEQ ID NO:14):
CATGACGGAGATTACCTCGAACTCCAGCTCGGATAGGTTTTGAGGACTA
CAACGTGTAATATTTTGCCTAAGGGTTAGCAATCCTGTCTAGCTAAAAC
ACGTAGTTTTCGAGCTCTGACGTGACGCCATCGATACCTCAGCGTATCG
CCTCGGACTCTACCACAGAGGGTATTTTCCTTATGCGCCCAACGGTGTG
TGGCTCCGTGCACCAATTCCTGCCAGCGTTGCTTACAGCGACTTTTGCG
CTCGACTCAATTCTCCACTGATC 4 (SEQ ID NO:15):
TCCGTCATGGATCAGTGGACGTGTCAGTCGAGCGCGTCGCTGTAAGCAA
CCAACAAAGGAATTGGTGCACGGAGCCACACACGTGCCTGCGCATAAGG
TACCCTCTGTGGTAGCACAGCAGGCGATACGCTGAGGTATCGATGGCCC
TGATTCAGAGCTCGCTACGTGTTTTAGCTGCCATTGATTGCTAACCCTT
AGGCAAAATATTGAAGCATGTAGTCCTCCCTATCCGAGCTGGACAGAGT
GGTAATC

Example 2

A comparison of single-stranded RNA tetrahedrons with or without knots was performed, including a comparison of their sequences, as shown in FIGS. 24-27. V. Kocar et al., Design principles for rapid folding of knotted DNA nanostructures. *Nat Commun* 7, (2016) refers to the construction of a significantly different form of knot than the knots of the present disclosure. The fundamental difference is the design of knot: Kocar et al. used the 2 single-stranded DNA on edge and adopted the natural double helix of DNA as knots. In the present work, in contrast, the knots are comprised of paranemic cohesion crossovers based on 4 single-stranded DNA. Kocar et al. failed to characterize their constructs and thus failed to confirm any structural features of the knots. In contrast, the RNA tetrahedron knotted nanostructures of this disclosure were characterized by AFM images to confirm their formation. The knots of the present disclosure are considerably larger and more complex than those referred to in Kocar et al., owing to the use of paranemic cohesion crossovers as the linking mechanism.

Example 3

Target tumor cell killing by knotted ssRNA nanostructures comprising an antibody to the tumor target is demonstrated as described below.

Programmed Death-Ligand-1 (PD-L1) antibody is obtained from a commercial vendor and chemically linked to a knotted ssRNA nanostructure by the methods described herein.

The yield of knotted ssRNA nanostructures conjugated to antibody is monitored by the different mobilities of unconjugated and conjugated ssRNA nanostructures in an SDS-PAGE gel. The mobility shift demonstrates that knotted ssRNA nanostructures comprising an antibody are generated.

MDA-MB-231 breast cells positive for (PD-L1) are incubated with anti-PD-L1 knotted ssRNA nanostructures for 12 hours. Knotted ssRNA nanostructures conjugated to the anti-PD-L1 antibody are bound to their cognate ligands on cancer cells, initiating tumor necrosis.

Example 4

Cancer cell killing by engineered T cells in a mouse model is demonstrated as discussed below.

The NSG mouse model is used to assess the in vivo anti-tumor effect of control ssRNA sequences not bearing an anti-PD-L1 antibody, as well as knotted ssRNA nanostructures comprising the anti-PD-L1 antibody. Alternatively, PTK7 siRNA are hybridized to ss RNA nanostructures. In another embodiment, anti-PTK7 antibodies are conjugated to ssRNA nanostructures. The CCRF-CEM cell line is used, which expresses PD-L1 and the PTK7 tumor marker, to monitor tumor growth in vivo. 8-10-week-old male and female NSG mice are injected intraperitoneally with CCRF-CEM cancer cells resuspended in Matrigel (BD Biosciences). Tumors are induced by subcutaneous injection of 5×10^6 tumor cells, and mice are treated by IV injection of compositions comprising knotted ssRNA nanostructures comprising the anti-PD-L1 antibody. Tumor growth and condition of mice are monitored every other day. For anti-tumoral efficacy, 6-8 mice per group are used.

The knotted ssRNA nanostructures comprising the anti-PD-L1 antibody is generated using the methods described herein. The knotted ssRNA nanostructures comprising the anti-PD-L1 antibodies (or PTK7 antibodies or PTK7siRNA) are used to eliminate CCFR-CEM cells in an NSG humanized mouse model. Mice are then injected with PD-L1 positive CCRF-CEM cells (Day 0). A pharmaceutical composition in the form of a saline solution comprising the knotted ssRNA nanostructures comprising the anti-PD-L1 antibody is injected at Day 8 to the cohort test mice. T cell survival and CCRF-CEM cells is analyzed by flow cytometry at day 10.

In addition, peripheral blood from adoptive transferred mice is collected for analysis. Serum is used to quantify different cytokine release by ELISA.

The results show that the knotted ssRNA nanostructures comprising the anti-PD-L1 antibody traffic to solid tumor area are used to successfully reduce tumor volume and prolong survival mouse life. Mouse survival of each cohort is also measured, and demonstrates that the mice cohort treated with the knotted ssRNA nanostructures comprising the anti-PD-L1 antibody exhibit a longer survival time than the control cohorts. The results confirm that knotted ssRNA nanostructures comprising the anti-PD-L1 antibody are used to kill cancer cells in the presence of a cancer cell. Targeting efficiency may lower than expected, peptides and DNA nanostructures including aptamers and origami are further optimized to get better outcomes. Furthermore, since the knotted ssRNA nanostructures comprising the anti-PD-L1 antibody are easy to customize, different combinations of targeting molecules, spacers domains, and/or targeting agents are tested to obtain higher anti-tumor potency. In some embodiments, three or four targeting molecules are simultaneously added to the knotted ssRNA nanostructures, or multiple targeting molecules plus cytokines are added to the knotted ssRNA nanostructures, or multiple targeting molecules plus checkpoint blockade are added to the knotted ssRNA nanostructures.

ssRNA Tetrahedron with 15 Crossing Numbers (SEQ ID NO:16):

GGGAGAGUUGCGAAGAAUCUAACACUAGUGUACAAGGGCUUCUCCUUAU
CAGAGAUCAUGAUGACAACAGGUGAAUGGAGGGUCUAACAUAAGAGUAA
UCCAAUGCUUCGAACUAACCUUCCCCUUGUGGUUAUCCUAGCCUAGCAU
AUACGUUCUGAGAAAACUUCCCUCUACUCACCAUCUGCAGCAAUACUCU
ACUACAGGUCUCUUUUCACUCUAGGGGAUGCAGCUAACGACCUACGUGU
UAUGAAGGUCCUAGAUUUGAGUAGCUCCACUCUCGUGCAUGGGGUGGAC
GGUAACGCCCUUCUGGGUUUCUCAAAAGGGGUGUUGCCAGCUGAACUAU
GGCUUUGGCGUUUCUUUCGGAAGCGAAGCUGAUGCUUGCUGAGGCAGAU
CCACUGAAAACCCUUGCCUCCAGACUCGAGCUUCGCGACAGCGUGGCCG
GAUCAUGCUCCCCUUAGUCAGAGUCUUACUGACGUAACAAAACAGGCAA
AUGGUCUCUGUCAAGAUGCCCCUUUGUGACCGUCGGGAUGUAUGUAACU
UAUGCGUGAUUUCACCGGCCAUACUCUGGUCGUCAUUCGCUGAUUGUAG
GGAUGCCAGCGGCCUCAACUACUAGUGGAUGUACAACCCCGGUAAUGCU
CUGCCAUACCGGUAAGGGGACUAUAAGACCCACGUGUUACUCGCGCGUU
AUAUGAUGGCUCAUCAGCCAUGUUAUCCAAAAGUCCAGUUACCUCUGAC
UCCUCGCCGUGCUGGGACUAUCUCGAGUCGCGAACUACAAUACGAGCAA
UUCCGCAUCCCAAAAGUCCAUAACUUGUAUUCGAUCCGCAUGCUAGAUG
ACAGUUUCUUGUCGGCUGUGAACUGGUUGCGACGUGAGCUCUAGCGCCC
UGUGUAACCUGAAGAAGUAGUUGUGCUAUUGAACUCUUGUGCUAGAACC
GAAUGACUCGAAGUCUAGAAAUAGACUUCGACAUGUACUGUUCUAGCAC
AAGAGUUCAAUAGCAAUCAGGUCUCUUCAGGUUACACAGGGCGCUAGAG
AAAACUCACGUCGCCUAGGCUACACAGCCGACAAGAGGAAGGUUUCUAG
CAUGCGGAUGAUUACUCAGUUAUGGACGGGAUGCGGAAUUGCUCGUAUU
GUAGGGAUCAUGUCGAGAUAGUCCCAGCACGGCGAGGUGGGCUUCGUAA
CUGGACGGAUAACAUGGCUGAAUCCCCUACAUAUAACGCGCGACUGUAG
UAUGGGUCUUAUAGUCAUGGUGAGGGUAUGGCAGAGCAUAAAAUACCGG
GGUUGUACAUCCACUGACCUGAUAGGCCGCUGGCAUCCCUACAAUCAGA
GUACAUGGACCAGAGUAUGGCCAAAAGGUGAAAUCAGCGUUACCUUACA
UACAUCCCGCGAGAGUGAAAGGGGCAUCUUGUAGGACCUCAUUUGCCUG
GUUACGUCAGUAAGAGAAGCCCAAAGGGGAGCAUGAUCCGGCCACGCUC
AUGAUCCGCUCGAGUCUGGAGGCAAGGGCAGUGGAUCUGCCUCAUGUCA

-continued

UCUCAGCUUCGCUUCCGAAAGAAACGCUGUACACUAAGUUCAGCUGGCA

ACACCCCGAGAAACCCAGAAGGCGCAUAAGGUCCACCCCAUGCAACGGU

CACGAGCUACUCAAAUCACAGAGACUCAUAACACGUAGGUAAAACGUUA

GCUGCUGAGCCAUGAGUGAAAAGAGACGUAACACGGAGUAUUGCUGCAG

CCCUUACCUAGAGGGAAGCUCAGAACGUAUAUGAACCAGUUGGAUAACC

ACAAGGAACUGUCAAGUUCGAAGCAUUGCGAAUACAUUAUGUUAGACCC

UCAAAACAUUCACCUGUGCAAGCAAUGAUCUCUGAUAAGGAGAAGCCCU

CAAAGCCAUGUGUUAGAUUCUUCGCAACUCUCCC ssRNA Tetrahedron without Crossing Numbers (SEQ ID NO:17):

GGGAGAUUACUCAUAAGGGCUGGCUUGGUUCACUAGGAGCUAGUUGGGU

AGCCCGUCACCAGUGCGUACAGCCCGUUCAUCCGCUUUGCGAUUGCUCA

CACAACGCUUCGAGUUUACCCGUUCUGCGAUUGAUCGAAAGAUCAGGAC

AUCGACGGGUGAACUCGAGUUGGGAAGUGAGCGAUCGCAAGCGAUCGAA

ACGGAAAACUCGCUGCUUACCGUAUGAAUAGGAGGUACCUUCUGCCGGU

AGUCGUUCGUUCAGUAAGCUGAGCUCGAAAGAGCUGUAGUAGUUGAACG

GACGACUAACUUAGAUCGUAGAGACCGAGGCAUACGGUUCCUUGAAAAA

GGACGCAAUGACCUCGGUUUCUACGGUCUAAGUAAAUCAAUAUCACCAC

UACUACCUAUGCCACGAAAACCCAUUGCCGAGGAUCCACAAUGGUGCUC

ACGCGUUUAUGUAGCAUUUUGAGCGGGAUCGGUUGAGAGAAAUCUCAUG

GAGUUACGCUCAAGAUGCUAGCACACGCCGAGCCUAUAGAGAUGGAUCC

UGCUUCGAAAGAAGCUCCUACGGUCUCUAUGGGCUCGGUGUGUGCCUAG

CUCGUAGCUCUAACUCCAAUCAUGGUGGAAAAUGAGUAGUCCAUCGCAG

AGUAUUCGGCCUGUGAGCGUUGUUACGGAUUUGCUGCAGCGGAUGGAGU

UUAUGCGAAAGCAUAGACUCUCGAUCGCGCAGCAGAUCCGUAUUCCCAA

CCACAGGUCGAAUACCGAUGUCCGGACUGCUCAAAAAGAGCGGGGUUAG

CAUGCGUUGCCAUCUCAACAUCUCCGUACUGCACUCUACAUGACAAGUA

CGAGGGUAUCUUGUUCGUGAGAUCGUUCAUGGUAGCACGCAGCUUCGGC

UGAGGAGCGAUCCACAACGCUCUAGAAAUAGAGCUGGUGACAUCGCUCU

UCAGCCGCUCCUAGGUGCUAUCAUGAACCCUUAUGAGAACAAAAAGUCG

CGUGGGCCCCAAUGCCUAGAGCUAAAUGCGAAAGGUGCAAGCUACGCAC

AGCGUCUGAUAAGGCGAGUGAAAACUCGUCUUAGUUCGUCUUGUGCGUG

GCUUGCCGCGAUUCCAUUUAGUUCUAGGUCGUCUAUCCCAUGCGACAAA

AAGAUAUCCUCCCUCUGACCAUGUAGCGUGCAGUGCGGAGAAGAGGUGU

GAGACGCGCAUGCUGCGUUGAAAAACGCUCGAAAACCGUCUCAUACCUC

UCUCCGUGAUAUCAGUAGGAUUCGUCAGAGGCGCAUGAAAAUGCGGUAC

UUGUGAAUCCUGCUGAUAUUACGGAGUGUUGAGGUGGCAAGUUUUCGAA

ACCUCGCUCCCACCGUGAUACCGAUCCGAGCUAUGAGCUAGCAUAAAUG

CGUGAGUACCAUUGCCGUAGGACGGCGAUGGGUUGCCUCAGACGCAGCC

CUAGUUAUCUACCUUUCGAUCCUUGGCCACUUCAUUGGGGACUUCGAAA

-continued

GAAGUAUAGACGAAAGUGGCUAAGGAUGAAUCGCGAGAUAAUUAGGGCU

AGACGAACGGCAAAAAACGUGGUAUAGCAGCUUACGGUGAUGUUGAUUU

CCGGCAGGAGGUACUUCCUAUUUCAUUGCGAAGCGGCGAGAAAAGCUGU

GCGCACGUUGUGGGGGCUACUCAACUAGAAGCUGCUGAACCGAGCCAGC

GAUCUCACGUAAUCUCCC

Although the foregoing specification and examples fully disclose and enable the embodiments of the present disclosure, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

We claim:

1. A knotted, self-assembled single-stranded nucleic acid (ssNA) nanostructure comprising a crossing number from 9 to 67 and comprising at least one paranemic cohesion crossover, wherein the ssNA is selected from DNA or RNA, wherein the ssNA length is from about 1500 to about 8000 nucleotides, wherein the nanostructure self-assembles by means of paranemic cohesion into knots comprising four ssNA regions, and wherein the ssNA comprises a sequence at least about 99% identical to SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO: 10, SEQ ID NO:11, or SEQ ID NO:16.

2. The knotted ssNA nanostructure of claim 1, wherein the ssNA comprises the sequence set forth by SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, or SEQ ID NO:16.

3. The knotted ssNA nanostructure of claim 1, wherein the ssNA is set forth by SEQ ID NO: 6 and self-assembles into a knotted hexagon comprising a crossing number of 67.

4. The knotted ssNA nanostructure of claim 1, wherein the knotted ssNA nanostructure has a 3-dimensional lattice shape.

5. The knotted ssNA nanostructure of claim 4, wherein the ssNA is set forth by SEQ ID NO:8 and self-assembles into a knotted tetrahedron having a crossing number of 15.

6. The knotted ssNA nanostructure of claim 4, wherein the ssNA is set forth by SEQ ID NO:9 and self-assembles into a knotted pyramid having a crossing number of 20.

7. The knotted ssNA nanostructure of claim 4, wherein the ssNA is set forth by SEQ ID NO: 10 and self-assembles into a knotted triangular prism having a crossing number of 22.

8. The knotted ssNA nanostructure of claim 4, wherein the ssNA is set forth by SEQ ID NO: 11 and self-assembles into a knotted pentagonal pyramid having a crossing number of 25.

9. The knotted ssNA nanostructure of claim 1, further comprising at least one anti-tumor agent operably linked to said nanostructure.

10. A pharmaceutical composition comprising the knotted ssNA nanostructure of claim 9 and a pharmaceutically acceptable carrier.

11. The knotted ssNA nanostructure of claim 1, wherein the nanostructure is replicable.

12. A method of treating breast cancer in a subject, comprising administering to the subject a therapeutically effective amount of the knotted ssNA nanostructure of claim 9.

13. The method of claim 12, further comprising administering at least one additional anti-tumor agent to the subject.

14. The method of claim 12, wherein the knotted ssNA nanostructure further comprises a tumor targeting agent selected from a tumor-specific monoclonal antibody and an aptamer.

15. The method of claim 12, wherein an anti-tumor immune response is boosted.

16. A complex comprising a knotted, self-assembled single-stranded nucleic acid (ssNA) nanostructure comprising a crossing number from 9 to 67 and comprising at least one paranemic cohesion crossover, wherein the ssNA is selected from DNA or RNA, wherein the ssNA length is from about 1500 to about 8000 nucleotides, wherein the nanostructure self-assembles by means of paranemic cohesion into knots comprising four ssNA regions, and a topological control strand comprising a sequence at least 99% identical to SEQ ID NO:12, SEQ ID NO:13, SEQ ID NO:14 or SEQ ID NO:15.

17. The complex of claim 16, wherein the topological control strand has the sequence set forth by SEQ ID NO:12, SEQ ID NO:13, SEQ ID NO:14 or SEQ ID NO:15.

* * * * *